(12) United States Patent
Chan et al.

(10) Patent No.: US 12,065,491 B2
(45) Date of Patent: Aug. 20, 2024

(54) ANTI-TREM1 ANTIBODIES AND RELATED METHODS

(71) Applicant: Pionyr Immunotherapeutics, Inc., South San Francisco, CA (US)

(72) Inventors: Christopher Chan, Pacifica, CA (US); Aritra Pal, San Carlos, CA (US); Venkataraman Sriram, Berkeley, CA (US); Leonard G. Presta, San Francisco, CA (US); Tiep Tu Le, Kensington, CA (US); Linda Liang, Mountain View, CA (US)

(73) Assignee: Pionyr Immunotherapeutics, Inc., South San Francisco, CA (US)

( * ) Notice: Subject to any disclaimer, the term of this patent is extended or adjusted under 35 U.S.C. 154(b) by 695 days.

(21) Appl. No.: 17/066,401

(22) Filed: Oct. 8, 2020

(65) Prior Publication Data
US 2021/0101983 A1  Apr. 8, 2021

Related U.S. Application Data

(60) Division of application No. 16/852,294, filed on Apr. 17, 2020, now Pat. No. 10,836,828, which is a continuation of application No. PCT/US2020/016949, filed on Feb. 6, 2020.

(60) Provisional application No. 62/889,994, filed on Aug. 21, 2019, provisional application No. 62/802,161, filed on Feb. 6, 2019.

(51) Int. Cl.
| | | |
|---|---|---|
| *C07K 16/28* | (2006.01) | |
| *A61K 39/395* | (2006.01) | |
| *A61P 35/00* | (2006.01) | |
| *A61K 39/00* | (2006.01) | |
| *A61K 45/06* | (2006.01) | |

(52) U.S. Cl.
CPC .......... *C07K 16/2827* (2013.01); *A61P 35/00* (2018.01); *C07K 16/2818* (2013.01); *A61K 2039/505* (2013.01); *A61K 2039/585* (2013.01); *A61K 45/06* (2013.01); *C07K 2317/24* (2013.01); *C07K 2317/41* (2013.01); *C07K 2317/565* (2013.01); *C07K 2317/732* (2013.01); *C07K 2317/92* (2013.01)

(58) Field of Classification Search
CPC ........ A61K 2039/505; A61K 2039/585; A61K 39/395; C07K 2317/24; C07K 2317/41; C07K 2317/565; C07K 2317/732; C07K 2317/92; A61P 35/00
See application file for complete search history.

(56) References Cited

U.S. PATENT DOCUMENTS

| | | |
|---|---|---|
| 8,021,836 B2 | 9/2011 | Kolopp-Sarda et al. |
| 8,106,165 B2 | 1/2012 | Ruben et al. |
| 8,114,603 B2 | 2/2012 | Margolin et al. |
| 8,231,878 B2 | 7/2012 | Colonna et al. |
| 8,258,268 B2 | 9/2012 | Wu et al. |
| 8,981,061 B2 | 3/2015 | Colonna et al. |
| 9,000,127 B2 | 4/2015 | Stennicke et al. |
| 9,550,830 B2 | 1/2017 | Stennicke et al. |
| 10,179,814 B2 | 1/2019 | Henriksen et al. |
| 10,906,975 B2 | 2/2021 | Stennicke et al. |
| 2003/0001658 A1 | 9/2003 | Colonna et al. |
| 2005/0001550 A1 | 7/2005 | Lal et al. |
| 2005/0002606 A1 | 11/2005 | Colonna et al. |
| 2010/0003053 A1 | 12/2010 | Colonna et al. |
| 2011/0028952 A1 | 2/2011 | Raksi et al. |
| 2013/0000289 A1 | 1/2013 | Colonna et al. |
| 2013/0001505 A1 | 6/2013 | Colonna et al. |
| 2013/0002110 A1 | 8/2013 | Stennicke et al. |
| 2013/0003092 A1 | 11/2013 | Stennicke et al. |
| 2015/0000185 A1 | 1/2015 | Stennicke et al. |
| 2015/0002748 A1 | 10/2015 | Stennicke et al. |
| 2015/0376294 A1 | 12/2015 | Nielsen et al. |
| 2016/0009086 A1 | 1/2016 | Choy et al. |
| 2016/0049641 A1 | 2/2016 | Li et al. |
| 2016/0244521 A1 | 8/2016 | White et al. |
| 2016/0002514 A1 | 9/2016 | Colonna et al. |
| 2017/0152102 A1 | 6/2017 | van Beek |
| 2017/0001907 A1 | 7/2017 | Stennicke et al. |
| 2017/0002981 A1 | 10/2017 | Henriksen et al. |
| 2017/0291946 A1 | 10/2017 | Krummel et al. |
| 2017/0306019 A1 | 10/2017 | Carriere et al. |
| 2017/0003209 A1 | 11/2017 | Colonna et al. |
| 2018/0001055 A1 | 4/2018 | Stennicke et al. |

(Continued)

FOREIGN PATENT DOCUMENTS

| | | |
|---|---|---|
| EP | 3026061 A1 | 6/2016 |
| JP | 2004-522742 A | 7/2004 |
| JP | 2015-508763 A | 3/2015 |

(Continued)

OTHER PUBLICATIONS

Padlan, Advances in Protein Chemistry, 1996, 49:57-133.*

(Continued)

*Primary Examiner* — Hong Sang
(74) *Attorney, Agent, or Firm* — Goodwin Procter LLP

(57) ABSTRACT

Provided herein are anti-TREM1 antibodies and related methods of making and using anti-TREM1 antibodies. Also provided are methods and compositions for enhancing an immune response and/or for the treatment of an immune-related condition in an individual, e.g., cancer, comprising killing, disabling, or depleting non-stimulatory myeloid cells using an anti-TREM1 antibody or antigen binding fragment thereof.

21 Claims, 48 Drawing Sheets

Specification includes a Sequence Listing.

(56) References Cited

U.S. PATENT DOCUMENTS

| | | | |
|---|---|---|---|
| 2019/0032624 A1 | 1/2019 | Schabasser | |
| 2020/0131264 A1 | 4/2020 | Pincetic et al. | |

FOREIGN PATENT DOCUMENTS

| | | | |
|---|---|---|---|
| WO | WO-02/058721 A1 | | 8/2002 |
| WO | 2011/028952 A1 | | 3/2011 |
| WO | WO-2013/120553 A1 | | 8/2013 |
| WO | WO-2013/120554 A1 | | 8/2013 |
| WO | 2016009086 A1 | | 1/2016 |
| WO | 2016049641 A1 | | 3/2016 |
| WO | WO-2017058866 A1 | * | 4/2017 |
| WO | 2017127933 A1 | | 8/2017 |
| WO | 2017152102 A2 | | 9/2017 |
| WO | WO-2018/191746 A1 | | 10/2018 |
| WO | 2019032624 A1 | | 2/2019 |

OTHER PUBLICATIONS

Berglund et al. (Berglund et al., Protein Science, 2008, 17:606-613.*

Tzartos et al., Methods in Molecular Biology, 1996, 66:55-66.*

Chen , Sci Adv. Apr. 1, 2020;6(14):eaaz7825.*

Bouchon, et al., "Cutting Edge: Inflammatory Responses Can Be Triggered by TREM-1, a Novel Receptor Expressed on Neutrophils and Monocytes", The Journal of Immunology, 2000, vol. 164: pp. 4991-4995.

Brynjolfsson, et al., "An Antibody Against Triggering Receptor Expressed on Myeloid Cells 1 (TREM-1) Dampens Proinflammatory Cytokine Secretion by Lamina Propria Cells from Patients with IBD", Inflamm Bowel Dis, Aug. 2016, vol. 22: pp. 1803-1811.

Carrasco, et al., "TREM-1 multimerization is essential for its activation on monocytes and neutrophils", Cellular & Molecular Immunology, Mar. 2018: pp. 1-13.

Fortin, et al., "Effects of TREM-1 activation in human neutrophils: activation of signaling pathways, recruitment into lipid rafts and association with TLR4", International Immunology, 2006, vol. 19: pp. 41-50.

Li, et al., "Expression and function of triggering receptor expressed on myeloid cells-1 (TREM-1) on canine neutrophils", Developmental and Comparative Immunology, 2011, vol. 35: pp. 872-880.

PCT/US2018/045680—International Preliminary Report on Patentability dated Feb. 11, 2020, 10 pages.

PCT/US2018/045680—International Search Report and Written Opinion dated Feb. 14, 2019, 10 pages.

Radsak et al., "Triggering Receptor Expressed on Myeloid Cells-1 in Neutrophil Inflammatory Responses: Differential Regulation of Activation and Survival", The Journal of Immunology, 2004, vol. 172: pp. 4956-4963.

Read et al., "Cutting Edge: Identification of Neutrophil PGLYRP1 as a Ligand for TREM-1", The Journal of Immunology, 2015, vol. 194: pp. 1417-1421.

Roe et al., "Triggering receptor expressed on myeloid cells-1 (TREM-1): a new player in antiviral immunity?", Frontiers in Microbiology, Nov. 2014, vol. 5, Article 627: pp. 1-11.

Tammaro et al., "TREM-1 and its potential ligands in non-infectious diseases: from biology to clinical perspectives", Pharmacology & Therapeutics, 2017, vol. 177: pp. 81-95.

Yang et al., "TREM-1 Signaling Promotes Host Defense during the Early Stage of Infection with Highly Pathogenic *Streptococcus suis*", Infection and Immunity, Aug. 2015, vol. 83, No. 8: pp. 3293-3301.

PCT/US2020/16949—International Search Report and Written Opinion dated Jul. 24, 2020, 17 pages.

Cohen, "TREM-1 in sepsis." The Lancet 358, No. 9284 (2001): 776-778.

Radaev et al., "Crystal structure of the, human myeloid cell activating receptor TREM-1." Structure 11, No. 12 (2003): 1527-1535.

Schenk et al., "TREM-1-expressing intestinal macrophages crucially amplify chronic inflammation in experimental colitis and inflammatory bowel diseases." The Journal of clinical investigation 117, No. 10 (2007): 3097-3106.

Ho et al., "TREM-1 expression in tumor-associated macrophages and clinical outcome in lung cancer." *American journal of respiratory and critical care medicine* 177, No. 7 (2008): 763-770.

PCT/US2020/016949—International Preliminary Report on Patentability, Aug. 10, 2021, 8 pages.

Rudikoff et al., "Single amino acid substitution altering antigen-binding specificity." Proceedings of the National Academy of Sciences 79, No. 6 (1982): 1979-1983.

Colman, P. M. "Research in Immunology." Elsevier, NY 145, No. 1 (1994): 33-36.

Kussie et al., "A single engineered amino acid substitution changes antibody fine specificity." The Journal of Immunology 152, No. 1 (1994): 146-152.

Chen et al., "Enhancement and destruction of antibody function by somatic mutation: unequal occurrence is controlled by V gene combinatorial associations." The EMBO journal 14, No. 12 (1995): 2784-2794.

D'Angelo et al., "Many routes to an antibody heavy-chain CDR3: necessary, yet insufficient, for specific binding." Frontiers in immunology 9 (2018): 395.

Biorad Datasheet: MCA4698PET Product Details, Feb. 1, 2018, XP055958227, Retrieved from the Internet: URL:https://www.biorad-antibodies.com/sta tic/datasheets/mca46/human-trem-1-antibody, 2 pages.

Warncke et al., "Different adaptations of IgG effector function in human and nonhuman primates and implications for therapeutic antibody treatment." The Journal of Immunology 188, No. 9 (2012): 4405-4411.

Nimmerjahn et al., "Fcγ receptors as regulators of immune responses." Nature Reviews Immunology 8, No. 1 (2008): 34-47.

Walter, Jochen. "The triggering receptor expressed on myeloid cells 2: a molecular link of neuroinflammation and neurodegenerative diseases." Journal of Biological Chemistry 291, No. 9 (2016): 4334-4341.

BioLegend Datasheet: PE anti-human CD354 (TREM-1) Antibody, Nov. 20, 2012, Retrieved from Internet: URL:https://www.biolegend.com/de-de/products/pe-anti-human-cd354-trem-1-antibody-2771?GroupID=BLDG10287, pp. 1-3 (5 pages total).

Mayes et al., "Thereapeutic targeting of TREM1 with PY159 promotes myeloid cell reprogramming and unleashes anti-tumor immunity," Mol Cancer Ther, Dec. 2021; 20 (12_Supplement): P104. (Year: 2021).

Piche-Nicholas et al., "Changes in complementary-determining regions significantly alter IgG binding to the neonatel Fc receptor (FcRn) and pharmacokinetics," MABS, 2018; vol. 10, No. 1: 81-94.

U.S. Appl. No. 16/852,294, filed Apr. 17, 2020, Published WO 2020/0247889 A1.

* cited by examiner

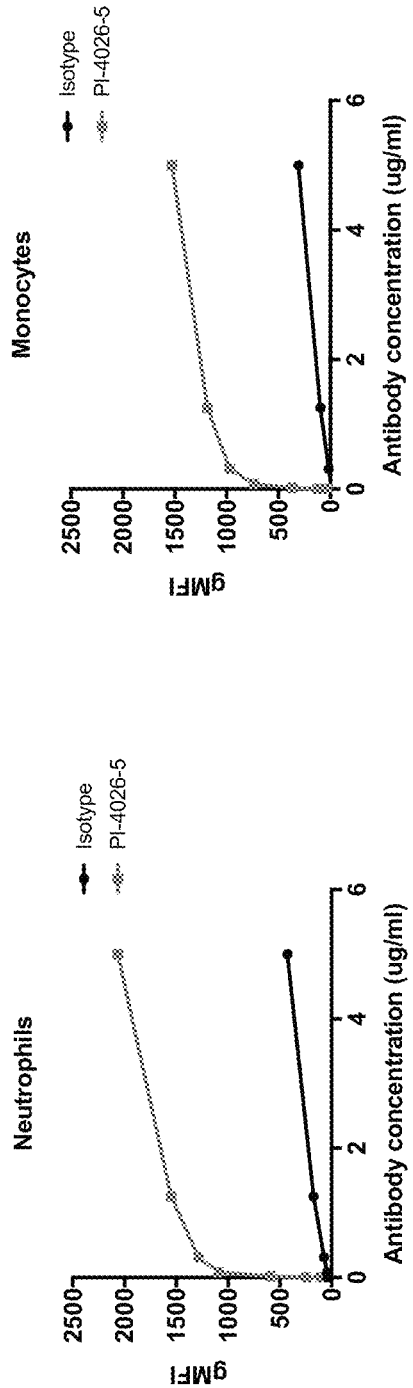

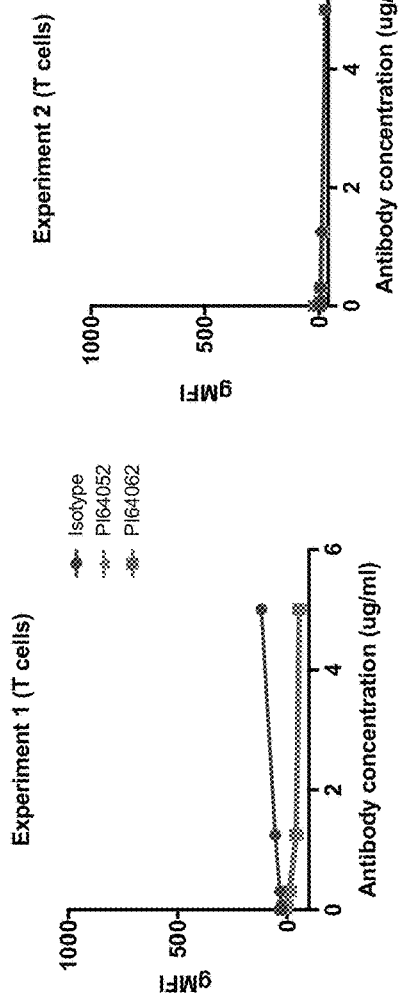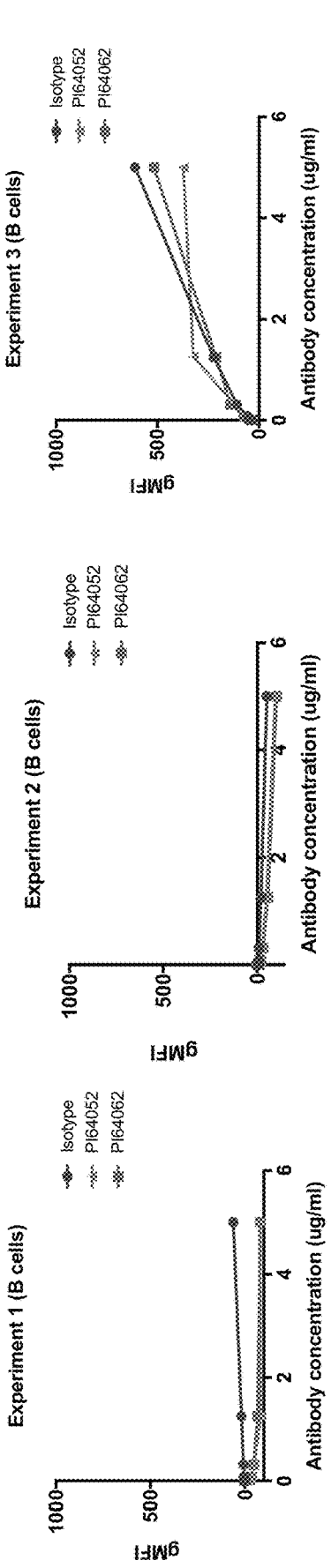

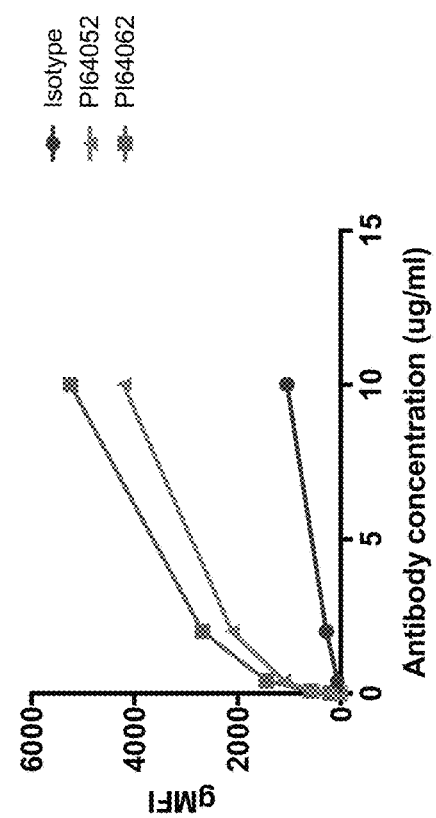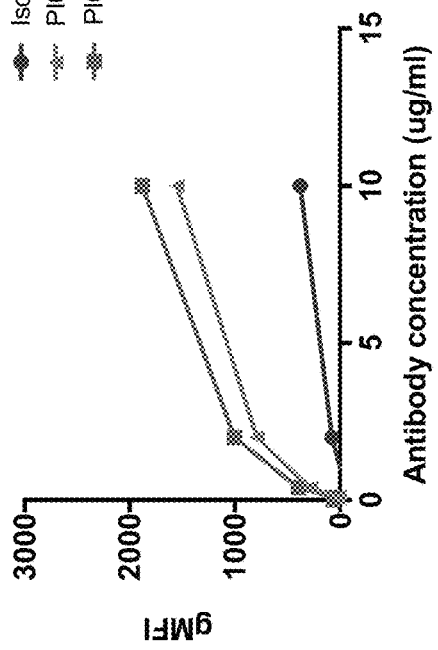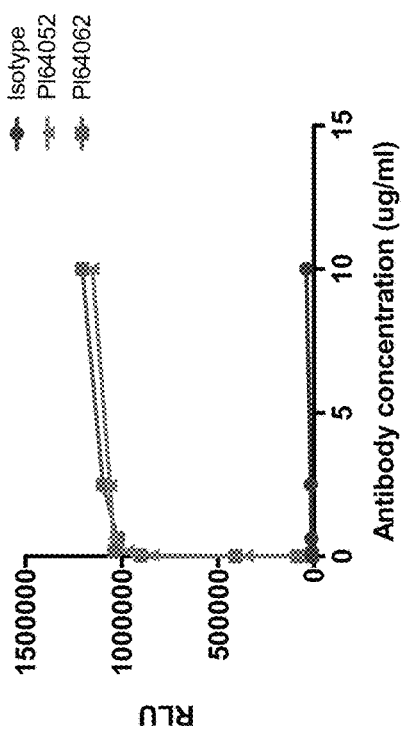

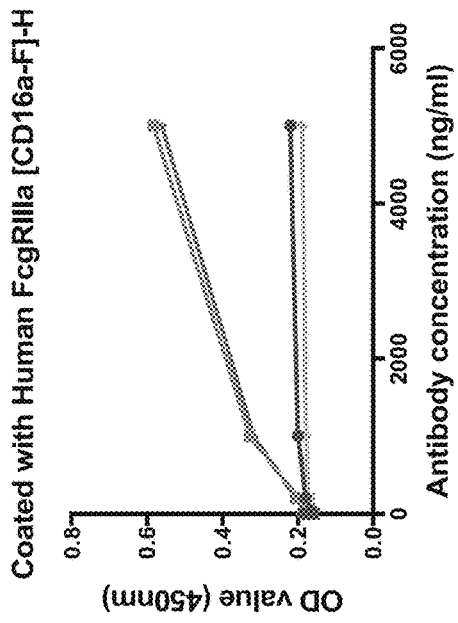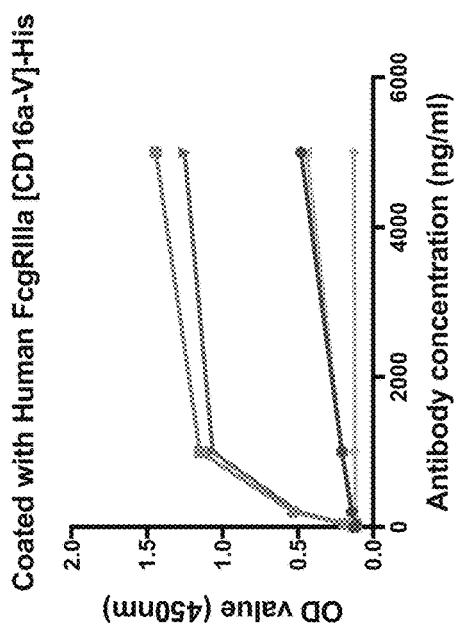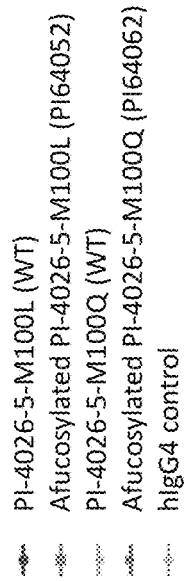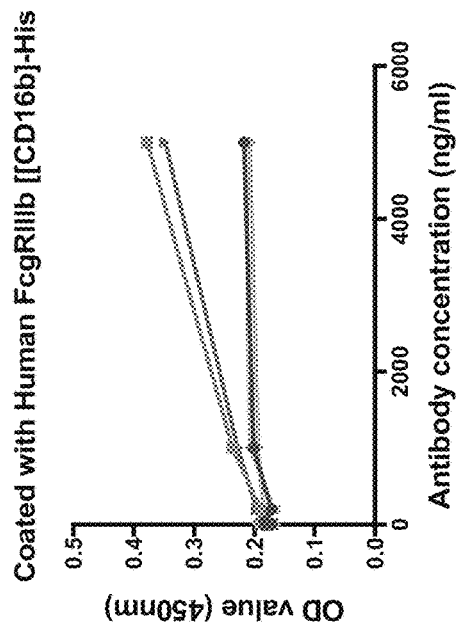
FIG. 26D, FIG. 26E, FIG. 26F

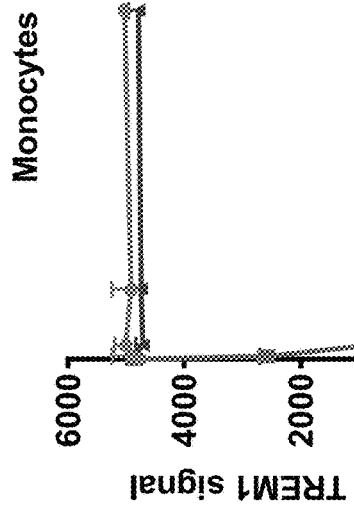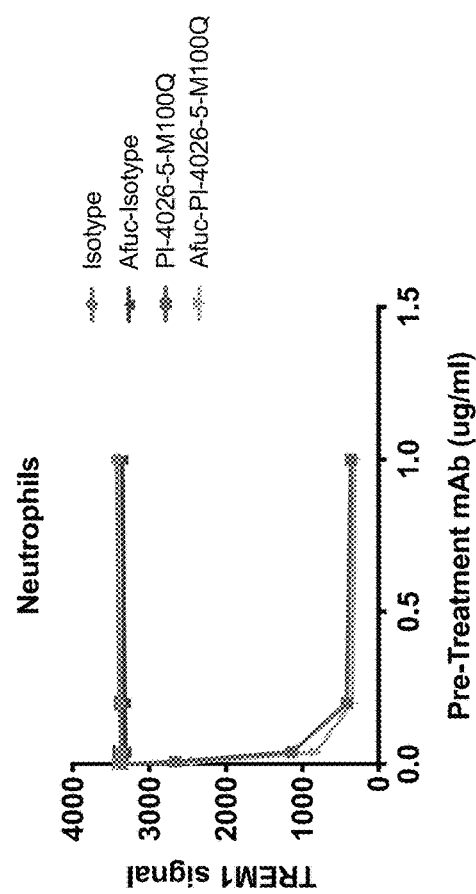

p<0.01, **p<0.0001

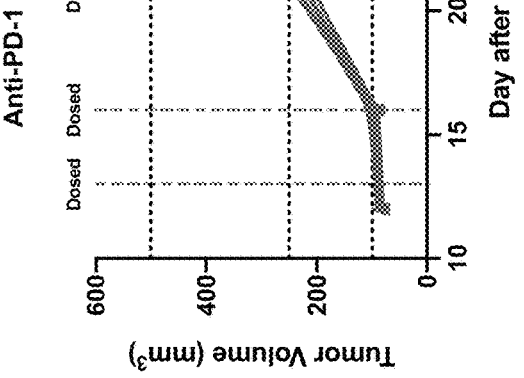
FIG. 31A Isotype
FIG. 31B Anti-PD-1
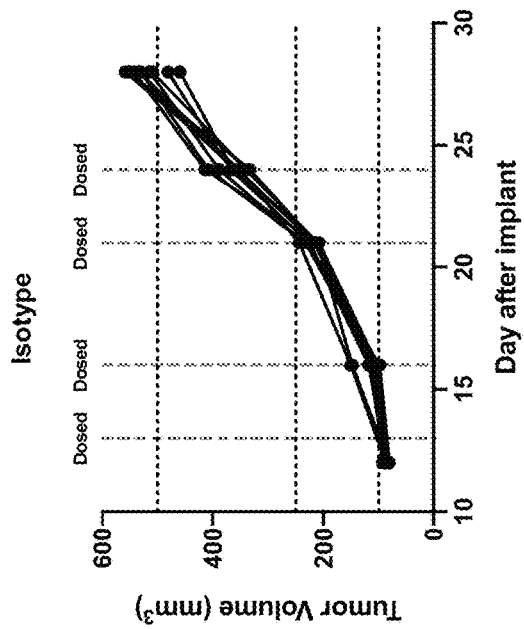
FIG. 31C Anti-TREM1
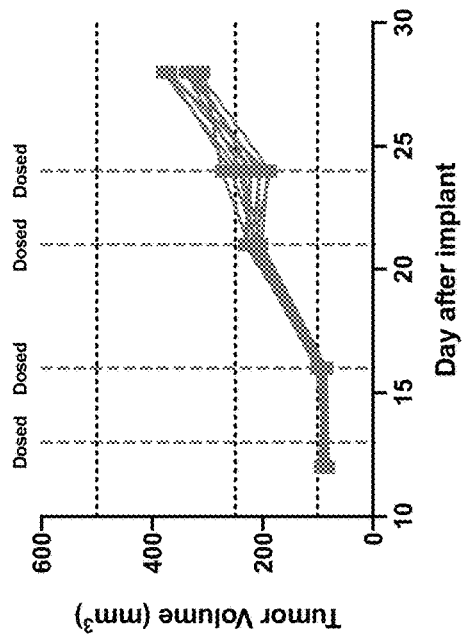
FIG. 31D Anti-TREM1 + Anti-PD-1

HLA-DR

CD40

CD80

CD86

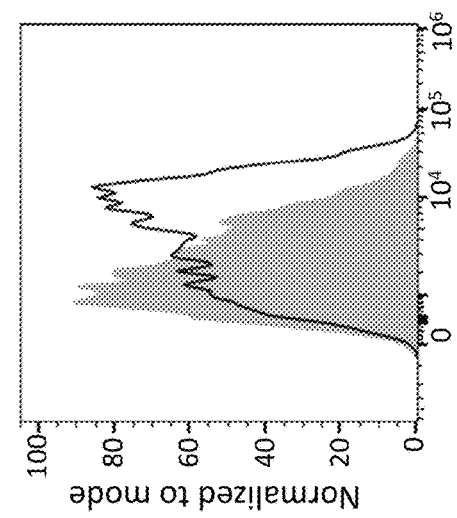
FIG. 37A HLA-DR
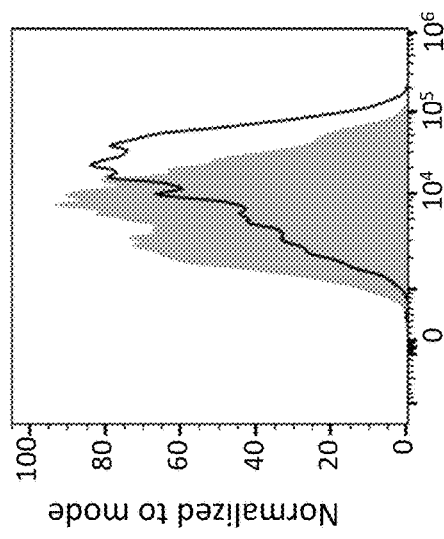
FIG. 37B CD40
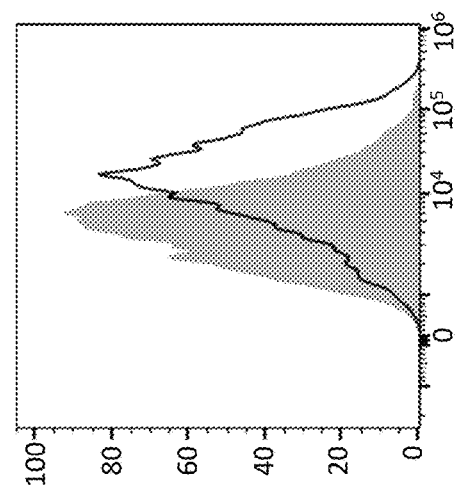
FIG. 37C CD80
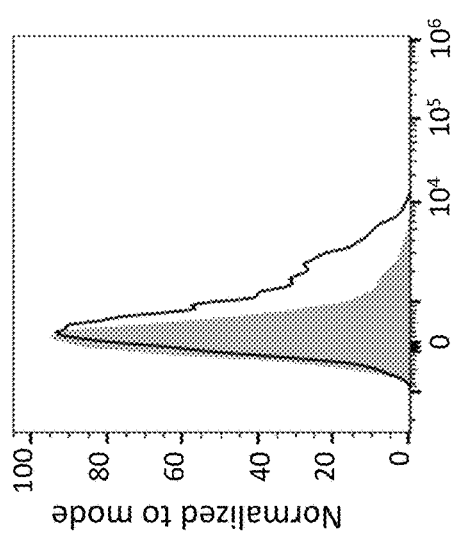
FIG. 37D CD86

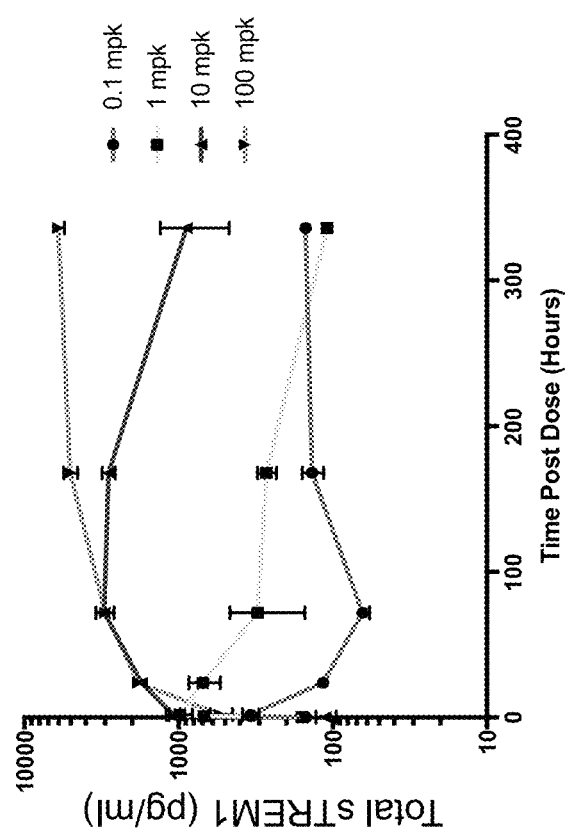
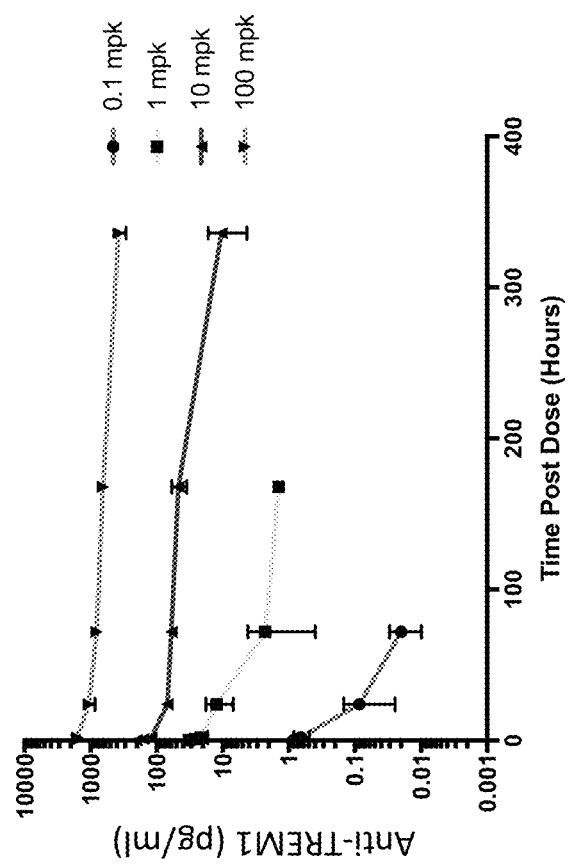

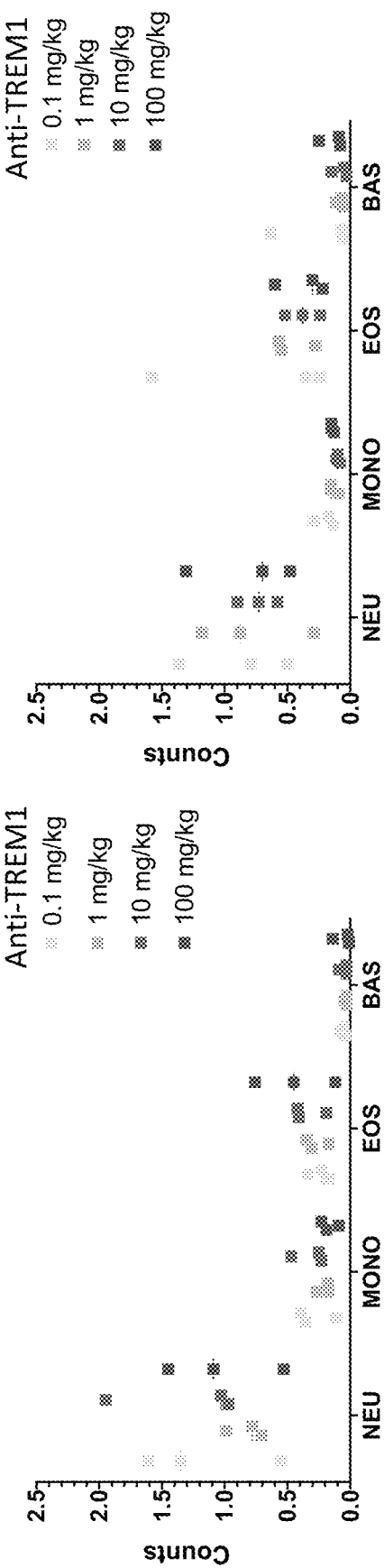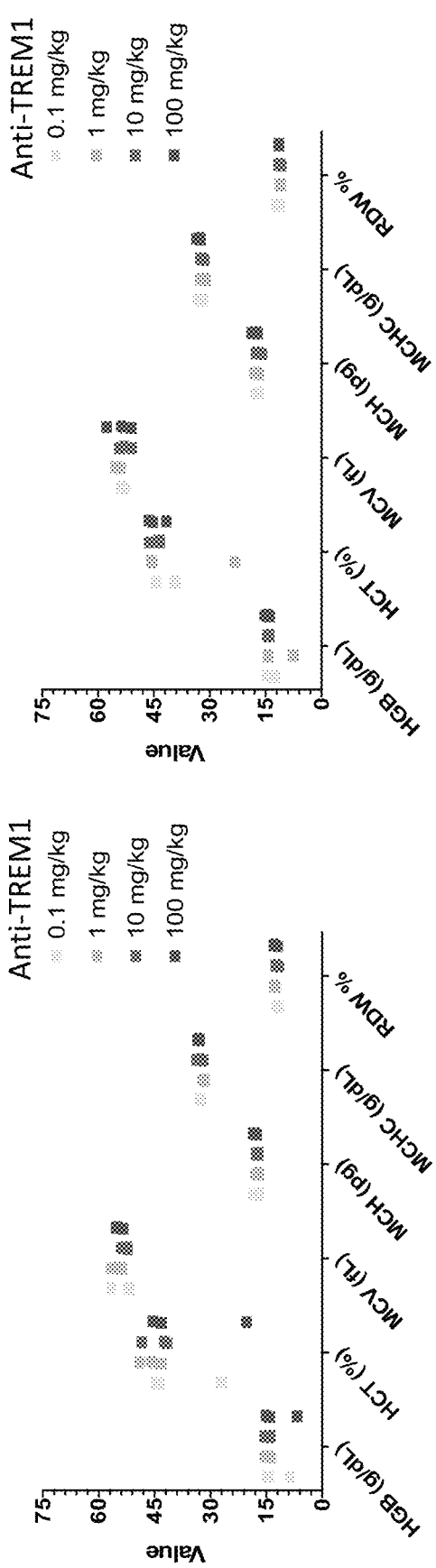

ANTI-TREM1 ANTIBODIES AND RELATED METHODS

CROSS REFERENCE TO RELATED APPLICATIONS

This application is a divisional application of U.S. application Ser. No. 16/852,294, filed Apr. 17, 2020, allowed, which is a continuation of International Application No. PCT/US2020/016949, filed Feb. 6, 2020, which claims the benefit of U.S. Provisional Application No. 62/802,161, filed Feb. 6, 2019, and U.S. Provisional Application No. 62/889, 994, filed on Aug. 21, 2019, which are hereby incorporated by reference in their entirety.

SEQUENCE LISTING

The instant application contains a Sequence Listing which has been submitted via EFS-Web and is hereby incorporated by reference in its entirety. Said ASCII copy, created on Oct. 8, 2020, is named PII010WOUSD1_SequenceListing.txt, and is 92,316 bytes in size.

BACKGROUND

Immunity plays a role in preventing tumor outgrowth. A complex microenvironment can develop within the lesion, and despite the recruitment of T-cells, there is often no effective control of the developing mass. Understanding the balance between tumor elimination and tumor escape may rely on a comprehension of the differential roles myeloid cells play in the tumor microenvironment.

Myeloid populations of the tumor microenvironment prominently include monocytes and neutrophils (sometimes loosely grouped as myeloid-derived suppressor cells), macrophages, and dendritic cells. Although intra-tumoral myeloid populations, as a whole, have long been considered non-stimulatory or suppressive, it has more recently been appreciated that not all tumor-infiltrating myeloid cells are functionally equivalent.

In normal tissues, many of these myeloid cells are essential for proper functioning of both innate and adaptive immunity and notably for wound repair. However, in the setting of cancer, a significant excess of macrophages and dysfunctional or skewed populations of these and other cell types are commonly described. When considered as an aggregate population defined by single markers, such as CD68 or CD163, "macrophage" infiltration is correlated with worse outcomes in patients across multiple tumor types ((de Visser, Cancer Immunol Immunother, 2008; 57:1531-9); (Hanada et al., Int J Urol 2000; 7:263-9); (Yao et al. Clin Cancer Res, 520, 2001; 7:4021-6); (Ruffell et al., PNAS, 523 2012; 109:2796-801)). But the phenotypic and functional subsetting of macrophages from the tumor microenvironment is complicated by the similarity of macrophages and dendritic cells, and is problematic in tumor biology. A morphologic criterion has been often applied to the issue; one approach to try to differentiate dendritic cells from macrophages was based on a more spikey or dendritic morphology for the former and more veiled or bulbous morphology for the latter (Bell et al., J Exp Med 555, 1999; 190:1417-26). Other groups are trying to differentiate on the basis of genetic and cell-surface markers.

There is diversity in the antigen-presenting compartment within tumors, and T-cells can differentiate features of antigen-presenting cells (APC). Because T cells are a major driver of tumor immunity, understanding the exact features of their cognate APCs will be important. Myeloid cells are prominent among cells capable of presenting tumor-derived antigens to T-cells and thereby maintaining the latter in an activated state. Antigen presentation occurs within the tumor itself and likely influences the functions of tumor cytotoxic T-lymphocytes (CTLs). T-cell activation by antigen presenting cells (APC) is an important component in antigen-specific immune responses and tumor cell killing. As these myeloid populations represent major T-cell-interacting partners and antigen-presenting cells for incoming tumor-reactive cytotoxic T lymphocytes, understanding their distinctions may guide therapeutic avenues.

Triggering Receptor Expressed on Myeloid Cells 1 (TREM1, but also known as CD354, HGNC: 17760, Entrez Gene: 54210, UniProtKB: Q9NP99) belongs to the Ig superfamily of receptors and is highly expressed on subsets of myeloid cells including neutrophils, monocytes and macrophages. TREM1 lacks signaling motifs and instead, receptor activation is mediated through the adapter DAP12 (DNAX-activating protein 12) that leads to amplification of inflammatory responses (Bouchon, et al (2000) J. Immunol. 164 (10): 4991-4995). Specifically, crosslinking of TREM1 induces expression of IL-8, myeloperoxidase, TNFα and MCP-1. TREM1 expression is up-regulated on myeloid cells in response to Toll-Like Receptor stimulation (bacterial and fungi stimulation), and has been shown to contribute to, and amplify the acute inflammatory response during septic shock and infection (Cohen, (2001) Lancet. 358: 776-778). While the ligand for TREM1 has remained elusive, recently, PGLYRP1 (peptidoglycan recognition protein 1) has been identified as a potent ligand of TREM1 (Read et al. (2015) J of Immunol. 194: 1417-1421). In mice there are 5 activating forms of TREM receptors including TREM 1, 2, 3, 4, and 5, with a soluble form of TREM1 (sTREM1) released during infection. Mouse TREM1 and the human homolog TREM1 share relatively low sequence identity of 46% (Radaev, et al. (2003) Structure 11: 1527-1535). Structurally TREM1 consists of a single V-type immunoglobulin (Ig)-like domain (Ig-V) of about 108 amino acids, followed by a 70 amino acid stalk region. In addition to the role TREM1 plays in sepsis, it has also been linked to inflammatory bowel disease. However very little is known about the role of TREM1 in the tumor microenvironment. (Schenk, et al (2007) JCI. 117: 3097-3106).

An unmet need exists for novel cancer therapeutic approaches that involve selectively decreasing the amount of cells that are ineffective at stimulating T-cell responses or repolarizing such cells, thereby enhancing an immune response within the tumor microenvironment.

Related patent applications include: PCT/US2018/045680, filed Aug. 7, 2018 which is herein incorporated by reference, in its entirety, for all purposes.

SUMMARY

In one aspect, provided herein are isolated antibodies that binds to human TREM1 (SEQ ID NO: 1), wherein the antibody i) binds within residues 21-34 (SEQ ID NO: 42), 103-109 (SEQ ID NO: 43), and 128-136 (SEQ ID NO: 44) of human TREM1 (SEQ ID NO: 1); and ii) comprises a human Fc region.

In one aspect, provided herein are isolated, humanized antibodies that binds to human TREM1 (SEQ ID NO: 1), wherein the antibody i) binds within residues 21-34 (SEQ ID NO: 42), 103-109 (SEQ ID NO: 43), and 128-136 (SEQ ID NO: 44) of human TREM1 (SEQ ID NO: 1); and ii) optionally comprises a human Fc region.

In one aspect, provided herein is an isolated antibody or antibodies that bind(s) to human TREM1 (SEQ ID NO: 1), comprising a variable heavy (VH) chain sequence comprising three heavy chain CDR sequences, CDR-H1, CDR-H2, and CDR-H3, and a variable light (VL) chain sequence comprising three light chain CDR sequences, CDR-L1, CDR-L2, and CDR-L3, wherein: CDR-H1 comprises the sequence set forth in SEQ ID NO: 23, CDR-H2 comprises the sequence set forth in SEQ ID NO: 24, CDR-H3 comprises the sequence set forth in SEQ ID NO: 29, wherein X is leucine (L), glutamine (Q), methionine (M), isoleucine (I), or glutamic acid (E), CDR-L1 comprises the sequence set forth in SEQ ID NO: 26, CDR-L2 comprises the sequence set forth in SEQ ID NO: 27, and CDR-L3 comprises the sequence set forth in SEQ ID NO: 28. In one aspect, provided herein is an isolated antibody or antibodies that bind(s) to human TREM1 (SEQ ID NO: 1), comprising a heavy chain comprising a variable heavy (VH) chain sequence comprising three heavy chain CDR sequences, CDR-H1, CDR-H2, and CDR-H3, and a light chain comprising a variable light (VL) chain sequence comprising three light chain CDR sequences, CDR-L1, CDR-L2, and CDR-L3, wherein: CDR-H1 comprises the sequence set forth in SEQ ID NO: 23, CDR-H2 comprises the sequence set forth in SEQ ID NO: 24, CDR-H3 comprises the sequence set forth in SEQ ID NO: 29, wherein X is leucine (L), glutamine (Q), methionine (M), isoleucine (I), or glutamic acid (E), CDR-L1 comprises the sequence set forth in SEQ ID NO: 26, CDR-L2 comprises the sequence set forth in SEQ ID NO: 27, and CDR-L3 comprises the sequence set forth in SEQ ID NO: 28.

In some embodiments, the antibody comprises a CDR-H3 comprising the sequence RXAAMDY (SEQ ID NO: 29), wherein X is leucine (L), glutamine (Q), methionine (M), isoleucine (I), or glutamic acid (E). In some embodiments, the antibody further comprises a CDR-H1 comprising the sequence set forth in SEQ ID NO: 23 and a CDR-H2 comprising the sequence set forth in SEQ ID NO: 24. In some embodiments, the CDR-H3 comprises the sequence set forth in SEQ ID NO: 33; and the antibody further comprises a CDR-H1 comprising the sequence set forth in SEQ ID NO: 23 and a CDR-H2 comprising the sequence set forth in SEQ ID NO: 24.

In some embodiments, the antibody further comprises a CDR-L1 comprising the sequence set forth in SEQ ID NO: 26, a CDR-L2 comprising the sequence set forth in SEQ ID NO: 27, and a CDR-L3 comprising the sequence set forth in SEQ ID NO: 28.

In some embodiments, the antibody comprises a VH sequence selected from the sequences set forth in SEQ ID NO: 16, 17, or 18. In some embodiments, the antibody comprises the VH sequence set forth in SEQ ID NO: 17.

In some embodiments, the antibody comprises a VL sequence selected from the sequences set forth in SEQ ID NOs: 20, 21, or 22. In some embodiments, the antibody comprises the VL sequence set forth in SEQ ID NO: 20.

In some embodiments, the antibody comprises the VH sequence set forth in SEQ ID NO: 17, and the VL sequence set forth in SEQ ID NO: 20.

In some embodiments, the antibody is an scFv. In some embodiments, the antibody is an scFv and comprises the VH sequence set forth in SEQ ID NO: 17, and the VL sequence set forth in SEQ ID NO: 20.

In some embodiments, the antibody is an scFv and comprises a VH sequence selected from the sequences set forth in SEQ ID NO: 16, 17, or 18 and a VL sequence selected from the sequences set forth in SEQ ID NOs: 20, 21, or 22. In some embodiments, the antibody comprises the VH sequence set forth in SEQ ID NO: 17, and the VL sequence set forth in SEQ ID NO: 20; and the human Fc region comprises wild-type, human IgG1 Fc.

In some embodiments, the antibody comprises the heavy chain sequence set forth in SEQ ID NO: 34 and the light chain sequence set forth in SEQ ID NO: 35.

In some embodiments, the antibody comprises the VH sequence selected from the sequences set forth in SEQ ID NOs: 4, 5, or 6.

In some embodiments, the antibody comprises a VL sequence selected from the sequences set forth in SEQ ID NOs: 20, 21, or 22.

In some embodiments, the antibody comprises the VH sequence selected from the sequences set forth in SEQ ID NOs: 8, 9 or 10.

In some embodiments, the CDR-H3 comprises the sequence set forth in SEQ ID NO: 32, and the antibody further comprises a CDR-H1 comprising the sequence set forth in SEQ ID NO:23 and a CDR-H2 comprising the sequence set forth in SEQ ID NO:24.

In some embodiments, the antibody comprises the VH sequence selected from the sequences set forth in SEQ ID NOs: 12, 13 or 14. In some embodiments, the antibody comprises the VH sequence set forth in SEQ ID NO: 13.

In some embodiments, the antibody comprises a VL sequence selected from the sequences set forth in SEQ ID NOs: 20, 21, or 22. In some embodiments, the antibody comprises the VL sequence set forth in SEQ ID NO: 20.

In some embodiments, the antibody comprises the VH sequence set forth in SEQ ID NO: 13, and the VL sequence set forth in SEQ ID NO: 20. In some embodiments, the antibody is an scFv and comprises the VH sequence set forth in SEQ ID NO: 13, and the VL sequence set forth in SEQ ID NO: 20.

In some embodiments, the antibody is an scFv and comprises a VH sequence selected from the sequences set forth in SEQ ID NO: 112, 13 or 14 and a VL sequence selected from the sequences set forth in SEQ ID NOs: 20, 21, or 22.

In some embodiments, the antibody comprises the VH sequence set forth in SEQ ID NO: 13, and the VL sequence set forth in SEQ ID NO: 20; and the human Fc region comprises wild-type, human IgG1 Fc.

In some embodiments, the antibody comprises the heavy chain sequence set forth in SEQ ID NO: 36 and the light chain sequence set forth in SEQ ID NO: 37.

In some embodiments, the antibody consists of the VH sequence set forth in SEQ ID NO: 17, 13, or 9; and the VL sequence set forth in SEQ ID NO: 20. In some embodiments, the antibody consists of the VH sequence set forth in SEQ ID NO: 17; and the VL sequence set forth in SEQ ID NO: 20. In some embodiments, the antibody consists of the VH sequence set forth in SEQ ID NO: 13; and the VL sequence set forth in SEQ ID NO: 20. In some embodiments, the antibody consists of the VH sequence set forth in SEQ ID NO: 9; and the VL sequence set forth in SEQ ID NO: 20.

In some embodiments, the antibody the heavy chain consists of the heavy chain sequence set forth in SEQ ID NO: 34 and the light chain sequence set forth in SEQ ID NO: 35.

In some embodiments, the antibody consists of the heavy chain sequence set forth in SEQ ID NO: 36 and the light chain sequence set forth in SEQ ID NO: 37.

In some embodiments, the antibody is afucosylated.

In another aspect, provided herein are isolated antibodies that binds to human TREM1 (SEQ ID NO: 1), wherein the antibody is afucosylated, and the antibody comprises the VH sequence set forth in SEQ ID NO: 17, 13, or 9; and the VL sequence set forth in SEQ ID NO: 20. In some embodiments, the antibody comprises the VH sequence set forth in SEQ ID NO: 17, and the VL sequence set forth in SEQ ID NO: 20.

In some embodiments, the antibody comprises the heavy chain sequence set forth in SEQ ID NO: 34 and the light chain sequence set forth in SEQ ID NO: 35.

In some embodiments, the antibody comprises the VH sequence set forth in SEQ ID NO: 13, and the VL sequence set forth in SEQ ID NO: 20.

In some embodiments, the antibody is afucosylated, and the antibody comprises the heavy chain sequence set forth in SEQ ID NO: 36 and the light chain sequence set forth in SEQ ID NO: 37.

In some embodiments, the antibody comprises the VH sequence set forth in SEQ ID NO: 9, and the VL sequence set forth in SEQ ID NO: 20.

In some embodiments, the antibody is afucosylated, and the antibody comprises the heavy chain sequence set forth in SEQ ID NO: 38 and the light chain sequence set forth in SEQ ID NO: 39.

In some embodiments, the antibody is a humanized, human, or chimeric antibody. In some embodiments, the antibody is a humanized antibody. In some embodiments, the antibody comprises a heavy chain human constant region of a class selected from IgG, IgA, IgD, IgE, and IgM. In some embodiments, the antibody comprises an Fc region. In some embodiments, the Fc region is a human Fc region. In some embodiments, the human Fc region comprises a human heavy chain constant region of the class IgG and a subclass selected from IgG1, IgG2, IgG3, and IgG4. In some embodiments, the human Fc region comprises wild-type, human IgG1 Fc.

In some embodiments, the antibody consists of the VH sequence set forth in SEQ ID NO: 17, and the VL sequence set forth in SEQ ID NO: 20; and the human Fc region comprises wild-type, human IgG1 Fc.

In some embodiments, the Fc region comprises one or more amino acid substitutions, wherein the one or more substitutions result in increased antibody half-life, increased ADCC activity, increased ADCP activity, or increased CDC activity compared with the Fc without the one or more substitutions. In some embodiments, the Fc region binds an Fcγ Receptor selected from the group consisting of: FcγRI, FcγRIIa, FcγRIIb, FcγRIIc, FcγRIIIa, and FcγRIIIb.

In some embodiments, the antibody is a monoclonal antibody.

In some embodiments, the antibody binds to human TREM1 with a KD of less than or equal to about 0.5, 1, 2, 3, 4, 5, 6, or 7×10$^{-9}$ M, as measured by surface plasmon resonance (SPR) assay. In some embodiments, the antibody binds to human TREM1 with a KD of less than or equal to about 7 nM as measured by surface plasmon resonance (SPR) assay.

In some embodiments, the antibody is an agonistic antibody.

In some embodiments, the antibody induces increased expression of at least one cytokine or chemokine in a cell as compared to an isotype control antibody.

In some embodiments, wherein the at least one cytokine or chemokine is selected from the group consisting of: IFN-γ, IL-1α, IL-12, IL-2, TNFSF9, TNFSF10, CXCL9, CXCL10, CCL17, CXCL1, CXCL5, CXCL8, CXCL11, CXCL15, CCL3, CCL4, CCL2, FasL, CD274, CRTAM, granzyme A (GzmA), or granzyme B (GzmB). In some embodiments, the cytokine or chemokine is CXCL10 or IFN-γ.

In some embodiments, the antibody induces increased expression of at least one myeloid co-stimulatory protein in a cell as compared to an isotype control antibody.

In some embodiments, the myeloid co-stimulatory protein is HLA-DR, CD40, CD80, or CD86 in a cell.

In some embodiments, the antibody induces increased activation of the ERK and/or STAT3 intracellular signaling pathways in a cell as compared to an isotype control antibody.

In some embodiments, the antibody induces an anti-tumor memory response as compared to an isotype control antibody.

In some embodiments, the antibody: competes for binding to human TREM1 with human TREM-26 antibody; binds to human TREM1; binds to cynomolgus TREM1; stimulates TREM1 signaling; induces immune signaling pathways; induces cytokine or chemokine secretion; induces co-stimulatory molecule expression; kills, disables, or depletes myeloid cells; or is capable of any combination of a.-h.

In some embodiments, the antibody has antibody-dependent cell-mediated cytotoxicity (ADCC) activity, In some embodiments, the antibody has antibody-mediated cellular phagocytosis (ADCP) activity. In some embodiments, the antibody has complement-dependent cytotoxicity (CDC) activity.

In some embodiments, the cell is a TREM1+ cell.

In some embodiments, the TREM1+ cell is selected from the group consisting of: dendritic cells, tumor associated macrophages (TAMs), myeloid-derived suppressive cells (MDSCs), neutrophils, and tumor associated neutrophils (TANs). In some embodiments, the TREM1+ cell is a myeloid-derived suppressive cell or a tumor associated neutrophil.

In some embodiments, the antibody crosslinks TREM1 to TREM1 on the cell surface of a TREM1+ cell.

In some embodiments, the isolated antibody is for use as a medicament. In some embodiments, the isolated antibody is for use in the treatment of a cancer or infection. In some embodiments, the isolated antibody is for use in the treatment of a cancer, wherein the cancer is selected from a solid tumor and a liquid tumor.

In another aspect, provided herein are isolated polynucleotides or set of polynucleotides encoding the antibody as described herein, a VH thereof, a VL thereof, a light chain thereof, a heavy chain thereof, or an antigen-binding portion thereof; optionally cDNA.

In another aspect, provided herein are vectors or set of vectors comprising the polynucleotide or set of polynucleotides as described herein.

In another aspect, provided herein are host cells comprising the polynucleotide or set of polynucleotides or the vector or set of vectors as described herein.

In another aspect, provided herein are methods of producing an antibody comprising expressing the antibody with the host cell and isolating the expressed antibody.

In another aspect, provided herein are pharmaceutical compositions comprising the antibody as described herein and a pharmaceutically acceptable excipient.

In another aspect, provided herein are kits comprising an antibody or a pharmaceutical composition as described herein and instructions for use.

In another aspect, provided herein are methods of increasing an immune response comprising administering to a subject a composition comprising an anti-TREM1 antibody or antigen binding fragment thereof.

In some embodiments, the composition comprises an antibody or the pharmaceutical composition as described herein.

In some embodiments, the antibody has receptor-ligand blocking, agonist, or antagonist activity.

In some embodiments, the antibody has agonist activity.

In some embodiments, the antibody induces increased expression of at least one cytokine or chemokine in a cell as compared to an isotype control antibody.

In some embodiments, the at least one cytokine or chemokine is selected from the group consisting of: IFN-γ, IL-1α, IL-12, IL-2, TNFSF9, TNFSF10, CXCL9, CXCL10, CCL17, CXCL1, CXCL5, CXCL8, CXCL11, CXCL15, CCL3, CCL4, CCL2, FasL, CD274, CRTAM, granzyme A (GzmA), or granzyme B (GzmB).

In some embodiments, the cytokine or chemokine is CXCL10 or IFN-γ.

In some embodiments, the antibody induces increased expression of at least one myeloid co-stimulatory protein as compared to an isotype control antibody.

In some embodiments, the myeloid co-stimulatory protein is HLA-DR, CD40, CD80, or CD86 in a cell.

In some embodiments, the antibody induces increased activation of the ERK and/or STAT3 intracellular signaling pathways in a cell as compared to an isotype control antibody.

In some embodiments, the antibody induces a memory immune response.

In some embodiments, the cell is a TREM1+ cell.

In some embodiments, the TREM1+ cell is selected from the group consisting of: dendritic cells, tumor associated macrophages (TAMs), myeloid-derived suppressive cells (MDSCs), neutrophils, and tumor associated neutrophils (TANs).

In some embodiments, the TREM1+ cell is a myeloid-derived suppressive cell or a tumor associated neutrophil.

In some embodiments, the antibody crosslinks TREM1 to TREM1 on the cell surface of a TREM1+ cell.

In some embodiments, the subject is human.

In another aspect, provided herein are methods of treating cancer, comprising administering to a subject a composition comprising an anti-TREM1 antibody or antigen binding fragment thereof.

In some embodiments, the composition comprises an antibody or a pharmaceutical composition as described herein.

In some embodiments, the antibody has receptor-ligand blocking, agonist, or antagonist activity.

In some embodiments, the antibody has agonist activity.

In some embodiments, the antibody induces increased expression of at least one cytokine or chemokine in a cell as compared to an isotype control antibody.

In some embodiments, the at least one cytokine or chemokine is selected from the group consisting of: IFN-γ, IL-1α, IL-12, IL-2, TNFSF9, TNFSF10, CXCL9, CXCL10, CCL17, CXCL1, CXCL5, CXCL8, CXCL11, CXCL15, CCL3, CCL4, CCL2, FasL, CD274, CRTAM, granzyme A (GzmA), or granzyme B (GzmB).

In some embodiments, the cytokine or chemokine is CXCL10 or IFN-γ.

In some embodiments, the antibody induces increased expression of at least one myeloid co-stimulatory protein as compared to an isotype control antibody.

In some embodiments, the myeloid co-stimulatory protein is HLA-DR, CD40, CD80, or CD86 in a cell.

In some embodiments, the antibody induces increased activation of the ERK and/or STAT3 intracellular signaling pathways in a cell as compared to an isotype control antibody.

In some embodiments, the antibody induces an anti-tumor memory response as compared to an isotype control antibody.

In some embodiments, the antibody has antibody-dependent cell-mediated cytotoxicity (ADCC) activity.

In some embodiments, the antibody has complement-dependent cytotoxicity (CDC) activity.

In some embodiments, the antibody has antibody-mediated phagocytosis (ADCP) activity.

In some embodiments, the cell is a TREM1+ cell.

In some embodiments, the TREM1+ cell is selected from the group consisting of: dendritic cells, tumor associated macrophages (TAMs), myeloid-derived suppressive cells (MDSCs), neutrophils, and tumor associated neutrophils (TANs).

In some embodiments, the TREM1+ cell is a myeloid-derived suppressive cell or a tumor associated neutrophil.

In some embodiments, the antibody crosslinks TREM1 to TREM1 on the cell surface of a TREM1+ cell.

In some embodiments, the subject is human.

In some embodiments, the cancer is a solid cancer.

In some embodiments, the cancer is a liquid cancer.

In some embodiments, the cancer is selected from the group consisting of: melanoma, kidney, hepatobiliary, head and neck squamous carcinoma (HNSC), pancreatic, colon, bladder, urothelial, glioblastoma, prostate, lung, breast, ovarian, gastric, esophageal, renal, endometrial, cervical, testicular, and mesothelioma cancers.

In some embodiments, the cancer is gastric cancer, ovarian cancer, colon cancer, or breast cancer.

In some embodiments, the contacting enhances an immune response in the subject.

In some embodiments, the enhanced immune response is an adaptive immune response.

In some embodiments, the enhanced immune response is an innate immune response.

In some embodiments, the subject has previously received, is concurrently receiving, or will subsequently receive an immunotherapy.

In some embodiments, the immunotherapy is at least one of: a checkpoint inhibitor; a checkpoint inhibitor of T cells; anti-PD1 antibody; anti-PDL1 antibody; anti-CTLA4 antibody; adoptive cell therapy; adoptive T cell therapy; CAR-T cell therapy; a dendritic cell vaccine; a STING agonist; a monocyte vaccine; Bacillus Calmette-Guerin vaccine; an antigen binding protein that binds both a T cell and an antigen presenting cell; a BiTE dual antigen binding protein; a toll-like receptor ligand; a cytokine; a cytotoxic therapy; a chemotherapy; a radiotherapy; a small molecule inhibitor; a small molecule agonist; an immunomodulator; an oncolytic virus; and an epigenetic modulator.

In some embodiments, the immunotherapy is selected from the group consisting of: an anti-PD1 antibody, an anti-PDL1 antibody; or an anti-CTLA4 antibody.

In another aspect, provided herein are methods of killing, disabling, or depleting myeloid cells that express Triggering Receptor Expressed on Myeloid Cells 1 (TREM1) on the cell surface, comprising contacting the myeloid cells with a antibody or a pharmaceutical composition as described herein.

In some embodiments, the antibody kills, disables, or depletes the myeloid cells by at least one of ADCC, CDC, and ADCP, optionally wherein the antibody kills, disables, or depletes the myeloid cells by ADCC, optionally wherein the antibody kills, disables, or depletes the myeloid cells by CDC, and optionally wherein the antibody kills, disables, or depletes the myeloid cells by ADCP.

In some embodiments, the antibody kills the myeloid cells by at least one of ADCC, CDC, and ADCP.

In some embodiments, the antibody disables the myeloid cells by at least one of ADCC, CDC, and ADCP.

In some embodiments, the antibody depletes the myeloid cells by at least one of ADCC, CDC, and ADCP.

In some embodiments, the antibody has antibody-dependent cell-mediated cytotoxicity (ADCC) activity.

In some embodiments, the antibody has complement-dependent cytotoxicity (CDC) activity.

In some embodiments, the antibody has antibody-mediated phagocytosis (ADCP) activity.

In some embodiments, the antibody has receptor-ligand blocking, agonist, or antagonist activity.

In some embodiments, the myeloid cells are stimulatory myeloid cells.

In some embodiments, the myeloid cells are non-stimulatory myeloid cells.

In some embodiments, the myeloid cells comprise at least one of dendritic cells, tumor-associated macrophages (TAMs), neutrophils, monocytes, or myeloid-derived suppressor cells.

In some embodiments, the myeloid cells are neutrophils or tumor associated neutrophils.

In some embodiments, the myeloid cells are tumor associated macrophages.

In some embodiments, the myeloid cells are monocytic myeloid-derived suppressor cells.

In some embodiments, the myeloid cells are intratumoral.

In some embodiments, the myeloid cells are in a population of immune cells comprising stimulatory myeloid cells and non-stimulatory myeloid cells.

In some embodiments, the contacting is in vitro or in vivo.

In some embodiments, the contacting occurs in vivo in a subject, optionally wherein the subject has cancer.

In some embodiments, the subject is human.

In some embodiments, the cancer is a solid cancer.

In some embodiments, the cancer is a liquid cancer.

In some embodiments, the cancer is selected from the group consisting of: melanoma, kidney, hepatobiliary, head and neck squamous carcinoma (HNSC), pancreatic, colon, bladder, urothelial, glioblastoma, prostate, lung, breast, ovarian, gastric, esophageal, renal, endometrial, cervical, testicular, and mesothelioma cancers.

In some embodiments, the cancer is gastric cancer, ovarian cancer, colon cancer, or breast cancer.

In some embodiments, the contacting enhances an immune response in the subject.

In some embodiments, the enhanced immune response is an adaptive immune response.

In some embodiments, the enhanced immune response is an innate immune response.

In some embodiments, the enhanced immune response comprises expression of at least one cytokine or chemokine.

In some embodiments, the at least one cytokine or chemokine is selected from the group consisting of: IFN-γ, IL-1α, IL-12, IL-2, TNFSF9, TNFSF10, CXCL9, CXCL10, CCL17, CXCL1, CXCL5, CXCL8, CXCL11, CXCL15, CCL3, CCL4, CCL2, FasL, CD274, CRTAM, granzyme A (GzmA), or granzyme B (GzmB).

In some embodiments, the at least one cytokine or chemokine is CXCL10 or IFN-γ.

In some embodiments, the subject has previously received, is concurrently receiving, or will subsequently receive an immunotherapy.

In some embodiments, the immunotherapy is at least one of: a checkpoint inhibitor; a checkpoint inhibitor of T cells; anti-PD1 antibody; anti-PDL1 antibody; anti-CTLA4 antibody; adoptive cell therapy; adoptive T cell therapy; CAR-T cell therapy; a dendritic cell vaccine; a STING agonist; a monocyte vaccine; Bacillus Calmette-Guerin vaccine; an antigen binding protein that binds both a T cell and an antigen presenting cell; a BiTE dual antigen binding protein; a toll-like receptor ligand; a cytokine; a cytotoxic therapy; a chemotherapy; a radiotherapy; a small molecule inhibitor; a small molecule agonist; an immunomodulator; an oncolytic virus; and an epigenetic modulator.

In some embodiments, the immunotherapy is selected from the group consisting of: an anti-PD1 antibody, an anti-PDL1 antibody; or an anti-CTLA4 antibody.

BRIEF DESCRIPTION OF THE DRAWINGS

These and other features, aspects, and advantages of the present invention will become better understood with regard to the following description, and accompanying drawings, where:

FIG. 3A shows the binding of PI-4026-5 to neutrophils in human peripheral blood. FIG. 3B shows the binding of PI-4026-5 to monocytes in human peripheral blood.

FIG. 13AB show the % aggregate of the PI64052 and PI64062 antibodies as determined by SEC in response to thermal stress. These are stability kinetics measurements.

FIG. 19A show no binding of PI64052 and PI64062 to lymphocytes (T cells). FIG. 19B show no binding of PI64052 and PI64062 to lymphocytes (T cells). FIG. 19C show no binding of PI64052 and PI64062 to lymphocytes (T cells). FIG. 19D show no binding of PI64052 and PI64062 to lymphocytes (B cells). FIG. 19E show no binding of PI64052 and PI64062 to lymphocytes (B cells). FIG. 19F show no binding of PI64052 and PI64062 to lymphocytes (B cells).

FIG. 23A shows binding of PI64052 and PI64062 to cynomolgus monocytes. FIG. 23B shows binding of PI64052 and PI64062 to cynomolgus monocytes.

FIG. 24 show the FcγR signaling induced by PI64052 and PI64062 using the hCD16 reporter assay system and is representative of 3 separate experiments.

FIG. 26D shows binding of PI64052 and PI64062 and their fucosylated parents to hFcγRIIIα. FIG. 26E shows binding of PI64052 and PI64062 and their fucosylated parents to hFcγRIIIα. FIG. 26F shows binding of PI64052 and PI64062 and their fucosylated parents to hFcγRIIIβ.

FIG. 27A shows dose-dependent receptor occupancy of PI-4026-5-M100Q and afucosylated PI-4026-5-M100Q on monocytes from peripheral blood. FIG. 27B shows dose-dependent receptor occupancy of PI-4026-5-M100Q and afucosylated PI-4026-5-M100Q on neutrophils from peripheral blood.

FIG. 31A provides the growth curves from each mouse from the isotype group in the Panc02 tumor model. FIG. 31B provides the growth curves from each mouse from the anti-PD-1 group in the Panc02 tumor model. FIG. 31C provides the growth curves from each mouse from the anti-TREM1 group in the Panc02 tumor model. FIG. 31D provides the growth curves from each mouse from the anti-TREM1 and anti-PD-1 group in the Panc02 tumor model.

FIG. 37A shows a representative histogram overlays for cell surface HLA-DR expression in monocytes after anti-TREM1 antibody (afucosylated PI64062) treatment. FIG. 37B shows a representative histogram overlays for cell surface CD40 expression in monocytes after anti-TREM1 antibody (afucosylated PI64062) treatment. FIG. 37C shows a representative histogram overlays for cell surface CD80 expression in monocytes after anti-TREM1 antibody (afucosylated PI64062) treatment.

FIG. 37D shows a representative histogram overlays for cell surface CD86 expression in monocytes after anti-TREM1 antibody (afucosylated PI64062) treatment.

FIG. 43A shows that the afucosylated PI-4928 anti-TREM1 antibody displays dose dependent pharmacokinetics. FIG. 43B shows soluble mouse TREM1 in serum after treatment with afucosylated PI-4928 anti-TREM1 antibody.

FIG. 44A shows the mouse blood cell count on day 7. FIG. 44B shows the mouse blood cell count on day 14. FIG. 44C shows the mouse red blood cell parameters on day 7. FIG. 44D shows the mouse red blood cell parameters values on day 14.

DETAILED DESCRIPTION

Definitions

Figure 1:
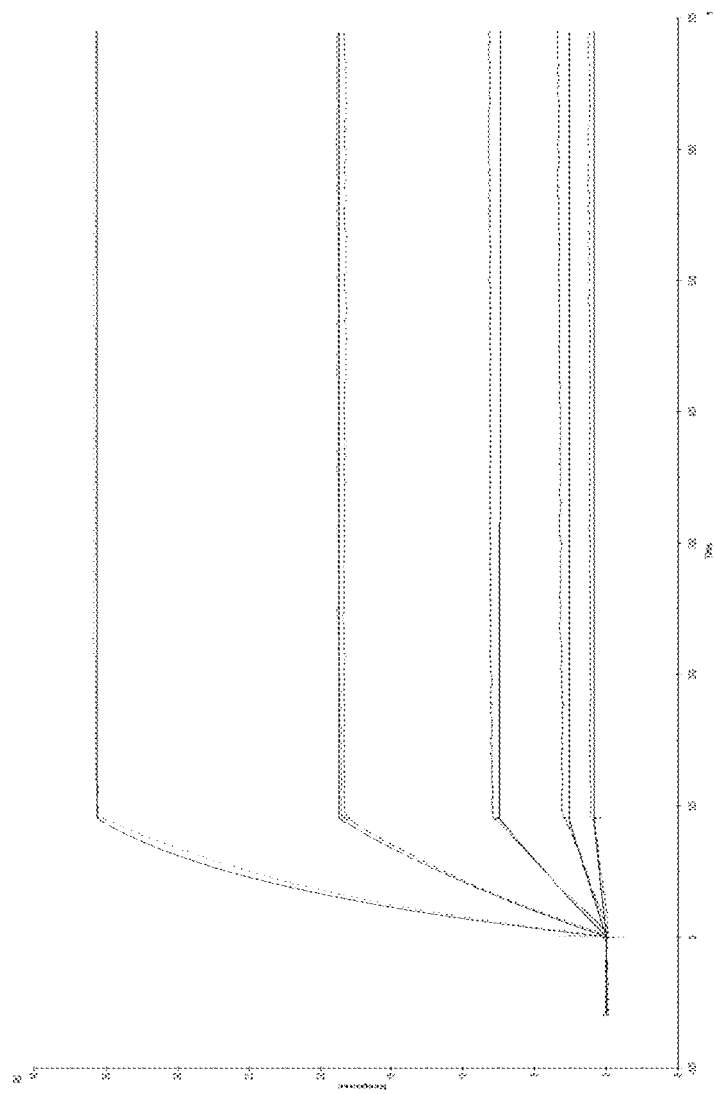
FIG. 1 shows the SPR binding kinetics of PI-4026-5.

Unless otherwise defined, all terms of art, notations and other scientific terminology used herein are intended to have the meanings commonly understood by those of skill in the art. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., Molecular Cloning: A Laboratory Manual 4th ed. (2012) Cold Spring Harbor Laboratory Press, Cold Spring Harbor, NY. As appropriate, procedures involving the use of commercially available kits and reagents are generally carried out in accordance with manufacturer-defined protocols and conditions unless otherwise noted.

As used herein, the singular form "a". "an", and "the" includes plural references unless indicated otherwise.

It is understood that aspects and embodiments of the invention described herein include "comprising." "consisting." and "consisting essentially of" aspects and embodiments.

For all compositions described herein, and all methods using a composition described herein, the compositions can either comprise the listed components or steps, or can "consist essentially of" the listed components or steps. When a composition is described as "consisting essentially of" the listed components, the composition contains the components listed, and may contain other components which do not substantially affect the condition being treated, but do not contain any other components which substantially affect the condition being treated other than those components expressly listed; or, if the composition does contain extra components other than those listed which substantially affect the condition being treated, the composition does not contain a sufficient concentration or amount of the extra components to substantially affect the condition being treated. When a method is described as "consisting essentially of" the listed steps, the method contains the steps listed, and may contain other steps that do not substantially affect the condition being treated, but the method does not contain any other steps which substantially affect the condition being treated other than those steps expressly listed. As a non-limiting specific example, when a composition is described as 'consisting essentially of' a component, the composition may additionally contain any amount of pharmaceutically acceptable carriers, vehicles, or diluents and other such components which do not substantially affect the condition being treated.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell." "host cell line," and "host cell culture" are used interchangeably and refer to cells into which an exogenous nucleic acid has been introduced, and the progeny of such cells. Host cells include "transformants" (or "transformed cells") and "transfectants" (or "transfected cells"), which each include the primary transformed or transfected cell and progeny derived therefrom. Such progeny may not be completely identical in nucleic acid content to a parent cell, and may contain mutations.

An "effective amount" or "therapeutically effective amount" as used herein refers to an amount of therapeutic compound, such as an anti-TREM1 antibody, administered to an individual, either as a single dose or as part of a series of doses, which is effective to produce or contribute to a desired therapeutic effect, either alone or in combination with another therapeutic modality. Examples of a desired therapeutic effect is enhancing an immune response, slowing or delaying tumor development; stabilization of disease; amelioration of one or more symptoms. An effective amount may be given in one or more dosages.

The term "treating" (and variations thereof such as "treat" or "treatment") refers to clinical intervention in an attempt to alter the natural course of a disease or condition in a subject in need thereof. Treatment can be performed during the course of clinical pathology. Desirable effects of treatment include preventing recurrence of disease, alleviation of symptoms, diminishment of any direct or indirect pathological consequences of the disease, preventing metastasis, decreasing the rate of disease progression, amelioration or palliation of the disease state, and remission or improved prognosis.

The term "sufficient amount" means an amount sufficient to produce a desired effect, e.g., an amount sufficient to modulate an immune response in a subject.

As used herein, the term "subject" or "individual" means a mammalian subject. Exemplary subjects include humans, monkeys, dogs, cats, mice, rats, cows, horses, camels, goats, rabbits, and sheep. In certain embodiments, the subject is a human. In some embodiments the subject has a disease or condition that can be treated with an antibody provided herein. In some aspects, the disease or condition is a cancer. In some aspects, the disease or condition is a viral infection.

The term "in vitro" refers to processes that occur in a living cell growing separate from a living organism, e.g., growing in tissue culture.

The term "in vivo" refers to processes that occur in a living organism.

The term "package insert" is used to refer to instructions customarily included in commercial packages of therapeutic or diagnostic products (e.g., kits) that contain information about the indications, usage, dosage, administration, combination therapy, contraindications and/or warnings concerning the use of such therapeutic or diagnostic products.

The term "cytotoxic agent." as used herein, refers to a substance that inhibits or prevents a cellular function and/or causes cell death or destruction.

A "chemotherapeutic agent" refers to a chemical compound useful in the treatment of cancer. Chemotherapeutic agents include "anti-hormonal agents" or "endocrine therapeutics" which act to regulate, reduce, block, or inhibit the effects of hormones that can promote the growth of cancer.

The term "cytostatic agent" refers to a compound or composition which arrests growth of a cell either in vitro or in vivo. In some embodiments, a cytostatic agent is an agent that reduces the percentage of cells in S phase. In some embodiments, a cytostatic agent reduces the percentage of cells in S phase by at least about 20%, at least about 40%, at least about 60%, or at least about 80%.

The term "tumor" refers to all neoplastic cell growth and proliferation, whether malignant or benign, and all precancerous and cancerous cells and tissues. The terms "cancer," "cancerous," "cell proliferative disorder." "proliferative disorder" and "tumor" are not mutually exclusive as referred to herein. The terms "cell proliferative disorder" and "proliferative disorder" refer to disorders that are associated with some degree of abnormal cell proliferation. In some embodiments, the cell proliferative disorder is a cancer. In some aspects, the tumor is a solid tumor. In some aspects, the tumor is a hematologic malignancy.

The term "pharmaceutical composition" refers to a preparation which is in such form as to permit the biological activity of an active ingredient contained therein to be effective in treating a subject, and which contains no additional components which are unacceptably toxic to the subject in the amounts provided in the pharmaceutical composition.

The terms "co-administration", "co-administer", and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to the administration of a second therapeutic agent.

The terms "modulate" and "modulation" refer to reducing or inhibiting or, alternatively, activating or increasing, a recited variable.

The terms "increase" and "activate" refer to an increase of 10%, 20%, 30%, 40%, 50%, 60%, 70%, 75%, 80%, 85%, 90%, 95%, 100%, 2-fold, 3-fold, 4-fold, 5-fold, 10-fold, 20-fold, 50-fold, 100-fold, or greater in a recited variable.

The terms "reduce" and "inhibit" refer to a decrease of 10%. 20%, 30%, 40%, 50%, 60%, 70%, 75%, 80%, 85%, 90%, 95%. 2-fold, 3-fold, 4-fold, 5-fold, 10-fold, 20-fold, 50-fold, 100-fold, or greater in a recited variable.

The term "about" indicates and encompasses an indicated value and a range above and below that value. In certain embodiments, the term "about" indicates the designated value ±10%, ±5%, or ±1%. In certain embodiments, where applicable, the term "about" indicates the designated value(s)±one standard deviation of that value(s).

The term "agonize" refers to the activation of receptor signaling to induce a biological response associated with activation of the receptor. An "agonist" is an entity that binds to and agonizes a receptor.

The term "antagonize" refers to the inhibition of receptor signaling to inhibit a biological response associated with activation of the receptor. An "antagonist" is an entity that binds to and antagonizes a receptor.

For any of the structural and functional characteristics described herein, methods of determining these characteristics are known in the art.

The term "optionally" is meant, when used sequentially, to include from one to all of the enumerated combinations and contemplates all subcombinations.

The term "amino acid" refers to the twenty common naturally occurring amino acids. Naturally occurring amino acids include alanine (Ala; A), arginine (Arg; R), asparagine (Asn; N), aspartic acid (Asp; D), cysteine (Cys; C); glutamic acid (Glu; E), glutamine (Gln; Q), Glycine (Gly; G); histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

The term percent "identity." in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., using publicly available computer software such as BLAST, BLASTP, BLASTN, BLAST-2, ALIGN, MEGALIGN (DNASTAR), CLUSTALW. CLUSTAL OMEGA, or MUSCLE software or other algorithms available to persons of skill) or by visual inspection. Software for performing BLAST analyses is publicly available through the National Center for Biotechnology Information (ncbi.nlm.nih.gov). Those skilled in the art can determine appropriate parameters for aligning sequences, including any algorithms needed to achieve maximal alignment over the full length of the sequences being compared. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

TREM1 Antibodies

Structure

The present application provides antibodies and compositions comprising an antibody which binds a TREM1 protein including antibodies that disable non-stimulatory myeloid cells.

The term "antibody" is used herein in its broadest sense and includes certain types of immunoglobulin molecules comprising one or more antigen-binding domains that specifically bind to an antigen or epitope. An antibody specifically includes intact antibodies (e.g., intact immunoglobulins), antibody fragments, and multi-specific antibodies.

The recognized immunoglobulin genes include the kappa, lambda, alpha, gamma, delta, epsilon and mu constant region genes, as well as the myriad immunoglobulin variable region genes. Light chains are classified as either kappa or lambda. The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called $\alpha$, $\delta$, $\epsilon$, $\gamma$, and $\mu$, respectively.

An exemplary immunoglobulin (antibody) structural unit is composed of two pairs of polypeptide chains, each pair having one "light" (about 25 kD) and one "heavy" chain (about 50-70 kD). The N-terminal domain of each chain defines a variable region of about 100 to 110 or more amino acids primarily responsible for antigen recognition. The terms variable light chain (VL) and variable heavy chain (VH) refer to these light and heavy chain domains respectively. The IgG1 heavy chain comprises of the VH, CH1, CH2 and CH3 domains respectively from the N to C-terminus. The light chain comprises of the VL and CL domains from N to C terminus. The IgG1 heavy chain comprises a hinge between the CH1 and CH2 domains. In certain embodiments, the immunoglobulin constructs comprise at least one immunoglobulin domain from IgG, IgM, IgA, IgD, or IgE connected to a therapeutic polypeptide. In some embodiments, the immunoglobulin domain found in an antibody provided herein, is from or derived from an immunoglobulin based construct such as a diabody, or a nanobody. In certain embodiments, the immunoglobulin constructs described herein comprise at least one immunoglobulin domain from a heavy chain antibody such as a camelid antibody. In certain embodiments, the immunoglobulin constructs provided herein comprise at least one immunoglobulin domain from a mammalian antibody such as a bovine antibody, a human antibody, a camelid antibody, a mouse antibody or any chimeric antibody.

In some embodiments, the antibodies provided herein comprise a heavy chain. In one embodiment, the heavy chain is an IgA. In one embodiment, the heavy chain is an IgD. In one embodiment, the heavy chain is an IgE. In one embodiment, the heavy chain is an IgG. In one embodiment, the heavy chain is an IgM. In one embodiment, the heavy chain is an IgG1. In one embodiment, the heavy chain is an IgG2. In one embodiment, the heavy chain is an IgG3. In one embodiment, the heavy chain is an IgG4. In one embodiment, the heavy chain is an IgA1. In one embodiment, the heavy chain is an IgA2.

In some embodiments, an antibody is an IgG1 antibody.
In some embodiments, an antibody is an IgG3 antibody.

In some embodiments, an antibody is an IgG2 antibody.

In some embodiments, an antibody is an IgG4 antibody.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as "complementarity determining regions" (CDRs), and these terms are used herein interchangeably in reference to portions of the variable region that form the antigen-binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The exact residue numbers which encompass a particular CDR will vary depending on the sequence and size of the CDR. Those skilled in the art can routinely determine which residues comprise a particular CDR given the variable region amino acid sequence of the antibody.

The amino acid sequence boundaries of a CDR can be determined by one of skill in the art using any of a number of known numbering schemes, including those described by Kabat et al., supra ("Kabat" numbering scheme); Al-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., *Dev. Comp. Immunol.*, 2003, 27:55-77 ("IMGT" numbering scheme); and Honegge and Plückthun, *J. Mol. Biol.*, 2001, 309:657-70 ("AHo" numbering scheme); each of which is incorporated by reference in its entirety.

Table A provides the positions of CDR-L1, CDR-L2, CDR-L3, CDR-H1, CDR-H2, and CDR-H3 as identified by the Kabat and Chothia schemes. For CDR-H1, residue numbering is provided using both the Kabat and Chothia numbering schemes.

CDRs may be assigned, for example, using antibody numbering software, such as Abnum, available at bioinf.org.uk/abs/abnum/, and described in Abhinandan and Martin, *Immunology*, 2008, 45:3832-3839, incorporated by reference in its entirety.

TABLE A

Residues in CDRs according to Kabat and Chothia numbering schemes.
Table A

| CDR | Kabat | Chothia |
| --- | --- | --- |
| L1 | L24-L34 | L24-L34 |
| L2 | L50-L56 | L50-L56 |
| L3 | L89-L97 | L89-L97 |
| H1 (Kabat Numbering) | H31-H35B | H26-H32 or H34* |

TABLE A-continued

Residues in CDRs according to Kabat and Chothia numbering schemes.
Table A

| CDR | Kabat | Chothia |
| --- | --- | --- |
| H1 (Chothia Numbering) | H31-H35 | H26-H32 |
| H2 | H50-H65 | H52-H56 |
| H3 | H95-H102 | H95-H102 |

*The C-terminus of CDR-H1, when numbered using the Kabat numbering convention, varies between H32 and H34, depending on the length of the CDR.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

The term "antigen-binding domain" means the portion of an antibody that is capable of specifically binding to an antigen or epitope. One example of an antigen-binding domain is an antigen-binding domain formed by a VH-VL dimer of an antibody. Another example of an antigen-binding domain is an antigen-binding domain formed by diversification of certain loops from the tenth fibronectin type III domain of an Adnectin. An antigen-binding domain can include CDRs 1, 2, and 3 from a heavy chain in that order; and CDRs 1, 2, and 3 from a light chain in that order.

The term "epitope" means a portion of an antigen that specifically binds to an antibody. Epitopes frequently consist of surface-accessible amino acid residues and/or sugar side chains and may have specific three-dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding, and other amino acid residues, which are not directly involved in the binding. The epitope to which an antibody binds can be determined using known techniques for epitope determination such as, for example, testing for antibody binding to TREM1 variants with different point-mutations, or to chimeric TREM1 variants.

To screen for antibodies which bind to an epitope on a target antigen bound by an antibody of interest (e.g., TREM1), a routine cross-blocking assay such as that described in *Antibodies, A Laboratory Manual*, Cold Spring Harbor Laboratory, Ed Harlow and David Lane (1988), can be performed. Alternatively, or additionally, epitope mapping can be performed by methods known in the art.

The term "chimeric antibody" refers to an antibody in which a portion of the heavy and/or light chain is derived from a particular source or species, while the remainder of the heavy and/or light chain is derived from a different source or species.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

A "humanized antibody" has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies can be found in U.S. Pat. Nos. 6,054,297, 5,886,152 and 5,877,293. For further details, see Jones et al., *Nature,* 1986, 321:522-525; Riechmann et al., *Nature,* 1988, 332:323-329; and Presta, *Curr. Op. Struct. Biol.,* 1992, 2:593-596, each of which is incorporated by reference in its entirety.

A "multispecific antibody" is an antibody that comprises two or more different antigen-binding domains that collectively specifically bind two or more different epitopes. The two or more different epitopes may be epitopes on the same antigen (e.g., a single TREM1 molecule expressed by a cell) or on different antigens (e.g., different TREM1 molecules expressed by the same cell, or a TREM1 molecule and a non-TREM1 molecule). In some aspects, a multi-specific antibody binds two different epitopes (i.e., a "bispecific antibody"). In some aspects, a multi-specific antibody binds three different epitopes (i.e., a "trispecific antibody").

A "monospecific antibody" is an antibody that comprises one or more binding sites that specifically bind to a single epitope. An example of a monospecific antibody is a naturally occurring IgG molecule which, while divalent (i.e., having two antigen-binding domains), recognizes the same epitope at each of the two antigen-binding domains. The binding specificity may be present in any suitable valency.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "single-chain" refers to a molecule comprising amino acid monomers linearly linked by peptide bonds. In a particular such embodiment, the C-terminus of the Fab light chain is connected to the N-terminus of the Fab heavy chain in the single-chain Fab molecule. As described in more detail herein, an scFv has a variable domain of light chain (VL) connected from its C-terminus to the N-terminal end of a variable domain of heavy chain (VH) by a polypeptide chain. Alternately the scFv comprises of polypeptide chain where in the C-terminal end of the VH is connected to the N-terminal end of VL by a polypeptide chain.

The "Fab fragment" (also referred to as fragment antigen-binding) contains the constant domain (CL) of the light chain and the first constant domain (CH1) of the heavy chain along with the variable domains VL and VH on the light and heavy chains respectively. The variable domains comprise the complementarity determining loops (CDR, also referred to as hypervariable region) that are involved in antigen-binding. Fab' fragments differ from Fab fragments by the addition of a few residues at the carboxy terminus of the heavy chain CH1 domain including one or more cysteines from the antibody hinge region.

"F(ab')2" fragments contain two Fab' fragments joined, near the hinge region, by disulfide bonds. F(ab')2 fragments may be generated, for example, by recombinant methods or by pepsin digestion of an intact antibody. The F(ab') fragments can be dissociated, for example, by treatment with ß-mercaptoethanol.

"Fv" fragments comprise a non-covalently-linked dimer of one heavy chain variable domain and one light chain variable domain.

"Single-chain Fv" or "sFv" or "scFv" includes the VH and VL domains of an antibody, wherein these domains are present in a single polypeptide chain. In one embodiment, the Fv polypeptide further comprises a polypeptide linker between the VH and VL domains which enables the scFv to form the desired structure for antigen-binding. For a review of scFv see Pluckthun in *The Pharmacology of Monoclonal Antibodies,* vol. 113, Rosenburg and Moore eds., Springer-Verlag, New York, pp. 269-315 (1994). HER2 antibody scFv fragments are described in WO93/16185; U.S. Pat. Nos. 5,571,894; and 5,587,458.

"scFv-Fc" fragments comprise an scFv attached to an Fc domain. For example, an Fc domain may be attached to the C-terminal of the scFv. The Fc domain may follow the VH or VL, depending on the orientation of the variable domains in the scFv (i.e., VH-VL or VL-VH). Any suitable Fc domain known in the art or described herein may be used. In some cases, the Fc domain comprises an IgG4 Fc domain.

The term "single domain antibody" or "sdAb" refers to a molecule in which one variable domain of an antibody specifically binds to an antigen without the presence of the other variable domain. Single domain antibodies, and fragments thereof, are described in Arabi Ghahroudi et al., *FEBS Letters,* 1998, 414:521-526 and Muyldermans et al., *Trends in Biochem. Sci.,* 2001, 26:230-245, each of which is incorporated by reference in its entirety. Single domain antibodies are also known as sdAbs or nanobodies. Sdabs are fairly stable and easy to express as fusion partner with the Fc chain of an antibody (Harmsen M M, De Haard H J (2007). "Properties, production, and applications of camelid single-domain antibody fragments". Appl. Microbiol Biotechnol. 77(1): 13-22).

The terms "full length antibody." "intact antibody." and "whole antibody" are used herein interchangeably to refer to an antibody having a structure substantially similar to a naturally occurring antibody structure and having heavy chains that comprise an Fc region. For example, when used to refer to an IgG molecule, a "full length antibody" is an antibody that comprises two heavy chains and two light chains.

An "antibody fragment" comprises a portion of an intact antibody, such as the antigen-binding or variable region of an intact antibody. Antibody fragments include, for example, Fv fragments, Fab fragments, F(ab')2 fragments, Fab' fragments, scFv (sFv) fragments, and scFv-Fc fragments.

Anti-TREM1 antibodies can include those described herein such as the clones set forth in the tables. In some embodiments, the antibody comprises an alternative scaffold. In some embodiments, the antibody consists of an alternative scaffold. In some embodiments, the antibody consists essentially of an alternative scaffold. In some embodiments, the antibody comprises an antibody fragment. In some embodiments, the antibody consists of an antibody fragment. In some embodiments, the antibody consists essentially of an antibody fragment. A "TREM1 antibody," "anti-TREM1 antibody," or "TREM1-specific antibody" is an antibody, as provided herein, which specifically binds to the antigen TREM1. In some embodiments, the antibody binds the extracellular domain of TREM1. In certain embodiments, a TREM1 antibody provided herein binds to an epitope of TREM1 that is conserved between or among TREM1 proteins from different species. An anti-TREM1 antibody can include a TREM-26 clone (BioLegend; catalog no. 314907; Li J, et al. 2011. Dev. Comp. Immunol. epub.).

In some embodiments the antibodies are monoclonal antibodies.

In some embodiments the antibodies are polyclonal antibodies.

In some embodiments the antibodies are produced by hybridomas. In other embodiments, the antibodies are produced by recombinant cells engineered to express the desired variable and constant domains.

In some embodiments the antibodies may be single chain antibodies or other antibody derivatives retaining the antigen specificity and the lower hinge region or a variant thereof.

In some embodiments, the antibodies may be polyfunctional antibodies, recombinant antibodies, human antibodies, humanized antibodies, fragments or variants thereof. In some embodiments, the antibody is a monoclonal antibody, a neutral antibody, an antagonistic antibody, an agonist antibody, a polyclonal antibody, an afucosylated antibody, a bispecific antibody, a human antibody, a chimeric antibody, a full-length antibody, and an antigen binding fragment thereof. In particular embodiments, the antibody fragment or a derivative thereof is selected from a Fab fragment, a Fab'2 fragment, a CDR, and ScFv. In some embodiments, the antibody is an antigen-binding fragment thereof, a Fab, Fab', F(ab')2, Fv, scFv, (scFv)2, single chain antibody molecule, dual variable domain antibody, single variable domain antibody, linear antibody, or V domain antibody.

In some embodiments, the antibodies are capable of forming an immune complex. For example, an immune complex can be a tumor cell covered by antibodies.

In some embodiments, the TREM1 antibodies compete for binding to human TREM1 (SEQ ID NO: 1) with a reference antibody.

Sequences of TREM1 Antibodies $V_H$ Domains

In some embodiments, an antibody provided herein comprises a VH sequence selected from SEQ ID NOs: 3, 4, 5, 6, 7, 8, 9, 10, 11, 12, 13, 14, 15, 16, 17, and 18. In some embodiments, an antibody provided herein comprises a $V_H$ sequence of SEQ ID NO: 3. In some embodiments, an antibody provided herein comprises a $V_H$ sequence of SEQ ID NO: 4. In some embodiments, an antibody provided herein comprises a $V_H$ sequence of SEQ ID NO: 5. In some embodiments, an antibody provided herein comprises a $V_H$ sequence of SEQ ID NO: 6. In some embodiments, an antibody provided herein comprises a $V_H$ sequence of SEQ ID NO: 7. In some embodiments, an antibody provided herein comprises a $V_H$ sequence of SEQ ID NO: 8. In some embodiments, an antibody provided herein comprises a $V_H$ sequence of SEQ ID NO: 9. In some embodiments, an antibody provided herein comprises a $V_H$ sequence of SEQ ID NO: 10. In some embodiments, an antibody provided herein comprises a $V_H$ sequence of SEQ ID NO: 11. In some embodiments, an antibody provided herein comprises a $V_H$ sequence of SEQ ID NO: 12. In some embodiments, an antibody provided herein comprises a $V_H$ sequence of SEQ ID NO: 13. In some embodiments, an antibody provided herein comprises a $V_H$ sequence of SEQ ID NO: 14. In some embodiments, an antibody provided herein comprises a $V_H$ sequence of SEQ ID NO: 15. In some embodiments, an antibody provided herein comprises a $V_H$ sequence of SEQ ID NO: 16. In some embodiments, an antibody provided herein comprises a $V_H$ sequence of SEQ ID NO: 17. In some embodiments, an antibody provided herein comprises a $V_H$ sequence of SEQ ID NO: 18.

In some embodiments, an antibody provided herein comprises a $V_H$ sequence having at least about 50%, 60%, 70%, 80%, 90%, 95%, or 99% identity to an illustrative $V_H$ sequence provided in SEQ ID NOs: 4, 5, 6, 8, 9, 10, 12, 13, 14, 16, 17, and 18. In some embodiments, an antibody provided herein comprises a $V_H$ sequence provided in SEQ ID NOs: 4, 5, 6, 8, 9, 10, 12, 13, 14, 16, 17, and 18, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

$V_L$ Domains

In some embodiments, an antibody provided herein comprises a VL sequence selected from SEQ ID NOs: 19, 20, 21, and 22. In some embodiments, an antibody provided herein comprises a VL sequence of SEQ ID NO: 19. In some embodiments, an antibody provided herein comprises a VL sequence of SEQ ID NO: 20. In some embodiments, an antibody provided herein comprises a VL sequence of SEQ ID NO: 21. In some embodiments, an antibody provided herein comprises a VL sequence of SEQ ID NO: 22.

In some embodiments, an antibody provided herein comprises a VL sequence having at least about 50%, 60%, 70%, 80%, 90%, 95%, or 99% identity to an illustrative VL sequence provided in SEQ ID NOs: 19, 20, 21, and 22. In some embodiments, an antibody provided herein comprises a VL sequence provided in SEQ ID NOs: 19, 20, 21, and 22, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

VH-VL Combinations

In some embodiments, an antibody provided herein comprises a $V_H$ sequence selected from SEQ ID NOs:3, 4, 5, 6, 7, 8, 9, 10, 11, 12, 13, 14, 15, 16, 17, and 18; and a $V_L$ sequence selected from SEQ ID NOs:19, 20, 21, and 22.

In some embodiments, an antibody provided herein comprises a $V_H$ sequence of SEQ ID NO:17 and a $V_L$ sequence of SEQ ID NO:20. In some embodiments, an antibody provided herein comprises a $V_H$ sequence of SEQ ID NO: 17 and a $V_L$ sequence of SEQ ID NO: 19. In some embodiments, an antibody provided herein comprises a $V_H$ sequence of SEQ ID NO: 17 and a $V_L$ sequence of SEQ ID NO:21. In some embodiments, an antibody provided herein comprises a $V_H$ sequence of SEQ ID NO: 17 and a $V_L$ sequence of SEQ ID NO:22.

In some embodiments, an antibody provided herein comprises a $V_H$ sequence of SEQ ID NO:16 and a $V_L$ sequence of SEQ ID NO: 19. In some embodiments, an antibody provided herein comprises a $V_H$ sequence of SEQ ID NO: 16 and a $V_L$ sequence of SEQ ID NO:20. In some embodiments, an antibody provided herein comprises a $V_H$ sequence of SEQ ID NO: 16 and a $V_L$ sequence of SEQ ID NO:21. In some embodiments, an antibody provided herein comprises a $V_H$ sequence of SEQ ID NO: 16 and a $V_L$ sequence of SEQ ID NO:22. In some embodiments, an antibody provided herein comprises a $V_H$ sequence of SEQ ID NO: 18 and a $V_L$ sequence of SEQ ID NO:19. In some embodiments, an antibody provided herein comprises a $V_H$ sequence of SEQ ID NO: 18 and a $V_L$ sequence of SEQ ID NO:20. In some embodiments, an antibody provided herein comprises a $V_H$ sequence of SEQ ID NO: 18 and a $V_L$ sequence of SEQ ID NO:21. In some embodiments, an antibody provided herein comprises a $V_H$ sequence of SEQ ID NO:18 and a $V_L$ sequence of SEQ ID NO:22.

In some embodiments, an antibody provided herein comprises a $V_H$ sequence of SEQ ID NO:13 and a $V_L$ sequence of SEQ ID NO:20. In some embodiments, an antibody provided herein comprises a $V_H$ sequence of SEQ ID NO: 13 and a $V_L$ sequence of SEQ ID NO:19. In some embodiments, an antibody provided herein comprises a $V_H$ sequence of SEQ ID NO:13 and a $V_L$ sequence of SEQ ID NO:21. In some embodiments, an antibody provided herein comprises a $V_H$ sequence of SEQ ID NO: 13 and a $V_L$ sequence of SEQ ID NO:22.

In some embodiments, an antibody provided herein comprises a $V_H$ sequence of SEQ ID NO:12 and a $V_L$ sequence of SEQ ID NO: 19. In some embodiments, an antibody provided herein comprises a $V_H$ sequence of SEQ ID NO: 12 and a $V_L$ sequence of SEQ ID NO:20. In some embodiments, an antibody provided herein comprises a $V_H$ sequence of SEQ ID NO: 12 and a $V_L$ sequence of SEQ ID NO:21. In some embodiments, an antibody provided herein comprises a $V_H$ sequence of SEQ ID NO: 12 and a $V_L$ sequence of SEQ ID NO:22. In some embodiments, an antibody provided herein comprises a $V_H$ sequence of SEQ ID NO: 14 and a $V_L$ sequence of SEQ ID NO: 19. In some embodiments, an antibody provided herein comprises a $V_H$ sequence of SEQ ID NO: 14 and a $V_L$ sequence of SEQ ID NO:21. In some embodiments, an antibody provided herein comprises a $V_H$ sequence of SEQ ID NO: 14 and a $V_L$ sequence of SEQ ID NO:22. In some embodiments, an antibody provided herein comprises a $V_H$ sequence of SEQ ID NO: 14 and a $V_L$ sequence of SEQ ID NO:20.

In some embodiments, an antibody provided herein comprises a $V_H$ sequence of SEQ ID NO:9 and a $V_L$ sequence of SEQ ID NO:20. In some embodiments, an antibody provided herein comprises a $V_H$ sequence of SEQ ID NO:9 and a $V_L$ sequence of SEQ ID NO: 19. In some embodiments, an antibody provided herein comprises a $V_H$ sequence of SEQ ID NO:9 and a $V_L$ sequence of SEQ ID NO:21. In some embodiments, an antibody provided herein comprises a $V_H$ sequence of SEQ ID NO:9 and a $V_L$ sequence of SEQ ID NO:22.

In some embodiments, an antibody provided herein comprises a $V_H$ sequence of SEQ ID NO:8 and a $V_L$ sequence of SEQ ID NO:19. In some embodiments, an antibody provided herein comprises a $V_H$ sequence of SEQ ID NO:8 and a $V_L$ sequence of SEQ ID NO:20. In some embodiments, an antibody provided herein comprises a $V_H$ sequence of SEQ ID NO:8 and a $V_L$ sequence of SEQ ID NO:21. In some embodiments, an antibody provided herein comprises a $V_H$ sequence of SEQ ID NO:8 and a $V_L$ sequence of SEQ ID NO:22. In some embodiments, an antibody provided herein comprises a Vu sequence of SEQ ID NO: 10 and a $V_L$ sequence of SEQ ID NO: 19. In some embodiments, an antibody provided herein comprises a $V_H$ sequence of SEQ ID NO:10 and a $V_L$ sequence of SEQ ID NO:21. In some embodiments, an antibody provided herein comprises a $V_H$ sequence of SEQ ID NO: 10 and a $V_L$ sequence of SEQ ID NO:22. In some embodiments, an antibody provided herein comprises a $V_H$ sequence of SEQ ID NO:10 and a $V_L$ sequence of SEQ ID NO:20.

In some embodiments, an antibody provided herein comprises a $V_H$ sequence of SEQ ID NO:5 and a $V_L$ sequence of SEQ ID NO:20. In some embodiments, an antibody provided herein comprises a $V_H$ sequence of SEQ ID NO:5 and a $V_L$ sequence of SEQ ID NO:19. In some embodiments, an antibody provided herein comprises a Vu sequence of SEQ ID NO:5 and a $V_L$ sequence of SEQ ID NO:21. In some embodiments, an antibody provided herein comprises a $V_H$ sequence of SEQ ID NO:5 and a $V_L$ sequence of SEQ ID NO:22.

In some embodiments, an antibody provided herein comprises a $V_H$ sequence of SEQ ID NO:4 and a $V_L$ sequence of SEQ ID NO: 19. In some embodiments, an antibody provided herein comprises a $V_H$ sequence of SEQ ID NO:4 and a $V_L$ sequence of SEQ ID NO:20. In some embodiments, an antibody provided herein comprises a $V_H$ sequence of SEQ ID NO:4 and a $V_L$ sequence of SEQ ID NO:21. In some embodiments, an antibody provided herein comprises a Vu sequence of SEQ ID NO:4 and a $V_L$ sequence of SEQ ID NO:22. In some embodiments, an antibody provided herein comprises a $V_H$ sequence of SEQ ID NO:6 and a $V_L$ sequence of SEQ ID NO: 19. In some embodiments, an antibody provided herein comprises a $V_H$ sequence of SEQ ID NO:6 and a $V_L$ sequence of SEQ ID NO:21. In some embodiments, an antibody provided herein comprises a $V_H$ sequence of SEQ ID NO:6 and a $V_L$ sequence of SEQ ID NO:22. In some embodiments, an antibody provided herein comprises a $V_H$ sequence of SEQ ID NO:6 and a $V_L$ sequence of SEQ ID NO:20.

In certain aspects, any of SEQ ID NOs:3, 4, 5, 6, 7, 8, 9, 10, 11, 12, 13, 14, 15, 16, 17, and 18 can be combined with any of SEQ ID NOs: 19, 20, 21, and 22. For example, SEQ ID NO:9 can be combined with any of SEQ ID NO: 19, 20, 21, and 22. As another example, SEQ ID NO: 17 can be combined with any of SEQ ID NO: 19, 20, 21, and 22.

In some embodiments, an antibody provided herein comprises a $V_H$ sequence having at least about 50%, 60%, 70%, 80%, 90%, 95%, or 99% identity to an illustrative $V_H$ sequence provided in SEQ ID NOs: 3, 4, 5, 6, 7, 8, 9, 10, 11, 12, 13, 14, 15, 16, 17, and 18; and a $V_L$ sequence having at least about 50%, 60%, 70%, 80%, 90%, 95%, or 99% identity to an illustrative $V_L$ sequence provided in SEQ ID NOs: 19, 20, 21, and 22. In some embodiments, an antibody provided herein comprises a VH sequence provided in SEQ ID NOs: 3, 4, 5, 6, 7, 8, 9, 10, 11, 12, 13, 14, 15, 16, 17, and 18, with up to 1, 2, 3, 4, 5, 6, 7, 8, 9, 10, 11, 12, 13, 14, 15, 16, 17, 18, 19, 20, 21, 22, 23, 24, or 25 amino acid substitutions, and a VL sequence provided in SEQ ID NOs: 19, 20, 21, and 22, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

CDRs

In some embodiments, an antibody provided herein comprises one to three CDRs of a VH domain selected from SEQ ID NOs: 3, 4, 5, 6, 7, 8, 9, 10, 11, 12, 13, 14, 15, 16, 17, and 18. In some embodiments, an antibody provided herein comprises two to three CDRs of a $V_H$ domain selected from SEQ ID NOs: 3, 4, 5, 6, 7, 8, 9, 10, 11, 12, 13, 14, 15, 16, 17, and 18. In some embodiments, an antibody provided herein comprises three CDRs of a VH domain selected from SEQ ID NOs: 3, 4, 5, 6, 7, 8, 9, 10, 11, 12, 13, 14, 15, 16, 17, and 18. In some aspects, the CDRs are Exemplary CDRs. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, the CDRs are CDRs having at least about 50%, 75%, 80%, 85%, 90%, or 95% identity with a CDR-H1, CDR-H2, or CDR-H3 of SEQ ID NOs: 3, 4, 5, 6, 7, 8, 9, 10, 11, 12, 13, 14, 15, 16, 17, and 18. In some embodiments, the CDR-H1 is a CDR-H1 of a VH domain selected from SEQ ID NOs: 3, 4, 5, 6, 7, 8, 9, 10, 11, 12, 13, 14, 15, 16, 17, and 18, with up to 1, 2, 3, 4, or 5 amino acid substitutions. In some embodiments, the CDR-H2 is a CDR-H2 of a VH domain selected from SEQ ID NOs: 3, 4, 5, 6, 7, 8, 9, 10, 11, 12, 13, 14, 15, 16, 17, and 18, with up to 1, 2, 3, 4, 5, 6, 7, or 8 amino acid substitutions. In some embodiments, the CDR-H3 is a CDR-H3 of a VH domain selected from SEQ ID NOs: 3, 4, 5, 6, 7, 8, 9, 10, 11, 12, 13, 14, 15, 16, 17, and 18, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises one to three CDRs of a VL domain selected from SEQ ID NOs: 19, 20, 21, and 22. In some embodiments, an antibody provided herein comprises two to three CDRs of a VL domain selected from SEQ ID NOs: 19, 20, 21, and 22. In some embodiments, an antibody provided herein comprises three CDRs of a VL domain selected from SEQ ID NOs: 19, 20, 21, and 22. In some aspects, the CDRs are Exemplary CDRs. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, the CDRs are CDRs having at least about 50%, 75%, 80%, 85%, 90%, or 95% identity with a CDR-L1, CDR-L2, or CDR-L3 of SEQ ID NOs: 19, 20, 21, and 22. In some embodiments, the CDR-L1 is a CDR-L1 of a VL domain selected from SEQ ID NOs: 19, 20, 21, and 22, with up to 1, 2, 3, 4, or 5 amino acid substitutions. In some embodiments, the CDR-L2 is a CDR-L2 of a VL domain selected from SEQ ID NOs: 19, 20, 21, and 22, with up to 1, 2, 3, 4, 5, 6, 7, or 8 amino acid substitutions. In some embodiments, the CDR-L3 is a CDR-L3 of a VL domain selected from SEQ ID NOs: 19, 20, 21, and 22, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises one to three CDRs of a VH domain selected from SEQ ID NOs: 3, 4, 5, 6, 7, 8, 9, 10, 11, 12, 13, 14, 15, 16, 17, and 18 and one to three CDRs of a VL domain selected from SEQ ID NOs: 19, 20, 21, and 22. In some embodiments, an antibody provided herein comprises two to three CDRs of a VH domain selected from SEQ ID NOs: 3, 4, 5, 6, 7, 8, 9, 10, 11, 12, 13, 14, 15, 16, 17, and 18 and two to three CDRs of a VL domain selected from SEQ ID NOs: 19, 20, 21, and 22. In some embodiments, an antibody provided herein comprises three CDRs of a VH domain selected from SEQ ID NOs: 3, 4, 5, 6, 7, 8, 9, 10, 11, 12, 13, 14, 15, 16, 17, and 18 and three CDRs of a VL domain selected from SEQ ID NOs: 19, 20, 21, and 22. In some aspects, the CDRs are Exemplary CDRs. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, an antibody provided herein comprises a CDR-H3 selected of SEQ ID NOs: 25, 29, 30, 31, 32, and 33. In some aspects, the CDR-H3 has at least about 50%, 75%, 80%, 85%. 90%, or 95% identity with a CDR-H3 of SEQ ID NOs: 25, 29, 30, 31, 32, and 33. In some embodiments, the CDR-H3 is a CDR-H3 selected of SEQ ID NO: 25, 29, 30, 31, 32, and 33, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 selected of SEQ ID NO:33. In some aspects, the CDR-H3 has at least about 50%, 75%, 80%, 85%, 90%, or 95% identity with a CDR-H3 of SEQ ID NO:33. In some embodiments, the CDR-H3 is a CDR-H3 selected of SEQ ID NO:33, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 selected of SEQ ID NO: 32. In some aspects, the CDR-H3 has at least about 50%, 75%, 80%, 85%, 90%, or 95% identity with a CDR-H3 of SEQ ID NO: 32. In some embodiments, the CDR-H3 is a CDR-H3 selected of SEQ ID NO: 32, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 selected of SEQ ID NO:25. In some aspects, the CDR-H3 has at least about 50%, 75%, 80%, 85%, 90%, or 95% identity with a CDR-H3 of SEQ ID NO:25. In some embodiments, the CDR-H3 is a CDR-H3 selected of SEQ ID NO:25, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H2 of SEQ ID NO: 24. In some aspects, the CDR-H2 has at least about 50%, 75%, 80%, 85%, 90%, or 95% identity with a CDR-H2 of SEQ ID NO: 24. In some embodiments, the CDR-H2 is a CDR-H2 of SEQ ID NO: 24, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H1 of SEQ ID NO: 23. In some aspects, the CDR-H1 has at least about 50%, 75%, 80%, 85%, 90%, or 95% identity with a CDR-H1 of SEQ ID NO: 23. In some embodiments, the CDR-H1 is a CDR-H1 of SEQ ID NO: 23, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 of SEQ ID NO: 29 and a CDR-H2 of SEQ ID NO:24. In some embodiments, an antibody provided herein comprises a CDR-H3 of SEQ ID NO: 29, a CDR-H2 of SEQ ID NO: 24, and a CDR-H1 of SEQ ID NO: 23. In some embodiments, the CDR-H3 has at least about 50%, 75%, 80%, 85%, 90%, or 95% identity with a CDR-H3 of SEQ ID NO: 29, the CDR-H2 has at least about 50%, 75%, 80%, 85%, 90%, or 95% identity with a CDR-H2 of SEQ ID NO: 24, and the CDR-H1 has at least about 50%, 75%, 80%, 85%, 90%, or 95% identity with a CDR-H1 of SEQ ID NO: 23. In some embodiments, the CDR-H3 is a CDR-H3 of SEQ ID NO: 29, with up to 1, 2, 3, 4, 5, 6, 7, or 8 amino acid substitutions; the CDR-H2 is a CDR-H2 of SEQ ID NO: 24, with up to 1, 2, 3, 4, 5, 6, 7, or 8 amino acid substitutions; and the CDR-H1 is a CDR-H1 of SEQ ID NO: 23, with up to 1, 2, 3, 4, or 5 amino acid substitutions.

In some embodiments, an antibody provided herein comprises a CDR-H3 of SEQ ID NO: 25 and a CDR-H2 of SEQ ID NO:24. In some embodiments, an antibody provided herein comprises a CDR-H3 of SEQ ID NO: 25, a CDR-H2 of SEQ ID NO: 24, and a CDR-H1 of SEQ ID NO: 23. In some embodiments, the CDR-H3 has at least about 50%, 75%, 80%, 85%, 90%, or 95% identity with a CDR-H3 of SEQ ID NO: 25, the CDR-H2 has at least about 50%, 75%, 80%, 85%, 90%, or 95% identity with a CDR-H2 of SEQ ID NO: 24, and the CDR-H1 has at least about 50%, 75%, 80%, 85%, 90%, or 95% identity with a CDR-H1 of SEQ ID NO: 23. In some embodiments, the CDR-H3 is a CDR-H3 of SEQ ID NO: 25, with up to 1, 2, 3, 4, 5, 6, 7, or 8 amino acid substitutions; the CDR-H2 is a CDR-H2 of SEQ ID NO: 24, with up to 1, 2, 3, 4, 5, 6, 7, or 8 amino acid substitutions; and the CDR-H1 is a CDR-H1 of SEQ ID NO: 23, with up to 1, 2, 3, 4, or 5 amino acid substitutions.

In some embodiments, an antibody provided herein comprises a CDR-H3 of SEQ ID NO: 33 and a CDR-H2 of SEQ ID NO:24. In some embodiments, an antibody provided herein comprises a CDR-H3 of SEQ ID NO: 33, a CDR-H2 of SEQ ID NO: 24, and a CDR-H1 of SEQ ID NO: 23. In some embodiments, the CDR-H3 has at least about 50%, 75%, 80%, 85%, 90%, or 95% identity with a CDR-H3 of SEQ ID NO: 33, the CDR-H2 has at least about 50%, 75%, 80%, 85%, 90%, or 95% identity with a CDR-H2 of SEQ ID NO: 24, and the CDR-H1 has at least about 50%, 75%, 80%, 85%, 90%, or 95% identity with a CDR-H1 of SEQ ID NO: 23. In some embodiments, the CDR-H3 is a CDR-H3 of SEQ ID NO: 33, with up to 1, 2, 3, 4, 5, 6, 7, or 8 amino acid substitutions; the CDR-H2 is a CDR-H2 of SEQ ID NO: 24, with up to 1, 2, 3, 4, 5, 6, 7, or 8 amino acid substitutions; and the CDR-H1 is a CDR-H1 of SEQ ID NO: 23, with up to 1, 2, 3, 4, or 5 amino acid substitutions.

In some embodiments, an antibody provided herein comprises a CDR-H3 of SEQ ID NO: 32 and a CDR-H2 of SEQ ID NO:24. In some embodiments, an antibody provided herein comprises a CDR-H3 of SEQ ID NO: 32, a CDR-H2 of SEQ ID NO: 24, and a CDR-H1 of SEQ ID NO: 23. In some embodiments, the CDR-H3 has at least about 50%, 75%, 80%, 85%, 90%, or 95% identity with a CDR-H3 of SEQ ID NO: 32, the CDR-H2 has at least about 50%, 75%, 80%, 85%, 90%, or 95% identity with a CDR-H2 of SEQ ID NO: 24, and the CDR-H1 has at least about 50%, 75%, 80%, 85%, 90%, or 95% identity with a CDR-H1 of SEQ ID NO: 23. In some embodiments, the CDR-H3 is a CDR-H3 of SEQ ID NO: 32, with up to 1, 2, 3, 4, 5, 6, 7, or 8 amino acid substitutions; the CDR-H2 is a CDR-H2 of SEQ ID NO: 24, with up to 1, 2, 3, 4, 5, 6, 7, or 8 amino acid substitutions; and the CDR-H1 is a CDR-H1 of SEQ ID NO: 23, with up to 1, 2, 3, 4, or 5 amino acid substitutions. In some aspects, the amino acid substitutions are conservative amino acid substitutions. In some embodiments, the antibody described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 of SEQ ID NO: 30 and a CDR-H2 of SEQ ID NO:24. In some embodiments, an antibody provided herein comprises a CDR-H3 of SEQ ID NO: 30, a CDR-H2 of SEQ ID NO: 24, and a CDR-H1 of SEQ ID NO: 23. In some embodiments, an antibody provided herein comprises a CDR-H3 of SEQ ID NO: 31 and a CDR-H2 of SEQ ID NO:24. In some embodiments, an antibody provided herein comprises a CDR-H3 of SEQ ID NO: 31, a CDR-H2 of SEQ ID NO: 24, and a CDR-H1 of SEQ ID NO: 23.

In some embodiments, an antibody provided herein comprises a CDR-L3 of SEQ ID NO: 28. In some aspects, the CDR-L3 has at least about 50%, 75%, 80%, 85%, 90%, or 95% identity with a CDR-L3 of SEQ ID NO: 28. In some embodiments, the CDR-L3 is a CDR-L3 of SEQ ID NO: 28, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-L2 of SEQ ID NO: 27. In some aspects, the CDR-L2 has at least about 50%, 75%, 80%, 85%, 90%, or 95% identity with a CDR-L2 of SEQ ID NO: 27. In some embodiments, the CDR-L2 is a CDR-L2 of SEQ ID NO: 27, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-L1 of SEQ ID NO: 26. In some aspects, the CDR-L1 has at least about 50%, 75%, 80%, 85%, 90%, or 95% identity with a CDR-L1 of SEQ ID NO: 26. In some embodiments, the CDR-L1 is a CDR-L1 of SEQ ID NO: 26, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-L3 of SEQ ID NO: 28 and a CDR-L2 of SEQ ID NO: 27. In some embodiments, an antibody provided herein comprises a CDR-L3 of SEQ ID NO: 28, a CDR-L2 of SEQ ID NO: 27, and a CDR-L1 of SEQ ID NO: 26. In some embodiments, the CDR-L3 has at least about 50%, 75%, 80%, 85%, 90%, or 95% identity with a CDR-L3 of SEQ ID NO: 28, the CDR-L2 has at least about 50%, 75%, 80%, 85%, 90%, or 95% identity with a CDR-L2 of SEQ ID NO: 27, and the CDR-L1 has at least about 50%, 75%, 80%, 85%, 90%, or 95% identity with a CDR-L1 of SEQ ID NO: 26. In some embodiments, the CDR-L3 is a CDR-L3 of SEQ ID NO: 28, with up to 1, 2, 3, 4, or 5 amino acid substitutions; the CDR-L2 is a CDR-L2 of SEQ ID NO: 27, with up to 1, 2, 3, or 4 amino acid substitutions; and the CDR-L1 is a CDR-L1 of SEQ ID NO: 26, with up to 1, 2, 3, 4, 5, or 6 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 of SEQ ID NO: 33, a CDR-H2 of SEQ ID NO: 24, a CDR-H1 of SEQ ID NO: 23, a CDR-L3 of SEQ ID NO: 28, a CDR-L2 of SEQ ID NO: 27, and a CDR-L1 of SEQ ID NO: 26. In some embodiments, the CDR-H3 has at least about 50%, 75%, 80%, 85%, 90%, or 95% identity with a CDR-H3 of SEQ ID NO: 33, the CDR-H2 has at least about 50%, 75%, 80%, 85%, 90%, or 95% identity with a CDR-H2 of SEQ ID NO: 24, the CDR-H1 has at least about 50%, 75%, 80%, 85%, 90%, or 95% identity with a CDR-H1 of SEQ ID NO: 23, the CDR-L3 has at least about 50%, 75%, 80%, 85%, 90%, or 95% identity with a CDR-L3 of SEQ ID NO: 28, the CDR-L2 has at least about 50%, 75%, 80%, 85%, 90%, or 95% identity with a CDR-L2 of SEQ ID NO: 27, and the CDR-L1 has at least about 50%, 75%, 80%, 85%, 90%, or 95% identity with a CDR-L1 of SEQ ID NO: 26. In some embodiments, the CDR-H3 is a CDR-H3 of SEQ ID NO: 33, with up to 1, 2, 3, 4, 5, 6, 7, or 8 amino acid substitutions; the CDR-H2 is a CDR-H2 of SEQ ID NO: 24, with up to 1, 2, 3, 4, 5, 6, 7, or 8 amino acid substitutions; the CDR-H1 is a CDR-H1 of SEQ ID NO: 23, with up to 1, 2, 3, 4, or 5 amino acid substitutions; the CDR-L3 is a CDR-L3 of SEQ ID NO: 28, with up to 1, 2, 3, 4, or 5 amino acid substitutions; the CDR-L2 is a CDR-L2 of SEQ ID NO: 27, with up to 1, 2, 3, or 4 amino acid substitutions; and the CDR-L1 is a CDR-L1 of SEQ ID NO: 26, with up to 1, 2, 3, 4, 5, or 6 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 of SEQ ID NO: 32, a CDR-H2 of SEQ ID NO: 24, a CDR-H1 of SEQ ID NO: 23, a CDR-L3 of SEQ ID NO: 28, a CDR-L2 of SEQ ID NO: 27, and a CDR-L1 of SEQ ID NO: 26. In some embodiments, the CDR-H3 has at least about 50%, 75%, 80%, 85%, 90%, or 95% identity with a CDR-H3 of SEQ ID NO: 32, the CDR-H2 has at least about 50%, 75%, 80%, 85%, 90%, or 95% identity with a CDR-H2 of SEQ ID NO: 24, the CDR-H1 has at least about 50%, 75%, 80%, 85%, 90%, or 95% identity with a CDR-H1 of SEQ ID NO: 23, the CDR-L3 has at least about 50%, 75%, 80%, 85%, 90%, or 95% identity with a CDR-L3 of SEQ ID NO: 28, the CDR-L2 has at least about 50%, 75%, 80%, 85%, 90%, or 95% identity with a CDR-L2 of SEQ ID NO: 27, and the CDR-L1 has at least about 50%, 75%, 80%, 85%, 90%, or 95% identity with a CDR-L1 of SEQ ID NO: 26. In some embodiments, the CDR-H3 is a CDR-H3 of SEQ ID NO: 32, with up to 1, 2, 3, 4, 5, 6, 7, or 8 amino acid substitutions; the CDR-H2 is a CDR-H2 of SEQ ID NO: 24, with up to 1, 2, 3, 4, 5, 6, 7, or 8 amino acid substitutions; the CDR-H1 is a CDR-H1 of SEQ ID NO: 23, with up to 1, 2, 3, 4, or 5 amino acid substitutions; the CDR-L3 is a CDR-L3 of SEQ ID NO: 28, with up to 1, 2, 3, 4, or 5 amino acid substitutions; the CDR-L2 is a CDR-L2 of SEQ ID NO: 27, with up to 1, 2, 3, or 4 amino acid substitutions; and the CDR-L1 is a CDR-L1 of SEQ ID NO: 26, with up to 1, 2, 3, 4, 5, or 6 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 of SEQ ID NO: 29, a CDR-H2 of SEQ ID NO: 24, a CDR-H1 of SEQ ID NO: 23, a CDR-L3 of SEQ ID NO: 28, a CDR-L2 of SEQ ID NO: 27, and a CDR-L1 of SEQ ID NO: 26. In some embodiments, the CDR-H3 has at least about 50%, 75%, 80%, 85%, 90%, or 95% identity with a CDR-H3 of SEQ ID NO: 29, the CDR-H2 has at least about 50%, 75%, 80%, 85%, 90%, or 95% identity with a CDR-H2 of SEQ ID NO: 24, the CDR-H1 has at least about 50%, 75%, 80%, 85%, 90%, or 95% identity with a CDR-H1 of SEQ ID NO: 23, the CDR-L3 has at least about 50%, 75%, 80%, 85%, 90%, or 95% identity with a CDR-L3 of SEQ ID NO: 28, the CDR-L2 has at least about 50%, 75%, 80%, 85%, 90%, or 95% identity with a CDR-L2 of SEQ ID NO: 27, and the CDR-L1 has at least about 50%, 75%, 80%, 85%, 90%, or 95% identity with a CDR-L1 of SEQ ID NO: 26. In some embodiments, the CDR-H3 is a CDR-H3 of SEQ ID NO: 29, with up to 1, 2, 3, 4, 5, 6, 7, or 8 amino acid substitutions; the CDR-H2 is a CDR-H2 of SEQ ID NO: 24, with up to 1, 2, 3, 4, 5, 6, 7, or 8 amino acid substitutions; the CDR-H1 is a CDR-H1 of SEQ ID NO: 23, with up to 1, 2, 3, 4, or 5 amino acid substitutions; the CDR-L3 is a CDR-L3 of SEQ ID NO: 28, with up to 1, 2, 3, 4, or 5 amino acid substitutions; the CDR-L2 is a CDR-L2 of SEQ ID NO: 27, with up to 1, 2, 3, or 4 amino acid substitutions; and the CDR-L1 is a CDR-L1 of SEQ ID NO: 26, with up to 1, 2, 3, 4, 5, or 6 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 of SEQ ID NO: 25, a CDR-H2 of SEQ ID NO: 24, a CDR-H1 of SEQ ID NO: 23, a CDR-L3 of SEQ ID NO: 28, a CDR-L2 of SEQ ID NO: 27, and a CDR-L1 of SEQ ID NO: 26. In some embodiments, the CDR-H3 has at least about 50%, 75%, 80%, 85%, 90%, or 95% identity with a CDR-H3 of SEQ ID NO: 25, the CDR-H2 has at least about 50%, 75%, 80%, 85%, 90%, or 95% identity with a CDR-H2 of SEQ ID NO: 24, the CDR-H1 has at least about 50%, 75%, 80%, 85%, 90%, or 95% identity with a CDR-H1 of SEQ ID NO: 23, the CDR-L3 has at least about 50%, 75%, 80%, 85%, 90%, or 95% identity with a CDR-L3 of SEQ ID NO: 28, the CDR-L2 has at least about 50%, 75%, 80%, 85%, 90%, or 95% identity with a CDR-L2 of SEQ ID NO: 27, and the CDR-L1 has at least about 50%, 75%, 80%, 85%, 90%, or 95% identity with a CDR-L1 of SEQ ID NO: 26. In some embodiments, the CDR-H3 is a CDR-H3 of SEQ ID NO: 25, with up to 1, 2, 3, 4, 5, 6, 7, or 8 amino acid substitutions; the CDR-H2 is a CDR-H2 of SEQ ID NO: 24, with up to 1, 2, 3, 4, 5, 6, 7, or 8 amino acid substitutions; the CDR-H1 is a CDR-H1 of SEQ ID NO: 23, with up to 1, 2, 3, 4, or 5 amino acid substitutions; the CDR-L3 is a CDR-L3 of SEQ ID NO: 28, with up to 1, 2, 3, 4, or 5 amino acid substitutions; the CDR-L2 is a CDR-L2 of SEQ ID NO: 27, with up to 1, 2, 3, or 4 amino acid substitutions; and the CDR-L1 is a CDR-L1 of SEQ ID NO: 26, with up to 1, 2, 3, 4, 5, or 6 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 of SEQ ID NO: 30 or 31, a CDR-H2 of SEQ ID NO: 24, a CDR-H1 of SEQ ID NO: 23, a CDR-L3 of SEQ ID NO: 28, a CDR-L2 of SEQ ID NO: 27, and a CDR-L1 of SEQ ID NO: 26. In some embodiments, the CDR-H3 has at least about 50%, 75%, 80%, 85%, 90%, or 95% identity with a CDR-H3 of SEQ ID NO: 30 or 31, the CDR-H2 has at least about 50%, 75%, 80%, 85%, 90%, or 95% identity with a CDR-H2 of SEQ ID NO: 24, the CDR-H1 has at least about 50%, 75%, 80%, 85%, 90%, or 95% identity with a CDR-H1 of SEQ ID NO: 23, the CDR-L3 has at least about 50%, 75%, 80%, 85%, 90%, or 95% identity with a CDR-L3 of SEQ ID NO: 28, the CDR-L2 has at least about 50%, 75%, 80%, 85%, 90%, or 95% identity with a CDR-L2 of SEQ ID NO: 27, and the CDR-L1 has at least about 50%, 75%, 80%, 85%, 90%, or 95% identity with a CDR-L1 of SEQ ID NO: 26. In some embodiments, the CDR-H3 is a CDR-H3 of SEQ ID NO: 30 or 31, with up to 1, 2, 3, 4, 5, 6, 7, or 8 amino acid substitutions; the CDR-H2 is a CDR-H2 of SEQ ID NO: 24, with up to 1, 2, 3, 4, 5, 6, 7, or 8 amino acid substitutions; the CDR-H1 is a CDR-H1 of SEQ ID NO: 23, with up to 1, 2, 3, 4, or 5 amino acid substitutions; the CDR-L3 is a CDR-L3 of SEQ ID NO: 28, with up to 1, 2, 3, 4, or 5 amino acid substitutions; the CDR-L2 is a CDR-L2 of SEQ ID NO: 27, with up to 1, 2, 3, or 4 amino acid substitutions; and the CDR-L1 is a CDR-L1 of SEQ ID NO: 26, with up to 1, 2, 3, 4, 5, or 6 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H1 of SEQ ID NO:23, a CDR-H2 of SEQ ID NO:24, a CDR-H3 of SEQ ID NO:33, a CDR-L1 of SEQ ID NO:26, a CDR-L2 of SEQ ID NO:27, and a CDR-L3 of SEQ ID NO:28.

In some embodiments, an antibody provided herein comprises a CDR-H1 of SEQ ID NO:23, a CDR-H2 of SEQ ID NO:24, a CDR-H3 of SEQ ID NO:25, a CDR-L1 of SEQ ID NO:26, a CDR-L2 of SEQ ID NO:27, and a CDR-L3 of SEQ ID NO:28.

In some embodiments, an antibody provided herein comprises a CDR-H1 of SEQ ID NO:23, a CDR-H2 of SEQ ID NO:24, a CDR-H3 of SEQ ID NO:29, a CDR-L1 of SEQ ID NO:26, a CDR-L2 of SEQ ID NO:27, and a CDR-L3 of SEQ ID NO:28.

In some embodiments, an antibody provided herein comprises a CDR-H1 of SEQ ID NO:23, a CDR-H2 of SEQ ID NO:24, a CDR-H3 of SEQ ID NO:32, a CDR-L1 of SEQ ID NO:26, a CDR-L2 of SEQ ID NO:27, and a CDR-L3 of SEQ ID NO:28.

In some embodiments, an antibody provided herein comprises a CDR-H1 of SEQ ID NO:23, a CDR-H2 of SEQ ID NO:24, a CDR-H3 of SEQ ID NO:30, a CDR-L1 of SEQ ID NO:26, a CDR-L2 of SEQ ID NO:27, and a CDR-L3 of SEQ ID NO:28.

In some embodiments, an antibody provided herein comprises a CDR-H1 of SEQ ID NO:23, a CDR-H2 of SEQ ID NO:24, a CDR-H3 of SEQ ID NO:31, a CDR-L1 of SEQ ID NO:26, a CDR-L2 of SEQ ID NO:27, and a CDR-L3 of SEQ ID NO:28.

Fc Region

The term "Fc domain" or "Fc region" herein is used to define a C-terminal region of an immunoglobulin heavy chain that contains at least a portion of the constant region. The term includes native sequence Fc regions and variant Fc regions. The structures of the Fc regions of various immunoglobulins, and the glycosylation sites contained therein, are known in the art. See Schroeder and Cavacini, J. Allergy Clin. Immunol., 2010, 125:S41-52, incorporated by reference in its entirety. The Fc region may be a naturally occurring Fc region, or an Fc region modified as described in the art or elsewhere in this disclosure.

Unless otherwise specified herein, numbering of amino acid residues in the Fc region or constant region is according to the EU numbering system, also called the EU index, as described in Kabat et al. Sequences of Proteins of Immunological Interest, 5th Ed. Public Health Service, National Institutes of Health, Bethesda, M D, 1991. An "Fc polypeptide" of a dimeric Fc as used herein refers to one of the two polypeptides forming the dimeric Fc domain, i.e. a polypeptide comprising C-terminal constant regions of an immunoglobulin heavy chain, capable of stable self-association. For example, an Fc polypeptide of a dimeric IgG Fc comprises an IgG CH2 and an IgG CH3 constant domain sequence. An Fc can be of the class IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$.

The terms "Fc receptor" and "FcR" are used to describe a receptor that binds to the Fc region of an antibody. For example, an FcR can be a native sequence human FcR. Generally, an FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Immunoglobulins of other isotypes can also be bound by certain FcRs (see, e.g., Janeway et al., Immuno Biology: the immune system in health and disease, (Elsevier Science Ltd., NY) (4th ed., 1999)). Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (reviewed in Daëron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976); and Kim et al., J. Immunol. 24:249 (1994)).

Modifications in the CH2 domain can affect the binding of FcRs to the Fc. A number of amino acid modifications in the Fc region are known in the art for selectively altering the affinity of the Fc for different Fcgamma receptors. In some aspects, the Fc comprises one or more modifications to promote selective binding of Fc-gamma receptors.

Exemplary mutations that alter the binding of FcRs to the Fc are listed below:

S298A/E333A/K334A, S298A/E333A/K334A/K326A (Lu Y, Vernes J M, Chiang N, et al. J Immunol Methods. 2011 Feb. 28; 365(1-2):132-41);

F243L/R292P/Y300L/V305I/P396L. F243L/R292P/Y300L/L235V/P396L (Stavenhagen J B, Gorlatov S. Tuaillon N, et al. Cancer Res. 2007 Sep. 15; 67(18): 8882-90; Nordstrom J L, Gorlatov S, Zhang W, et al. Breast Cancer Res. 2011 Nov. 30; 13(6):R123);

F243L (Stewart R, Thom G, Levens M, et al. Protein Eng Des Sel. 2011 September; 24(9):671-8.). S298A/E333A/K334A (Shields R L, Namenuk A K, Hong K, et al. J Biol Chem. 2001 Mar. 2; 276(9):6591-604);

S239D/I332E/A330L, S239D/I332E (Lazar G A, Dang W, Karki S, et al. Proc Natl Acad Sci USA. 2006 Mar. 14; 103(11):4005-10);

S239D/S267E, S267E/L328F (Chu S Y, Vostiar I, Karki S, et al. Mol Immunol. 2008 September; 45(15):3926-33);

S239D/D265S/S298A/I332E, S239E/S298A/K326A/A327H, G237F/S298A/A330L/I332E, S239 D/I332E/S298A. S239D/K326E/A330L/I332E/S298A, G236A/S239D/D270L/I332E, S239E/S267E/H26 8D, L234F/S267E/N325L, G237F/V266L/S267D and other mutations listed in WO2011/120134 and WO2011/120135, herein incorporated by reference. Therapeutic Antibody Engineering (by William R. Strohl and Lila M. Strohl, Woodhead Publishing series in Biomedicine No 11, ISBN 1 907568 37 9, October 2012) lists mutations on page 283.

In some embodiments an antibody described herein includes modifications to improve its ability to mediate effector function. Such modifications are known in the art and include afucosylation, or engineering of the affinity of the Fc towards an activating receptor, mainly FCGR3a for ADCC, and towards C1q for CDC. The following Table B summarizes various designs reported in the literature for effector function engineering.

Methods of producing antibodies with little or no fucose on the Fc glycosylation site (Asn 297 EU numbering) without altering the amino acid sequence are well known in the art. The GlymaX® technology (ProBioGen AG) is based on the introduction of a gene for an enzyme which deflects the cellular pathway of fucose biosynthesis into cells used for antibody production. This prevents the addition of the sugar "fucose" to the N-linked antibody carbohydrate part by antibody-producing cells. (von Horsten et al. (2010) Glycobiology. 2010 December; 20 (12):1607-18. Another approach to obtaining antibodies with lowered levels of fucosylation can be found in U.S. Pat. No. 8,409,572, which teaches selecting cell lines for antibody production for their ability to yield lower levels of fucosylation on antibodies Antibodies can be fully afucosylated (meaning they contain no detectable fucose) or they can be partially afucosylated, meaning that the isolated antibody contains less than 95%, less than 85%, less than 75%, less than 65%, less than 55%, less than 45%, less than 35%, less than 25%, less than 15% or less than 5% of the amount of fucose normally detected for a similar antibody produced by a mammalian expression system.

Thus, in one embodiment, an antibody described herein can include a dimeric Fc that comprises one or more amino acid modifications as noted in Table B that confer improved effector function. In another embodiment, the antibody can be afucosylated to improve effector function.

TABLE B

CH2 domains and effector function engineering
Table B

| Reference | Mutations | Effect |
|---|---|---|
| Lu, 2011, Ferrara 2011, Mizushima 2011 | Afucosylated | Increased ADCC |
| Lu, 2011 | S298A/E333A/K334A | Increased ADCC |
| Lu, 2011 | S298A/E333A/K334A/K326A | Increased ADCC |
| Stavenhagen, 2007 | F243L/R292P/Y300L/V305I/P396L | Increased ADCC |
| Nordstrom, 2011 | F243L/R292P/Y300L/L235V/P396L | Increased ADCC |
| Stewart, 2011 | F243L | Increased ADCC |
| Shields, 2001 | S298A/E333A/K334A | Increased ADCC |
| Lazar, 2006 | S239D/I332E/A330L | Increased ADCC |
| Lazar, 2006 | S239D/I332E | Increased ADCC |
| Bowles, 2006 | AME-D, not specified mutations | Increased ADCC |
| Heider, 2011 | 37.1, mutations not disclosed | Increased ADCC |
| Moore, 2010 | S267E/H268F/S324T | Increased CDC |

Fc modifications reducing FcγR and/or complement binding and/or effector function are known in the art. Recent publications describe strategies that have been used to engineer antibodies with reduced or silenced effector activity (see Strohl, W R (2009), Curr Opin Biotech 20:685-691, and Strohl, W R and Strohl L M, "Antibody Fc engineering for optimal antibody performance" In Therapeutic Antibody Engineering, Cambridge: Woodhead Publishing (2012), pp 225-249). These strategies include reduction of effector function through modification of glycosylation, use of IgG2/IgG4 scaffolds, or the introduction of mutations in the hinge or CH2 regions of the Fc. For example, US Patent Publication No. 2011/0212087 (Strohl), International Patent Publication No. WO 2006/105338 (Xencor), US Patent Publication No. 2012/0225058 (Xencor), US Patent Publication No. 2012/0251531 (Genentech), and Strop et al ((2012) J. Mol. Biol. 420: 204-219) describe specific modifications to reduce FcγR or complement binding to the Fc.

Specific, non-limiting examples of known amino acid modifications to reduce FcγR or complement binding to the Fc include those identified in the following Table C:

TABLE C

Modifications to reduce FcγR or complement binding to the Fc
Table C

| Company | Mutations |
|---|---|
| GSK | N297A |
| Ortho Biotech | L234A/L235A |
| Protein Design labs | IGG2 V234A/G237A |
| Wellcome Labs | IGG4 L235A/G237A/E318A |
| GSK | IGG4 S228P/L236E |
| Alexion | IGG2/IGG4combo |
| Merck | IGG2 H268Q/V309L/A330S/A331S |
| Bristol-Myers | C220S/C226S/C229S/P238S |
| Seattle Genetics | C226S/C229S/E3233P/L235V/L235A |
| Amgen | *E. coli* production, non glyco |
| Medimune | L234F/L235E/P331S |
| Trubion | Hinge mutant, possibly C226S/P230S |

Methods of producing antibodies with little or no fucose on the Fc glycosylation site (Asn 297 EU numbering) without altering the amino acid sequence are well known in the art. The GlymaxX® technology (ProBioGen AG) is based on the introduction of a gene for an enzyme which deflects the cellular pathway of fucose biosynthesis into cells used for antibody production. This prevents the addition of the sugar "fucose" to the N-linked antibody carbohydrate part by antibody-producing cells. (von Horsten et al. (2010) Glycobiology. 2010 December; 20 (12):1607-18.) Examples of cell lines capable of producing defucosylated antibody include CHO-DG44 with stable overexpression of the bacterial oxidoreductase GDP-6-deoxy-D-lyxo-4-hexylose reductase (RMD) (see Henning von Horsten et al., Glycobiol 2010, 20:1607-1618) or Lec13 CHO cells, which are deficient in protein fucosylation (see Ripka et al., Arch. Biochem. Biophys., 1986, 249:533-545; U.S. Pat. Pub. No. 2003/0157108; WO 2004/056312; each of which is incorporated by reference in its entirety), and knockout cell lines, such as alpha-1,6-fucosyltransferase gene or FUT8 knockout CHO cells (see Yamane-Ohnuki et al., Biotech. Bioeng., 2004, 87: 614-622; Kanda et al., Biotechnol. Bioeng., 2006, 94:680-688; and WO 2003/085107; each of which is incorporated by reference in its entirety). Another approach to obtaining antibodies with lowered levels of fucosylation can be found in U.S. Pat. No. 8,409,572, which teaches selecting cell lines for antibody production for their ability to yield lower levels of fucosylation on antibodies Examples of cell lines capable of producing defucosylated antibody include CHO-DG44 with stable overexpression of the bacterial oxidoreductase GDP-6-deoxy-D-lyxo-4-hexylose reductase (RMD) (see Henning von Horsten et al., Glycobiol 2010, 20:1607-1618) or Lec13 CHO cells, which are deficient in protein fucosylation (see Ripka et al., Arch. Biochem. Biophys., 1986, 249:533-545; U.S. Pat. Pub. No. 2003/0157108; WO 2004/056312; each of which is incorporated by reference in its entirety), and knockout cell lines, such as alpha-1,6-fucosyltransferase gene or FUT8 knockout CHO cells (see Yamane-Ohnuki et al., Biotech. Bioeng., 2004, 87: 614-622; Kanda et al., Biotechnol. Bioeng., 2006, 94:680-688; and WO 2003/085107; each of which is incorporated by reference in its entirety).

Antibodies can be fully afucosylated (meaning they contain no detectable fucose) or they can be partially afucosylated, meaning that the isolated antibody contains less than 95%, less than 85%, less than 75%, less than 65%, less than 55%, less than 45%, less than 35%, less than 25%, less than 15% or less than 5% of the amount of fucose normally detected for a similar antibody produced by a mammalian expression system.

In some aspects, an antibody provided herein comprises an IgG1 domain with reduced fucose content at position Asn 297 compared to a naturally occurring IgG1 domain. Such Fc domains are known to have improved ADCC. See Shields et al., J. Biol. Chem., 2002, 277:26733-26740, incorporated by reference in its entirety. In some aspects, such antibodies do not comprise any fucose at position Asn 297. The amount of fucose may be determined using any suitable method, for example as described in WO 2008/077546, incorporated by reference in its entirety.

In certain embodiments, an antibody provided herein comprises an Fc region with one or more amino acid substitutions which improve ADCC, such as a substitution at one or more of positions 298, 333, and 334 of the Fc region. In some embodiments, an antibody provided herein comprises an Fc region with one or more amino acid substitutions at positions 239, 332, and 330, as described in Lazar et al., Proc. Natl. Acad. Sci. USA, 2006, 103:4005-4010, incorporated by reference in its entirety.

Other illustrative glycosylation variants which may be incorporated into the antibodies provided herein are described, for example, in U.S. Pat. Pub. Nos. 2003/0157108, 2004/0093621, 2003/0157108, 2003/0115614, 2002/0164328, 2004/0093621, 2004/0132140, 2004/0110704, 2004/0110282, 2004/0109865; International Pat. Pub. Nos. 2000/61739, 2001/29246, 2003/085119, 2003/084570, 2005/035586, 2005/035778; 2005/053742, 2002/031140; Okazaki et al., J. Mol. Biol., 2004, 336:1239-1249; and Yamane-Ohnuki et al., Biotech. Bioeng., 2004, 87: 614-622; each of which is incorporated by reference in its entirety.

In some embodiments, an antibody provided herein comprises an Fc region with at least one galactose residue in the oligosaccharide attached to the Fc region. Such antibody variants may have improved CDC function. Examples of such antibody variants are described, for example, in WO 1997/30087; WO 1998/58964; and WO 1999/22764; each of which his incorporated by reference in its entirety.

In some embodiments, an antibody provided herein comprises one or more alterations that improves or diminishes C1q binding and/or CDC. See U.S. Pat. No. 6,194,551; WO 99/51642; and Idusogie et al., J. Immunol., 2000, 164:4178-4184; each of which is incorporated by reference in its entirety.

In some embodiments, the antibody comprises a heavy chain human constant region of a class selected from IgG, IgA, IgD, IgE, and IgM. In some embodiments, the antibody comprises an Fc region. In some embodiments, the Fc region is a human Fc region. In some embodiments, the human Fc region comprises a human heavy chain constant region of the class IgG and a subclass selected from IgG1, IgG2. IgG3, and IgG4. In some embodiments, the human Fc region comprises wild-type, human IgG1 Fc.

Binding

"Affinity" refers to the strength of the sum total of non-covalent interactions between a single binding site of a molecule (e.g., an antibody) and its binding partner (e.g., an antigen or epitope). Unless indicated otherwise, as used herein, "affinity" refers to intrinsic binding affinity, which reflects a 1:1 interaction between members of a binding pair (e.g., antibody and antigen or epitope). The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein, such as surface plasmon resonance (SPR) technology (e.g., BIACORE®) or biolayer interferometry (e.g., FORTEBIO®).

With regard to the binding of an antibody to a target molecule, the terms "bind." "specific binding," "specifically binds to," "specific for," "selectively binds," and "selective for" a particular antigen (e.g., a polypeptide target) or an epitope on a particular antigen mean binding that is measurably different from a non-specific or non-selective interaction (e.g., with a non-target molecule). Specific binding can be measured, for example, by measuring binding to a target molecule and comparing it to binding to a non-target molecule. Specific binding can also be determined by competition with a control molecule that mimics the epitope recognized on the target molecule. In that case, specific binding is indicated if the binding of the antibody to the target molecule is competitively inhibited by the control molecule. In some embodiments, the affinity of a TREM1 antibody for a non-target molecule is less than about 50% of the affinity for TREM1. In some embodiments, the affinity of a TREM1 antibody for a non-target molecule is less than about 40% of the affinity for TREM1. In some embodiments, the affinity of a TREM1 antibody for a non-target molecule is less than about 30% of the affinity for TREM1. In some embodiments, the affinity of a TREM1 antibody for a non-target molecule is less than about 20% of the affinity for TREM1. In some embodiments, the affinity of a TREM1 antibody for a non-target molecule is less than about 10% of the affinity for TREM1. In some embodiments, the affinity of a TREM1 antibody for a non-target molecule is less than about 1% of the affinity for TREM1. In some embodiments, the affinity of a TREM1 antibody for a non-target molecule is less than about 0.1% of the affinity for TREM1.

The term "$k_d$" ($sec^{-1}$), as used herein, refers to the dissociation rate constant of a particular antibody-antigen interaction. This value is also referred to as the $k_{off}$ value.

The term "$k_a$" ($M^{-1} \times sec^{-1}$), as used herein, refers to the association rate constant of a particular antibody-antigen interaction. This value is also referred to as the $k_{on}$ value.

The term "$K_D$" (M), as used herein, refers to the dissociation equilibrium constant of a particular antibody-antigen interaction. $K_D = k_d/k_a$. In some embodiments, the affinity of an antibody is described in terms of the $K_D$ for an interaction between such antibody and its antigen. For clarity, as known in the art, a smaller $K_D$ value indicates a higher affinity interaction, while a larger $K_D$ value indicates a lower affinity interaction.

The term "$K_A$" ($M^{-1}$), as used herein, refers to the association equilibrium constant of a particular antibody-antigen interaction. $K_A = k_a/k_d$.

When used herein in the context of two or more antibodies, the term "competes with" or "cross-competes with" indicates that the two or more antibodies compete for binding to an antigen (e.g., TREM1). In one exemplary assay, TREM1 is coated on a surface and contacted with a first TREM1 antibody, after which a second TREM1 antibody is added. In another exemplary assay, a first TREM1 antibody is coated on a surface and contacted with TREM1, and then a second TREM1 antibody is added. If the presence of the first TREM1 antibody reduces binding of the second TREM1 antibody, in either assay, then the antibodies compete with each other. The term "competes with" also includes combinations of antibodies where one antibody reduces binding of another antibody, but where no competition is observed when the antibodies are added in the reverse order. However, in some embodiments, the first and second antibodies inhibit binding of each other, regardless of the order in which they are added. In some embodiments, one antibody reduces binding of another antibody to its antigen by at least 25%, at least 50%, at least 60%, at least 70%, at least 80%, at least 85%, at least 90%, at least 95%, or at least 99% as measured in a competitive binding assay. A skilled artisan can select the concentrations of the antibodies used in the competition assays based on the affinities of the antibodies for TREM1 and the valency of the antibodies. The assays described in this definition are illustrative, and a skilled artisan can utilize any suitable assay to determine if antibodies compete with each other. Suitable assays are described, for example, in Cox et al., "Immunoassay Methods," in Assay Guidance Manual [Internet], Updated Dec. 24, 2014 (ncbi.nlm.nih.gov/books/NBK92434/; accessed Sep. 29, 2015); Silman et al., Cytometry, 2001, 44:30-37; and Finco et al., J. Pharm. Biomed. Anal., 2011, 54:351-358; each of which is incorporated by reference in its entirety.

A test antibody competes with a reference antibody if an excess of a test antibody (e.g., at least 2×, 5×, 10×, 20×, or 100×) inhibits or blocks binding of the reference antibody by, e.g., at least 50%, 60%, 70%, 75%, 80%, 85%, 90%, 95%, or 99% as measured in a competitive binding assay. Antibodies identified by competition assay (competing antibody) include antibodies binding to the same epitope as the reference antibody and antibodies binding to an adjacent epitope sufficiently proximal to the epitope bound by the reference antibody for steric hindrance to occur. For example, a second, competing antibody can be identified that competes for binding to TREM1 with a first antibody described herein. In certain instances, the second antibody can block or inhibit binding of the first antibody by, e.g., at least 50%, 60%, 70%, 75%, 80%, 85%, 90%, 95%, or 99% as measured in a competitive binding assay. In certain instances, the second antibody can displace the first antibody by greater than 50%, 60%, 70%. 75%, 80%, 85%, 90%, 95%, or 99%.

In some embodiments, an anti-TREM1 antibody does not substantially bind myeloid cells present outside of cancer tissue. In some embodiments, an anti-TREM1 antibody does not substantially bind stimulatory myeloid cells present in cancer tissue.

In some embodiments, an anti-TREM1 antibody binds to residues 21-34 (SEQ ID NO: 42), 103-109 (SEQ ID NO: 43), and 128-136 (SEQ ID NO: 44) of human TREM1. The binding epitope includes the residues within the numerical range (e.g., residues 22-33 of TREM1), the beginning residue of each range (e.g., residues 21-33 of TREM1) and the end residue of each range (e.g., residues 22-34 of TREM1), or any combination thereof. In some embodiments, the anti-TREM1 antibody binds to residues 22-33, 104-108, and 129-135 of human TREM1. In some embodiments, the anti-TREM1 antibody binds to residues 21-33, 103-108, and 128-135 of human TREM1. In some embodiments, the anti-TREM1 antibody binds to residues 22-34, 104-109, and 129-136 of human TREM1. In some embodiments, the anti-TREM1 antibody binds to residues selected from residues 21-34, 22-33, 21-33, or 22-34; 103-109, 104-108, 103-108, or 104-109; and 128-136, 129-135, 128-135, or 129-136.

In some embodiments, an antibody provided herein binds human TREM1 with a $K_D$ of less than or equal to about 0.001, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 1.95, 2, 2.5, 3, 3.5, 4, 4.5, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 8, 9, or $10 \times 10^{-9}$ M, as measured by Biacore assay. In some embodiments, the KD of the antibody provided herein is between about 0.001-0.01, 0.01-0.1, 0.01-0.05, 0.05-0.1, 0.1-0.5, 0.5-1, 0.25-0.75, 0.25-0.5, 0.5-0.75, 0.75-1, 0.75-2, 1.1-1.2, 1.2-1.3, 1.3-1.4, 1.4-1.5, 1.5-1.6, 1.6-1.7, 1.7-1.8, 1.8-1.9, 1.9-2, 1-2, 1-5, 2-7, 3-8, 3-5, 4-6, 5-6, 5-5.5, 5.5-6, 5-7, 6-7, 6-6.5, 6.5-7, 6-8, 7-9, 7-10, or $5-10 \times 10^{-9}$ M, as measured by Biacore assay.

In some embodiments, the antibody provided herein binds human TREM1 with a $K_D$ of less than or equal to about 10, 9, 8, 7, 6, 5, 4.5, 4, 3.5, 3, 2.5, 2, 1.98, 1.95, 1.9, 1.85, 1.8, 1.75, 1.7, 1.65, 1.6, 1.55, 1.50, 1.45, 1.4, 1.3, 1.2, 1.1, 1, 0.9, 0.85, 0.8, 0.75, 0.7, 0.65, 0.6, 0.55, 0.5, 0.45, 0.4, 0.35, 0.3, 0.25, 0.2, 0.15, or $0.1 \times 10^{-9}$ M, or less, as measured by Biacore assay. In some embodiments, the antibody provided herein binds human TREM1 with a $K_D$ between 5-3, 4-2, 3-1, 1.9-1.8, 1.8-1.7, 1.7-1.6, 1.6-1.5, 1.9-1.5, 1.5-1, 1-0.8, 1-0.5, 0.9-0.6, 0.7-0.4, 0.6-0.2, 0.5-0.3, 0.3-0.2, or $0.2-0.1 \times 10^{-9}$ M as measured by Biacore assay. In some embodiments, the antibody provided herein binds human TREM1 with a $K_d$ of less than or equal to about 10, 9.56, 9.5, 9.0, 8.88, 8.84, 8.5, 8, 7.5, 7.32, 7, 6.5, 6, 5.5, 5, 4.5, 4, 3.5, 3, 2.5, 2, 1.5, or $1 \times 10^{-4}$ (l/s), or less, as measured by Biacore assay. In some embodiments, the antibody provided herein binds human TREM1 with a $K_a$ between 7-10, 7-8, 8-9, 9-10, 7-7.5, 7.5-8, 8-8.5, 8.5-9, 9-9.5, or 9.5-10×10$^{-4}$ (l/s) as measured by Biacore assay. In some embodiments, the antibody provided herein binds human TREM1 with a $K_a$ of greater than or equal to about 4, 4.1, 4.2, 4.3, 4.4, 4.5, 4.6, 4.7, 4.8, 4.9, 45, 5.1, 5.2, 5.3, 5.4, 5.5, 5.6, 5.7, 5.8, 5.9, 6, 7, 8, 9, or 10×10$^5$ (l/Ms), or more, as measured by Biacore assay. In some embodiments, the antibody provided herein binds human TREM1 with a $K_a$ between 4-7, 4-4.5, 4.5-5, 5-5.5, 5.5-6, 6-6.5, or 6.5-7, 7-8, 8-9, or 9-10×10$_5$ (l/Ms) as measured by Biacore assay.

In some embodiments, the antibody binds human monocytes with an EC50 of about 0.1, 0.15, 0.2, 0.22, 0.25, 0.27, 0.3, 0.32, 0.35, 0.37, 0.4, 0.05, 0.5, 0.55, 0.6, 0.65, 0.7, 0.8, 0.9, 1, 1.1, 1.2, 1.3, 1.4, 1.5, 1.6, 1.7, 1.8, 1.9, or 2 nM as measured by measured by flow cytometry. In some embodiments, the antibody provided herein binds human monocytes with an EC50 of less than or equal to 2, 1.9, 1.8, 1.7, 1.6, 1.5, 1.4, 1.3, 1.2, 1.1, 0.9, 0.8, 0.7, 0.6, 0.5, 0.4, 0.3, 0.2, or 0.1 nM as measured by measured by flow cytometry. In some embodiments, the antibody binds human monocytes with an EC50 between about 0.2-1.4, 0.2-0.3, 0.3-0.5, 0.5-0.7, 0.7-1, 1-1.2, or 1.2-1.4 nM as measured by measured by flow cytometry.

In some embodiments, the antibody binds human neutrophils with an EC50 of about 0.1, 0.15, 0.2, 0.22, 0.25, 0.27, 0.3, 0.32, 0.35, 0.37, 0.4, 0.05, 0.5, 0.55, 0.6, 0.65, 0.7, 0.8, 0.9, 1, 1.1, 1.2, 1.3, 1.4, 1.5, 1.6, 1.7, 1.8, 1.9, or 2 nM as measured by measured by flow cytometry. In some embodiments, the antibody provided herein binds neutrophils with an EC50 of less than or equal to about 2, 1.9, 1.8, 1.7, 1.6, 1.5, 1.4, 1.3, 1.2, 1.1, 0.9, 0.8, 0.7, 0.6, 0.5, 0.4, 0.3, 0.2, or 0.1 nM as measured by measured by flow cytometry. In some embodiments, the antibody binds human neutrophils with an EC50 between about 0.15-1, 0.15-0.3, 0.3-0.5, 0.5-0.7, 0.7-1, 1-1.5, or 1.5-2 nM as measured by measured by flow cytometry.

In some embodiments, the antibody provided herein does not bind human neutrophils with an EC50 greater than or equal to 3 nM or more as measured by measured by flow cytometry.

Function

"Effector functions" refer to those biological activities mediated by the Fc region of an antibody, which activities may vary depending on the antibody isotype. Examples of antibody effector functions include C1q binding to activate complement dependent cytotoxicity (CDC), Fc receptor binding to activate antibody-dependent cellular cytotoxicity (ADCC), and antibody dependent cellular phagocytosis (ADCP), receptor ligand blocking, agonism, or antagonism.

In some embodiments, the antibody has antibody-dependent cellular cytotoxicity (ADCC) activity. ADCC can occur when antibodies bind to antigens on the surface of pathogenic or tumorigenic target-cells. Effector cells bearing Fc gamma receptors (FcγR or FCGR) on their cell surface, including cytotoxic T-cells, natural killer (NK) cells, macrophages, neutrophils, eosinophils, dendritic cells, or monocytes, recognize and bind the Fc region of antibodies bound to the target-cells. Such binding can trigger the activation of intracellular signaling pathways leading to cell death. In particular embodiments, the antibody's immunoglobulin Fc region subtypes (isotypes) include human IgG1 and IgG3. As used herein, ADCC refers to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, Annu. Rev. Immunol 9:457-92 (1991). To assess ADCC activity of a molecule of interest, an in vitro ADCC assay, such as that described in U.S. Pat. Nos. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al., Proc. Natl. Acad. Sci. (USA) 95:652-656 (1998).

In some embodiments, the antibody has complement-dependent cytotoxicity (CDC) activity. Antibody-induced CDC is mediated through the proteins of the classical complement cascade and is triggered by binding of the complement protein C1q to the antibody. Antibody Fc region binding to C1q can induce activation of the complement cascade. In particular embodiments, the antibody's immunoglobulin Fc region subtypes (isotypes) include human IgG1 and IgG3. As used herein, CDC refers to the ability of a molecule to lyse a target in the presence of complement. The complement activation pathway is initiated by the binding of the first component of the complement system (C1q) to a molecule (e.g. polypeptide (e.g., an antibody)) complexed with a cognate antigen. To assess complement activation, a CDC assay, e.g. as described in Gazzano-Santoro et al., J. Immunol. Methods 202:163 (1996), may be performed.

In some embodiments, an antibody has antibody-dependent cellular phagocytosis (ADCP) activity. ADCP can occur when antibodies bind to antigens on the surface of pathogenic or tumorigenic target-cells. Phagocytic cells bearing Fc receptors on their cell surface, including monocytes and macrophages, recognize and bind the Fc region of antibodies bound to target-cells. Upon binding of the Fc receptor to the antibody-bound target cell, phagocytosis of the target cell can be initiated. ADCP can be considered a form of ADCC.

In some embodiments, a TREM1 antibody induces reprogramming of a non-stimulatory myeloid cell to a stimulatory myeloid cell. In some embodiments, a TREM1 antibody induces expression of pro-inflammatory cytokine or chemokine, and/or induction of expression of co-stimulatory molecules. In some embodiments, a co-stimulatory molecule is CD40 or HLA-DR. In some embodiments, a pro-inflammatory cytokine or chemokine is IFN-γ, IL-1α, IL-12, IL-2, TNFSF9, TNFSF10, CXCL9, CXCL10, CCL17, CXCL1, CXCL5, CXCL8, CXCL11, CXCL15, CCL3, CCL4, CCL2, FasL, CD274, CRTAM, granzyme A (GzmA), or granzyme B (GzmB).

In some embodiments, an antibody is an agonistic antibody. An agonistic antibody can induce (e.g., increase) one or more activities or functions of NSMs after the antibody binds a TREM1 protein expressed on the cell. The agonistic antibody may bind to and activate NSMs, causing changes in proliferation of the cell or modifying antigen presentation capabilities. The agonistic antibody may bind to and activate NSMs, triggering intracellular signaling pathways that lead to modified cell growth or apoptosis. The agonistic antibody may bind to TREM1 and induce signaling downstream of TREM1. In some embodiments, the TREM1 signaling increases an immune response in the cell. In some embodiments, the immune response is activation, cytokine or chemokine secretion, or expression of myeloid co-stimulatory proteins.

In some embodiments, an antibody is an antagonistic antibody. An antagonistic antibody can block (e.g. decrease) one or more activities or functions of NSMs after the antibody binds a TREM1 protein expressed on the cell. For example, the antagonist antibody may bind to and block ligand binding to one or more NSM proteins, preventing differentiation and proliferation of the cell or modifying antigen presentation capabilities. The antagonist antibody may bind to and prevent activation of a TREM1 protein by its ligand, modifying intracellular signaling pathways that contribute to cell growth and survival.

In some embodiments an antibody is a depleting antibody. A depleting antibody is one that would kill a non-stimulatory myeloid cell upon contact through the antibody's interaction with other immune cells of molecules. For example, antibodies, when bound to cells bearing TREM1 proteins, could engage complement proteins and induce complement-dependent cell lysis. Antibodies, when bound to cells bearing TREM1 proteins, could also trigger neighboring cells bearing Fc receptors to kill them by antibody-dependent cellular cytotoxicity (ADCC).

In some embodiments, an antibody is a neutralizing antibody, and the antibody neutralizes one or more biological activities of NSMs. In some embodiments, TREM1 protein is expressed on the surface of non-stimulatory myeloid cells and the antibody recognizes the extracellular domain of TREM1 protein.

In some embodiments an antibody is selective for NSMs (preferentially binds to TREM1). In certain embodiments, an antibody that selectively binds to NSMs has a dissociation constant (Kd) of range of 0.0001 nM to 1 µM. In certain embodiments, an antibody specifically binds to an epitope on a TREM1 protein that is conserved among the protein from different species. In another embodiment, selective binding includes, but does not require, exclusive binding.

In one embodiment an anti-TREM1 antibody bound to its target is responsible for causing the in vivo depletion of non-stimulatory myeloid cells to which it is bound. In some embodiments, effector proteins induced by clustered antibodies can trigger a variety of responses, including release of inflammatory cytokines, regulation of antigen production, endocytosis, or cell killing. In one embodiment the antibody is capable of recruiting and activating complement or mediating antibody-dependent cellular cytotoxicity (ADCC) in vivo, or mediating phagocytosis by binding Fc receptors in vivo. The antibody may also deplete non-stimulatory myeloid cells by inducing apoptosis or necrosis of the non-stimulatory myeloid cell upon binding.

In some embodiments, the antibodies are capable of forming an immune complex. For example, an immune complex can be a tumor cell covered by antibodies.

In some embodiments, an anti-TREM1 antibody does not substantially bind myeloid cells present outside of cancer tissue. In some embodiments, an anti-TREM1 antibody does not substantially bind stimulatory myeloid cells present in cancer tissue.

In some embodiments the disabling of non-stimulatory myeloid cells is in vitro and is achieved: a) by killing of the non-stimulatory myeloid cells; b) magnetic bead depletion of the non-stimulatory myeloid cells; or c) Fluorescence-activated cell sorting (FACS) sorting of the non-stimulatory myeloid cells.

An "immunoconjugate" is an antibody conjugated to one or more heterologous molecule(s), such as an effector molecule, or a therapeutic (cytokine, for example) or diagnostic agent.

In certain embodiments an antibody is conjugated to a drug, e.g., a toxin, a chemotherapeutic agent, an immune modulator, or a radioisotope. Several methods of preparing ADCs (antibody drug conjugates) are known in the art and are described in U.S. Pat. No. 8,624,003 (pot method), 8,163,888 (one-step), and 5,208,020 (two-step method), for example. An antibody or antigen-binding fragment thereof can be conjugated to at least one agent including a radionuclide, a cytotoxin, a chemotherapeutic agent, a drug, a pro-drug, a toxin, an enzyme, an immunomodulator, an anti-angiogenic agent, a pro-apoptotic agent, a cytokine, a hormone, an oligonucleotide, an antisense molecule, a siRNA, a second antibody, and a second antibody fragment that is antigen binding.

Non-Stimulatory Myeloid Cells (NSMs)

Provided herein are methods and compositions for disabling and/or detecting non-stimulatory myeloid cells (NSMs) comprising the use of an anti-TREM1 antibody. Also provided herein are methods and compositions for targeting and/or detecting non-stimulatory myeloid cells expressing a NSM protein.

Also provided herein are methods and compositions for disabling and/or detecting non-stimulatory myeloid cells comprising the use of antibody directed at a non-human homolog of human NSM protein, in that non-human individual.

As used herein, non-stimulatory myeloid cells are myeloid cells that are not sufficiently effective at stimulating an immune response (e.g. not as effective at stimulating an anti-tumor response in a tumor microenvironment compared to stimulatory myeloid cells). In some embodiments, non-stimulatory myeloid cells are not as effective at presenting an antigen (e.g., a tumor antigen) to T-cells or not as effective at stimulating tumor specific T-cell responses as compared to a stimulatory myeloid cell. In some embodiments, non-stimulatory myeloid cells can display a decreased ability to uptake, process, and/or present tumor-associated antigens to a T cell as compared to a stimulatory myeloid cell. Non-stimulatory myeloid cells may contain a reduced ability or no ability to re-prime cytotoxic T lymphocytes or in some cases cannot stimulate effective tumor-cell killing. Non-stimulatory myeloid cells may display lower expression of gene and cell-surface markers involved in antigen processing, antigen presentation and/or antigen co-stimulation including, without limitation, CD80, CD86, MHCI, and MHCII compared to stimulatory myeloid cells.

Non-stimulatory myeloid cells, when compared to stimulatory myeloid cells, may display the lower expression of genes associated with cross-presentation, co-stimulation, and/or stimulatory cytokines, including, without limitation, any one or more of TAP1, TAP2, PSMB8, PSMB9, TAPBP, PSME2, CD24a, CD274, BTLA, CD40, CD244, ICOSL, ICAM1, TIM3, PDL2, RANK, FLT3, CSF2RB, CSF2RB2, CSF2RA, IL12b, XCR1, CCR7, CCR2, CCL22, CXCL9, and CCL5, and increased expression of anti-inflammatory cytokine IL-10. In some embodiments, non-stimulatory myeloid cells are dependent on the transcription factor IRF4 and the cytokines GM-CSF or CSF-1 for differentiation and survival. In some embodiments, non-stimulatory myeloid cells can contribute to tumoral angiogenesis by secreting vascular endothelial growth factor (VEGF) and nitric oxide synthase (NOS) and support tumor growth by secreting epidermal growth factor (EGF).

In some embodiments, non-stimulatory myeloid cells are tumor-associated macrophages (TAM) or dendritic cells (DC). In some embodiments, the non-stimulatory myeloid cell is not a dendritic cell (DC).

In some embodiments, non-stimulatory myeloid cells are tumor-associated macrophages (TAMs). TAMs are macrophages present near or within cancerous tumors, and are derived from circulating monocytes or resident tissue macrophages.

In some embodiments, non-stimulatory myeloid cells are tumor-associated neutrophils (TANs). TANs are neutrophils present near or within cancerous tumors.

In some embodiments the non-stimulatory myeloid cells and the stimulatory myeloid cells are distinguished on the basis of the markers they express, or the markers they selectively express. The expression of a cell surface markers can be described as '+' or 'positive'. The absence of a cell surface marker can be described as '−' or 'negative'. The expression of a cell surface marker can be further described as 'high' (cells expressing high levels of the makers) or 'low' (cells expressing low levels of the markers), which indicates the relative expression of each marker on the cell surface. The level of markers may be determined by various methods known in the art, e.g. immuno-staining and FACS analysis, or gel electrophoresis and Western blotting.

In some embodiments, non-stimulatory myeloid cells are dendritic cells (DCs). In some embodiments, dendritic cells can be distinguished by a spikey or dendritic morphology. In one embodiment, the non-stimulatory dendritic cell is at least CD45+, HLA-DR+, CD14−, CD11c+, and BDCA1+ (also referred to as DC1 cells). In one embodiment, the non-stimulatory dendritic cell is not CD45+, HLA-DR+, CD14−, CD11c+, and BDCA3+(also referred to as DC2 cells). In one embodiment, a dendritic cell that is CD45+, HLA-DR+, CD14−, CD11c+, and BDCA3+ is a stimulatory-myeloid cell.

In some embodiments, non-stimulatory myeloid cells are tumor associated macrophages (TAMs). In some embodiments, for example in humans, the non-stimulatory tumor associated macrophages are at least CD45+, HLA-DR+, CD14+. In some embodiments the non-stimulatory tumor associated macrophages are at least $CD45^+$, $HLA\text{-}DR^+$, $CD14^+$, $CD11b^+$. In some embodiments the non-stimulatory tumor associated macrophages are at least $CD45^+$, $HLA\text{-}DR^+$, $CD14^+$, $CD11c^+$. In some embodiments the non-stimulatory tumor associated macrophages are at least $CD45^+$, $HLA\text{-}DR^+$, $CD14^+$, $BDCA3^-$. In some embodiments the non-stimulatory tumor associated macrophages are at least $CD45^+$, $HLA\text{-}DR^+$, $CD14^+$, $BDCA3^-$, $CD11b^+$. In some embodiments the non-stimulatory tumor associated macrophages are at least $CD45^+$, $HLA\text{-}DR^+$, $CD14^+$, $BDCA3^-$, $CD11c^+$. In some embodiments the non-stimulatory tumor associated macrophages are at least $CD45^+$, $HLA\text{-}DR^+$, $CD14^+$, $CD11b^+$, and $CD11c^+$. In some embodiments the non-stimulatory tumor associated macrophages are at least $CD45^+$, $HLA\text{-}DR^+$, $CD14^+$, $BDCA3^-$, $CD11b^+$, and $CD11c^+$.

In some embodiments the methods and compositions of the present invention are useful for targeting TAMs and DCs in other mammals, for example in mice. In such embodiments, mouse TAMs and DCs are contacted with a TREM1 antibody. In one embodiment, for example in mice, the tumor-associated macrophage is at least CD45+, I-A/I-E+, CD14+, $CD11b^{high}$, and $CD11c^{low}$ (also referred to as TAM1). In one embodiment, for example in mice, tumor-associated macrophages are at least CD45+, I-A/I-E+, CD14+, $CD11b^{low}$, and $CD11c^{high}$ (also referred to as TAM2). The term "$CD11b^{high}$ macrophages", as used herein, relates to macrophages expressing high levels of CD11b. The term "$CD11b^{low}$ macrophages," as used herein, relates to macrophages that express on their surface a level of CD11b that is substantially lower than that of $CD11b^{high}$ macrophages. The term "$CD11c^{high}$", as used herein, relates to macrophages expressing high levels of CD11c. The term "$CD11c^{low}$ macrophages", as used herein, relates to macrophages that express on their surface a level of CD11c that is substantially lower than that of $CD11c^{high}$ macrophages.

In some embodiments, the non-stimulatory myeloid cells of the invention include one or more of TAM and DC1 cells.

In some embodiments, for example in mice, the non-stimulatory myeloid cells of the invention include one or more of TAM1. TAM2, and DC1 cells. In such embodiments the non-stimulatory myeloid cells of the invention are contacted with a TREM1 antibody.

In some embodiments, the non-stimulatory myeloid cells are myeloid-derived suppressive cells (MDSCs). In some embodiments, the non-stimulatory myeloid cells are tumor-associate neutrophils (TANs).

In some embodiments, the non-stimulatory myeloid cells are localized within the margins of the tumoral lesions or in the transformed tumor ducts, where they come into contact with cognate T-cells. In one embodiment, the localization of the non-stimulatory myeloid cell is modified, so that the cells are no longer localized at the tumor margin or are no longer in contact with T-cells.

In some embodiments, the non-stimulatory myeloid cells are in a population of immune cells comprising stimulatory myeloid cells and non-stimulatory myeloid cells. In some embodiments, the non-stimulatory myeloid cells are in a population of immune cells comprising only non-stimulatory myeloid cells. The populations of immune cells of the present invention may be pure, homogenous, heterogeneous, derived from a variety of sources (e.g. diseased tissue, tumor tissue, healthy tissue, cell banks), maintained in primary cell cultures, maintained in immortalized cultures, and/or maintained in ex vivo cultures.

In some embodiments, the non-stimulatory myeloid cells are tumor-associated macrophages.

In some embodiments, the non-stimulatory myeloid cells are dendritic cells.

In some embodiments, the non-stimulatory myeloid cells are $CD45^+$, $HLA\text{-}DR^+$, $CD14^-$, $CD11c^+$, and $BDCA1^+$. In some embodiments, the non-stimulatory myeloid cells comprise cells that are $CD45^+$, $HLA\text{-}DR^+$, $CD14^-$, $CD11c^+$, and $BDCA1^+$. In some embodiments, the non-stimulatory myeloid cells consist of cells that are $CD45^+$, $HLA\text{-}DR^+$, $CD14^-$, $CD11c^+$, and $BDCA1^+$. In some embodiments, the non-stimulatory myeloid cells consist essentially of cells that are $CD45^+$, $HLA\text{-}DR^+$, $CD14^-$, $CD11c^+$, and $BDCA1^+$.

In some embodiments, the non-stimulatory myeloid cells are $CD45^+$, $HLA\text{-}DR^+$, $CD14^+$, $BDCA3^-$. In some embodiments, the non-stimulatory myeloid cells comprise cells that are $CD45^+$, $HLA\text{-}DR^+$, $CD14^+$, $BDCA3^-$. In some embodiments, the non-stimulatory myeloid cells consist of cells that are $CD45^+$, $HLA\text{-}DR^+$, $CD14^+$, $BDCA3^-$. In some embodiments, the non-stimulatory myeloid cells consist essentially of cells that are $CD45^+$, $HLA\text{-}DR^+$, $CD14^+$, $BDCA3^-$.

In some embodiments, the non-stimulatory myeloid cells are $CD45^+$, $HLA\text{-}DR^+$, $CD14^+$, $CD11b^+$. In some embodiments, the non-stimulatory myeloid cells comprise cells that are $CD45^+$, $HLA\text{-}DR^+$, $CD14^+$, $CD11b^+$. In some embodiments, the non-stimulatory myeloid cells consist of cells that are $CD45^+$, $HLA\text{-}DR^+$, $CD14^+$, $CD11b^+$. In some embodiments, the non-stimulatory myeloid cells consist essentially of cells that are CD45+, HLA-DR+, CD14+, CD11b+.

In some embodiments, the non-stimulatory myeloid cells are CD45+, HLA-DR+, CD14+, CD11c+. In some embodiments, the non-stimulatory myeloid cells comprise cells that are CD45+, HLA-DR+, CD14+, CD11c+. In some embodiments, the non-stimulatory myeloid cells consist of cells that are CD45+, HLA-DR+, CD14+, CD11c+. In some embodiments, the non-stimulatory myeloid cells consist essentially of cells that are CD45+, HLA-DR+, CD14+, CD11c+.

In some embodiments, the non-stimulatory myeloid cells are CD45+, HLA-DR+, CD14+, BDCA3−, and CD11c+. In some embodiments, the non-stimulatory myeloid cells comprise cells that are CD45+, HLA-DR+, CD14+, BDCA3−, and CD11c+. In some embodiments, the non-stimulatory myeloid cells consist of cells that are CD45+, HLA-DR+, CD14+, BDCA3−, and CD11c+. In some embodiments, the non-stimulatory myeloid cells consist essentially of cells that are CD45+, HLA-DR+, CD14+, BDCA3−, and CD11c+.

In some embodiments, the non-stimulatory myeloid cells are CD45+, HLA-DR+, CD14+, BDCA3−, CD11b+. In some embodiments, the non-stimulatory myeloid cells comprise cells that are CD45+, HLA-DR+, CD14+, BDCA3−, CD11b+. In some embodiments, the non-stimulatory myeloid cells consist of cells that are CD45+, HLA-DR+, CD14+, BDCA3−, CD11b+. In some embodiments, the non-stimulatory myeloid cells consist essentially of cells that are CD45+, HLA-DR+, CD14+, BDCA3−, CD11b+.

In some embodiments, the non-stimulatory myeloid cells are CD45+, HLA-DR+, CD14+, CD11b+, and CD11c+. In some embodiments, the non-stimulatory myeloid cells comprise cells that are CD45+, HLA-DR+, CD14+, CD11b+, and CD11c+. In some embodiments, the non-stimulatory myeloid cells consist of cells that are CD45+, HLA-DR+, CD14+, CD11b+, and CD11c+. In some embodiments, the non-stimulatory myeloid cells consist essentially of cells that are CD45+, HLA-DR+, CD14+, CD11b+, and CD11c+.

In some embodiments, the non-stimulatory myeloid cells are CD45+, HLA-DR+, CD14+, BDCA3−, CD11b+, and CD11c+. In some embodiments, the non-stimulatory myeloid cells comprise cells that are CD45+, HLA-DR+, CD14+, BDCA3−, CD11b+, and CD11c+. In some embodiments, the non-stimulatory myeloid cells consist of cells that are CD45+, HLA-DR+, CD14+, BDCA3−, CD11b+, and CD11c+. In some embodiments, the non-stimulatory myeloid cells consist essentially of cells that are CD45+, HLA-DR+, CD14+, BDCA3−, CD11b+, and CD11c+.

In some embodiments, the non-stimulatory myeloid cells are not CD45+, HLA-DR+, CD14−, CD11c+, and BDCA3+. In some embodiments, the non-stimulatory myeloid cells comprise cells that are not CD45+, HLA-DR+, CD14−, CD11c+, and BDCA3+.

In some embodiments, for example in mice, the non-stimulatory myeloid cells are CD45+, I-A/I-E+, CD14+, CD11b$^{high}$, and CD11c$^{low}$. In some embodiments, for example in mice, the non-stimulatory myeloid cells comprise cells that are CD45+, I-A/I-E+, CD14+, CD11b$^{high}$, and CD11c$^{low}$. In some embodiments, for example in mice, the non-stimulatory myeloid cells consist of cells that are CD45+, I-A/I-E+, CD14+, CD11b$^{high}$, and CD11c$^{low}$. In some embodiments, for example in mice, the non-stimulatory myeloid cells consist essentially of cells that are CD45+, I-A/I-E+, CD14+, CD11b$^{high}$, and CD11c$^{low}$. In such embodiments the non-stimulatory mice myeloid cells are contacted with a TREM1 antibody.

In some embodiments, for example in mice, the non-stimulatory myeloid cells are CD45+, I-A/I-E+, CD14+, CD11b$^{low}$, and CD11c$^{high}$. In some embodiments, for example in mice, the non-stimulatory myeloid cells comprise cells that are CD45+, I-A/I-E+, CD14+, CD11b$^{low}$, and CD11c$^{high}$. In some embodiments, for example in mice, the non-stimulatory myeloid cells consist of cells that are CD45+, I-A/I-E+, CD14+, CD11b$^{low}$, and CD11c$^{high}$. In some embodiments, for example in mice, the non-stimulatory myeloid cells consist essentially of cells that are CD45+, I-A/I-E+, CD14+, CD11b$^{low}$, and CD11c$^{high}$. In such embodiments the non-stimulatory mice myeloid cells are contacted with a TREM1 antibody.

In some embodiments, the non-stimulatory myeloid cells are in a cancer tissue.

In some embodiments, the population of immune cells is in a cancer tissue.

In some embodiments, the non-stimulatory cells and stimulatory myeloid cells are in a cancer tissue.

In some embodiments, the biological sample comprises a population of immune cells comprising non-stimulatory myeloid cells and stimulatory myeloid cells.

NSM cells can refer collectively to DC1, TAM1, and TAM2 cells present in tumor tissues and which may be distinguished from other cell types by their expression of NSM cell markers. For example, genes and associated proteins which are expressed or translated in greater abundance in NSM cells than SDCs may act as NSM markers. An exemplary NSM marker is CD11b. Additional exemplary NSM markers are listed in Table A. NSM cells can express TREM1, MS4A7, C5AR1, LYVE1, ABCC3, LILRB4, MRC1/CD206, SIGLEC1, STAB1, TMEM37, MERTK, and TMEM119 on their cell surface. In some aspects, NSM cells do not express at least one of KIT, CCR7, BATF3, FLT3, ZBTB46, IRF8, BTLA, MYCL1, CLEC9A, BDCA3, and XCR1.

In one embodiment, NSM cells express one or more of the NSM marker genes listed in Table D. In another embodiment, NSM cells express 2, 3, 4, 5, 6, 7, 8, 9, 10, 11, 12, 13, 14, 15, 16, 17, 18 or more of the NSM markers listed in Table A. In another embodiment, NSM cells express most or all of the NSM markers listed in Table A. In another embodiment, NSM cells are identified as expressing MRC1, MS4A7, C1QC, APOE, C1QB, C1QA, and C5AR1.

TABLE D

| Table D | |
|---|---|
| SDC Markers | NSM Markers |
| KIT | C5AR1 |
| CCR7 | LYVE1 |
| BATF3 | ABCC3 |
| FLT3 | MRC1 |
| ZBTB46 | SIGLEC1 |
| IRF8 | STAB1 |
| BTLA | C1QB |
| MYCL1 | C1QA |
| CLEC9A | TMEM37 |
| BDCA3 | MERTK |

TABLE D-continued

Table D

| SDC Markers | NSM Markers |
| --- | --- |
| XCR1 | C1QC |
| | TMEM119 |
| | MS4A7 |
| | APOE |
| | CYP4F18 |
| | TREM1 |
| | TREM2 |
| | TLR7 |
| | LILRB4 |

Stimulatory Myeloid Cells

As used herein, stimulatory myeloid cells (also called SDCs in certain aspects) are myeloid cells that are effective at stimulating an immune response (e.g. more effective at stimulating an anti-tumor response in a tumor microenvironment compared to non-stimulatory myeloid cells). In some embodiments, stimulatory myeloid cells are effective at presenting an antigen (e.g. a tumor antigen) to T-cells or are effective at stimulating tumor specific T-cell responses as compared to a non-stimulatory myeloid cell. In some embodiments, stimulatory myeloid cells can display an increased ability to uptake, process, and/or present tumor-associated antigens to a T cell as compared to a non-stimulatory myeloid cell. Stimulatory myeloid cells can have an increased ability to re-prime cytotoxic T lymphocytes or in some cases stimulate effective tumor-cell killing relative to non-stimulatory myeloid cells. Stimulatory myeloid cells may display higher expression of gene and cell-surface markers involved in antigen processing, antigen presentation and/or antigen co-stimulation including, without limitation, CD80, CD86, MHCI, and MHCII compared to non-stimulatory myeloid cells.

Exemplary stimulatory myeloid cell markers are listed in Table A. For example, in human SDCs, the expression of Xcr1, Clec9a, and BDCA3 (CD141) are markers of SDC identity. It will be noted that in mice, CD103 can also be used as a strong marker of SDC identity, although it is not expressed in human SDCs.

In one embodiment, SDCs are tumor infiltrating myeloid cells having dendritic cell identity and which also express one or more of the SDC markers listed in Table A. In another embodiment, SDCs are tumor infiltrating myeloid cells having dendritic cell identity and which also express two, three, four, five, six, seven, eight, nine or all of the SDC markers listed in Table A. In another embodiment, SDCs are identified as tumor infiltrating myeloid dendritic cells expressing BDCA3, KIT, CCR7, BATF3, FLT3, ZBTB46, IRF8, BTLA, MYCL1, XCR1 and CLEC9A. SDC cells can express at least one of KIT, CCR7, BATF3, FLT3, ZBTB46, IRF8, BTLA, MYCL1, CLEC9A, BDCA3, and XCR1. In some embodiments, SDCs do not substantially express TREM1, MS4A7, C5AR1, LYVE1, ABCC3, LILRB4, MRC1/CD206, SIGLEC1, STAB1, TMEM37, MERTK, and/or TMEM119 on their cell surface. In some embodiments, SDCs do not substantially express C5AR1, LYVE1, ABCC3, MRC1, SIGLEC1, STAB1, C1QB, C1QA, TMEM37, MERTK, C1QC. TMEM119, MS4A7, APOE, CYP4F18, TREM1, TLR7, and/or LILRB4. Flow cytometry and PCR, among other art recognized assays, can be used to assess expression of a marker disclosed herein.

Stimulatory myeloid cells can be CD45$^+$, HLA-DR$^+$, CD14$^-$, CD11c$^+$, and BDCA3$^+$. Stimulatory myeloid cells can be CD45$^+$, HLA-DR$^+$, and BDCA3$^+$. Stimulatory myeloid cells can be CD45$^+$, HLA-DR$^+$, CD14$^-$, and BDCA3$^+$. Stimulatory myeloid cells can be CD45$^+$, HLA-DR$^+$, CD11c$^+$, and BDCA3$^+$.

Pharmaceutical Compositions

The present application provides compositions comprising the antibodies including pharmaceutical compositions comprising any one or more of the antibodies described herein with one or more pharmaceutically acceptable excipients. In some embodiments the composition is sterile. The pharmaceutical compositions generally comprise an effective amount of an antibody.

These compositions can comprise, in addition to one or more of the antibodies disclosed herein, a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g. oral, intravenous, cutaneous or subcutaneous, nasal, intramuscular, intraperitoneal routes.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives can be included, as required.

Whether it is a polypeptide, antibody (e.g., anti-TREM1 antibody), nucleic acid, small molecule or other pharmaceutically useful compound according to the present invention that is to be given to an individual, administration is preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of protein aggregation disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

A composition can be administered alone or in combination with other treatments, either simultaneously or sequentially dependent upon the condition to be treated.

Methods

Methods of Preparation

Antibodies described herein can be produced using recombinant methods and compositions, e.g., as described in U.S. Pat. No. 4,816,567.

In one embodiment, isolated nucleic acid encoding an antibody described herein is provided. Such nucleic acid may encode an amino acid sequence comprising the VL and/or an amino acid sequence comprising the VH of the antibody (e.g., the light and/or heavy chains of the antibody) or an amino acid sequence comprising the VHH of a single domain antibody. In a further embodiment, one or more vectors (e.g., expression vectors) comprising such nucleic acid are provided. In one embodiment, the nucleic acid is provided in a multicistronic vector. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antigen-binding polypeptide construct, or (2) a first vector comprising a nucleic acid that encodes an amino acid sequence comprising the VL of the antigen-binding polypeptide construct and a second vector comprising a nucleic acid that encodes an amino acid sequence comprising the VH of the antigen-binding polypeptide construct. In one embodiment, the host cell is eukaryotic, e.g. a Chinese Hamster Ovary (CHO) cell, or human embryonic kidney (HEK) cell, or lymphoid cell (e.g., Y0, NS0, Sp20 cell). In one embodiment, a method of making an antibody is provided, wherein the method comprises culturing a host cell comprising nucleic acid encoding the antibody, as provided above, under conditions suitable for expression of the antibody, and optionally recovering the antibody from the host cell (or host cell culture medium).

For recombinant production of the antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

The term "substantially purified" refers to a construct described herein, or variant thereof that may be substantially or essentially free of components that normally accompany or interact with the protein as found in its naturally occurring environment, i.e. a native cell, or host cell in the case of recombinantly produced heteromultimer that in certain embodiments, is substantially free of cellular material includes preparations of protein having less than about 30%, less than about 25%, less than about 20%, less than about 15%, less than about 10%, less than about 5%, less than about 4%, less than about 3%, less than about 2%, or less than about 1% (by dry weight) of contaminating protein. When the heteromultimer or variant thereof is recombinantly produced by the host cells, the protein in certain embodiments is present at about 30%, about 25%, about 20%, about 15%, about 10%, about 5%, about 4%, about 3%, about 2%, or about 1% or less of the dry weight of the cells. When the heteromultimer or variant thereof is recombinantly produced by the host cells, the protein, in certain embodiments, is present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. In certain embodiments, "substantially purified" heteromultimer produced by the methods described herein, has a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis.

Suitable host cells for cloning or expression of antibody-encoding vectors include prokaryotic or eukaryotic cells described herein.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome. Host cells can include CHO, derivatives of CHO, NS0, Sp20, CV-1, VERO-76, HeLa, HepG2, Per.C6, or BHK.

As used herein, the term "eukaryote" refers to organisms belonging to the phylogenetic domain Eucarya such as animals (including but not limited to, mammals, insects, reptiles, birds, etc.), ciliates, plants (including but not limited to, monocots, dicots, algae, etc.), fungi, yeasts, *flagellates*, microsporidia, protists, etc.

As used herein, the term "prokaryote" refers to prokaryotic organisms. For example, a non-eukaryotic organism can belong to the Eubacteria (including but not limited to, *Escherichia coli, Thermus thermophilus, Bacillus stearothermophilus, Pseudomonas fluorescens, Pseudomonas aeruginosa, Pseudomonas putida*, etc.) phylogenetic domain, or the Archaea (including but not limited to, *Methanococcus jannaschii, Methanobacterium* thermoautotrophicum, *Halobacterium* such as *Haloferax volcanii* and *Halobacterium* species NRC-1, *Archacoglobus fulgidus, Pyrococcus furiosus, Pyrococcus horikoshii, Aeuropyrum pernix*, etc.) phylogenetic domain.

For example, antibody may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized." resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibodies are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

In one embodiment, the antibodies described herein are produced in stable mammalian cells, by a method comprising: transfecting at least one stable mammalian cell with: nucleic acid encoding the antibody, in a predetermined ratio; and expressing the nucleic acid in the at least one mammalian cell. In some embodiments, the predetermined ratio of nucleic acid is determined in transient transfection experiments to determine the relative ratio of input nucleic acids that results in the highest percentage of the antibody in the expressed product.

In some embodiments is the method of producing an antibody in stable mammalian cells as described herein wherein the expression product of the at least one stable mammalian cell comprises a larger percentage of the desired glycosylated antibody as compared to the monomeric heavy or light chain polypeptides, or other antibodies.

In some embodiments is the method of producing a glycosylated antibody in stable mammalian cells described herein, said method comprising identifying and purifying the desired glycosylated antibody. In some embodiments, the said identification is by one or both of liquid chromatography and mass spectrometry.

If required, the antibodies can be purified or isolated after expression. Proteins may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. As is well known in the art, a variety of natural proteins bind Fc and antibodies, and these proteins can find use in the present invention for purification of antibodies. For example, the bacterial proteins A and G bind to the Fc region. Likewise, the bacterial protein L binds to the Fab region of some antibodies. Purification can often be enabled by a particular fusion partner. For example, antibodies may be purified using glutathione resin if a GST fusion is employed, Ni+2 affinity chromatography if a His-tag is employed or immobilized anti-flag antibody if a flag-tag is used. For general guidance in suitable purification techniques, see, e.g. incorporated entirely by reference Protein Purification: Principles and Practice, 3rd Ed., Scopes, Springer-Verlag, NY, 1994, incorporated entirely by reference. The degree of purification necessary will vary depending on the use of the antibodies. In some instances no purification is necessary.

In certain embodiments the antibodies are purified using Anion Exchange Chromatography including, but not limited to, chromatography on Q-sepharose, DEAE sepharose, poros HQ, poros DEAF, Toyopearl Q, Toyopearl QAE, Toyopearl DEAE, Resource/Source Q and DEAE, Fractogel Q and DEAE columns.

In specific embodiments the proteins described herein are purified using Cation Exchange Chromatography including, but not limited to, SP-sepharose, CM sepharose, poros HS, poros CM. Toyopearl SP. Toyopearl CM, Resource/Source S and CM, Fractogel S and CM columns and their equivalents and comparables.

In addition, antibodies described herein can be chemically synthesized using techniques known in the art (e.g., see Creighton, 1983, Proteins: Structures and Molecular Principles, W. H. Freeman & Co., N. Y and Hunkapiller et al., Nature, 310:105-111 (1984)). For example, a polypeptide corresponding to a fragment of a polypeptide can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4diaminobutyric acid, alpha-amino isobutyric acid, 4aminobutyric acid, Abu, 2-amino butyric acid, g-Abu, e-Ahx, 6amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, alanine, fluoro-amino acids, designer amino acids such as methyl amino acids, C-methyl amino acids, N-methyl amino acids, and amino acid analogs in general. Furthermore, the amino acid can be D (dextrorotary) or L (levorotary).

Methods of Immune Modulation of Myeloid Cells

Methods of administration of a TREM1 antibody as described herein can result in induction of pro-inflammatory molecules, such as cytokines, chemokines, or expression of myeloid activation receptors by myeloid cells. Generally, induced pro-inflammatory molecules are present at levels greater than that achieved with isotype control. In some embodiments, the myeloid cells are non-stimulatory myeloid cells. In some embodiments, the non-stimulatory myeloid cells are TREM1-expressing (TREM1+) cells. In some embodiments, the myeloid cell is a myeloid-derived suppressive cell or a tumor associated neutrophil. In some embodiments, the TREM1+ cell is a myeloid-derived suppressive cell or a tumor associated neutrophil. Such pro-inflammatory molecules in turn result in activation of anti-tumor immunity, including, but not limited to, T cell activation, M1-like macrophage activation, and NK cell activation. Thus, the administration of an anti-TREM1 antibody can induce multiple anti-tumor immune mechanisms that lead to tumor destruction.

In another aspect, the invention provides methods of increasing an immune response in an individual comprising administering to the individual an effective amount of a composition comprising an anti-TREM1 antibody or antigen-binding fragment thereof. In some embodiments, the method of increasing an immune response in a subject comprises comprising administering to the subject an antibody that competes for binding to human TREM1 (SEQ ID NO: 1) with a reference antibody. In some embodiments, the method of increasing an immune response in a subject comprises comprising administering to the subject an antibody that competes for binding to human TREM1 (SEQ ID NO: 1), wherein the antibody binds within residues 21-34 (SEQ ID NO: 42), 103-109 (SEQ ID NO: 43), and 128-136 (SEQ ID NO: 44) of human TREM1 (SEQ ID NO: 1). In some embodiments, the method of increasing an immune response in a subject comprises comprising administering to the subject an antibody that competes for binding to human TREM1 (SEQ ID NO: 1), wherein the antibody i) binds within residues 21-34 (SEQ ID NO: 42), 103-109 (SEQ ID NO: 43), and 128-136 (SEQ ID NO: 44) of human TREM1 (SEQ ID NO: 1); and ii) optionally comprises a human Fc region. In some embodiments, the antibody is present in a pharmaceutical composition further comprising a pharmaceutically acceptable excipient.

In any and all aspects of increasing an immune response as described herein, any increase or decrease or alteration of an aspect of characteristic(s) or function(s) is as compared to a cell not contacted with an anti-TREM1 antibody.

Increasing an immune response can be both enhancing an immune response or inducing an immune response. For instance, increasing an immune response encompasses both the start or initiation of an immune response, or ramping up or amplifying an on-going or existing immune response. In some embodiments, the treatment induces an immune response. In some embodiments, the induced immune response is an adaptive immune response. In some embodiments, the induced immune response is an innate immune response. In some embodiments, the treatment enhances an immune response. In some embodiments, the enhanced immune response is an adaptive immune response. In some embodiments, the enhanced immune response is an innate immune response. In some embodiments, the treatment increases an immune response. In some embodiments, the increased immune response is an adaptive immune response. In some embodiments, the increased immune response is an innate immune response. In some embodiments, the immune response is started or initiated by administration of an anti-TREM1 antibody. In some embodiments, the immune response is enhanced by administration of an anti-TREM1 antibody.

In another aspect, the present application provides methods of contacting a cell with an anti-TREM1 antibody, which results in the modulation of the immune function of the cell. The modulation can be increasing an immune response or reprogramming of non-stimulatory myeloid cells to become stimulatory myeloid cells. In some embodiments, the modulation is an increase in immune function. In some embodiments, the modulation is reprogramming the non-stimulatory myeloid cells to become stimulatory myeloid cells. In some embodiments, the modulation of function leads to the activation of non-stimulatory myeloid cells. In some embodiments, the modulation of function leads to the reprogramming of TREM1-expressing myeloid cells.

In some embodiments, the cells are non-stimulatory myeloid cells. In some embodiments, the cells are TREM1-expressing cells (TREM1+ cells). In some embodiments, the non-stimulatory cells are TREM1+ cells. In some embodiments, the TREM1+ cells are one or more of DC1 cells, TAM1 cells, TAM2 cells, myeloid-derived suppressive cells (MDSCs), neutrophils, and tumor associated neutrophils (TANs). In some embodiments, the TREM1+ cell is a myeloid-derived suppressive cell. In some embodiments, the TREM1+ cell is a a tumor associated neutrophil (TAN). In some embodiments, contacting a non-stimulatory myeloid cell with a TREM1 antibody induces the non-stimulatory cell to become a stimulatory myeloid cell (SDC).

In some embodiments, the modulation of function of the non-stimulatory myeloid cells or TREM1+ cells leads to an increase in the cells' abilities to stimulate both native and activated CD8+ T-cells, for example, by increasing the ability of non-stimulatory cells to cross-present tumor antigen on MHCI molecules to naive CD8+ T-cells or by increasing cytokine or chemokine secretion by the non-stimulatory myeloid cells. In some embodiments, the modulation of function of the non-stimulatory myeloid cells or TREM1+ cells leads to an increase in the cells' abilities to stimulate both native and activated CD4+ T-cells, for example, by increasing the ability of non-stimulatory cells or TREM1+ to cross-present tumor antigen on MHCII molecules to naive CD4+ T-cells. In some embodiments, the modulation of function enhances or increases the cells' ability to produce cytokines, chemokines, or costimulatory or activating receptors. In some embodiments, the modulation increases the T-cell stimulatory function of the myeloid cells or TREM1+ cells, including, for example, the cells' abilities to trigger T-cell receptor (TCR) signaling. T-cell proliferation, or T-cell cytokine production.

In some embodiments, the increased immune response is secretion of cytokines and chemokines. In some embodiments, the antibody has agonist activity. In some embodiments, the antibody induces increased expression of at least one cytokine or chemokine in a cell as compared to an isotype control antibody. In some embodiments, the at least one cytokine or chemokine is selected from the group consisting of: IFN-γ, IL-1α, IL-12, IL-2, TNFSF9, TNFSF10, CXCL9, CXCL10, CCL17, CXCL1, CXCL5, CXCL8, CXCL11, CXCL15, CCL3, CCL4, CCL2, CCL8, CCL20, IL-6, CCL2, CCL7, CSF-1, CCL13, CCL19, TNFα, GZMH, PD-L1, MMP7, CCL23, CD70, CD8a, FasL, CD274, CRTAM, granzyme A (GzmA), or granzyme B (GzmB). In some embodiments, the cytokine or chemokine is CXCL10. In some embodiments, the cytokine or chemokine is IFN-γ. In some embodiments, the cytokine or chemokine secretion is increased a between bout 1-100-fold 1, 5, 10, 20, 30, 40, 50, 60, 70, 80, 90, 100, 1-10, 10-20, 20-30, 30-40, 40-50, 50-60, 60-70, 70-80, 80-90, or 90-100 fold as compared to an untreated cell or a cell treated with an isotype control antibody. In some embodiments, the chemokine is CXCL10 and the secretion is increased between about 1-100-fold, 1-fold, 5-fold, 10-fold, 20-fold, 30-fold, 40-fold, 50-fold, 60-fold, 70-fold, 80-fold, 90-fold, 100-fold, 1-10-fold, 10-20-fold, 20-30-fold, 30-40-fold, 40-50-fold, 50-60-fold, 60-70-fold, 70-80-fold, 80-90-fold, or 90-100-fold as compared to an untreated cell or a cell treated with an isotype control antibody. In some embodiments, the sytokine is IFN-γ and the secretion is increased between about 1-100-fold, 1-fold, 5-fold, 10-fold, 20-fold, 30-fold, 40-fold, 50-fold, 60-fold, 70-fold, 80-fold, 90-fold, 100-fold, 1-10-fold, 10-20-fold, 20-30-fold, 30-40-fold, 40-50-fold, 50-60-fold, 60-70-fold, 70-80-fold, 80-90-fold, or 90-100-fold as compared to an untreated cell or a cell treated with an isotype control antibody.

In some embodiments, the modulation increases the expression of at least one myeloid co-stimulatory protein as compared to an isotype control antibody. In some embodiments, the myeloid co-stimulatory protein is HLA-DR, CD40, CD80, or CD86 in a cell. HLA-DR is an MHC class II cell surface receptor that mainly functions to present peptide antigens to T cells in order to elicit an immune response. HLA-DR is a heterodimer of an a unit and a ß unit.

HLA-DR is expressed by antigen presenting cells such as macrophages, B cells, and dendritic cells. CD40 is a co-stimulatory protein found on antigen-presenting cells and is required for activation of the antigen-presenting cell. CD80 is a receptor largely expressed by immune cells such as dendritic cells, B cells, monocytes, and antigen-presenting cells, and is closely related to CD86. CD80 interacts with CD28 and CTLA4 on T cells and works in tandem with CD86 to prime T cell and B cell activation, proliferation, and differentiation, including signaling of T cells to differentiate into cytotoxic T cells. CD80 can also stimulate dendritic cells and enhance cytokine production. Co-stimulatory proteins are required in order for an antigen-presenting cell to fully activate a T cell, along with a primary antigen-specific signal. T cell co-stimulation is required to T cell proliferation, differentiation, and survival. T cells activated without co-stimulation can lead to T cell anergy or deletion.

In some embodiments, the treatment increases HLA-DR expression. In some embodiments, the treatment increases CD40 expression. In some embodiments, the treatment increases CD80 expression. In some embodiments, the treatment increases CD86 expression. In some embodiments, the co-stimulatory molecule is increased between about 1-100-fold, 1-fold, 5-fold, 10-fold, 20-fold, 30-fold, 40-fold, 50-fold, 60-fold, 70-fold, 80-fold, 90-fold, 100-fold, 1-10-fold, 10-20-fold, 20-30-fold, 30-40-fold, 40-50-fold, 50-60-fold, 60-70-fold, 70-80-fold, 80-90-fold, or 90-100-fold or more as compared to an untreated cell or a cell treated with an isotype control antibody.

In some embodiments, the enhanced immune response is anti-tumor immune cell recruitment and activation.

In some embodiments, the antibody induces increased activation of the ERK and/or JAK-STAT intracellular signaling pathways in a cell as compared to an isotype control antibody. In some embodiments, the antibody induces increased activation of STAT3 in a cell as compared to an isotype control antibody. In some embodiments, the antibody induces increased activation of the ERK intracellular signaling pathway in a cell as compared to an isotype control antibody. In some embodiments, the antibody induces increased activation of the JAK-STAT intracellular signaling pathway in a cell as compared to an isotype control antibody. The ERK pathway is involved in cell proliferation. STAT3 is a transcription factor and a member of the JAK-STAT signaling pathway. STAT3 mediates transcription of genes involved in cell growth and is essential for the differentiation of $T_H17$ helper T cells. Loss of STAT3 in vivo has also been implicated in the failure to maintain antibody based immunity.

In some embodiments, the antibody induces a memory immune response as compared to an isotype control antibody. In general, a memory immune response is a protective immune response upon a subsequent exposure to pathogens or antigens that the immune system encountered previously. Exemplary memory immune responses include the immune response after infection or vaccination with an antigen. In general, memory immune responses are mediated by lymphocytes such as T cells or B cells. In some embodiments, the memory immune response is a protective immune response to cancer, including cancer cell growth, proliferation, or metastasis. In some embodiments, the memory immune response inhibits, prevents, or reduces cancer cell growth, proliferation, or metastasis.

In some embodiments, the antibody crosslinks TREM1 to TREM1 on the cell surface of a TREM1+ cell. In some embodiments, the contacting is in vitro. In some embodiments, the contacting is in vivo. In some particular embodiments, the contacting is in vivo in a human. In some embodiments, the contacting is effected by administering an anti-TREM1 antibody. In some embodiments, the individual receiving the antibody (such as a human) has cancer.

Methods of Disabling, Killing, or Depleting Non-Stimulatory Myeloid Cells

In one aspect, the present application provides methods of contacting non-stimulatory myeloid cells with an anti-TREM1 antibody, such as a human or humanized antibody, which results in the disabling of the non-stimulatory myeloid cells.

In another aspect, the present application provides methods of contacting non-stimulatory myeloid cells with an anti-TREM1 antibody, which results in the disabling of the non-stimulatory myeloid cells.

In some embodiments, the non-stimulatory cells are one or more of DC1 cells, and TAM cells. In some embodiments, the non-stimulatory cells are one or more of TAM cells, myeloid-derived suppressive cells (MDSCs) and tumor associated neutrophils (TANs).

In some embodiments, the present application provides methods of disabling non-stimulatory myeloid cells, comprising contacting the non-stimulatory myeloid cells with a TREM1 antibody, thereby killing the non-stimulatory myeloid cells. Disabling refers to rendering a cell partially or completely non-functional. In some embodiments, the disabling of the non-stimulatory myeloid cells leads to inducing growth arrest in the cells. In some embodiments, the disabling of the non-stimulatory myeloid cells leads to apoptosis in the cells. In some embodiments, the disabling of the non-stimulatory cells leads to lysis of the cells, as for example by complement dependent cytotoxicity (CDC) or antibody-dependent cell cytotoxicity (ADCC). In some embodiments, the disabling of the non-stimulatory myeloid cells leads to necrosis in the cells. In some embodiments, the disabling of the non-stimulatory myeloid cells leads to inducing growth arrest in the cells. In some embodiments, the disabling of the non-stimulatory myeloid cells leads to inactivating the cells. In some embodiments, the disabling of the non-stimulatory myeloid cells leads to neutralizing the activity of a TREM1 protein in the cells. In some embodiments, the disabling of the non-stimulatory myeloid cells leads to reduction in proliferation of the cells. In some embodiments, the disabling of the non-stimulatory myeloid cells leads to differentiation of the cells. In some embodiments, the disabling of the non-stimulatory myeloid cells leads to a decrease in the cells' ability to act as inhibitory antigen presenting cells or leads to an increase in the cells' ability to act as activating antigen-presenting cells. In some embodiments, the disabling of the non-stimulatory myeloid cells leads to the mislocalization of the cells within tumor tissue or tumor microenvironment (TME). In some embodiments, the disabling of the non-stimulatory myeloid cells leads to an altered spatial organization of the cells within tumor tissue or tumor microenvironment. In some embodiments, the disabling of the non-stimulatory myeloid cells leads to an altered temporal expression of the cells within tumor tissue or TME. In some embodiments, the method further comprises removing the non-stimulatory myeloid cells.

In any and all aspects of disabling non-stimulatory myeloid cells as described herein, any increase or decrease or alteration of an aspect of characteristic(s) or function(s) is as compared to a cell not contacted with an anti-TREM1 antibody.

In another aspect, the present application provides methods of contacting non-stimulatory myeloid cells with an anti-TREM1 antibody, which results in the modulation of function of the non-stimulatory myeloid cells. The modulation can be any one or more of the following. In some embodiments the non-stimulatory cells are one or more of DC1 cells, TAM1 cells, TAM2 cells, MDSCs, and TANs. In some embodiments, the modulation of function leads to the disabling of non-stimulatory myeloid cells. In some embodiments, the modulation of function of the non-stimulatory myeloid cells leads to an increase in the cells' abilities to stimulate both native and activated CD8+ T-cells, for example, by increasing the ability of non-stimulatory cells to cross-present tumor antigen on MHCI molecules to naive CD8+ T-cells. In some embodiments, the modulation of function of the non-stimulatory myeloid cells leads to an increase in the cells' abilities to stimulate both native and activated CD4+ T-cells, for example, by increasing the ability of non-stimulatory cells to cross-present tumor antigen on MHCII molecules to naive CD4+ T-cells. In some embodiments, the modulation increases the T-cell stimulatory function of the myeloid cells, including, for example, the cells' abilities to trigger T-cell receptor (TCR) signaling, T-cell proliferation, or T-cell cytokine production. In some embodiments, the modulation of function enhances or increases the cells' ability to produce cytokines, chemokines, or costimulatory or activating receptors. In one embodiment, the survival of the non-stimulatory cell is decreased or the proliferation of the non-stimulatory cell is decreased. In one embodiment, the ratio of stimulatory myeloid cells to non-stimulatory myeloid cells is increased.

In any and all aspects of decreasing the function of non-stimulatory myeloid cells as described herein, any increase or decrease or alteration of an aspect of characteristic(s) or function(s) is as compared to a cell not contacted with an anti-TREM1 antibody.

In some embodiments, the present application provides methods of killing (also referred to as inducing cell death) non-stimulatory myeloid cells, comprising contacting the non-stimulatory myeloid cells with an anti-TREM1 antibody, thereby killing the non-stimulatory myeloid cells. In some embodiments the killing is increased relative to non-stimulatory myeloid cells that have not been contacted with an anti-TREM1 antibody. In some embodiments, the contacting induces apoptosis in the non-stimulatory myeloid cells. In some embodiments, the non-stimulatory myeloid cells are in a population of immune cells comprising non-stimulatory myeloid cells and stimulatory myeloid cells. In some embodiments, the method further comprises removing the non-stimulatory myeloid cells. In some embodiments, 10%-100% of the cells are killed. In some embodiments, at least 10%, 20%, 30%, 40%, 50%, 60%, 70%, 80%, 90% or 100% of the cells are killed.

In some embodiments, the present application provides methods of increasing the ratio of stimulatory myeloid cells to non-stimulatory myeloid cells in a population of immune cells comprising stimulatory myeloid cells and non-stimulatory myeloid cells, comprising contacting the population of immune cells with an anti-TREM1 antibody. In some embodiments the ratio is increased relative to a population of cells that have not been contacted with an anti-TREM1 antibody. In some embodiments the ratio of DC2 cells to DC1 cells is increased. In some embodiments the ratio of DC2 cells to TAM1 cells is increased. In some embodiments the ratio of DC2 cells to TAM2 cells is increased. In some embodiments the ratio of DC2 cells to TAM1+TAM2 cells is increased. In some embodiments the ratio of DC2 cells to TAM1+DC1 cells is increased. In some embodiments the ratio of DC2 cells to DC1+TAM2 cells is increased. In some embodiments the ratio of DC2 cells to DC1+TAM1+TAM2 cells is increased. In some embodiments, at least the ratio is increased by 10%, 20%, 30%, 40%, 50%, 60%, 70%, 80%, 90%, or 100%.

In some embodiments the ratio of stimulatory myeloid cells to non-stimulatory myeloid cells prior to contacting ranges from 0.001:1-0.1:1. In some embodiments the ratio of stimulatory myeloid cells to non-stimulatory myeloid cells following the contacting ranges from 0.1:1-100:1.

In some embodiments, the non-stimulatory myeloid cells are reduced in number. In some embodiments the stimulatory myeloid cells are DC2 cells. In some embodiments, the non-stimulatory myeloid cells are killed, for example by necrosis, or apoptosis. In some embodiments, the non-stimulatory myeloid cells are induced to undergo growth arrest. In some embodiments the non-stimulatory myeloid cells no longer proliferate. In some embodiments the spatial localization of the non-stimulatory myeloid cells is altered, and the ratio is increased in a particular region of the TME. In some embodiments the temporal expression of the non-stimulatory myeloid cells is altered, and the ratio is increased during a particular time during the development of the tumor.

In some embodiments, the contacting is in vitro. In some embodiments, the contacting is in vivo. In some particular embodiments, the contacting is in vivo in a human. In some embodiments, the contacting is effected by administering an anti-TREM1 antibody. In some embodiments, the individual receiving the antibody (such as a human) has cancer.

Methods of Cancer Treatment

In another aspect, the invention provides methods of treating an immune-related condition (such as methods of enhancing an immune response or effecting the disabling of non-stimulatory myeloid cells) in an individual comprising administering to the individual an effective amount of a composition comprising an anti-TREM1 antibody. In some embodiments, the methods provided herein are useful for the treatment of cancer and as such an individual receiving an anti-TREM1 antibody or an anti-TREM1 antibody has cancer.

Any suitable cancer may be treated with the antibodies provided herein. The cancer can be, but is not limited to, any carcinoma, adenocarcinoma, soft tissue, sarcoma, teratomas, melanoma, leukemia, Hodgkin lymphoma, non-Hodgkin lymphoma, or brain cancer, or any other cancer known in the medical field. In some embodiments, the cancer is a solid cancer. In some embodiments, the cancer is a liquid cancer. In some embodiments, the cancer is immunoevasive. In some embodiments, the cancer is immunoresponsive.

In some embodiments, the cancer is melanoma, kidney, hepatobiliary, head-neck squamous carcinoma (HNSC), pancreatic, colon, bladder, urothelial, glioblastoma, prostate, lung, breast (mammary), ovarian, gastric, esophageal, renal, endometrial, cervical, testicular, melanoma, leukemia, lymphoma, or mesothelioma. In some embodiments, the cancer is colon cancer, pancreatic cancer, or breast cancer.

In some embodiments, the treatment results in a decrease in the cancer volume or size. In some embodiments, the treatment is effective at reducing a cancer volume as compared to the cancer volume prior to administration of the antibody. In some embodiments, the treatment results in a decrease in the cancer growth rate. In some embodiments, the treatment is effective at reducing a cancer growth rate as compared to the cancer growth rate prior to administration of the antibody. In some embodiments, the treatment is effective at eliminating the cancer.

In some embodiments the immune-related condition is an immune-related condition associated with the expression of TREM1 protein on non-stimulatory myeloid cells (in humans) or the expression of a homolog of TREM1 protein in a non-human species. In some embodiments the immune-related condition is an immune-related condition associated with the overexpression of TREM1 protein on non-stimulatory myeloid cells, as compared to stimulatory myeloid-cells. In some embodiments the overexpression of the TREM1 mRNA or the TREM1 protein is about at least 2 fold, 5 fold, 10 fold, 25 fold, 50 fold, or 100 fold higher as compared to stimulatory myeloid cells.

In some embodiments these methods are further provided in combination with other co-therapies such as a PD-1/PD-L1/PD-L2 blockade therapy, anti-PD-1 antibodies, anti-PD-L1 antibodies, anti-PD-L2 antibodies, a CTLA4 blockade therapy, anti-CTLA-4 antibodies, generalized checkpoint blockade therapy in which inhibitory molecules on T cells are blocked, adoptive T-cell therapy, CAR T-cell therapy, dendritic cell or other cellular therapies, as well as conventional chemotherapies.

In some embodiments, the method further comprises determining the expression level of TREM1 protein in a biological sample from the individual. In some embodiments the biological sample includes, but is not limited to a body fluid, a tissue sample, an organ sample, urine, feces, blood, saliva, CSF and any combination thereof. In some embodiments the biological sample is derived from a tumor tissue. In some embodiments, the expression level comprises the mRNA expression level of mRNA encoding TREM1 protein. In some embodiments, the expression level of TREM1 protein comprises the protein expression level of NSM. In some embodiments the expression level of TREM1 protein is detected in the sample using a method selected from the group consisting of FACS, Western blot, ELISA, immunoprecipitation, immunohistochemistry, immunofluorescence, radioimmunoassay, dot blotting, immunodetection methods, HPLC, surface plasmon resonance, optical spectroscopy, mass spectrometry, HPLC, qPCR, RT-qPCR, multiplex qPCR or RT-qPCR, RNA-seq, microarray analysis, SAGE, MassARRAY technique, and FISH, and combinations thereof.

In another aspect, the present application provides methods for determining the presence or absence of non-stimulatory myeloid cells in general, or for determining the presence or absence of particular non-stimulatory myeloid cells (for example DC1 cells, TAMIcells, and/or TAM2 cells) comprising: contacting a population of cells comprising non-stimulatory myeloid cells with an anti-TREM1 antibody; and quantifying the number non-stimulatory myeloid cells. In another aspect, the present application provides methods for determining the presence or absence of non-stimulatory myeloid cells comprising: contacting a population of immune cells comprising non-stimulatory myeloid cells and stimulatory myeloid cells with an anti-TREM1 antibody; detecting a complex or moiety indicating the binding of the antibody to the cell and optionally quantifying the number of non-stimulatory myeloid cells in the population. In another aspect, methods of determining the relative ratio of non-stimulatory myeloid cells to stimulatory myeloid cells are provided, comprising: contacting a population of immune cells comprising non-stimulatory myeloid cells and stimulatory myeloid cells with an anti-TREM1 antibody; quantifying the number of stimulatory myeloid cells and non-stimulatory myeloid cells; and determining the relative ratio of non-stimulatory myeloid cells to stimulatory myeloid cells.

In embodiments described herein for detection and/or quantification, an anti-TREM1 antibody binds to a TREM1 protein, but does not necessarily have to affect a biological response, such as ADCC, although it may have an effect on a biological response.

In another aspect, the present invention provides methods for identifying an individual who may respond to immunotherapy (e.g. with an anti-TREM1 antibody) for the treatment of an immune-related condition (e.g. cancer) comprising: detecting the expression level of TREM1 protein in a biological sample from the individual; and determining based on the expression level of TREM1 protein, whether the individual may respond immunotherapy, wherein an elevated level of TREM1 protein in the individual relative to that in a healthy individual indicates that the individual may respond to immunotherapy. In some embodiments, these methods may also be used for diagnosing an immune-related condition (e.g. cancer) in the individual and are based the expression level of TREM1 protein, wherein an elevated level of TREM1 protein in the individual relative to that in a healthy individual indicates that the individual suffers from cancer. In some embodiments, the expression level comprises the mRNA expression level of mRNA encoding TREM1 protein. In other embodiments, the expression level of TREM1 protein comprises the protein expression level of TREM1 protein. In some embodiments the expression level of TREM1 protein is detected in the sample using a method selected from the group consisting of FACS, Western blot, ELISA, immunoprecipitation, immunohistochemistry, immunofluorescence, radioimmunoassay, dot blotting, immunodetection methods, HPLC, surface plasmon resonance, optical spectroscopy, mass spectrometery, HPLC, qPCR, RT-qPCR, multiplex qPCR or RT-qPCR, RNA-seq, microarray analysis, SAGE, MassARRAY technique, and FISH, and combinations thereof. In these embodiments, an anti-TREM1 antibody binds to the TREM1 protein, but does not necessarily have to affect a biological response, such as ADCC. In some embodiments the biological sample is derived from a tumor tissue. In some embodiments the biological sample includes, but is not limited to a body fluid, a tissue sample, an organ sample, urine, feces, blood, saliva, CSF and any combination thereof.

Also disclosed herein is a method of enhancing a subject immune response to tumors or enhancing the efficacy of immunotherapy treatments. In general, a treatment that increases the abundance of SDCs will improve subject outcome, such as recurrence-free survival time, and will enhance the efficacy of cancer immunotherapy treatments. A treatment can increase the relative or absolute abundance of SDC cells in a subject's tumor. A treatment can decrease the relative or absolute abundance of NSM cells in a subject's tumor.

Exemplary methods of the general treatment strategy include increasing the numbers of SDCs by systemic introduction of Flt3L. Another method is treatment of a subject's autologous bone-marrow or blood cells with Flt3L while simultaneously blocking CSF1. Expression, for example by retrovirus, of SDC transcription factors such as IRF8, Mycl1 or BATF3 or ZBTB46 in bone-marrow or blood progenitor populations may also be used to drive SDC development. Another strategy of treatment includes the systematic elimination of NSM cells while selectively sparing the SDC. This can generate an overall favorable change in the ratio of these populations. Elimination of NSM cells may be accomplished by any means, including the administration (systemic or localized to the tumor) of antibodies against TREM1 surface proteins.

In some embodiments, SDC-enhancing treatments are applied as a therapeutic treatment to better enable the subject's native immune system in controlling or eradicating the cancer. In another embodiment, the SDC-enhancing treatments of the invention are applied in combination with a therapeutic treatment such as an immunotherapy treatment (such application being prior to, concurrent with, or after the immunotherapy treatment) wherein the SDC-enhancing treatment acts as an accessory or adjuvant treatment to increase the efficacy of the therapeutic treatment.

Methods of Administration

In some embodiments, the methods provided herein are useful for the treatment of an immune-related condition in an individual. In one embodiment, the individual is a human and the antibody is a TREM1 antibody. In another embodiment, the individual is a mouse and the antibody is a TREM1 antibody.

In some embodiments, an antibody is administered intravenously, intramuscularly, subcutaneously, topically, orally, transdermally, intraperitoneally, intraorbitally, by implantation, by inhalation, intrathecally, intraventricularly, or intranasally. An effective amount of an anti-TREM1 antibody may be administered for the treatment of cancer. The appropriate dosage of the anti-TREM1 antibody may be determined based on the type of cancer to be treated, the type of the anti-TREM1 antibody, the severity and course of the cancer, the clinical condition of the individual, the individual's clinical history and response to the treatment, and the discretion of the attending physician.

Combination Therapies

In some embodiments, an antibody provided herein is administered with at least one additional therapeutic agent. Any suitable additional therapeutic or immunotherapeutic agent may be administered with an antibody provided herein. In some embodiments, the immunotherapy is selected from, but is not limited to, a checkpoint inhibitor; a checkpoint inhibitor of T cells; anti-PD1 antibody; anti-PDL1 antibody; anti-CTLA4 antibody; adoptive cell therapy; adoptive T cell therapy; CAR-T cell therapy; a dendritic cell vaccine; a STING agonist; a monocyte vaccine; Bacillus Calmette-Guerin vaccine; an antigen binding protein that binds both a T cell and an antigen presenting cell; a BiTE dual antigen binding protein; a toll-like receptor ligand; a cytokine; a cytotoxic therapy; a chemotherapy; a radiotherapy; a small molecule inhibitor; a small molecule agonist; an immunomodulator; an oncolytic virus; and an epigenetic modulator, and combinations thereof.

In some embodiments, the additional therapeutic agent is an antibody. In some embodiments, the additional therapeutic agent is an antibody that binds a protein or proteins on a tumor cell surface.

For the treatment of cancer, the anti-TREM1 antibody may be combined with one or more antibodies that inhibit immune checkpoint proteins. Of particular interest are immune checkpoint proteins displayed on the surface of a tumor cell. The immune-checkpoint receptors that have been most actively studied in the context of clinical cancer immunotherapy, cytotoxic T-lymphocyte-associated antigen 4 (CTLA4; also known as CD152) and programmed cell death protein 1 (PD1; also known as CD279), are both inhibitory receptors. The clinical activity of antibodies that block either of these receptors implies that antitumor immunity can be enhanced at multiple levels and that combinatorial strategies can be intelligently designed, guided by mechanistic considerations and preclinical models.

The two ligands for PD-1 are PD-1 ligand 1 (PD-L1; also known as B7-H1 and CD274) and PD-L2 (also known as B7-DC and CD273). PD-L1 is expressed on cancer cells and through binding to its receptor PD-1 on T cells it inhibits T cell activation/function. Inhibitors that block the interaction of PD-1 with its cognate ligands on the cancer cells, PD-L1 and PD-L2, can result in both increased T cell activation and function, and prevent cancer cells from evading the immune system.

In some embodiments, the immunotherapy is an agent that interferes with PD-1 and PD-L1 or PD-L2 binding. In some embodiments, the immunotherapy is an anti-PD1 antibody. In some embodiments, the immunotherapy is an anti-PD-L1 antibody. In some embodiments, the immunotherapy is an anti-PD-L2 antibody.

Various PD-1, PD-L1, and PD-L2 antibodies are known in the art. In some embodiments, the additional therapeutic agent is at least one of: Atezolizumab (PD-L1), Avelumab (PD-L1), Durvalumab (PD-L1), Nivolumab (PD-1), Pembrolizumab (PD-1), Cemiplimab (PD-1), Ipilimumab (CTLA-4), Tremelimumab (CTLA-4), or any combination thereof.

The additional therapeutic agent can be administered by any suitable means. In some embodiments, an antibody provided herein and the additional therapeutic agent are included in the same pharmaceutical composition. In some embodiments, an antibody provided herein and the additional therapeutic agent are included in different pharmaceutical compositions.

In embodiments where an antibody provided herein and the additional therapeutic agent are included in different pharmaceutical compositions, administration of the antibody can occur prior to, simultaneously, and/or following, administration of the additional therapeutic agent. In some embodiments, administration of an antibody provided herein and the additional therapeutic agent occur within about one month of each other. In some embodiments, administration of an antibody provided herein and the additional therapeutic agent occur within about one week of each other. In some embodiments, administration of an antibody provided herein and the additional therapeutic agent occur within about one day of each other. In some embodiments, administration of an antibody provided herein and the additional therapeutic agent occur within about twelve hours of each other. In some embodiments, administration of an antibody provided herein and the additional therapeutic agent occur within about one hour of each other.

Kits and Articles of Manufacture

The present application provides kits comprising any one or more of the antibody compositions described herein. In some embodiments, the kits further contain a component selected from any of secondary antibodies, reagents for immunohistochemistry analysis, pharmaceutically acceptable excipient and instruction manual and any combination thereof. In one specific embodiment, the kit comprises a pharmaceutical composition comprising any one or more of the antibody compositions described herein, with one or more pharmaceutically acceptable excipients.

The present application also provides articles of manufacture comprising any one of the antibody compositions or kits described herein. Examples of an article of manufacture include vials (including sealed vials).

Additional Embodiments

Below are paragraphs enumerating specific embodiments.

An isolated antibody that binds to human TREM1 (SEQ ID NO: 1), comprising a heavy chain comprising a variable heavy (VH) chain sequence comprising three heavy chain CDR sequences, CDR-H1, CDR-H2, and CDR-H3, and a light chain comprising a variable light (VL) chain sequence comprising three light chain CDR sequences, CDR-L1, CDR-L2, and CDR-L3, wherein:
  a. CDR-H1 comprises the sequence set forth in SEQ ID NO: 23,
  b. CDR-H2 comprises the sequence set forth in SEQ ID NO: 24,
  c. CDR-H3 comprises the sequence set forth in SEQ ID NO: 33,
  d. CDR-L1 comprises the sequence set forth in SEQ ID NO: 26,
  e. CDR-L2 comprises the sequence set forth in SEQ ID NO: 27, and
  f. CDR-L3 comprises the sequence set forth in SEQ ID NO: 28.

The isolated antibody of claim 1, wherein the VH chain sequence comprises the VH sequence set forth in SEQ ID NO: 17, and the VL chain sequence comprises the VL sequence set forth in SEQ ID NO: 20.

The isolated antibody of claim 1, wherein the VH chain sequence comprises the VH sequence selected from the sequences set forth in SEQ ID NO: 16, 17, or 18; and the VL chain sequence comprises the VL sequence selected from the sequences set forth in SEQ ID NOs: 20, 21, or 22.

The isolated antibody of claim 1, wherein the antibody comprises the heavy chain sequence set forth in SEQ ID NO: 34 and the light chain sequence set forth in SEQ ID NO: 35.

The isolated antibody of claim 1, wherein the VH chain sequence consists of the VH sequence set forth in SEQ ID NO: 17; and the VL chain sequence consists of the VL sequence set forth in SEQ ID NO: 20.

The isolated antibody claim 1, wherein the VH chain sequence consists of the VH sequence selected from the sequences set forth in SEQ ID NO: 16, 17, or 18; and the VL chain sequence consists of the VL sequence selected from the sequences set forth in SEQ ID NOs: 20, 21, or 22.

The isolated antibody of claim 1, wherein the antibody consists of the heavy chain sequence set forth in SEQ ID NO: 34 and the light chain sequence set forth in SEQ ID NO: 35.

The isolated antibody of claim 1, wherein the antibody is afucosylated, and wherein the VH chain sequence comprises the VH sequence set forth in SEQ ID NO: 17, and the VL chain sequence comprises the VL sequence set forth in SEQ ID NO: 20.

The isolated antibody claim 1, wherein the antibody is afucosylated, and wherein the VH chain sequence comprises the VH sequence selected from the sequences set forth in SEQ ID NO: 16, 17, or 18; and the VL chain sequence comprises the VL sequence selected from the sequences set forth in SEQ ID NOs: 20, 21, or 22.

The isolated antibody of claim 1, wherein the antibody is afucosylated, and the antibody comprises the heavy chain sequence set forth in SEQ ID NO: 34 and the light chain sequence set forth in SEQ ID NO: 35.

The isolated antibody of claim 1, wherein the antibody is afucosylated, and wherein the VH chain sequence consists of the VH sequence set forth in SEQ ID NO: 17, and the VL chain sequence comprises the VL sequence set forth in SEQ ID NO: 20.

The isolated antibody claim 1, wherein the antibody is afucosylated, and wherein the VH chain sequence consists of the VH sequence selected from the sequences set forth in SEQ ID NO: 16, 17, or 18; and the VL chain sequence comprises the VL sequence selected from the sequences set forth in SEQ ID NOs: 20, 21, or 22.

The isolated antibody of claim 1, wherein the antibody is afucosylated, and the antibody consists of the heavy chain sequence set forth in SEQ ID NO: 34 and the light chain sequence set forth in SEQ ID NO: 35.

The isolated antibody of claim 1, wherein the antibody is afucosylated.

The isolated antibody of claim 1, wherein antibody comprises an active human Fc.

The isolated antibody of claim 15, wherein the human Fc is a wild-type human IgG1 Fc.

The isolated antibody of claim 1, wherein the antibody is afucosylated and comprises a wild type human IgG1 Fc, and wherein the VH chain sequence comprises the VH sequence set forth in SEQ ID NO: 17, and the VL chain sequence comprises the VL sequence set forth in SEQ ID NO: 20.

The isolated antibody of claim 1, wherein the antibody binds to human TREM1 with a KD of less than or equal to about 0.5, 1, 2, 3, 4, 5, 6, or 7×10-9 M, as measured by surface plasmon resonance (SPR) assay.

The isolated antibody of claim 1, wherein the antibody is humanized.

A method of producing an antibody comprising expressing the antibody of claim 1 from a host cell and isolating the expressed antibody.

A pharmaceutical composition comprising the antibody of claim 1 and a pharmaceutically acceptable excipient.

A kit comprising the antibody of claim 1 and instructions for use.

An isolated antibody that binds to human TREM1 (SEQ ID NO: 1), comprising a heavy chain comprising a variable heavy (VH) chain sequence comprising three heavy chain CDR sequences, CDR-H1, CDR-H2, and CDR-H3, and a light chain comprising a variable light (VL) chain sequence comprising three light chain CDR sequences, CDR-L1, CDR-L2, and CDR-L3, wherein:
  a. CDR-H1 comprises the sequence set forth in SEQ ID NO: 23,
  b. CDR-H2 comprises the sequence set forth in SEQ ID NO: 24,
  c. CDR-H3 comprises the sequence set forth in SEQ ID NO: 32,
  d. CDR-L1 comprises the sequence set forth in SEQ ID NO: 26,
  e. CDR-L2 comprises the sequence set forth in SEQ ID NO: 27, and
  f. CDR-L3 comprises the sequence set forth in SEQ ID NO: 28.

The isolated antibody of claim 23, wherein the VH chain sequence comprises the VH sequence set forth in SEQ ID NO: 13, and the VL chain sequence comprises the VL sequence set forth in SEQ ID NO: 20.

The isolated antibody of claim 23, wherein the antibody comprises the heavy chain sequence set forth in SEQ ID NO: 36 and the light chain sequence set forth in SEQ ID NO: 37.

A pharmaceutical composition comprising the antibody of claim 23 and a pharmaceutically acceptable excipient.

A method of treating cancer in a subject, comprising administering to the subject an antibody that competes for binding to human TREM1 (SEQ ID NO: 1) with a reference antibody comprising a heavy chain comprising a variable heavy (VH) chain sequence comprising three heavy chain CDR sequences, CDR-H1, CDR-H2, and CDR-H3, and a light chain comprising a variable light (VL) chain sequence comprising three light chain CDR sequences, CDR-L1, CDR-L2, and CDR-L3, wherein:
  a. CDR-H1 comprises the sequence set forth in SEQ ID NO: 23,
  b. CDR-H2 comprises the sequence set forth in SEQ ID NO: 24, c. CDR-H3 comprises the sequence set forth in SEQ ID NO: 33,
d. CDR-L1 comprises the sequence set forth in SEQ ID NO: 26,
e. CDR-L2 comprises the sequence set forth in SEQ ID NO: 27, and
f. CDR-L3 comprises the sequence set forth in SEQ ID NO: 28.

The method of claim 27, wherein the subject has previously received, is concurrently receiving, or will subsequently receive an immunotherapy, wherein the immunotherapy is at least one of: a checkpoint inhibitor; a checkpoint inhibitor of T cells; anti-PD1 antibody; anti-PDL1 antibody; anti-CTLA4 antibody; adoptive T cell therapy; CAR-T cell therapy; a dendritic cell vaccine; a monocyte vaccine; an antigen binding protein that binds both a T cell and an antigen presenting cell; a BiTE dual antigen binding protein; a toll-like receptor ligand; a cytokine; a cytotoxic therapy; a chemotherapy; a radiotherapy; a small molecule inhibitor; a small molecule agonist; an immunomodulator; and an epigenetic modulator.

The method of claim 28, wherein the immunotherapy is an anti-PD1 antibody, an anti-PDL1 antibody, or an anti-CTLA4 antibody.

A method of increasing an immune response in a subject, comprising administering to the subject an antibody that competes for binding to human TREM1 (SEQ ID NO: 1) with a reference antibody comprising a heavy chain comprising a variable heavy (VH) chain sequence comprising three heavy chain CDR sequences, CDR-H1, CDR-H2, and CDR-H3, and a light chain comprising a variable light (VL) chain sequence comprising three light chain CDR sequences, CDR-L1, CDR-L2, and CDR-L3, wherein:
a. CDR-H1 comprises the sequence set forth in SEQ ID NO: 23,
b. CDR-H2 comprises the sequence set forth in SEQ ID NO: 24,
c. CDR-H3 comprises the sequence set forth in SEQ ID NO: 33
d. CDR-L1 comprises the sequence set forth in SEQ ID NO: 26,
e. CDR-L2 comprises the sequence set forth in SEQ ID NO: 27, and
f. CDR-L3 comprises the sequence set forth in SEQ ID NO: 28.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pennsylvania: Mack Publishing Company, 1990); Carey and Sundberg *Advanced Organic Chemistry* $3^{rd}$ Ed. (Plenum Press) Vols A and B (1992).

Example 1: Sequencing and Humanization of Anti-TREM1 Antibody

A monoclonal mouse IgG1 Clone TREM-26 specific for human TREM1 was obtained and used for sequence determination and humanization. In brief, disulfide bonds in the antibody were reduced with dithiothreitol (DTT) and free sulfhydryl groups were alkylated with iodoacetamide. The alkylated antibody was digested with sequencing-grade endoproteinases, purified using spin columns, and sequence was determined by LC-MS/MS analysis (see below).

A chimera antibody (PI-4026) was constructed by grafting the mouse antibody VL and VH regions to human IgG1 constant regions. The chimera was further humanized by cloning the antibody CDRs into human variable domain frameworks and ten additional humanized variants were made with different framework mutations, 4 VH variants and 4 VL variants (PI-4026-1-10).

The VH and VL sequences were compared to libraries of known human germline sequences on the NCBI website (ncbi.nlm.nih.gov/igblast/; Ye, J. et al. Nucleic Acids Research 41: W34-W40 (2013)). The databases used were IMGT human VH genes (F+ORF, 273 germline sequences) and IMGT human VLkappa genes (F+ORF, 74 germline sequences).

For the humanized PI-4026 VH, human germline IGHV1-46 (allele 1) was chosen as the acceptor sequence and the human heavy chain IGHJ4 (allele 1) joining region (J gene) was chosen from human joining region sequences compiled at IMGT® the international ImMunoGeneTics information System® imgt.org (founder and director: Marie-Paule Lefranc, Montpellier, France).

For the humanized PI-4026 VL, human germline IGKV1-39 (allele 1) was chosen as the acceptor sequence and human light chain IGKJ2 (allele 1) joining region (J gene) was chosen from human joining region sequences compiled at IMGT® the international ImMunoGeneTics information System® imgt.org (founder and director: Marie-Paule Lefranc, Montpellier, France).

CDRs were defined according to the AbM definition (see the website of Dr. Andrew C. R. Martin bioinf.org.uk/abs/for a table comparing CDR definitions). Alteration of human germline framework (i.e., non-CDR residues in VH and VL) positions to corresponding parental murine sequence were used, e.g., to optimize binding of the humanized antibody.

Table 1A shows VH and VL sequences of the humanized versions of mAb PI-4026 that were created. 4026 VH-1 and 4026 VL-1 are the parent, humanized VH and VL clones from which the other humanized versions were created via additional framework mutations. Three humanized clones of the VH (4026 VH-2, VH-3, VH-4) and VL regions were made (4026 VL-2, VL-3, VL-4). Table 1B shows the CDR sequences.

TABLE 1A

| SEQ ID NO | Name | Sequence |
|---|---|---|
| | 4026 VH-1 | QVQLVQSGAEVKKPGASVKVSCKASGYTF TDYVINWVRQAPGQGLEWMGEIYPGSGST FYAQKFQGRVTMTRDTSTSTVYMELSSLR SEDTAVYYCARRMAAMDYWGQGTLVTVSS |

TABLE 1A-continued

| SEQ ID NO | Name | Sequence |
|---|---|---|
| | 4026 VH-2 | QVQLVQSGAEVKKPGASVKVSCKASGYTF TDYVINWVRQAPGQGLEWMGEIYPGSGST FYAQKFQGRVTMTADTSTSTVYMELSSLR SEDTAVYYCTRRMAAMDYWGQGTLVTVSS |
| | 4026 VH-3 | QVQLVQSGAEVKKPGASVKMSCKASGYTF TDYVINWVRQAPGQGLEWIGEIYPGSGST FYAQKFQGRATLTADTSTSTAYMEVSSLR SEDTAVYYCTRRMAAMDYWGQGTLVTVSS |
| | 4026 VH-4 | QVQLVQSGAEVKKPGASVKMSCKASGYTF TDYVINWVRQAPGQGLEWIGEIYPGSGST FYAQKFQGRATLTADKSTSTAYMEVSSLR SEDTAVYYCTRRMAAMDYWGQGTLVTVSS |
| | 4026 VL-1 | DIQMTQSPSSLSASVGDRVTITCSASSSV SYMHWYQQKPGKAPKLLIYTTSNLASGVP SRFSGSGSGTDFTLTISSLQPEDFATYYC HQWSGYPTFGQGTKLEIK |
| | 4026 VL-2 | DIQLTQSPSSLSASVGDRVTITCSASSSV SYMHWYQQKPGKAPKLLLYTTSNLASGVP SRFSGSGSGTDYTLTISSLQPEDFATYYC HQWSGYPTFGQGTKLEIK |
| | 4026 VL-3 | DIQLTQSPSSLSASVGDRITLTCSASSSV SYMHWYQQKPGKAPKLLLYTTSNLASGVP SRFSGSGSGTDYTLTISSVQPEDFATYYC HQWSGYPTFGQGTKLEIK |
| | 4026 VL-4 | DIQLTQSPSSLSASVGDRITLTCSASSSV SYMHWYQQKPGKAPKLLLYTTSNLASGVP SRFSGSGSGTDYTLTISSVQPEDAATYYC HQWSGYPTFGQGTKLEIK |

Table 1C—CDRs of humanized antibodies

TABLE 1C

CDRs of humanized antibodies
Table 1B

| SEQ ID NO | Name | Sequence |
|---|---|---|
| | CDR H1 | GYTFTDYVIN |
| | CDR H2 | EIYPGSGSTF |
| | CDR H3 | RMAAMDY |
| | CDR L1 | SASSSVSYMH |
| | CDR L2 | TTSNLAS |
| | CDR L3 | HQWSGYPT |

Ten humanized variants of TREM1 antibody were made using the different framework mutations. Table 1C shows the number of framework mutations and the heavy and light chain pairing used in each humanized variant.

TABLE 1C

| mAb | # of Framework mutations (VH + VL) | VH used | VL used |
|---|---|---|---|
| PI-4026 (chimera) | N/A | N/A | N/A |
| PI-4026-1 | 0 (CDR swap only) | 1 | 1 |
| PI-4026-2 | 5 | 2 | 2 |

TABLE 1C-continued

| mAb | # of Framework mutations (VH + VL) | VH used | VL used |
|---|---|---|---|
| PI-4026-3 | 8 | 2 | 3 |
| PI-4026-4 | 9 | 2 | 4 |
| PI-4026-5 | 11 | 3 | 2 |
| PI-4026-6 | 14 | 3 | 3 |
| PI-4026-7 | 15 | 3 | 4 |
| PI-4026-8 | 12 | 4 | 2 |
| PI-4026-9 | 15 | 4 | 3 |
| PI-4026-10 | 16 | 4 | 4 |

Example 2: Production and Characterization of Anti-TREM1 Antibodies

Antibody Production and Characterization

Heavy and light chain expression vectors were transfected into expi293 cells using standard methods. Cells were grown for up to 7 days after which supernatants were harvested for antibody purification. In addition to expi293, antibodies were also produced in expi293 cells that were made deficient in mammalian α1,6-fucosyltransferase (FUT8) by CRISPR/Cas9 editing (Alexander Weiss, University of Toronto). Supernatant pH was adjusted with 1M HEPES pH 7.4 and sodium azide was added to prevent microbial growth. Kan-Cap A resin was used to capture proteins and the antibodies were eluted with 50 mM Citrate pH 3.5, 100 mM NaCl after washing with PBS and PBS containing 1M NaCl. Immediately after elution, the solution was neutralized with 1M Tris (pH 8) containing 0.5M Arginine. Biophysical characterization was conducted on protein that was buffer exchanged to PBS using standard techniques. Protein was quantified by OD280, quantity and concentration was determined using calculated extinction coefficient. Reduced and non-reduced SDS-PAGE (Biorad criterion Tris/Glycine/SDS, 4-20%) or Perkin Elmer GXII capillary electrophoresis system, was used to determine purity and approximate molecular mass. Aggregation status was determined by UHPLC, with detection at 280 nm using a Sepax Zenix-C SEC-300, 3 um, 300 Å, 4.6*150 mm size exclusion column and PBS running buffer.

Human Avid $K_D$ Measurement Using Surface Plasmon Resonance (SPR)

The affinity of human TREM1 binding to PI-4026 variants were measured by SPR on the BIAcore T200 (GE Healthcare, UK). All data were collected at 25° C. 10 mM HEPES pH 7.4, 150 mM NaCl, 3 mM EDTA, 0.05% (v/V) surfactant P20 was used as mobile buffer and for all dilution of mAbs. Anti-mouse Fc was immobilized on a CM4 biosensor chip (GE Healthcare) using amine coupling chemistry. Human chimeric TREM1-mIgG Fc was captured on one flow cell, and another flow cell (used as reference surface) was left blank. A range of concentrations of PI-4026 variants (as analyte, all hIgG1 isotype) were injected through both flow cells in multiple cycles. After each cycle, the surface was regenerated by injecting a glycine HCl buffer (10 mM, pH 2.0). BIAevaluation software was used to perform the kinetic evaluation. Kinetic evaluation was through generation of sensorgrams which were fitted with a 1:1 Langmuir binding model.

Human Monomeric $K_D$ Measurement Using Surface Plasmon Resonance (SPR)

The affinity of human TREM1 binding to PI-4026 variants were measured by SPR on the BIAcore T200 (GE Healthcare, UK). All data were collected at 25° C. 10 mM HEPES pH 7.4, 150 mM NaCl, 3 mM EDTA, 0.05% (v/V) surfactant P20 was used as mobile buffer and for all dilution of mAbs. Anti-human Fc was immobilized on a CM4 biosensor chip (GE Healthcare) using amine coupling chemistry. PI-4026 variants (all hIgG1 isotype) were captured by the anti-human Fc on one flow cell, and another flow cell (used as reference surface) was left blank. A range of concentrations of His tagged-human TREM1 (as analyte) were injected through flow cells with captured PI-4026 variants and the reference cell in multiple cycles. After each cycle, the surface was regenerated by injecting a 3M $MgCl_2$. BIAevaluation software was used to perform the kinetic evaluation. Kinetic evaluation was through generation of sensorgrams which were fitted with a 1:1 Langmuir binding model.

Differential Scanning Fluorimetry

The melting temperatures of PI-4026 variants were determined by nano differential scanning fluorimetry (DSF). PI-4026 variant samples were run at a ramp rate of 1.5° C./min from 20° C. to 100° C. Samples were loaded into the nanoDSF grade capillaries by dipping into the sample. To minimize evaporation during the thermal scan, both ends of the capillary were sealed with an inert oil-based liquid rubber sealing paste.

$T_m$ was calculated from the changes in tryptophan fluorescence intensity or the ratio of tryptophan emission at 350 and 330 nm which accurately monitor the conformational changes during unfolding of the protein as a function of temperature. $T_m$ is the temperature at which the protein is 50% unfolded.

Cell Binding

HEK293 control cells in log phase growth were harvested from culture, washed, and plated in 96 well U bottom plates at $1 \times 10^5$ cells/well. Titrations of the indicated PI-4026 variants and an isotype control were added to the cells and incubated for 30 mins on ice. An Alexa 647—conjugated anti-human Fcγ secondary antibody (Jackson Immunoresearch) diluted at 1:500 was used to detect bound primary antibody. The secondary antibody was incubated with the cells for 30 mins on ice. Cells were then washed and stained with Zombie NIR (Biolegend) to determine cell viability for 15 mins at room temperature. Fluorescence signal from bound antibody was assessed by flow cytometry (ThermoFisher Attune NxT).

Results

Table 2 shows antibody avidity, monomeric affinity, cell binding, and DSF results for each of the humanized TREM1 antibodies.

Based on the results shown PI-4026-5 was selected for further characterization and testing.

Next, the affinity of human TREM1 binding to PI-4026-5 was further measured by SPR on the BIAcore T200 (GE Healthcare). All data were collected at 25° C. 10 mM HEPES pH 7.4, 150 mM NaCl, 3 mM EDTA, 0.05% (v/V) surfactant P20 was used as mobile buffer and dilutions of PI-4026-5. Anti-mouse Fc was immobilized on a CM4 biosensor chip (GE Healthcare) using amine coupling chemistry. Human chimeric TREM1-mIgG Fc was captured on one flow cell, and another flow cell, used as reference surface, was left blank. A range of concentrations of PI-4026-5 were injected through both flow cells in multiple cycles. After each cycle, the surface was regenerated by injecting a glycine HCl buffer (10 mM, pH 2.0). BIAevaluation software was used to perform the kinetic evaluation. Kinetic evaluation was through generation of sensorgrams which were fitted with a 1:1 Langmuir binding model. The SPR binding kinetics of PI-4026-5 are shown in FIG. 1.

Example 3: Cellular Binding of Anti-TREM1 Antibodies

Species Specificity of Humanized TREM1 Antibodies hTREM1 Overexpressing Cells

HEK293 control or human TREM1 over-expressing cells in log phase growth were harvested from culture, washed, and plated in 96 well U bottom plates at $1 \times 10^5$ cells/well. Titrations of unconjugated hIgG1 control or PI-4026-5 antibodies at the indicated concentrations were added to the cells and incubated for 30 mins on ice. An Alexa 647-conjugated anti-human Fcγ secondary antibody (Jackson Immunoresearch) diluted at 1:500 was used to detect bound primary antibody. The secondary antibody was incubated with the cells for 30 mins on ice. Cells were then washed and stained with Zombie NIR (Biolegend) to determine cell viability for 15 mins at room temperature. Fluorescence signal from bound antibody was assessed by flow cytometry (ThermoFisher Attune NxT). EC50 values were calculated in Prism Software (Graphpad).

CynoTREM1 and mTREM1 Overexpressing Cells

HEK293 over-expressing cynomolgus or mouse TREM1 in log phase growth were harvested from culture, washed, and plated in 96 well U bottom plates at $1 \times 10^5$ cells/well. Titrations of unconjugated hIgG1 control or PI-4026-5 antibodies at the indicated concentrations were added to the cells and incubated for 30 mins on ice. An Alexa 647-conjugated anti-human Fcγ secondary antibody (Jackson Immunoresearch) diluted at 1:500 was used to detect bound

TABLE 2

| Anti-hTREM1 mAb | Avid $K_D$ (nM) | Monomeric $K_D$ (nM) | Monomeric '$K_{off}$' (M) | Background binding | $EC_{50}$ (nM) Neutrophils | DSF (Tm2, ° C.) |
|---|---|---|---|---|---|---|
| PI-4026 chimera | <0.1 | 1.13 | 4.92e−4 | N | 0.46 | — |
| PI-4026-1 | Poor fit | Poor fit | Poor fit | Y | 3.25 | — |
| PI-4026-2 | <0.1 | 2.65 | 1.04e−3 | N | 0.33 | — |
| PI-4026-3 | <0.1 | 2.42 | 1.11e−3 | N | 0.30 | — |
| PI-4026-4 | <0.1 | 3.63 | 1.60e−3 | N | 0.27 | — |
| PI-4026-5 | <0.1 | 2.01 | 4.38e−4 | N | 0.21 | 82.73 |
| PI-4026-6 | <0.1 | 1.55 | 6.99e−4 | N | 0.26 | 82.47 |
| PI-4026-7 | <0.1 | 2.31 | 7.84e−4 | N | 0.19 | 76.17 |
| PI-4026-8 | <0.1 | 2.51 | 5.17e−4 | Y | 0.22 | — |
| PI-4026-9 | <0.1 | 2.83 | 5.19e−4 | Y | 0.17 | — |
| PI-4026-10 | <0.1 | 2.77 | 8.34e−4 | Y | 0.20 | — | primary antibody. The secondary antibody was incubated with the cells for 30 mins on ice. Cells were then washed and stained with Zombie NIR (Biolegend) to determine cell viability for 15 mins at room temperature. Fluorescence signal from bound antibody was assessed by flow cytometry (ThermoFisher Attune NxT). EC50 values were calculated in Prism Software (Graphpad).

Cellular Binding

Fresh blood from human donors (Stanford Blood Centre) was red cell lysed and washed to enrich PBMC and granulocyte content. Cells were plated and Fc receptors were blocked with a combination of human serum (Jackson Immunoresearch), human FcX (Biolegend), and a peptide-based FcR block solution (Innovex Biosciences). Cells were also stained with Zombie NIR (Biolegend) to determine cell viability. After staining with Zombie NIR, cells were stained with a flow cytometry cocktail encompassing markers for major immune subsets and titrations of either human IgG1 control or PI-4026-5. All antibodies used were directly conjugated. Data was acquired by flow cytometry (ThermoFisher Attune NxT). EC50 values were calculated in Prism Software (Graphpad).

Results

Figure 2A:
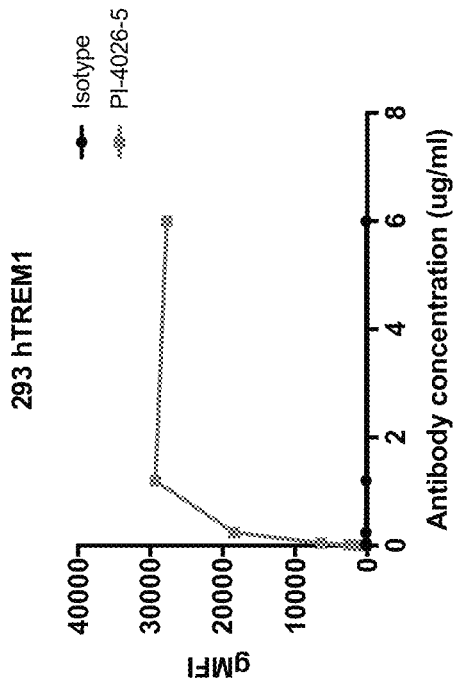
FIG. 2A shows the binding of PI-4026-5 to HEK293 control cells.
Figure 2B:
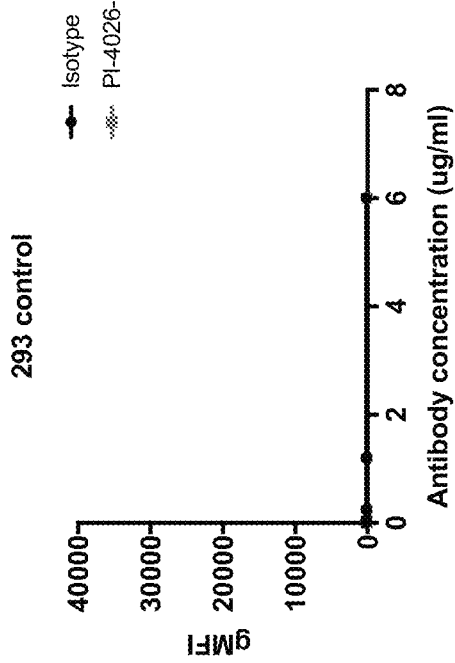
FIG. 2B shows the binding of PI-4026-5 to human TREM1 over-expressing HEK293 cells.

As shown in FIGS. 2A and 2B, PI-4026-5 binds to human TREM1 over-expressing cells with high specificity, but does not bind to cells that do not overexpress human TREM1. Furthermore, PI-4026-5 binds to neutrophils and monocytes in human peripheral blood (FIGS. 3A and 3B).

To confirm the species specificity of the humanized TREM1 antibodies, binding of PI-4026-5 to cynomolgus and mouse TREM1 was assessed.

Figure 4B:
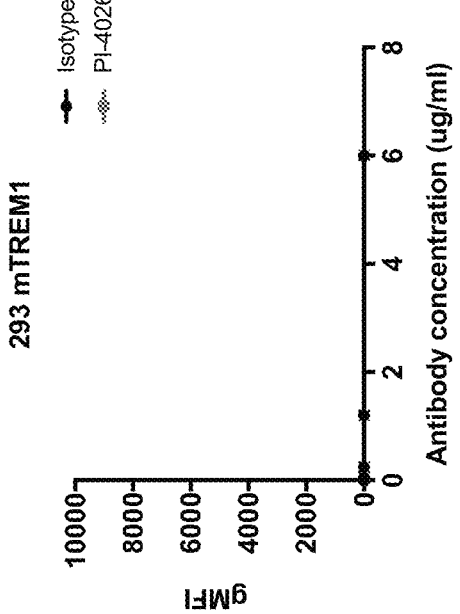
FIG. 4B shows no binding of PI-4026-5 to cells expressing mouse TREM1.
Figure 4A:
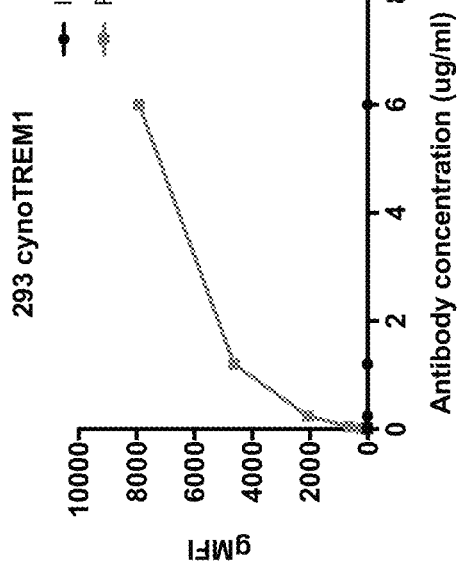
FIG. 4A show the binding of PI-4026-5 to cells expressing cynomolgus TREM1.

As shown in FIGS. 4A and 4B, PI-4026-5 binds to cynomolgus TREM1 but not mouse TREM1 over-expressing cells.

Example 4: Induction of ADCC and ADCP by Anti-TREM1 Antibodies

ADCC and ADCP Assays

HEK293 target cells over-expressing human TREM1 were incubated with a titration of PI-4026-5 or a hIgG1 isotype control at the indicated concentrations in flat bottom white 96 well plates (ThermoFisher). After a 15 minute incubation at room temperature, hCD16 or hCD32 expressing NFAT-luciferase reporter Jurkat cells (Promega, Madison, WI) were added to the target cell/antibody mixture at a ratio of 3:1. After the addition of reporter cells, the assay was incubated at 37° c. in 5% $CO_2$ atmosphere for 6 hrs. The amount of luciferase activity was determined by exposure to luciferase substrate (Promega, Madison, WI) and detected by a luminescence reader (EnVision, Perkin Elmer). EC50 values were calculated in Prism Software (Graphpad).

GFP-positive expi293 parental or human TREM1 over-expressing cells were incubated with titrations of unconjugated hIgG1 control or PI-4026-5 antibodies for 15-30 mins at room temperature. Without washing, human macrophages polarized from CD14+ monocytes labelled with Cell Trace Violet (ThermoFisher) were then added to the expi293 and antibody mixture at a ratio of 1:1. The assay was incubated for 6 hrs at 37°c in a 5% $CO_2$ atmosphere, after which the assay was assessed by flow cytometry (ThermoFisher Attune NxT). ADCP was measured by enumerating the number of GFP positive and Cell Trace Violet positive macrophages from the singlet gate. EC50 values were calculated in Prism Software (Graphpad).

Results

Figures 5A, 5B:
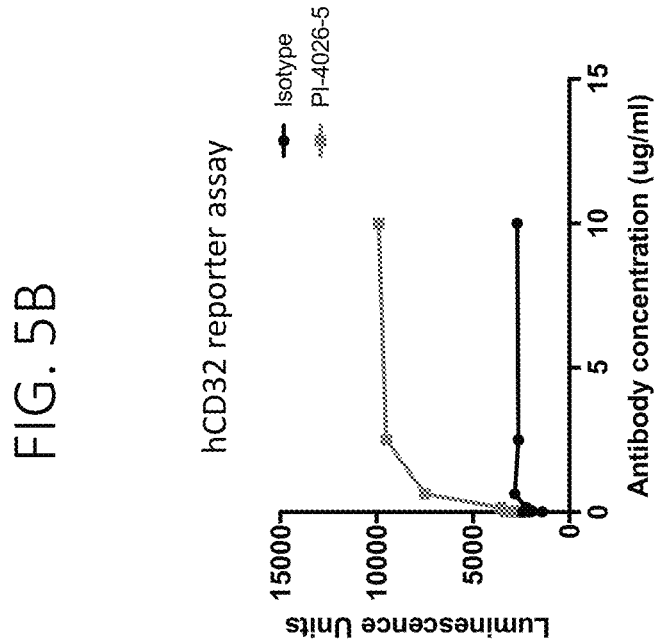
FIG. 5A show FcγR signaling induced by PI-4026-5 using the hCD16 reporter assay systems.
FIG. 5B show FcγR signaling induced by PI-4026-5 using the hCD32 reporter assay systems.

As shown in FIGS. 5A and 5B, PI-4026-5 induces downstream FcγR-mediated signaling in a dose-dependent. TREM1-specific manner. FIG. 5A shows induction of FcγR signaling using the hCD16 reporter assay system, and FIG. 5B shows induction of FcγR signaling using the hCD32 reporter assay system.

Next, the ability of the humanized TREM1 antibody to induce ADCP by primary human macrophages was assessed.

Figure 6A:
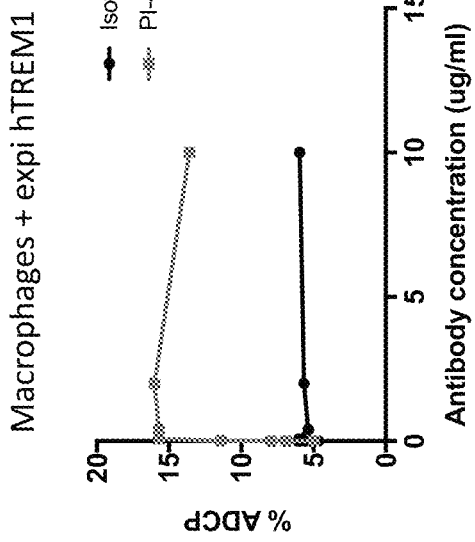
FIG. 6A shows that PI-4026-5 does not induces ADCP of parental expi293 cells by primary human macrophages.
Figure 6B:
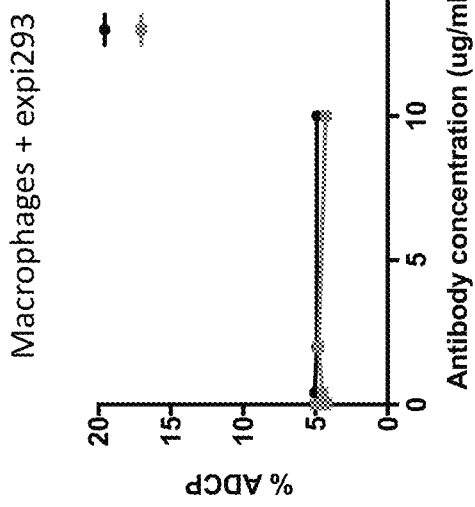
FIG. 6B show that PI-4026-5 induces ADCP of expi293 cells expressing hTREM1 by primary human macrophages.

As shown in FIGS. 6A and 6B, PI-4026-5 induces ADCP by primary human macrophages of expi293 cells over-expressing hTREM1 (FIG. 6B) but not parental expi293 cells (FIG. 6A).

Example 5: Crystallization of the Chimera PI-4026 Fab with Human TREM1 IgV

Protein Crystallization

Diffraction quality crystals of the SEC purified complex of the hTREM1 IgV:chimera PI-4026 Fab were obtained by sitting drop vapor diffusion at 20° C. Crystals were cryo-protected and X-ray diffraction data was collected at the European Synchrotron (ESRF) in Grenoble, France. The structure of the hTREM1 IgV:PI-4026 Fab complex was determined by molecular replacement using the program MOLREP in CCP4. The final model was refined to a Rwork and Rfree of 16.4% and 21.6%, respectively, at a resolution of 1.93 Å. Analysis of final refined structure showed one PI-4026 Fab interacting with one TREM1 IgV molecule.

Results

FIG. 7A-E show the interaction of specific residues in each CDR of the PI-4026 Fab with specific residues of the TREM1 IgV domain. In each panel, the dark grey structure represents the indicated antibody CDR and the light grey structure represents the TREM1 IgV domain. Interacting residues are denoted with the single letter amino acid nomenclature followed by their position in the human TREM1 sequence, or the PI-4026 heavy or light chain. Dotted lines indicate hydrogen bonds between the CDR residues and TREM1 IgV residues. The numbers associated with dotted lines are the distances between residues measured in angstroms (Å). CDRL2 of the PI-4026 Fab was not critical for the interaction with the TREM1 IgV domain. All figures and interactions were generated and modelled using PyMOL software.

Figure 7A:
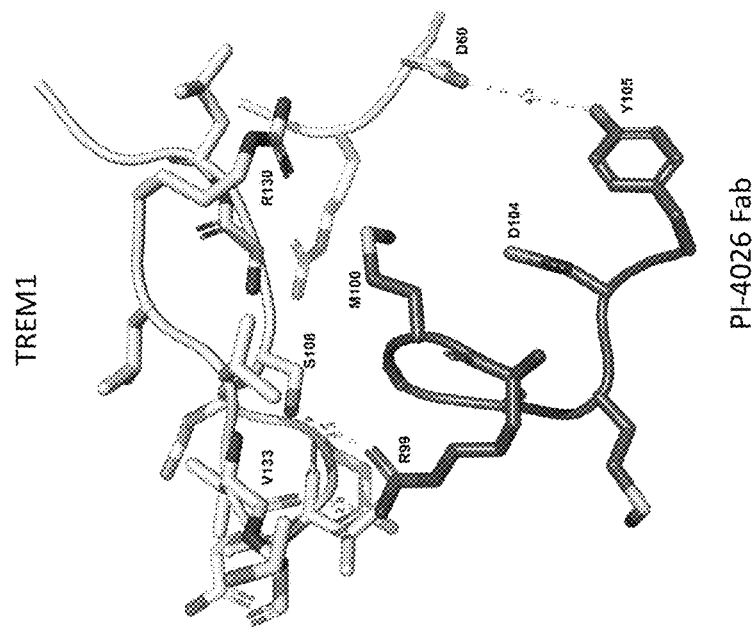
FIG. 7A shows the interaction of residues within the CDRH1 of the PI-4026 Fab and the TREM1 IgV domain.
Figure 7B:
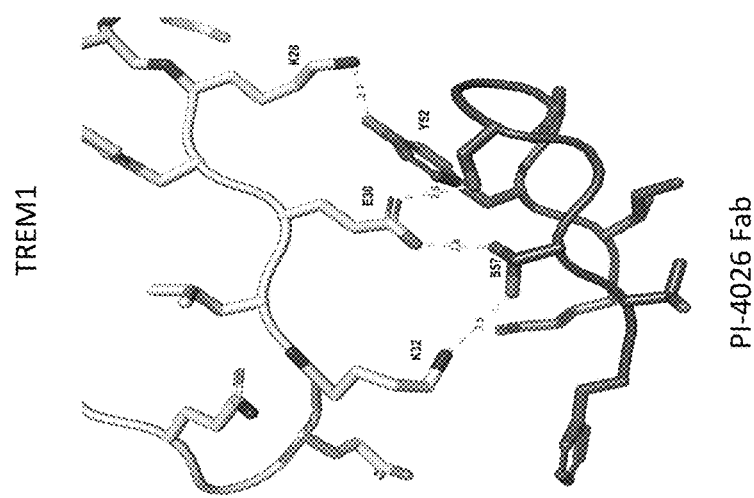
FIG. 7B shows the interaction of residues within the CDRH2 of the PI-4026 Fab and the TREM1 IgV domain.
Figure 7C:
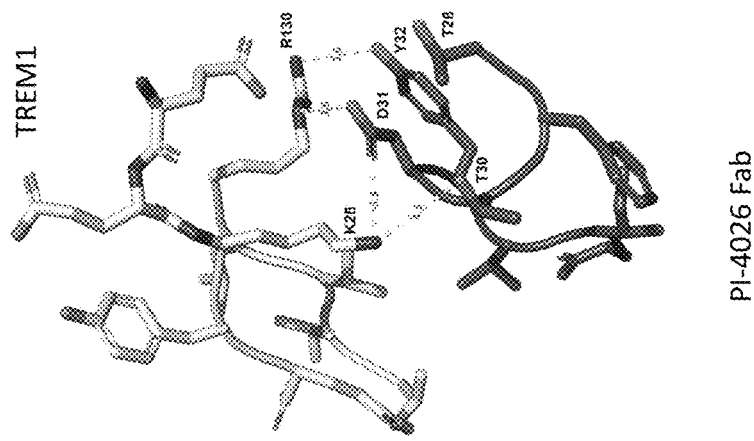
FIG. 7C shows the interaction of residues within the CDRH3 of the PI-4026 Fab and the TREM1 IgV domain.
Figure 7E:
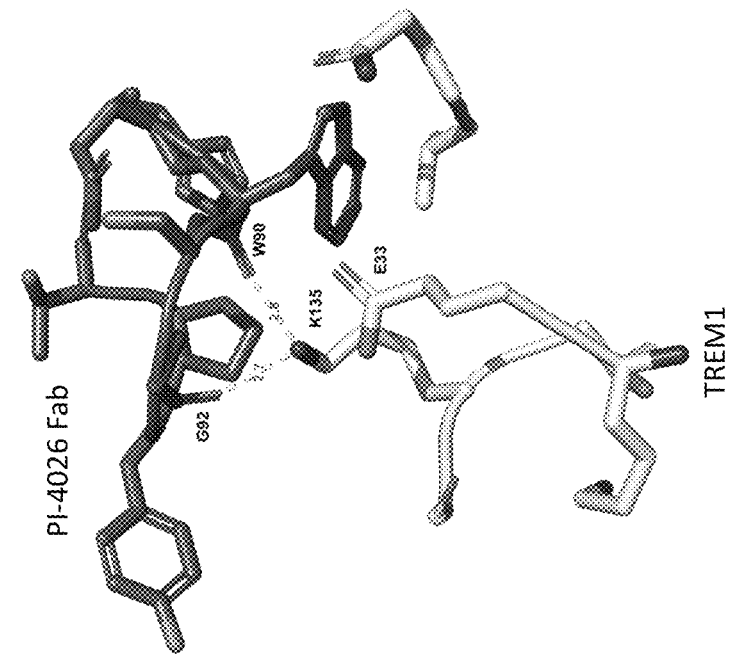
FIG. 7E shows the interaction of residues within the CDRL3 of the PI-4026 Fab and the TREM1 IgV domain.
Figure 7D:
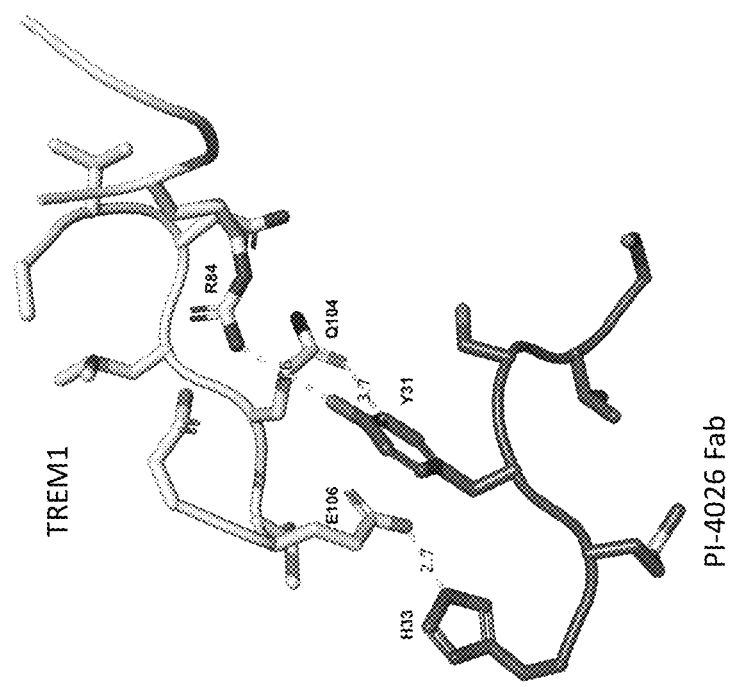
FIG. 7D shows the interaction of residues within the CDRL1 of the PI-4026 Fab and the TREM1 IgV domain.

FIG. 7A shows the interaction of residues within the CDRH1 of the PI-4026 Fab and the TREM1 IgV domain. FIG. 7B shows the interaction of residues within the CDRH2 of the PI-4026 Fab and the TREM1 IgV domain. FIG. 7C shows the interaction of residues within the CDRH3 of the PI-4026 Fab and the TREM1 IgV domain. FIG. 7D shows the interaction of residues within the CDRL1 of the PI-4026 Fab and the TREM1 IgV domain. FIG. 7E shows the interaction of residues within the CDRL3 of the PI-4026 Fab and the TREM1 IgV domain.

The epitope sequence of the chimera PI-4026 antibody is the non-contiguous residues encompassing amino acids 21-34 (SEQ ID NO: 42), 103-109 (SEQ ID NO: 43), and 128-136 (SEQ ID NO: 44) of human TREM1.

Example 6: CDRH3 Mutation to Reduce Oxidation Risk and Characterization of Variant CDRH3 mAbs $H_2O_2$ Oxidation Assessment by Size Exclusion Chromatography (SEC)

Analysis of oxidation was achieved by incubating PI-4026-5 and PI-4026-7 variants in the indicated concentrations of $H_2O_2$ for 1 h at 40° C. at a final antibody concentration of 1 mg/mL. Samples were analyzed by SEC at various concentrations and time points using ThermoFisher analytical UHPLC system on a Superdex 200 Increase 10/300 GL column (GE Healthcare). PBS pH 7.4 was used as the mobile phase buffer and the flow rate was 0.5 mL/min. Data were analyzed and the AUC of peaks at A280 were integrated using Chromeleon 7 instrument software (ThermoFisher).

Cynomolgus Avid KD

The affinity of cynomolgus TREM1 binding to the PI-4026-5 variants were measured by SPR on the BIAcore T200 (GE Healthcare). All data were collected at 25° C. 10 mM HEPES pH 7.4, 150 mM NaCl, 3 mM EDTA, 0.05% (v/V) surfactant P20 was used as mobile buffer and for all dilution of mAbs. Anti-mouse Fc was immobilized on a CM4 biosensor chip (GE Healthcare) using amine coupling chemistry. Chimeric cynomolgus TREM1-mIgG Fc was captured on one flow cell and another flow cell (used as reference surface) was left blank. A range of concentrations of PI-4026-5 variants (as analytes, hIgG1 isotype) were injected through flow cells with captured cynomolgus TREM1-mIgG Fc and the reference cell. After each cycle, the surface was regenerated by injecting a glycine HCl buffer (10 mM. pH 2.0). BIAevaluation software was used to perform the kinetic evaluation. Kinetic evaluation was through generation of sensorgrams which were fitted with a 1:1 Langmuir binding model.

Afucosylated Antibody Production

Afucosylated antibodies were produced by transfection of heavy and light chain plasmids of the antibody of interest (e.g. PI-4026-5) into expi293 cells which were made deficient in mammalian α1,6-fucosyltransferase (FUT8) by CRISPR/Cas9 editing (Alexander Weiss, University of Toronto). Once cells were transfected, they were expanded for up to 7 days after which media was harvested and antibodies purified by a one-step protein A column purification step (HiTrap MabSelect SuRe, GE Healthcare). Antibodies were subsequently buffer exchanged into PBS and assessed for endotoxin (LAL Endotoxin test, Charles River Laboratories), concentration (Nanodrop, ThermoFisher Scientific), and any aggregation by UHPLC (ThermoFisher Scientific). Antibodies are SEC purified to monomer dependent on their aggregation properties (monomericity below 95%). Afucosylation is validated by a western blot with an antibody against Lens Culinaris Agglutination (LCA) antigen (L-1040-10, Vector Biolabs) or assessing the full glycan profile of the antibody of interest (Bionova Scientific).

Results

Figure 8:
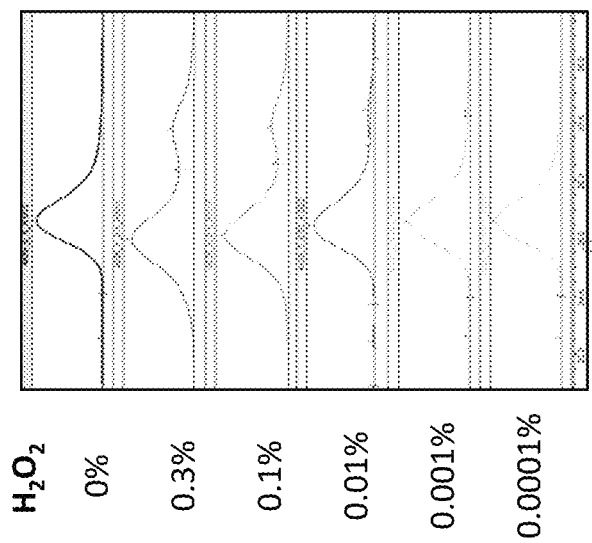
FIG. 8 shows the SEC profiles of PI-4026-5 after exposure to differential concentrations of $H_2O_2$.

As shown in FIG. 8, PI-4026-5 has an oxidation risk at Met100 in CDRH3 (RMAAMDY) as assessed by SEC. The percent heterogeneity of the antibody increases and the percent monomer decreases in an $H_2O_2$ dose dependent manner. This is indicated by the double peaks observed in the SEC profiles of the samples treated with 0.3%, 0.1%, and 0.01% $H_2O_2$. Table 3 provides quantification of the SEC results.

TABLE 3

| % $H_2O_2$ | % monomer | % heterogeneity |
|---|---|---|
| 0 | 100 | 0 |
| 0.3 | 60.43 | 39.57 |
| 0.1 | 67.57 | 32.43 |
| 0.01 | 86.63 | 13.37 |
| 0.001 | 96.73 | 3.27 |
| 0.0001 | 100 | 0 |

To address this, the methionine at residue 100 in PI-4026-7 was mutated to isoleucine and the mutant antibody was tested as described above. As shown in Table 4, mutation of the methionine residue (RMAAMDY (SEQ ID NO: 25)) to isoleucine (RIAAMDY (SEQ ID NO: 30)) eliminated the oxidation risk. Incubation of the PI-4026-7M100I antibody with $H_2O_2$ did not result in any increase in protein heterogeneity.

TABLE 4

|  | PI-4026-7-M100 | | PI-4026-7-M100I | |
|---|---|---|---|---|
| % $H_2O_2$ | % monomer | % heterogeneity | % monomer | % heterogeneity |
| 0 | 100 | 0 | 100 | 0 |
| 0.3 | 54.37 | 45.63 | 100 | 0 |
| 0.1 | 71.74 | 28.26 | 100 | 0 |
| 0.01 | 86.81 | 13.19 | 100 | 0 |
| 0.001 | 100 | 0 | 100 | 0 |
| 0.0001 | 100 | 0 | 100 | 0 |

Next, additional mutations were made in PI-4026-5 to determine one or more preferred mutation(s) at this residue position for clinical development. M100 was mutated to isoleucine (M100I), glutamic acid (M100E), leucine (M100L), or glutamine (M100Q). These mutations were rationally selected based on an analysis of the solved crystal structure of the interaction between the PI-4026 Fab and the TREM1 IgV domain (Example 5). Table 5 shows a summary of the CDR-H3 substitutions and sequences.

TABLE 5

| M100x substitutions | CDRH3 mutation | CDRH3 sequence |
|---|---|---|
| PI-4026-5-M100 | None | RMAAMDY |
| PI-4026-5-M100I | M→I | RIAAMDY |
| PI-4026-5-M100E | M→E | REAAMDY |
| PI-4026-5-M100L | M→L | RLAAMDY |
| PI-4026-5-M100Q | M→Q | RQAAMDY |

Each PI-4026-5 CDRH3 mutant was characterized as previously described in Examples 2, 3, and 4 for binding affinity to human and cynomolgus TREM1, SEC, cellular binding and $EC_{50}$ to human monocytes, DSF, and FcγR signaling using the hCD16 reporter assay system.

In addition, binding of the antibodies to cells overexpressing cynomolgus TREM1 was assessed. The results for the PI-4026-5 CDRH3 mutants are summarized in Table 6.

TABLE 6

| Anti-hTREM1 mAb (fucosylated) | Human Avid $K_D$ (nM) | Cyno Avid $K_D$ (nM) | % Monomer SEC | Human Monomeric $K_D$ (nM) | Human Monomeric '$K_{off}$' (M) | Background binding | $EC_{50}$ (nM) Monocytes (Human) | $EC_{50}$ (nM) Cyno TREM1 cells | hCD16 ADCC assay $EC_{50}$ (nM) | DSF (Tm2, °C) |
|---|---|---|---|---|---|---|---|---|---|---|
| PI-4026-5-M100 (parent) | 0.68 | 1.76 | >95 | 4.81 | 6.67e-4 | N | 0.3 | 4.61 | 2.54 | 77.4 |
| PI-4026-5-M100I | 0.88 | 11.8 | >95 | 10.2 | 1.31e-3 | N | 0.94 | 28.62 | 6.92 | 76.7 |
| PI-4026-5-M100E | 0.19 | 6.19 | >95 | 3.33 | 4.76e-4 | Y | 0.45 | 57.99 | 3.18 | 77.6 |
| PI-4026-5-M100L | 0.27 | 1.43 | >95 | 4.93 | 6.33e-4 | N | 0.67 | 4.85 | 5.86 | 77.3 |
| PI-4026-5-M100Q | 0.37 | 0.66 | >95 | 5.61 | 9.06e-4 | N | 0.65 | 6.04 | 8.60 | 78.1 |

Next, afucosylated PI-4026-5 CDRH3 mutant antibodies were similarly characterized.

The results for the afucosylated PI-4026-5 CDRH3 mutants are summarized in Table 7.

TABLE 7

| Anti-hTREM1 mAb (afucosylated) | Human Avid $K_D$ (nM) | Cyno Avid $K_D$ (nM) | % Monomer SEC | Human Monomeric $K_D$ (nM) | Human Monomeric '$K_{off}$' (M) | Background binding | $EC_{50}$ (nM) Monocytes (Human) | $EC_{50}$ (nM) Cyno TREM1 cells | hCD16 ADCC assay $EC_{50}$ (nM) | DSF (Tm2, °C) |
|---|---|---|---|---|---|---|---|---|---|---|
| PI-4026-5-M100 (parent) | 0.55 | 2.99 | >95 | 6.21 | 9.26e-4 | N | 0.60 | 6.61 | 0.36 | 77.5 |
| PI-4026-5-M100I | 0.88 | 13.4 | >95 | 10.1 | 1.31e-3 | N | 1.06 | 22.02 | 0.39 | 76.7 |
| PI-4026-5-M100E | <0.1 | 8.66 | >95 | 3.74 | 5.05e-4 | Y | 0.3 | 55.97 | 0.33 | 77.2 |
| PI-4026-5-M100L | 0.15 | 1.41 | >95 | 4.34 | 7.46e-4 | N | 0.75 | 3.62 | 0.28 | 76.7 |
| PI-4026-5-M100Q | 0.39 | 0.45 | >95 | 6.32 | 9.68e-4 | N | 1.32 | 2.07 | 0.29 | 77.2 |

PI-4026-5-M100I and PI-4026-5-M100E showed higher non-specific binding to non-TREM1 expressing cells and lost the ability to bind to cells that express cynomolgus TREM1. PI-4026-5-M100L and PI-4026-5-M100Q were chosen for further development as they retained the qualities of PI-4026-5-M100 (parent antibody) such as binding to human and cynomolgus TREM1, specificity, biophysical characteristics, and functionality. Importantly, afucosylated PI-4026-5-M100L and PI-4026-5-M100Q showed similar biophysical and binding characteristics compared to their fucosylated counterparts except for significantly enhanced FcγR signaling in the hCD16 reporter assay.

Example 7: Cellular Binding and Induction of ADCC and ADCP Signaling by Fucosylated and Afucosylated PI-4026-5 Variant CDRH3 Antibodies Human Cell Binding Assay Fresh blood from human donors (Stanford Blood Centre) was red cell lysed and washed to enrich PBMC and granulocyte content. Cells were plated and Fc receptors were blocked with a combination of human serum (Jackson Immunoresearch), Human FcX (Biolegend), and a peptide-based FcR block solution (Innovex Biosciences). Cells were also stained with Zombie NIR (Biolegend) to determine cell viability. After Zombie NIR, cells were stained with a flow cytometry cocktail with markers for major immune subsets, and a titration of either human IgG1 control, PI-4170, PI-4026-5, or PI-4026-5 mutants that contain specific mutations at residue 100 of the heavy chain. PI-4026-5 and PI-4026-5 mutants were either fully fucosylated or afucosylated. All antibodies used were directly conjugated and data was acquired by flow cytometry (ThermoFisher Attune NxT). EC50 values were calculated in Prism Software (Graphpad).

Cynomolgus Cell Binding Assay

Fresh cynomolgus monkey blood (Worldwide Primates Inc) was red cell lysed and washed to enrich PBMC and granulocyte content. Cells were plated and Fc receptors were blocked with a combination of human serum (Jackson Immunoresearch) and a peptide-based FcR block solution (Innovex Biosciences). Cells were also stained with Zombie NIR (Biolegend) to determine cell viability. After Zombie NIR, cells were stained with a flow cytometry cocktail with markers for major immune subsets, and a titration of either human IgG1 control, PI-4170, PI-4026-5, or PI-4026-5 mutants that contain specific mutations at residue 100 of the heavy chain. PI-4026-5 and PI-4026-5 mutants were either fully fucosylated or afucosylated. All antibodies used were directly conjugated and data was acquired by flow cytometry (ThermoFisher Attune NxT). EC50 values were calculated in Prism Software (Graphpad).

ADCC and ADCP Assays

Figure 9A:
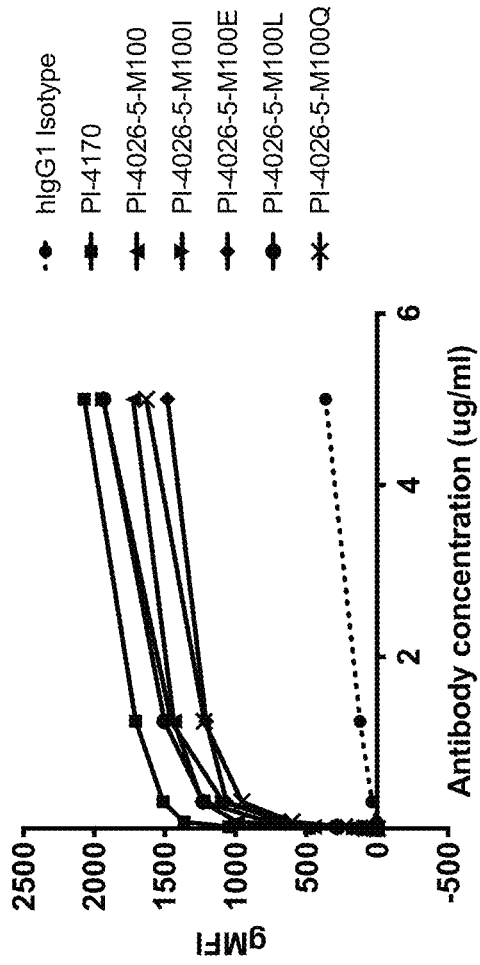
FIG. 9A shows that fucosylated PI-4026-5 antibodies bind to human peripheral monocytes.
Figure 9B:
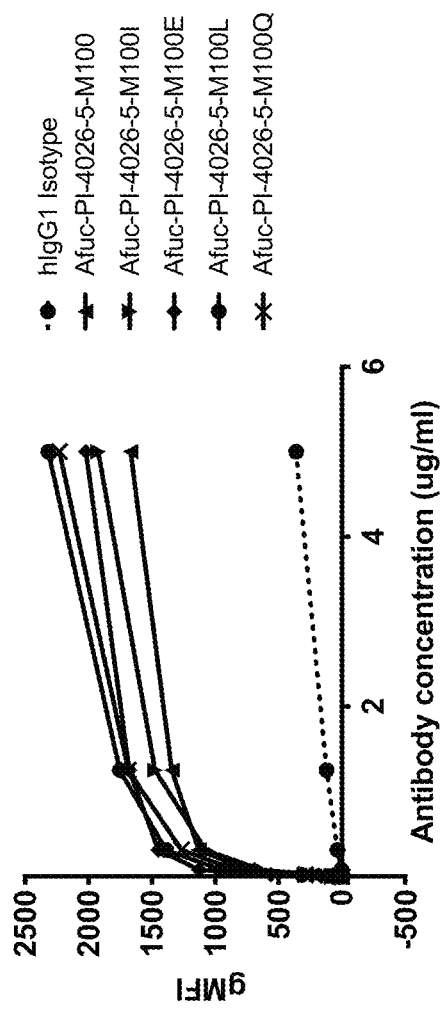
FIG. 9B shows that afucosylated PI-4026-5 antibodies bind to human peripheral monocytes.
Figure 10A:
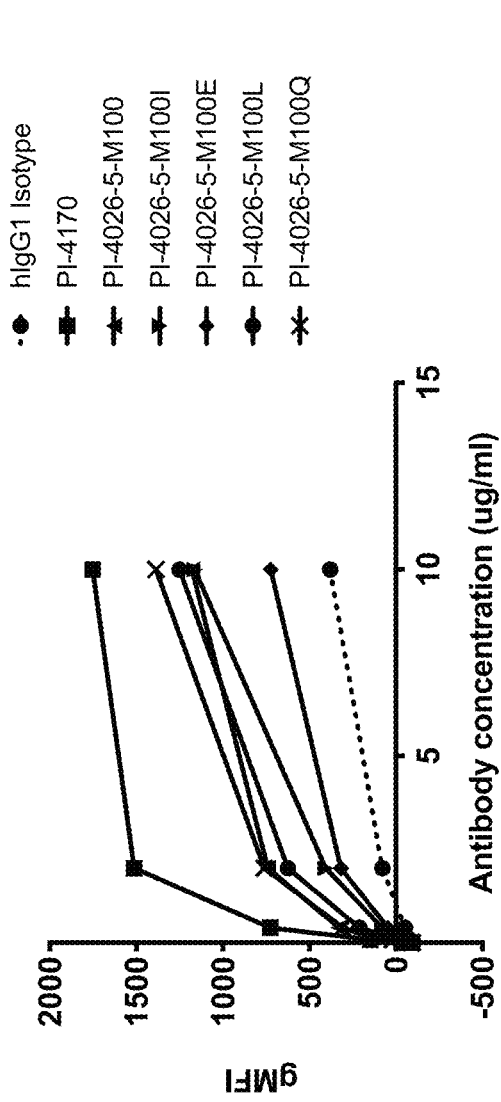
FIG. 10A shows that fucosylated PI-4026-5 antibodies bind to cynomolgus peripheral monocytes.
Figure 10B:
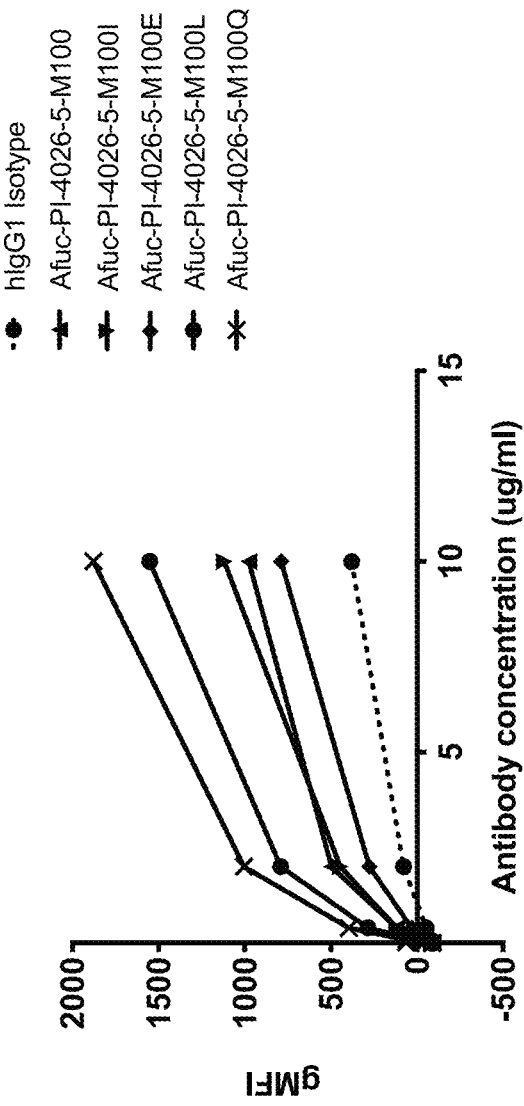
FIG. 10B show that afucosylated PI-4026-5 antibodies bind to cynomolgus peripheral monocytes.

HEK293 target cells over-expressing human TREM1 were incubated with a titration of PI-4170, PI-4026-5, PI-4026-5 mutants or a hIgG1 isotype control in fucosylated or afucosylated format at the indicated concentrations in flat bottom white 96 well plates (ThermoFisher). After a 15 minute incubation at room temperature, hCD16 expressing NFAT-luciferase reporter Jurkat cells (Promega, Madison, WI) were added to the target cell/antibody mixture at a ratio of 3:1. After the addition of reporter cells, the assay was incubated at 37° c. in 5% $CO_2$ atmosphere for 6 hrs. The amount of luciferase activity was determined by exposure to luciferase substrate (Promega, Madison, WI) and detected by a luminescence reader (Envision, Perkin Elmer). EC50 values were calculated in Prism Software (Graphpad).
Results As shown in FIGS. 9A and 9B the fucosylated PI-4026-5 antibodies and afucosylated PI-4026-5 antibodies bind to human peripheral monocytes. FIG. 9A shows the binding of the fucosylated antibodies, while FIG. 9B shows the binding of the afucosylated antibodies. Similarly, the fucosylated PI-4026-5 antibodies and afucosylated PI-4026-5 antibodies bind to cynomolgus monocytes (FIGS. 10A and 10B). The PI-4026-5-M100L and PI-4026-5-M100Q CDRH3 variants showed the best binding to the cynomolgus monocytes.

Figure 11A:
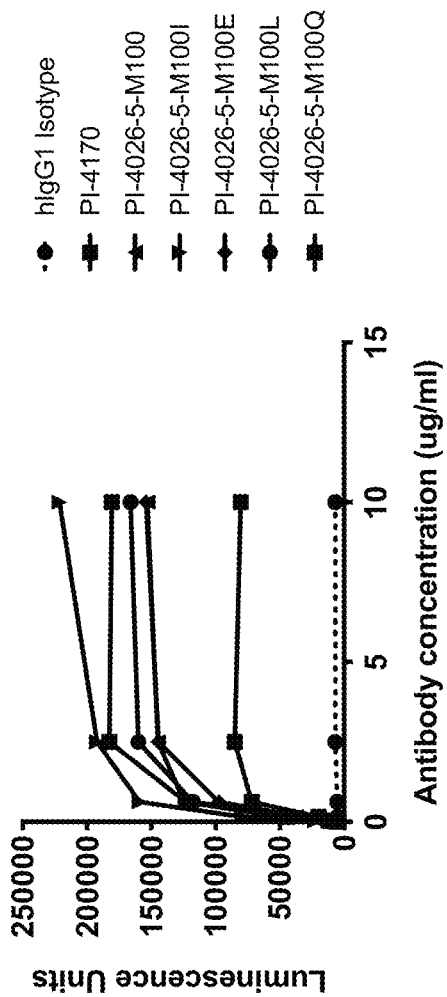
FIG. 11A shows FcγR signaling induced by fucosylated PI-4026-5 using the hCD16 reporter assay system.
Figure 11B:
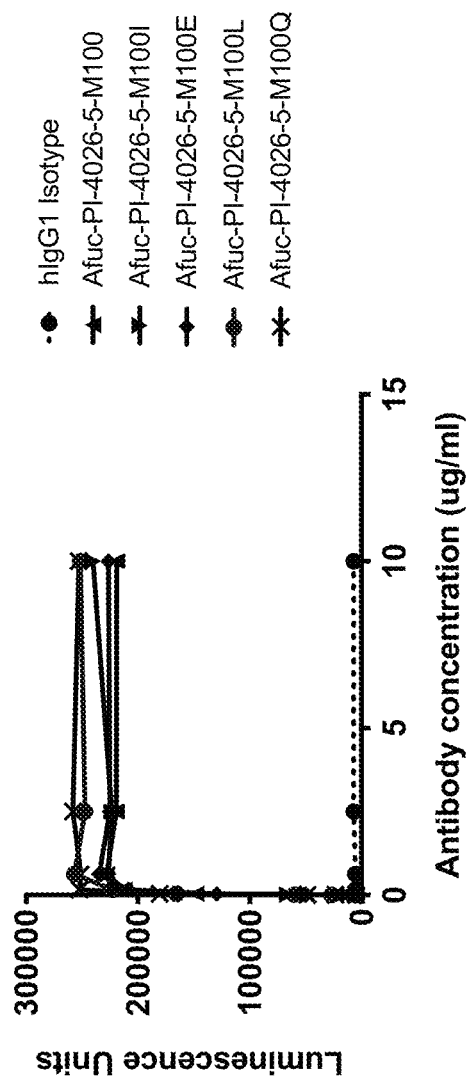
FIG. 11B show FcγR signaling induced by afucosylated PI-4026-5 antibodies using the hCD16 reporter assay system.

In addition, afucosylation of the antibodies resulted in increased FcγR signaling through hCD16 as compared to fucosylated antibodies (FIGS. 11A and 11B). FIG. 11A shows the FcγR signaling activity of the fucosylated antibodies, while FIG. 11B shows the FcγR signaling activity of the afucosylated antibodies.

Example 8: Biochemical Characterization of PI-4026-5-M100L and PI-4026-5-M100Q Antibodies Based on the previous data, two afucosylated CDRH3 mutant antibodies were further characterized using various biochemical assays. These were afucosylated PI-4026-5-M100L, renamed PI64052, and afucosylated PI-4026-5-M100Q, renamed PI64062.

Antibody $K_D$ for human and cynomolgus cells were determined as previously described.
Aggregation/Stability (Size Exclusion Chromatography/SEC)

Afucosylated PI-4026-5 M100L (PI64052) and afucosylated PI-4026-5 M100Q (PI64062) were analyzed by SEC at various concentrations and time points using ThermoFisher analytical UHPLC system on a Superdex 200 Increase 10/300 GL column (GE Healthcare). PBS pH 7.4 was used as the mobile phase buffer and the flow rate was 0.5 mL/min. Data were analyzed and the AUC of peaks at A280 were integrated using Chromeleon 7 instrument software (ThermoFisher).
Aggregation/Stability (Dynamic Light Scattering "DLS")

Data for afucosylated PI-4026-5-M100L (PI64052) and afucosylated PI-4026-5-M100Q (PI64062) at the indicated concentrations and time points were acquired at 37° C. using the temperature controlled DynaPro Plate Reader (Wyatt) equipped with an 830 nm laser. Samples were loaded on a 384-well plate to enable automated, high throughput data collection. The scattered light was monitored at 169ºC. DYNAMICS software was used to analyze and calculate the hydrodynamic diameter as well as the polydispersity index.
Differential Species & Relative Hydrophobicity (Hydrophobic Interaction Chromatography/HIC)

Afucosylated PI-4026-5-M100L (PI64052) and afucosylated PI-4026-5-M100Q (PI64062) were analyzed by HIC using an analytical UHPLC system on a MAbPac HIC-10, Analytical column, 5 µm, 4.6×100 mm (ThermoFisher). 0.1M Sodium Phosphate pH 6.0, 1M Ammonium Sulfate was used as the mobile phase 1 and 0.1M Sodium Phosphate pH 6.0 was used as mobile phase 2 to generate a gradient at a flow rate of 1 mL/min. Samples eluted in the gradient were monitored by A280. Data were analyzed and the AUC of peaks were integrated using Chromeleon 7 instrument software (ThermoFisher) and Prism Software (Graphpad).
Thermal Stress (Dynamic Light Scattering "DLS")

Data for afucosylated PI-4026-5-M100L (PI64052) and afucosylated PI-4026-5-M100Q (PI64062) at the indicated concentrations and time points were acquired at 37° C. using the temperature controlled DynaPro Plate Reader (Wyatt) equipped with an 830 nm laser. Samples were loaded on a 384-well plate to enable automated, high throughput data collection. The scattered light was monitored at 169° C. DYNAMICS software was used to analyze and calculate the hydrodynamic diameter as well as the polydispersity index.
Thermal Stress (Differential Scanning Fluorimetry "DSF")

The melting temperatures of afucosylated PI-4026-5-M100L (PI64052) and afucosylated PI-4026-5-M100Q (PI64062) were determined by nano differential scanning fluorimetry (DSF). Samples were run at a ramp rate of 1.5° C./min from 20° C. to 100° C. Samples were loaded into the nanoDSF grade capillaries by dipping into the sample. To minimize evaporation during the thermal scan, both ends of the capillary were sealed with an inert oil-based liquid rubber sealing paste.

Tm was calculated from the changes in tryptophan fluorescence intensity or the ratio of tryptophan emission at 350 and 330 nm which accurately monitor the conformational changes during unfolding of the protein as a function of temperature. Tm is the temperature at which the protein is 50% unfolded.
Thermal Stress (SEC)

Data for afucosylated PI-4026-5-M100L (PI64052) and afucosylated PI-4026-5-M100Q (PI64062) at the indicated concentrations, temperature (37° c.), and time points was collected using ThermoFisher analytical UHPLC system on a Superdex 200 Increase 10/300 GL column (GE Healthcare). PBS pH 7.4 was used as the mobile phase buffer and the flow rate was 0.5 mL/min. Data were analyzed and the AUC of peaks at A280 were integrated using Chromeleon 7 instrument software (ThermoFisher) and Prism Software (Graphpad).
Oxidative Stress (HIC)

Analysis of oxidation was achieved by incubating afucosylated PI-4026-5-M100L (PI64052) and afucosylated PI-4026-5-M100Q (PI64062) in the indicated concentrations of $H_2O_2$ for 1 h at 40° C. at a final antibody concentration of 1 mg/mL. Samples were analyzed by HIC at the indicated time points using a ThermoFisher analytical UHPLC system on a MAbPac HIC-10, Analytical column, 5 µm, 4.6×100 mm (ThermoFisher). 0.1M Sodium Phosphate pH 6.0, 1M Ammonium Sulfate was used as the mobile phase 1, and 0.1M Sodium Phosphate pH 6.0 was used as mobile phase 2 to generate a gradient at a flow rate of 1 mL/min. Samples eluted in the gradient were monitored by A280. Data were analyzed and the AUC of peaks were integrated using Chromeleon 7 instrument software (ThermoFisher) and Prism Software (Graphpad).
Oxidative Stress (SEC)

Analysis of oxidation was achieved by incubating afucosylated PI-4026-5-M100L (PI64052) and afucosylated PI-4026-5-M100Q (PI64062) in the indicated concentrations of $H_2O_2$ for 1 h at 40° C. at a final antibody concentration of 1 mg/mL. Samples were analyzed by SEC at the indicated time points using the ThermoFisher analytical UHPLC system on a Superdex 200 Increase 10/300 GL column (GE Healthcare). PBS pH 7.4 was used as the mobile phase buffer and the flow rate was 0.5 mL/min. Data were analyzed and the AUC of peaks at A280 were integrated using Chromeleon 7 instrument software (ThermoFisher).
Deamidation Risk (Charge Variant Analysis by Capillary Electrophoresis-Iso Electric Focusing "CE-IEF")

Afucosylated PI-4026-5-M100L (PI64052) and afucosylated PI-4026-5-M100Q (PI64062) were incubated for 12 h at a final antibody concentration of 1 mg/mL in the indicated buffers (PBS pH 7.4, Tris pH 8, or citrate pH 4.5) at the indicated pH values and the indicated temperatures (4° C. or 40° C.). After 12 h, samples were prepared in accordance with the charge variant kit (Perkin Elmer) and samples were run and analyzed on a LabChipII GX instrument and LabChip GX software (Perkin Elmer).

Results

Table 8 shows the results of the binding properties of PI64052 and PI64062 to human and cynomolgus TREM1 protein. PI64052 had better human avidity and binding to monomeric human TREM1, but PI64062 had better cynomolgus avidity.

TABLE 8

| Anti-hTREM1 mAb | Human Avid $K_D$ (nM) | Cyno Avid $K_D$ (nM) | Human Monomeric $K_D$ (nM) |
|---|---|---|---|
| PI64052 (PI-4026-5 M100L) | 0.15 | 1.41 | 4.34 |
| PI64062 (PI-4026-5 M100Q) | 0.39 | 0.45 | 6.32 |

Figure 12A:
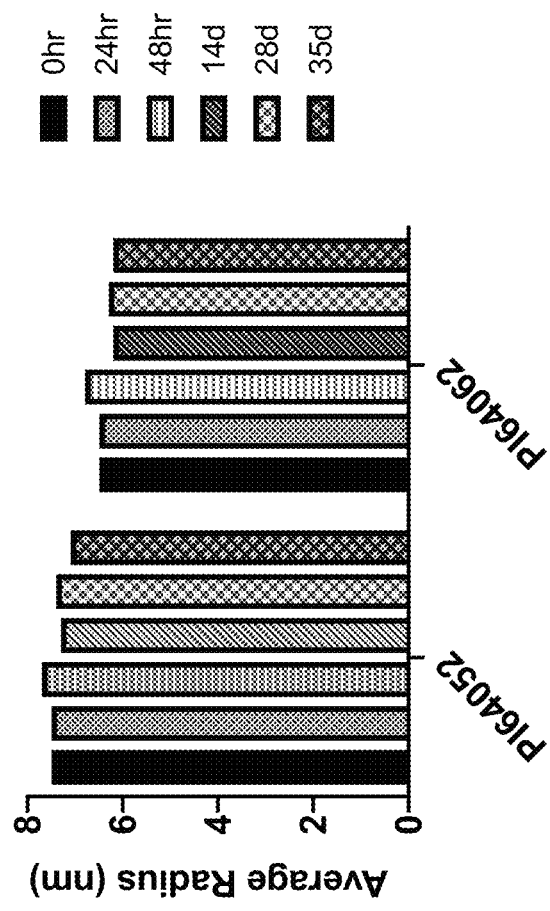
FIG. 12A shows the average radius of the PI64052 (PI-4026-5-M100L) and PI64062 (PI-4026-5-M100Q) antibodies as determined by DLS in response to thermal stress.
Figure 12B:
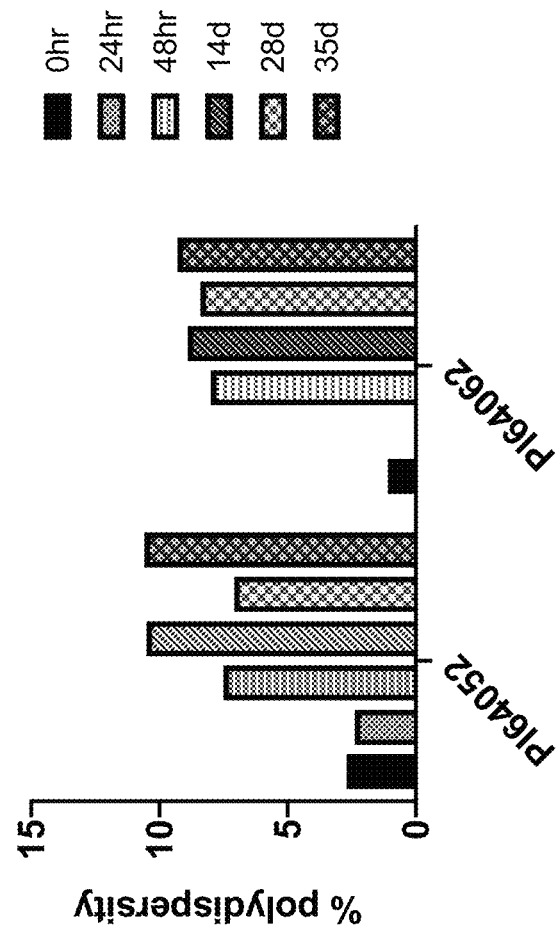
FIG. 12B shows the % polydispersity of the PI64052 and PI64062 antibodies as determined by DLS in response to thermal stress. These are stability kinetics measurements.

The stability kinetics in response to thermal stress (37°C) of the PI64052 and PI64062 antibodies as determined by DLS are shown in FIGS. 12A and 12B. FIG. 12A shows the average radius of each antibody over time (bars from left to right: 0 h, 24 h, 48 h, 14 d, 28 d, and 35 d), while FIG. 12B shows the % polydispersity over time (bars from left to right: 0 h, 24 h, 48 h, 14 d, 28 d, and 35 d). Both antibodies showed increased polydispersity at later timepoints, but is well below the industry-accepted definition of monodispersity (<20% polydispersity). The results are quantified in Table 9, below.

Figure 14A:
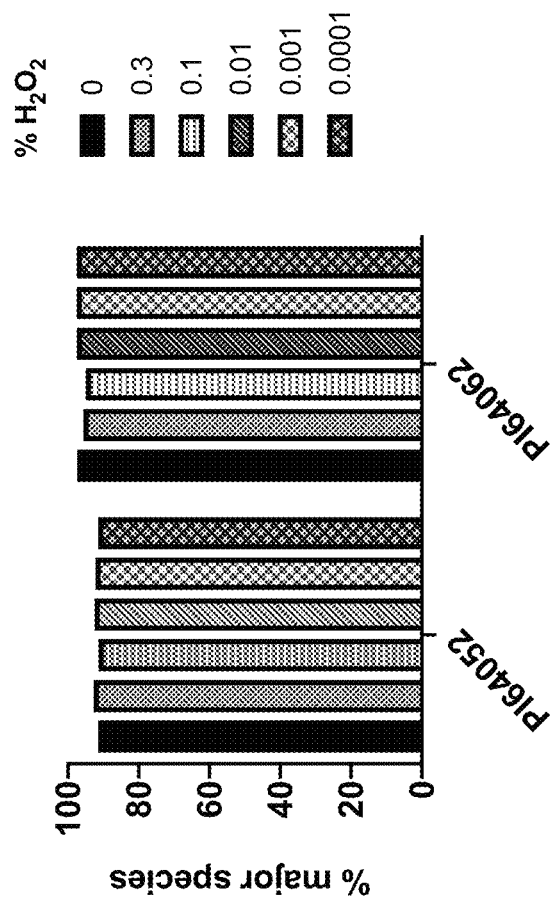
FIG. 14A show the % major species of the PI64052 and PI64062 antibodies at 24 hours post exposure to differential concentrations of $H_2O_2$ by hydrophobic interaction chromatography.
Figure 14B:
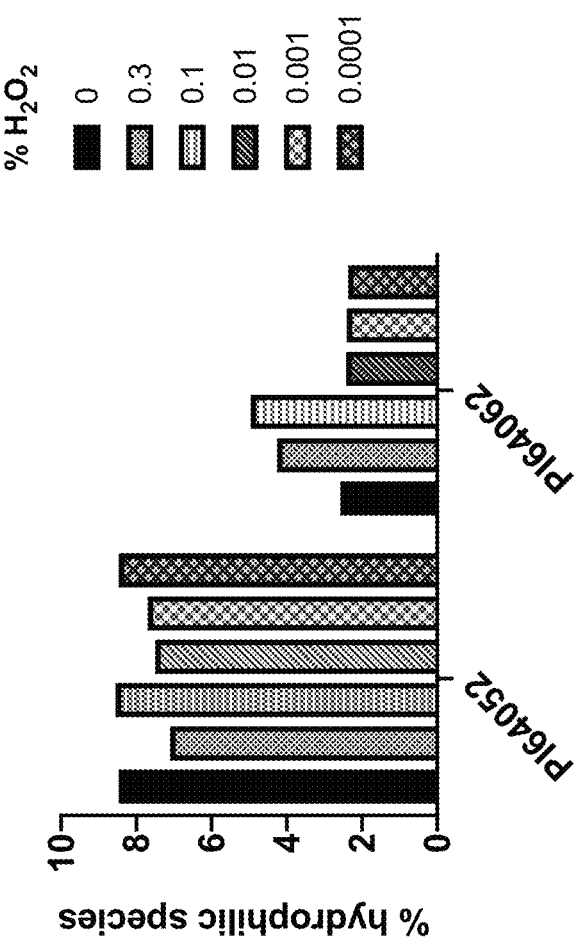
FIG. 14B show the % hydrophilic species of the PI64052 and PI64062 antibodies at 24 hours post exposure to differential concentrations of $H_2O_2$ by hydrophobic interaction chromatography. These are oxidative stress susceptibility measurements.
Figure 15A:
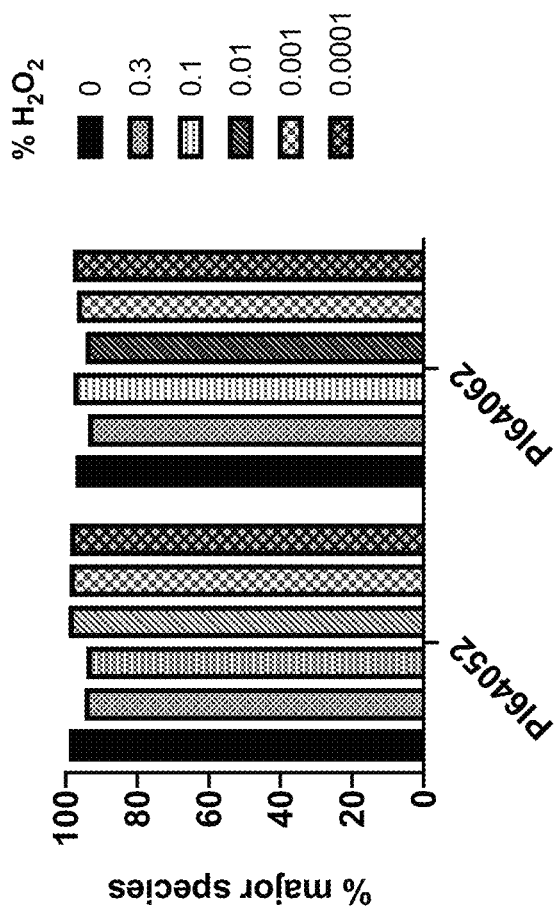
FIG. 15A shows the % major species of the PI64052 and PI64062 antibodies at 14 days post exposure to differential concentrations of $H_2O_2$ by hydrophobic interaction chromatography.
Figure 15B:
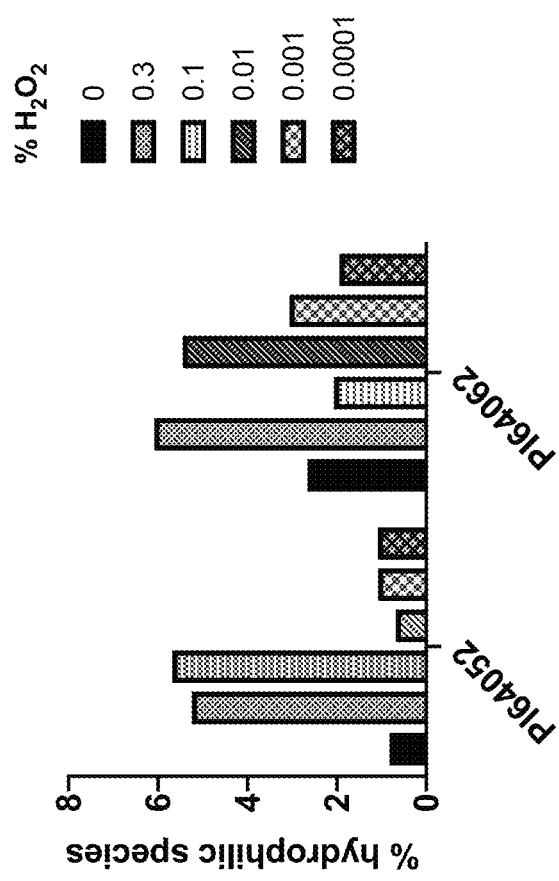
FIG. 15B shows % hydrophilic species of the PI64052 and PI64062 antibodies at 14 days post exposure to differential concentrations of $H_2O_2$ by hydrophobic interaction chromatography. These are oxidative stress susceptibility measurements.
Figure 16A:
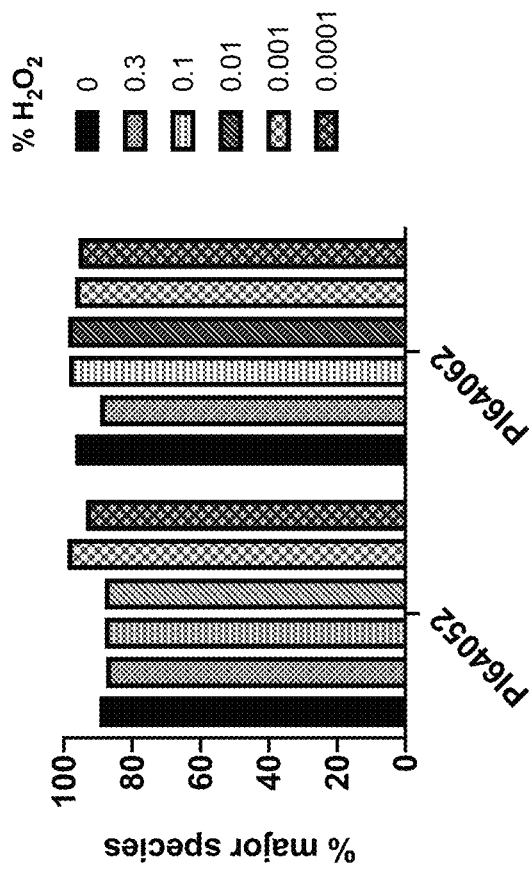
FIG. 16A shows the % major species of the PI64052 and PI64062 antibodies at 28 days post exposure to differential concentrations of $H_2O_2$ by hydrophobic interaction chromatography.
Figure 16B:
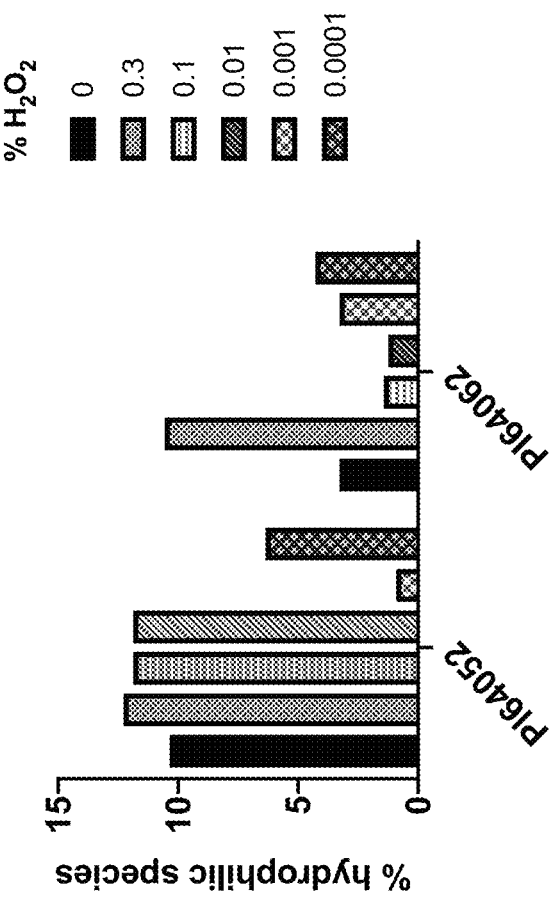
FIG. 16B shows % hydrophilic species, of the PI64052 and PI64062 antibodies at 28 days post exposure to differential concentrations of $H_2O_2$ by hydrophobic interaction chromatography.

The oxidative stress susceptibility of the PI64052 and PI64062 antibodies are shown in FIGS. 14A and 14B (24 h, bars from left to right 0, 0.3, 0.1, 0.01, 0.001, 0.0001), FIGS. 15A and 15B (14 d, bars from left to right 0, 0.3, 0.1, 0.01, 0.001, 0.0001), and FIGS. 16A and 16B (28 d, bars from left to right 0, 0.3, 0.1, 0.01, 0.001, 0.0001) as measured by hydrophobic interaction chromatography (HIC). The results are also quantified in Tables 11, 12, and 13, below. Incubation with $H_2O_2$ did not result in significant increases in oxidized species of either antibody at 24 h or 14 d after $H_2O_2$ treatment. However, 28 d after $H_2O_2$ exposure, PI64052 showed more heterogeneity than PI64062 as a function of $H_2O_2$ concentration.

TABLE 11

| | PI64052 | | PI64062 | |
|---|---|---|---|---|
| 24 hrs % $H_2O_2$ | Major species | Hydrophilic species | Major species | Hydrophilic species |
| 0 | 91.520 | 8.480 | 97.42 | 2.58 |
| 0.3 | 92.900 | 7.100 | 95.74 | 4.26 |
| 0.1 | 91.440 | 8.560 | 95.04 | 4.96 |
| 0.01 | 92.500 | 7.500 | 97.57 | 2.43 |
| 0.001 | 92.300 | 7.700 | 97.59 | 2.41 |
| 0.0001 | 91.520 | 8.480 | 97.63 | 2.37 |

TABLE 9

| | | 0 h | | 24 h | | 48 h | | 14 d | | 28 d | | 35 d | |
|---|---|---|---|---|---|---|---|---|---|---|---|---|---|
| DC | Conc. | Radius (nm) | % Poly-dispersity | Radius (nm) | % Poly-dispersity | Radius (nm) | % Poly-dispersity | Radius (nm) | % Poly-dispersity | Radius (nm) | % Poly-dispersity | Radius (nm) | % Poly-dispersity |
| PI64052 | 50 mg/ml | 7.5 | 2.7 | 7.5 | 2.4 | 7.7 | 7.5 | 7.3 | 10.5 | 7.4 | 7.1 | 7.1 | 10.6 |
| PI64062 | 50 mg/ml | 6.5 | 1.1 | 6.5 | 0 | 6.8 | 8 | 6.2 | 8.9 | 6.3 | 8.4 | 6.2 | 9.3 |

Figure 13A:
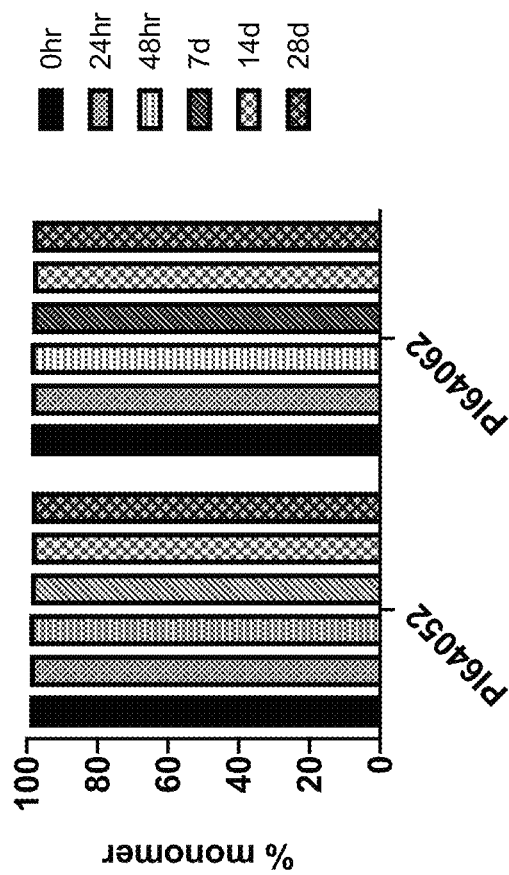
FIG. 13A shows the % monomer of the PI64052 and PI64062 antibodies as determined by SEC in response to thermal stress.
Figure 13B:
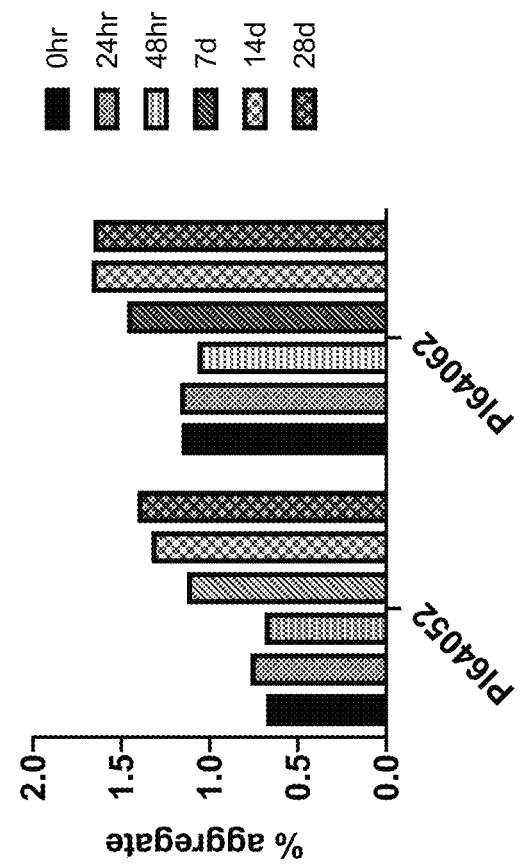

The stability kinetics of the PI64052 and PI64062 antibodies as determined by SEC are shown in FIGS. 13A and 13B. FIG. 13A shows the % monomer (bars from left to right: 0 h, 24 h, 48 h, 7 d, 14 d, and 28 d), while FIG. 13B shows the % aggregation over time (bars from left to right: 0 h, 24 h, 48 h, 7 d, 14 d, and 28 d). Both antibodies had a very minimal increase in % aggregation over time, but maintained monomericity of >98%. The results are quantified in Table 10, below.

TABLE 12

| | PI64052 | | PI64062 | |
|---|---|---|---|---|
| DAY 14 % $H_2O_2$ | Major species | Hydrophilic species | Major species | Hydrophilic species |
| 0 | 99.17 | 0.83 | 97.34 | 2.66 |
| 0.3 | 94.75 | 5.25 | 93.91 | 6.09 |

TABLE 10

| | | 0 h | | 24 h | | 48 h | | 7 d | | 14 d | | 28 d | |
|---|---|---|---|---|---|---|---|---|---|---|---|---|---|
| DC | Conc. | % Mono | % Agg | % Mono | % Agg | % Mono | % Agg | % Mono | % Agg | % Mono | % Agg | % Mono | % Agg |
| PI64052 | 50 mg/ml | 99.32 | 0.68 | 99.23 | 0.77 | 99.31 | 0.69 | 98.87 | 1.13 | 98.67 | 1.33 | 98.59 | 1.41 |
| PI64062 | 50 mg/ml | 98.84 | 1.16 | 98.83 | 1.17 | 98.93 | 1.07 | 98.53 | 1.47 | 98.33 | 1.67 | 98.34 | 1.66 |

TABLE 12-continued

| DAY 14 % $H_2O_2$ | PI64052 | | PI64062 | |
| --- | --- | --- | --- | --- |
| | Major species | Hydrophilic species | Major species | Hydrophilic species |
| 0.1 | 94.31 | 5.69 | 97.93 | 2.07 |
| 0.01 | 99.31 | 0.69 | 94.54 | 5.46 |
| 0.001 | 98.92 | 1.08 | 96.93 | 3.07 |
| 0.0001 | 98.91 | 1.09 | 98.05 | 1.95 |

TABLE 13

| DAY 28 % $H_2O_2$ | PI64052 | | PI64062 | |
| --- | --- | --- | --- | --- |
| | Major species | Hydrophilic species | Major species | Hydrophilic species |
| 0 | 89.63 | 10.37 | 96.71 | 3.29 |
| 0.3 | 87.71 | 12.29 | 89.42 | 10.58 |
| 0.1 | 88.12 | 11.88 | 98.55 | 1.45 |
| 0.01 | 88.12 | 11.88 | 98.75 | 1.25 |
| 0.001 | 99.08 | 0.92 | 96.72 | 3.28 |
| 0.0001 | 93.63 | 6.37 | 95.71 | 4.29 |

Figure 17A:
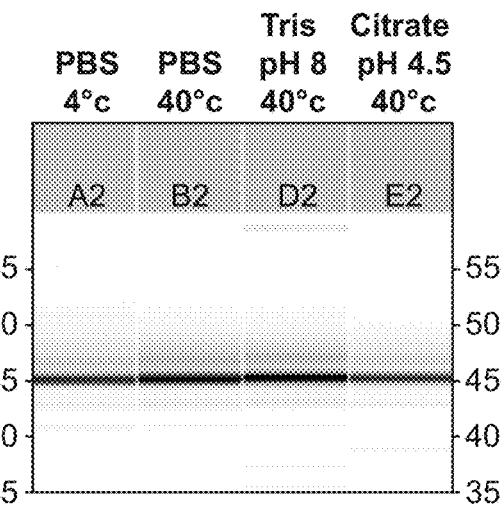
FIG. 17A shows the results of the deamidation assay of the PI64052 and PI64062 antibodies.
Figure 17B:
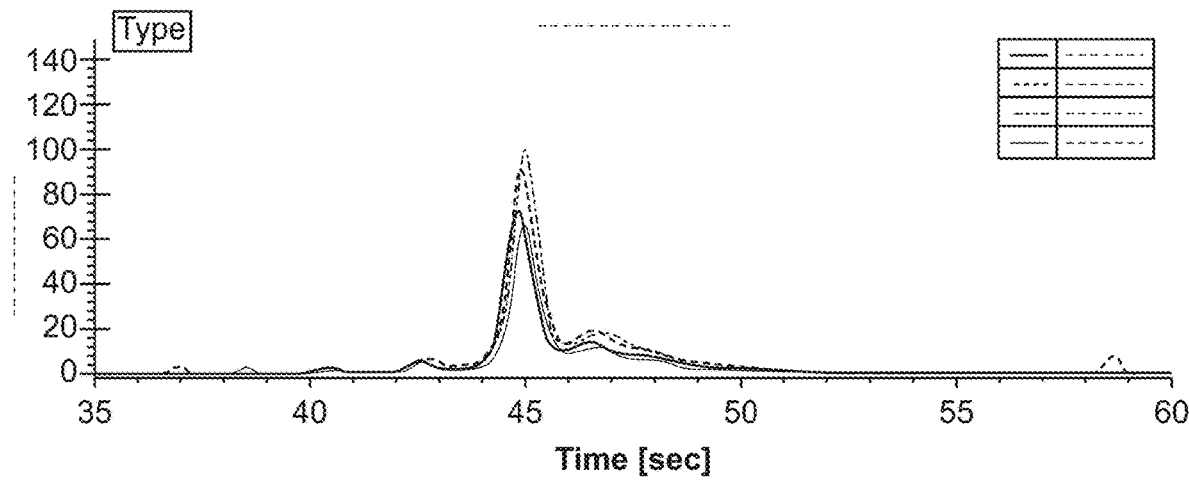
FIG. 17B shows the results of the deamidation assay of the PI64052 and PI64062 antibodies.
Figure 17C:
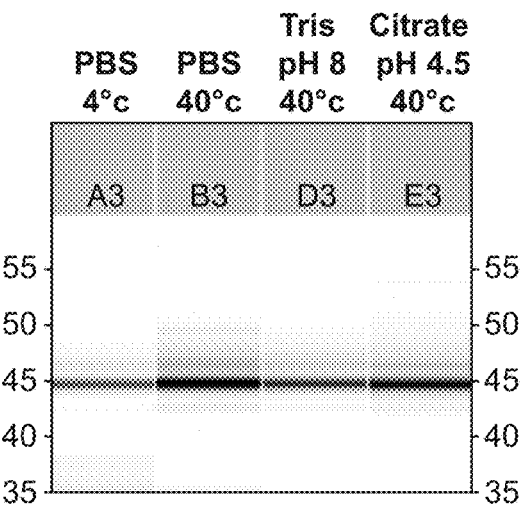
FIG. 17C shows the results of the deamidation assay of the PI64052 and PI64062 antibodies.
Figure 17D:
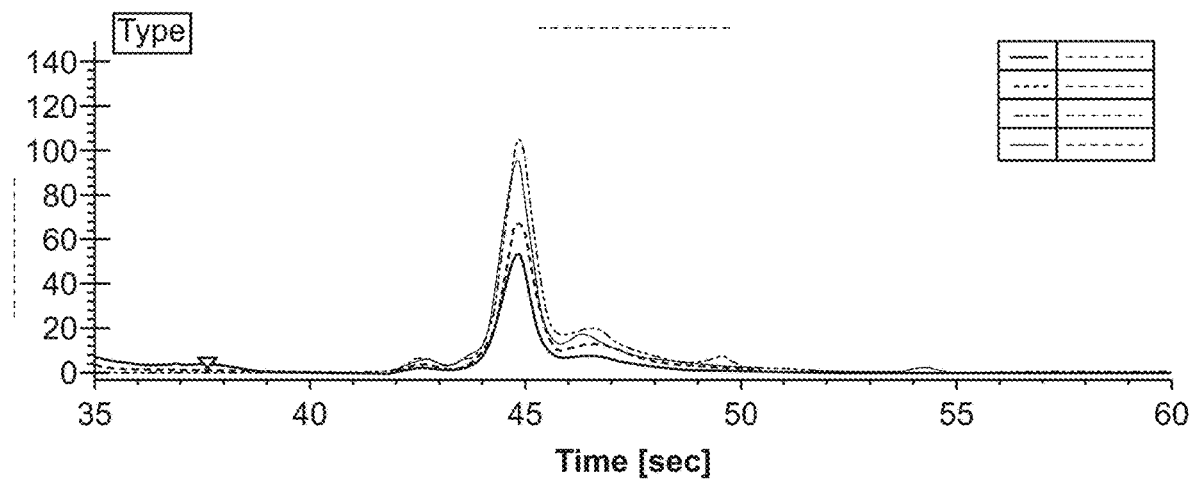
FIG. 17D shows the results of the deamidation assay of the PI64052 and PI64062 antibodies.

The results of the deamidation assay of the PI64052 and PI64062 antibodies are shown in FIGS. 17A-17D. Neither PI64052 (FIGS. 17A and 17B) or PI64062 (FIGS. 17C and 17D) showed deamidation risk by CE-IEF analysis. FIGS. 17A and 17C are capillary electrophoresis gels that detect any protein charge variants that may arise as a function of deamidating conditions. FIGS. 17B and 17D shows the data from the capillary electrophoresis gels represented as intensity of the protein bands detected.

A summary of the biophysical characterization of the PI64052 and PI64062 antibodies is shown in Table 14. The superiority of one antibody over the other for each criterion is indicated by (+). Criteria in which neither antibody is superior to the other is indicated by (−). Overall, PI64062, containing the M100Q mutation in the CDR-H3 region, had better biophysical properties than PI64052.

TABLE 14

| Criteria/Test | PI64052 (M100L) | PI64062 (M100Q) |
| --- | --- | --- |
| $K_D$ human (avid) | + | − |
| $K_D$ cyno (avid) | − | + |
| $K_D$ human (monomer) | + | − |
| Aggregation (SEC, DLS) | − | − |
| Differential species (HIC) | − | + |
| Thermal Stress (DLS, DSF) | − | − |
| Oxidative stress (HIC, SEC) | − | + |
| Stability over time (DLS, SEC) | − | − |
| Relative Hydrophilicity (HIC) | − | + |
| Deamidation Risk (Charge variants) | − | − |

Example 9: Cellular Binding and and Induction of ADCC and ADCP Signaling by PI64052 and PI64062 Antibodies Next, PI64052 and PI64062 were characterized using various functional assays, including cellular binding and induction of ADCC and ADCP.
Background Binding
HEK293 GFP control cells in log phase growth were harvested from culture, washed, and plated in 96 well U bottom plates at $1 \times 10^5$ cells/well. Titrations of afucosylated PI-4026-5-M100L (PI64052) and afucosylated PI-4026-5-M100Q (PI64062), as well as an isotype control were added to the cells and incubated for 30 mins on ice. An Alexa 647-conjugated anti-human Fcγ secondary antibody (Jackson Immunoresearch) diluted at 1:500 was used to detect bound primary antibody. The secondary antibody was incubated with the cells for 30 mins on ice. Cells were then washed and stained with Zombie NIR (Biolegend) to determine cell viability for 15 mins at room temperature. Fluorescence signal from bound antibody was assessed by flow cytometry (ThermoFisher Attune NxT).
Lymphocyte Binding
Fresh blood from human donors (Stanford Blood Centre) was red cell lysed and washed to enrich PBMC and granulocyte content. Cells were plated and Fc receptors were blocked with a combination of human serum (Jackson Immunoresearch), Human FcX (Biolegend), and a peptide-based FcR block solution (Innovex Biosciences). Cells were also stained with Zombie NIR (Biolegend) to determine cell viability. After Zombie NIR, cells were stained with a flow cytometry cocktail encompassing markers for major immune subsets, and a titration of either human IgG1 control, afucosylated PI-4026-5-M100L (PI64052), or afucosylated PI-4026-5-M100Q (PI64062). All antibodies used were directly conjugated and data was acquired by flow cytometry (ThermoFisher Attune NxT).
EC50 of Binding to hTREM1 Over-Expressing Cells
HEK293 cells over-expressing human TREM1 in log phase growth were harvested from culture, washed, and plated in 96 well U bottom plates at $1 \times 10^5$ cells/well. Titrations of unconjugated hIgG1 control, afucosylated PI-4026-5-M100L (PI64052), or afucosylated PI-4026-5-M100Q (PI64062) at the indicated concentrations were added to the cells and incubated for 30 mins on ice. An Alexa 647-conjugated anti-human Fcγ secondary antibody (Jackson Immunoresearch) diluted at 1:500 was used to detect bound primary antibody. The secondary antibody was incubated with the cells for 30 mins on ice. Cells were then washed and stained with Zombie NIR (Biolegend) to determine cell viability for 15 mins at room temperature. Fluorescence signal from bound antibody was assessed by flow cytometry (ThermoFisher Attune NXT). EC50 values were calculated in Prism Software (Graphpad).
EC50 of Binding to cynoTREM1 Over-Expressing Cells
HEK293 cells over-expressing cynomolgus TREM1 in log phase growth were harvested from culture, washed, and plated in 96 well U bottom plates at $1 \times 10^5$ cells/well. Titrations of unconjugated hIgG1 control, afucosylated PI-4026-5-M100L (PI64052), or afucosylated PI-4026-5-M100Q (PI64062) at the indicated concentrations were added to the cells and incubated for 30 mins on ice. An Alexa 647-conjugated anti-human Fcγ secondary antibody (Jackson Immunoresearch) diluted at 1:500 was used to detect bound primary antibody. The secondary antibody was incubated with the cells for 30 mins on ice. Cells were then washed and stained with Zombie NIR (Biolegend) to determine cell viability for 15 mins at room temperature. Fluorescence signal from bound antibody was assessed by flow cytometry (ThermoFisher Attune NXT). EC50 values were calculated in Prism Software (Graphpad).
EC50 of Binding to Human Monocytes
Fresh blood from human donors (Stanford Blood Centre) was red cell lysed and washed to enrich PBMC and granulocyte content. Cells were plated and Fc receptors were blocked with a combination of human serum (Jackson Immunoresearch), Human FcX (Biolegend), and a peptide-based FcR block solution (Innovex Biosciences). Cells were also stained with Zombie NIR (Biolegend) to determine cell viability. After Zombie NIR, cells were stained with a flow cytometry cocktail encompassing markers for major immune subsets, and a titration of either human IgG1 control, afucosylated PI-4026-5-M100L (PI64052), or afucosylated PI-4026-5-M100Q (PI64062). All antibodies used were directly conjugated and data was acquired by flow cytometry (ThermoFisher Attune NxT). EC50 values were calculated in Prism Software (Graphpad).

EC50 of Binding to Cynomolgus Monocytes

Fresh cynomolgus monkey blood (Worldwide Primates Inc) was red cell lysed and washed to enrich PBMC and granulocyte content. Cells were plated and Fc receptors were blocked with a combination of human serum (Jackson Immunoresearch) and a peptide-based FcR block solution (Innovex Biosciences). Cells were also stained with Zombie NIR (Biolegend) to determine cell viability. After Zombie NIR, cells were stained with a flow cytometry cocktail encompassing markers for major immune subsets, and a titration of either human IgG1 control, afucosylated PI-4026-5-M100L (PI64052), or afucosylated PI-4026-5-M100Q (PI64062). All antibodies used were directly conjugated and data was acquired by flow cytometry (ThermoFisher Attune NXT). EC50 values were calculated in Prism Software (Graphpad).

hCD16 ADCC Reporter Assay

HEK293 target cells over-expressing human TREM1 were incubated with a titration of afucosylated PI-4026-5-M100L (PI64052), afucosylated PI-4026-5-M100Q (PI64062), or hIgG1 isotype control at the indicated concentrations in flat bottom white 96 well plates (ThermoFisher). After a 15 minute incubation at room temperature, hCD16 expressing NFAT-luciferase reporter Jurkat cells (Promega, Madison, WI) were added to the target cell/antibody mixture at a ratio of 3:1. After the addition of reporter cells, the assay was incubated at 37°c in 5% $CO_2$ atmosphere for 6 hrs. The amount of luciferase activity was determined by exposure to luciferase substrate (Promega, Madison, WI) and detected by a luminescence reader (Envision, Perkin Elmer). EC50 values were calculated in Prism Software (Graphpad).

Primary Macrophage ADCP Assay

GFP-positive expi293 cells over-expressing human TREM1 were incubated with titrations of unconjugated hIgG1 control, afucosylated PI-4026-5-M100L (PI64052), or afucosylated PI-4026-5-M100Q (PI64062) for 15-30 mins at room temperature. Without washing, human macrophages polarized from CD14+ monocytes from two donors labelled with Cell Trace Violet (ThermoFisher) were then added to the expi293 and antibody mixture at a ratio of 1:1. The assay was incubated for 6 hrs at 37°c in a 5% $CO_2$ atmosphere, after which the assay was assessed by flow cytometry (ThermoFisher Attune NxT). ADCP was measured by enumerating the number of GFP positive and Cell Trace Violet positive macrophages gated on single cells. EC50 values were calculated in Prism Software (Graphpad).

FcγR binding 1 ug/ml of the indicated recombinant human His-tagged FcγR proteins (Sino Biologicals) were coated on MaxiSorp plates overnight at 4°c. The next day, plates were washed, and a titration of fucosylated or afucosylated PI-4026-5-M100L and PI-4026-5 M100Q, or a hIgG4 isotype control (Biolegend) at the indicated concentrations were added to the coated plates. Fc-mediated binding of the antibodies to the coated FcγR proteins was detected with a HRP-conjugated Fab'2 fragment against the Fab'2 portion of human IgG (Jackson Immunoresearch). TMB substrate (ThermoFisher) was used to quantitate the amount of HRP-conjugated secondary reagent bound to primary antibodies and $H_3PO_4$ was used to stop the reaction. Absorbance at 450 nm was measured using the Spectramax plate reader (Life Technologies).

Results

Figure 18A:
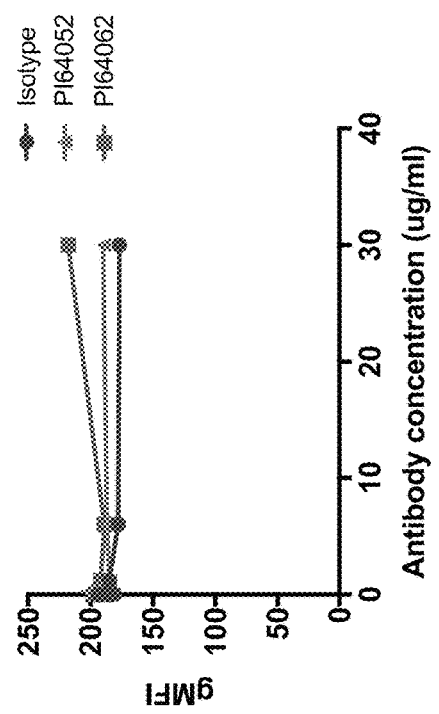
FIG. 18A shows no background binding of PI64052 and PI64062 to HEK293 cells.
Figure 18B:
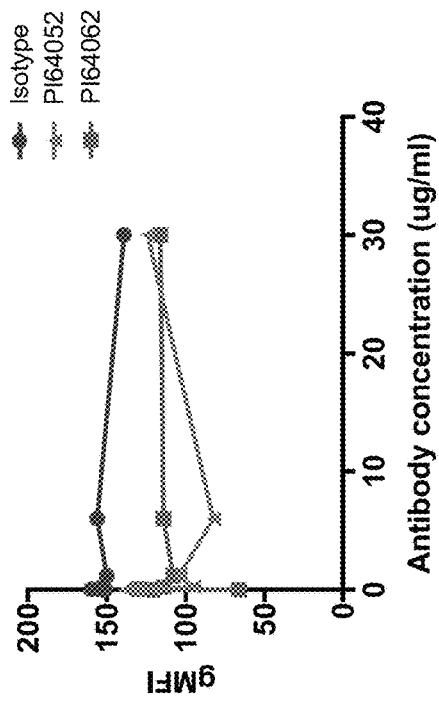
FIG. 18B shows no background binding of PI64052 and PI64062 to HEK293 cells.
Figure 18C:
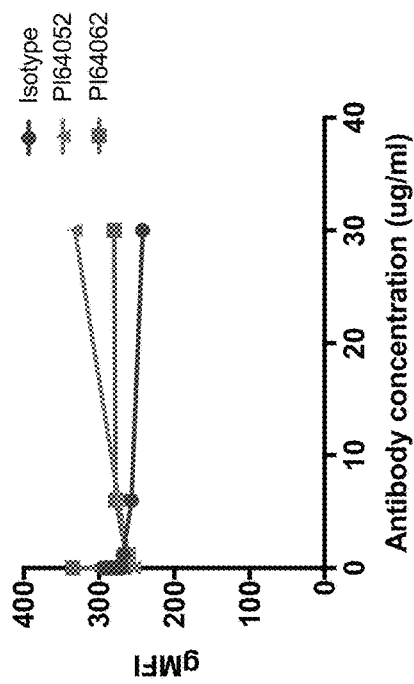
FIG. 18C shows no background binding of PI64052 and PI64062 to HEK293 cells.

Individual experimental replicates for HEK293 parental cell binding are shown in FIGS. 18A, 18B, and 18C. There was no detectable binding of PI64052 and PI64062 to HEK293 cells relative to isotype control.

As shown in FIGS. 19A-F, there was no detectable binding of PI64052 and PI64062 to human lymphocytes (T cells or B cells) relative to isotype control. Each assay was repeated three times and each graph shows results from the individual experiments. FIGS. 19A, 19B, and 19C show individual experiments gated on T cells, while FIGS. 19D, 19E, and 19F show individual experiments gated on B cells.

Figure 20A:
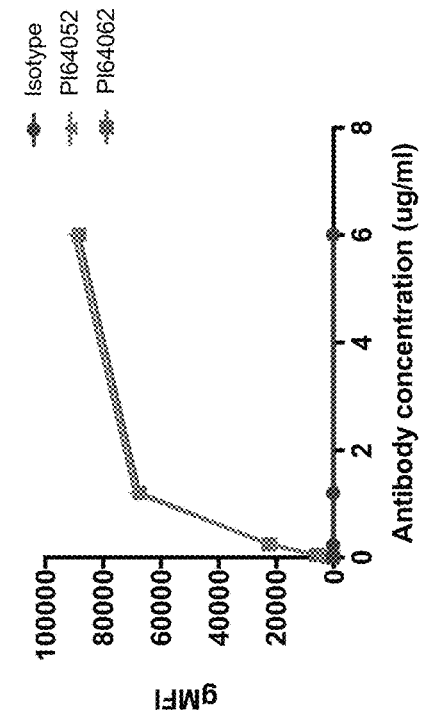
FIG. 20A shows binding of PI64052 and PI64062 antibodies to HEK293 cells overexpressing human TREM1.
Figure 20B:
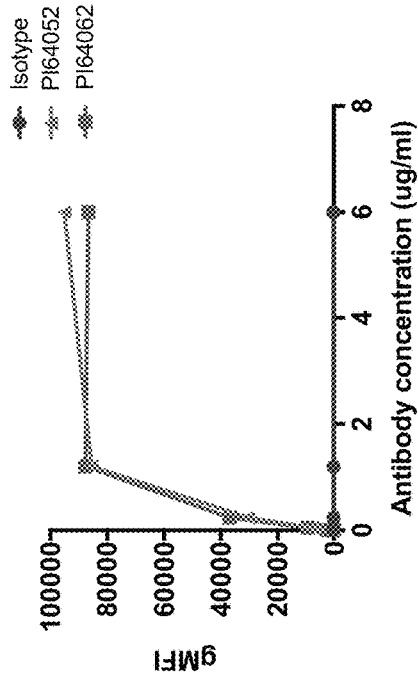
FIG. 20B shows binding of PI64052 and PI64062 antibodies to HEK293 cells overexpressing human TREM1.
Figure 20C:
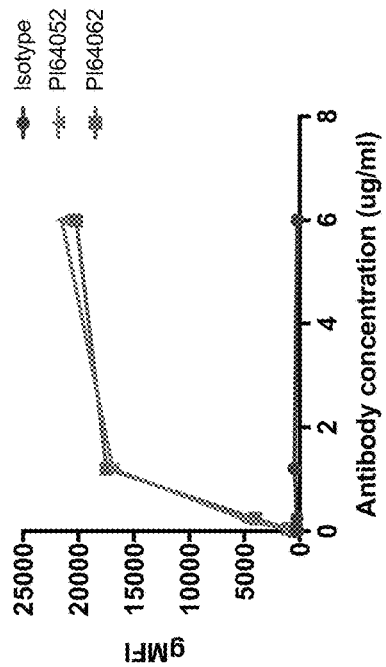
FIG. 20C shows binding of PI64052 and PI64062 antibodies to HEK293 cells overexpressing human TREM1.

Neither was there a difference in the EC50 of the two afucosylated antibodies to cells overexpressing human TREM1 (FIGS. 20A, 20B, and 20C). The experiment was repeated three times and each graph shows the result of each individual experiment. The data is quantified in Table 15 below.

TABLE 15

| Antibody | Experiment | $EC_{50}$ (nM) |
|---|---|---|
| PI64052 | 1 | 3.26 |
| PI64062 | 1 | 2.32 |
| PI64052 | 2 | 3.97 |
| PI64062 | 2 | 3.88 |
| PI64052 | 3 | 5.34 |
| PI64062 | 3 | 4.88 |

Figure 21A:
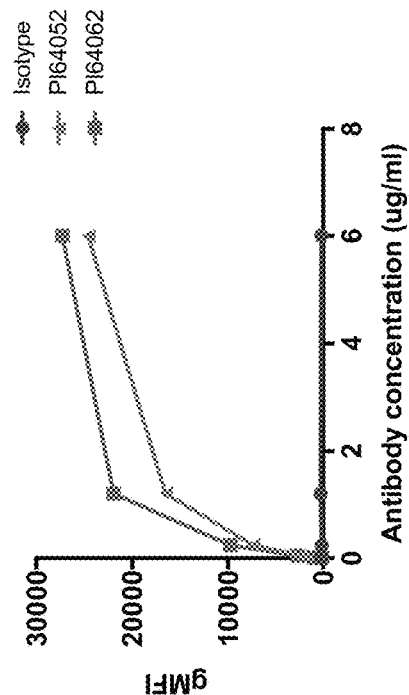
FIG. 21A shows binding of PI64052 and PI64062 antibodies to HEK293 cells overexpressing cynomolgus TREM1.
Figure 21B:
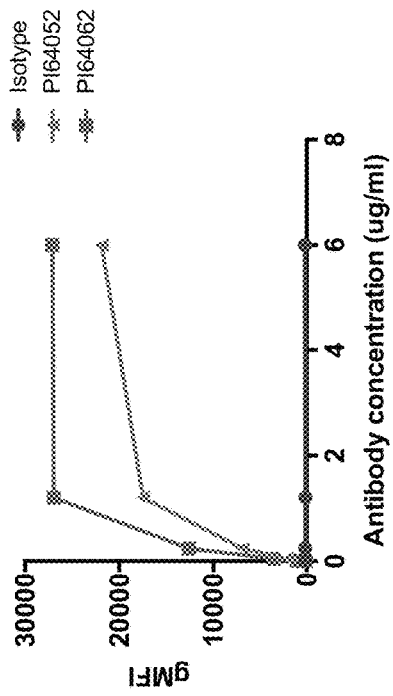
FIG. 21B shows binding of PI64052 and PI64062 antibodies to HEK293 cells overexpressing cynomolgus TREM1.
Figure 21C:
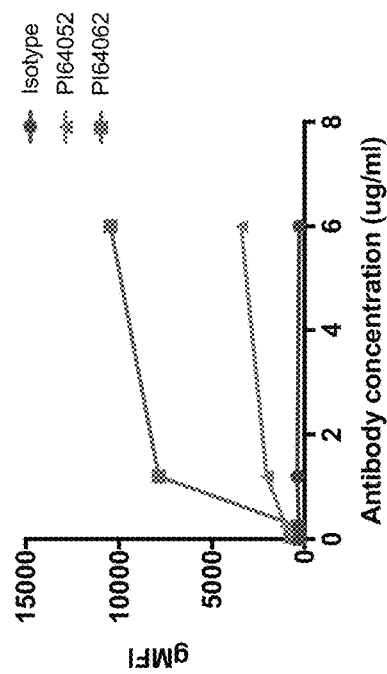
FIG. 21C shows binding of PI64052 and PI64062 antibodies to HEK293 cells overexpressing cynomolgus TREM1.

PI64062 did show consistently better binding to cells overexpressing cynomolgus TREM1 (FIGS. 21A, 21B, 21C). The experiment was repeated three times and each graph shows the result of each individual experiment. The data is quantified in Table 16 below.

TABLE 16

| Antibody | Experiment | $EC_{50}$ (nM) |
|---|---|---|
| PI64052 | 1 | 3.62 |
| PI64062 | 1 | 2.07 |
| PI64052 | 2 | 4.67 |
| PI64062 | 2 | 3.25 |
| PI64052 | 3 | 42.75 |
| PI64062 | 3 | 7.89 |

Figure 22A:
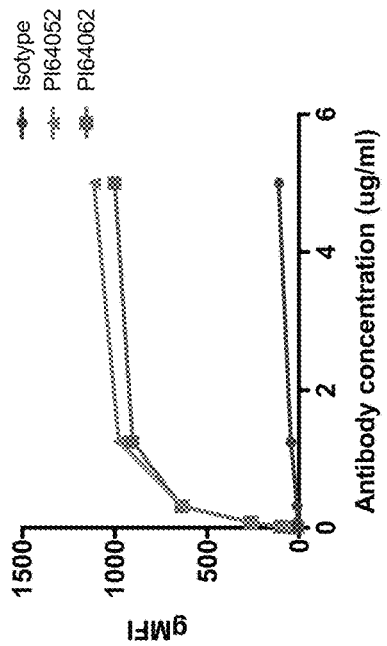
FIG. 22A shows binding of PI64052 and PI64062 to human monocytes.
Figure 22B:
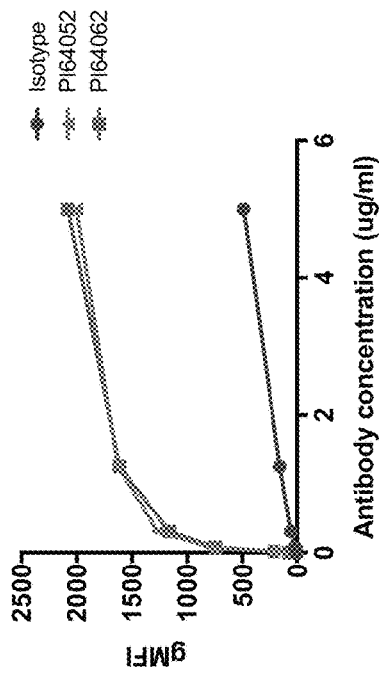
FIG. 22B shows binding of PI64052 and PI64062 to human monocytes.
Figure 22C:
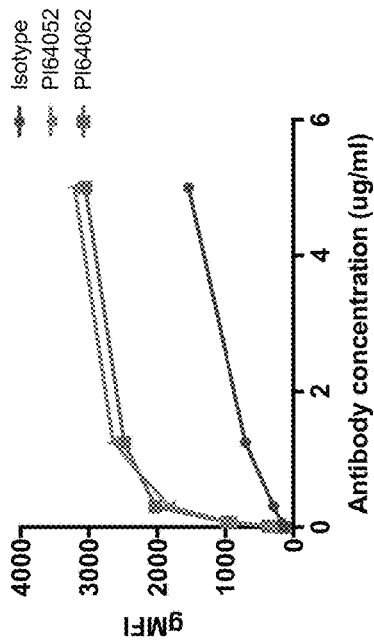
FIG. 22C shows binding of PI64052 and PI64062 to human monocytes.

There was no difference in the EC50 of the two afucosylated antibodies to human monocytes (FIGS. 22A, 22B, and 22C). The experiment was repeated three times and each graph shows the result of each individual experiment. The data is quantified in Table 17 below.

TABLE 17

| Antibody | Experiment | $EC_{50}$ (nM) |
|---|---|---|
| PI64052 | 1 | 0.75 |
| PI64062 | 1 | 1.32 |
| PI64052 | 2 | 1.40 |
| PI64062 | 2 | 1.27 |
| PI64052 | 3 | 0.73 |
| PI64062 | 3 | 0.57 |

There was no difference in the EC50 of the two afucosylated antibodies to cynomolgus monocytes (FIGS. 23A and 23B). The assay was repeated twice and each graph shows the result of each individual experiment. The data is quantified in Table 18 below.

TABLE 18

| Antibody | Experiment | EC$_{50}$ (nM) |
| --- | --- | --- |
| PI64052 | 1 | 7.84 |
| PI64062 | 1 | 7.94 |
| PI64052 | 2 | 7.16 |
| PI64062 | 2 | 7.84 |

As shown in FIG. 24, there was no significant difference in FcγR signaling mediated by PI64052 and PI64062 in the hCD16 reporter assay system. The assay was repeated three times and each graph shows the result of each individual experiment. The data is quantified in Table 19 below. FIG. 24 is the third experiment and is representative of the three separate experiments.

TABLE 19

| Antibody | Experiment | EC$_{50}$ (nM) |
| --- | --- | --- |
| PI64052 | 1 | 0.09 |
| PI64062 | 1 | 0.08 |
| PI64052 | 2 | 0.28 |
| PI64062 | 2 | 0.29 |
| PI64052 | 3 | 0.11 |
| PI64062 | 3 | 0.09 |

Figure 25A:
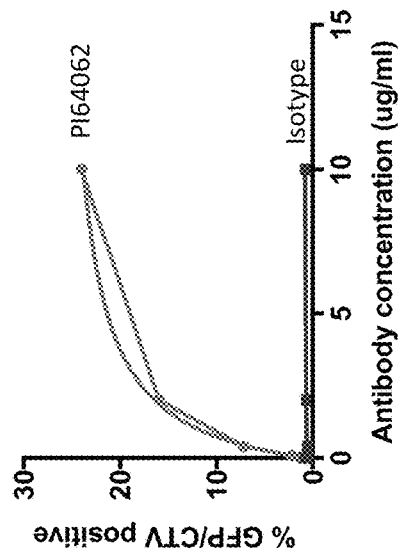
FIG. 25A show that PI64052 induces ADCP of expi cells expressing hTREM1, but not parental expi cells, by primary human macrophages.
Figure 25B:
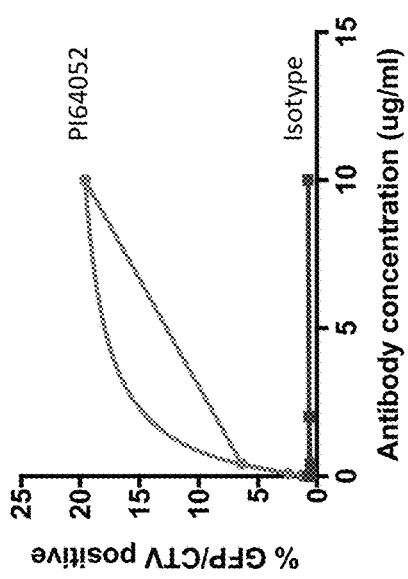
FIG. 25B show that PI64062 induces ADCP of expi cells expressing hTREM1, but not parental expi cells, by primary human macrophages.
Figure 25C:
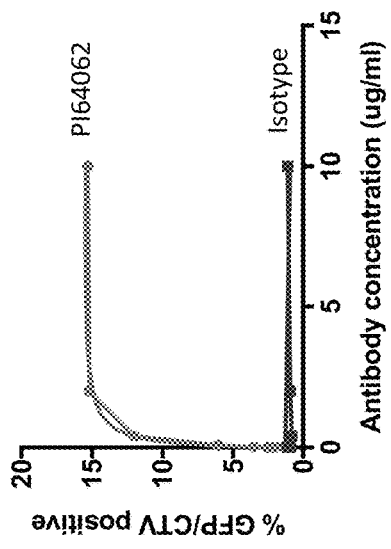
FIG. 25C show that PI64052 induces ADCP of expi cells expressing hTREM1, but not parental expi cells, by primary human macrophages.
Figure 25D:
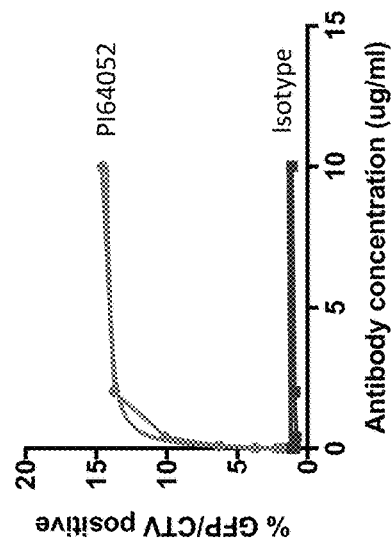
FIG. 25D show that PI64062 induces ADCP of expi cells expressing hTREM1, but not parental expi cells, by primary human macrophages.

As shown in FIGS. 25A, 25B, 25C, and 25D there was no significant difference in the ability of PI64052 and PI64062 to induce ADCP of hTREM1 expressing cells by primary human macrophages. The assay was performed using two donors. FIGS. 25A and 25B show results from Donor 1, while FIGS. 25C and 25D show results from Donor 2. The data is quantified in Table 20 below.

TABLE 20

| Antibody | Donor | EC$_{50}$ (nM) |
| --- | --- | --- |
| PI64052 | 1 | 6.86 |
| PI64062 | 1 | 8.69 |
| PI64052 | 2 | 0.86 |
| PI64062 | 2 | 0.96 |

Figure 26A:
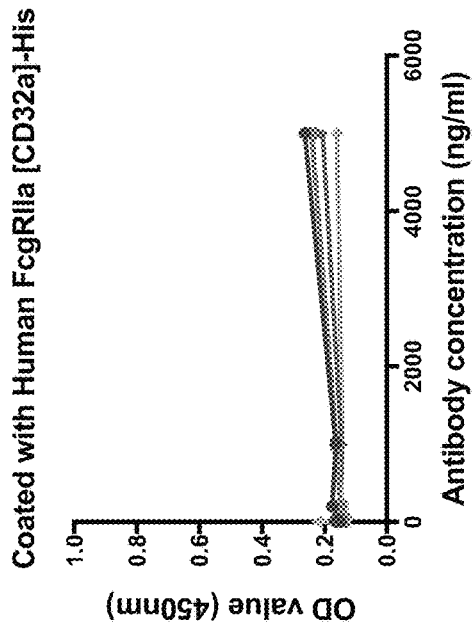
FIG. 26A shows binding of PI64052 and PI64062 and their fucosylated parents (PI-4026-5-M100L and PI-4026-5-M100Q respectively) to hFcγRI.
Figure 26B:
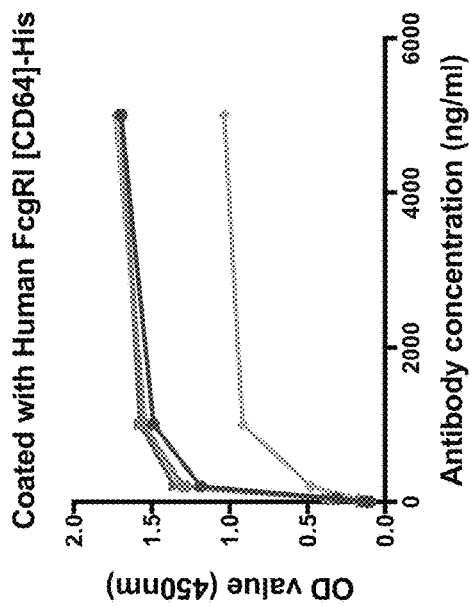
FIG. 26B shows binding of PI64052 and PI64062 and their fucosylated parents to hFcγRIIα.
Figure 26C:
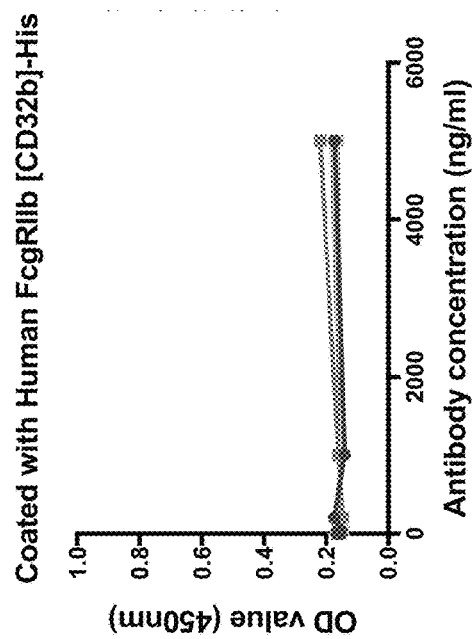
FIG. 26C shows binding of PI64052 and PI64062 and their fucosylated parents to hFcγRIIβ.

As shown in FIGS. 26A-F, there was no significant difference in FcγR binding between PI64052 and PI64062. PI64052 and PI64062 showed enhanced binding to certain FcγR such as FcγRIIIa (V), FcγRIIIa (F), and FcγRIIIb as compared to their fucosylated counterparts, PI-4026-5-M100L and PI-4026-5-M100Q respectively. FIG. 26A shows binding to FcγRI, FIG. 26B shows binding to FcγRIIa, FIG. 26C shows binding to FcγRIIb, FIG. 26D shows binding to FcγRIIIa (CD16a-V), FIG. 26E shows binding to FcγRIIIa (CD16a-F), and FIG. 26F shows binding to FcγRIIIb.

A summary of the binding and functional characterization of the PI64052 and PI64062 antibodies is shown in Table 21. The superiority of one antibody over the other for each criterion is indicated by (+). Criteria in which neither antibody is superior to the other is indicated by (-). Overall, PI64062, containing the M100Q mutation in the CDRH3 region had better binding properties than PI64052 to cynomolgus TREM1, while other properties were not substantially different.

TABLE 21

| Criteria/Test | PI64052 (M100L) | PI64062 (M100Q) |
| --- | --- | --- |
| Absence of background (HEK293 cells) | − | − |
| Absence of lymphocyte binding | − | − |
| EC$_{50}$ human (over-expressing) | − | − |
| EC$_{50}$ cyno (over-expressing) | − | + |
| EC$_{50}$ human monocytes | − | − |
| EC$_{50}$ cyno monocytes | − | − |
| CD16 ADCC Reporter Assay | − | − |
| Primary Macrophage ADCP Assay | − | − |
| FcγR binding | − | − |

Example 10: Receptor Occupancy and Cytokine Release by PI-4026-5-M100Q and Afucosylated PI-4026-5-M100Q (PI64062) Antibodies Receptor Occupancy Whole blood was sourced from multiple human donors (Stanford Blood Centre) and erythrocytes were removed. The remaining leukocytes were plated at 5×10$^6$ cells per well in a 96 well plate. Once plated, cells were incubated with unconjugated hIgG1 isotype, afucosylated hIgG1 isotype, PI-4026-5-M100Q, or afucosylated PI-4026-5-M100Q (PI64062) for 24 hr in a titration dependent manner.

After 24 hr, cells were washed once in PBS and stained with Zombie NIR (Biolegend) to determine cell viability. Fc receptors (FcγR) were also blocked with a combination of human serum (Jackson Immunoresearch), human FcX (Biolegend), and a peptide-based FcγR block solution (Innovex Biosciences). After incubation with FcγR blocking reagents, surface receptors of interest were stained with a flow cytometry cocktail encompassing markers for major intratumoral immune subsets as well as a mIgG1 isotype or mouse anti-human TREM1 antibody (clone TREM26, Biolegend). All antibodies used for phenotyping by flow cytometry were directly conjugated. Data was acquired using an Attune NxT analyzer (ThermoFisher) and analyzed using FlowJo (BD Biosciences), Prism (Graphpad), and Excel (Microsoft).

Receptor occupancy was determined by assessing the loss of specific signal from binding of the conjugated TREM1 antibody to relevant cell subsets (monocytes and neutrophils) as a function of the concentration of unconjugated antibody.

IC$_{50}$ values were calculated based on the titration curves plotted in Prism (Graphpad) and were normalized to nanomolar concentrations.

In Vitro Cytokine and Chemokine Detection

Whole blood was sourced from multiple human donors (Stanford Blood Centre) and erythrocytes were removed. The remaining leukocytes were plated at 5×10$^6$ cells per well in a 96 well plate. Once plated, cells were incubated with unconjugated hIgG1 isotype, afucosylated hIgG1 isotype, PI-4026-5-M100Q, or afucosylated PI-4026-5-M100Q (PI64062) for 24 hr in a titration dependent manner.

After 24 hr, supernatants were harvested and the levels of the indicated cytokines and chemokines were assessed in each condition using a Human Proinflammatory and Chemokine Kit (Panel 1, Meso Scale Diagnostics). Data was acquired using Meso Scale Diagnostics Technology and analyzed in Excel (Microsoft) and Prism (Graphpad).

EC$_{50}$ values were calculated based on the titration curves plotted in Prism (Graphpad) and were normalized to nanomolar concentrations.

Results

PI-4026-5-M100Q and afucosylated PI-4026-5-M100Q (PI64062) did not show substantially different dose dependent receptor occupancy (RO) on monocytes (FIG. 27A) or neutrophils (FIG. 27B).

Table 22 provides a quantification of the RO IC50 on monocytes for PI-4026-5-M100Q and afucosylated PI-4026-5-M100Q.

TABLE 22

| mAb | $IC_{50}$ (nM) |
|---|---|
| PI-4026-5-M100Q | 0.05 |
| Afuc-PI-4026-5-M100Q | 0.06 |

Table 23 provides a quantification of the RO IC50 on neutrophils for PI-4026-5-M100Q and afucosylated PI-4026-5-M100Q.

TABLE 23

| mAb | $IC_{50}$ (nM) |
|---|---|
| PI-4026-5-M100Q | 0.13 |
| Afuc-PI-4026-5-M100Q | 0.09 |

Figure 28A:
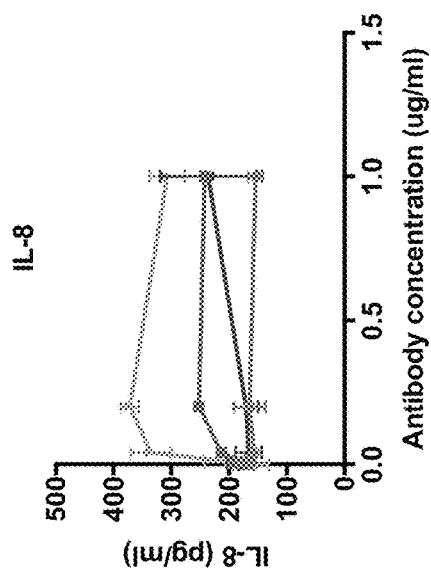
FIG. 28A shows that afucosylated PI-4026-5-M100Q induces a more robust dose-dependent cytokine release of IFN-γ from human peripheral blood leukocytes than PI-4026-5-M100Q.
Figure 28B:
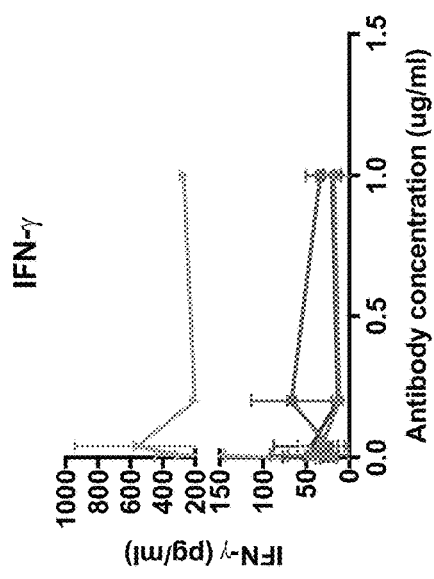
FIG. 28B shows that afucosylated PI-4026-5-M100Q induces a more robust dose-dependent cytokine release of IL-8 from human peripheral blood leukocytes than PI-4026-5-M100Q.
Figure 28D:
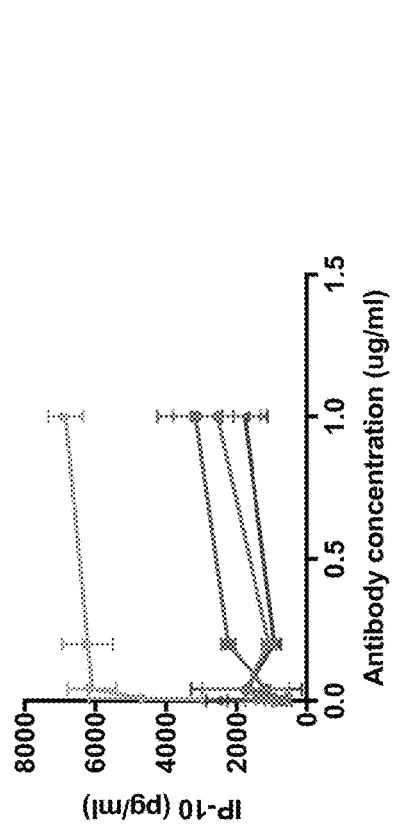
FIG. 28D shows that afucosylated PI-4026-5-M100Q induces a more robust dose-dependent cytokine release of IP-10 from human peripheral blood leukocytes than PI-4026-5-M100Q.
Figure 28C:
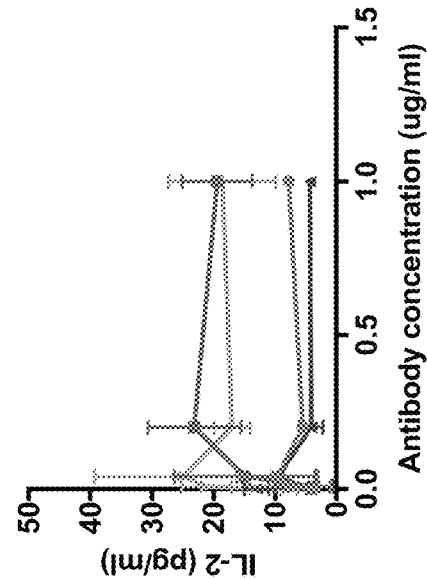
FIG. 28C shows that afucosylated PI-4026-5-M100Q induces a more robust dose-dependent cytokine release of IL-2 from human peripheral blood leukocytes than PI-4026-5-M100Q.

PI-4026-5-M100Q and afucosylated PI-4026-5-M100Q (PI64062) also induced a dose-dependent cytokine signature from human leukocytes. The IFN-γ induction is shown in FIG. 28A, IL-8 induction shown in FIG. 28B, IL-2 induction is shown in FIG. 28C, and IP-10 induction is shown in FIG. 28D. Other cytokines, including IL-6, TNFα, and IL-1β, were detected at <10 pg/ml. The $EC_{50}$ of each cytokine response is shown in Table 24.

TABLE 24

| Cytokine | mAb | $EC_{50}$ (nM) |
|---|---|---|
| IFN-γ | PI-4026-5-M100Q | 0.74 |
|  | Afuc-PI-4026-5-M100Q | 0.02 |
| IL-8 | PI-4026-5-M100Q | 0.32 |
|  | Afuc-PI-4026-5-M100Q | 0.10 |
| IL-2 | PI-4026-5-M100Q | 0.28 |
|  | Afuc-PI-4026-5-M100Q | 0.009 |
| IP-10 | PI-4026-5-M100Q | 0.71 |
|  | Afuc-PI-4026-5-M100Q | 0.03 |

Example 11: In Vivo Anti-TREM1 and Anti-PD-1 Combination Therapy Cytokine Profile In Vivo Cytokine Detection The Py8119 breast carcinoma line (ATCC, Manassas, VA) was harvested in log phase and injected subcutaneously into the right ventral flank of female C57BL/6 mice (Jackson Laboratories) at a dose of 2×10⁶ cells/mouse mixed with an equal volume of Matrigel. After tumors in the majority of mice had reached 70-130 mm³, mice were randomized and dosing with the indicated antibodies was commenced. Antibodies were dosed intraperitoneally at 15 mg/kg for anti-TREM1 and a mIgG2a isotype, and 5 mg/kg for anti-PD-1 and a mIgG1 isotype at a frequency of every 5 days for 2 doses. Anti-TREM1 and mIgG2a isotype were both afucosylated and the anti-TREM1 antibody used was PI-4928.

48 hrs after the second dose of antibody, blood from mice was harvested and fractionated for serum analysis. IFN-γ and TNFα serum cytokines were assessed from each group using Meso Scale Diagnostics Technology (Mouse proinflammatory panel 1). Data was acquired using Meso Scale Diagnostics Technology and analyzed in Excel (Microsoft) and Prism (Graphpad). Statistical test used was an ordinary one-way ANOVA with a Tukey's multiple comparisons correction.

PI-4928 was previously described in PCT/US2018/045680, herein incorporated by reference, and was shown to bind to mouse TREM1 on neutrophils (see e.g., Example 10) and cells overexpressing mouse TREM1 (see e.g., Example 11). Afucosylated PI-4928 also bound FcγR and induced FcγR-mediated signaling and ADCC (see e.g., Example 11). In addition, the therapeutic efficacy of afucosylated PI-4928 in combination with anti-PD-1 was also assessed in the Py8119 mouse model. The combination therapy resulted in decreased tumor volume size compared to control groups (see e.g., Example 15), indicating that an ADCC-based depletion of TREM1+ cells can lead to antitumor activity.

In this example, PI-4928 was used as an in vivo surrogate for the antibodies described above as it binds mouse TREM1, it also induces FcγR signaling in Jurkat reporter cells over-expressing mFcγRIV, and has been shown to provide an anti-cancer therapeutic effect in vivo.

Results

Figure 29B:
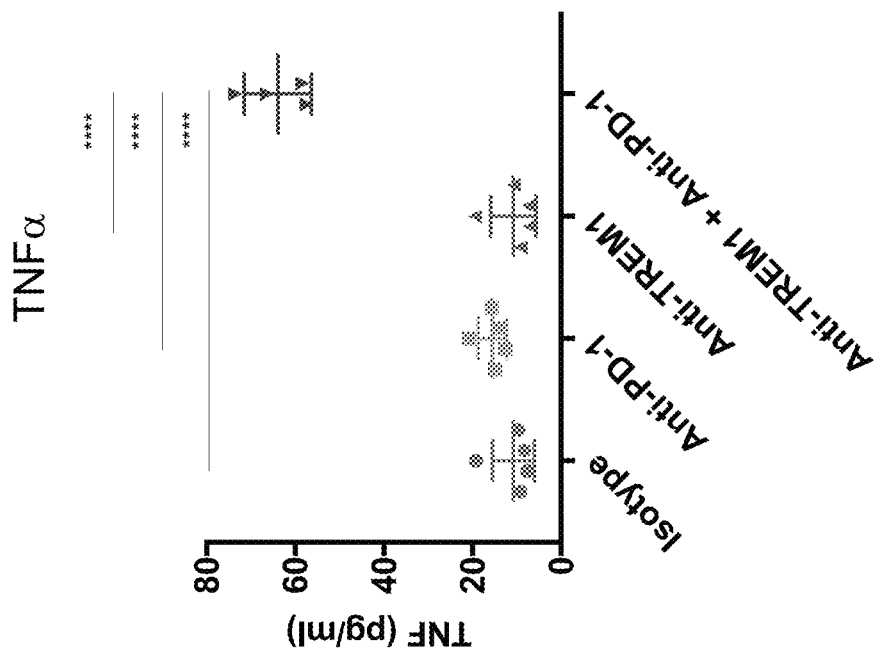
FIG. 29B shows that combination therapy of afucosylated PI-4928 anti-TREM1 and anti-PD-1 antibodies induce a peripheral cytokine signature in vivo.
Figure 29A:
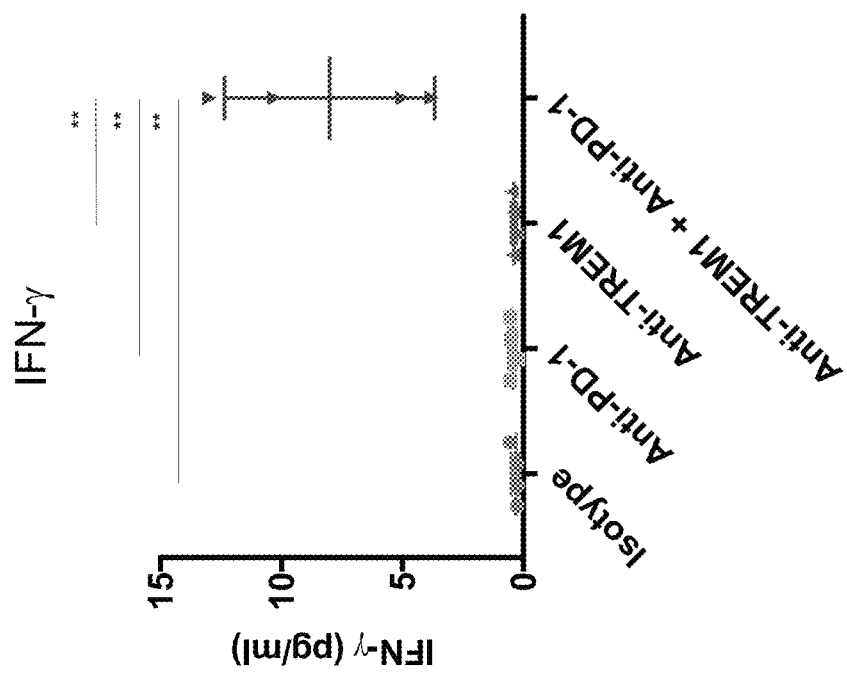
FIG. 29A shows that combination therapy of afucosylated PI-4928 anti-TREM1 and anti-PD-1 antibodies induce a peripheral cytokine signature in vivo.

The combination of the anti-TREM1 antibody (afucosylated-PI-4928) and PD-1 induced both an IFN-γ (FIG. 29A) and a TNFα (FIG. 29B) cytokine response in vivo,  indicates p<0.01, ** indicates p<0.0001.

Example 12: In Vivo Anti-TREM1 and anti-PD-1 Combination Therapy Efficacy

Panc02 Efficacy Study

The Panc02 pancreatic ductal adenocarcinoma cell line (NCI cell repository) was harvested in log phase and injected subcutaneously into the right flank of female C57BL/6 mice (Charles River Laboratories) at a dose of 2×10⁶ cells/mouse. After tumors in the majority of mice had reached 80-100 mm³, mice were randomized and dosing with the indicated antibodies was commenced. Antibodies were dosed intraperitoneally at 15 mg/kg for anti-TREM1 and a mIgG2a isotype, and 10 mg/kg for anti-PD-1 and a mIgG1 isotype at a frequency of every 3 or 5 days for 4 doses. Anti-TREM1 and mIgG2a isotype were both afucosylated and the anti-TREM1 antibody used was PI-9067L. Tumor size was assessed using the formula V (mm³)=(L×W×W)=2 where V=volume, L=length, and W=width. Tumors were measured using calipers and mice were euthanized when tumor volumes reached 2000 mm³.

Tumor growth was plotted as mean per group over time, individual mice per group over time, and tumor volume per group at Day 28. Statistical test used was an ordinary one-way ANOVA with a Holm-Sidak multiple comparisons correction.

PI-9067L was previously described in PCT/US2018/045680, herein incorporated by reference, and was shown to bind to mouse TREM1 on neutrophils (see e.g., Example 10) and cells overexpressing mouse TREM1 (see e.g., Example 11). Afucosylated PI-9067L also bound FcγR and induced FcγR-mediated signaling and ADCC (see e.g., Example 11). In addition, the therapeutic efficacy of fucosylated and afucosylated PI-9067L alone or in combination with anti-PD-1 in the MC38 and CT26 mouse models was also assessed. Mono- or combination therapy with PI-9067L resulted in decreased tumor volume size compared to control groups in the MC38 and CT26 models respectively (see e.g., Examples 13 and 14), indicating that an ADCC-based depletion of TREM1+ cells can lead to antitumor activity.

In this example, PI-9067L was used as an in vivo surrogate for the antibodies described above as it binds to mouse TREM1, it also induces FcγR signaling in Jurkat reporter cells over-expressing mFcγRIV, and has been shown to provide an anti-cancer therapeutic effect in vivo.

Results

Figure 30:
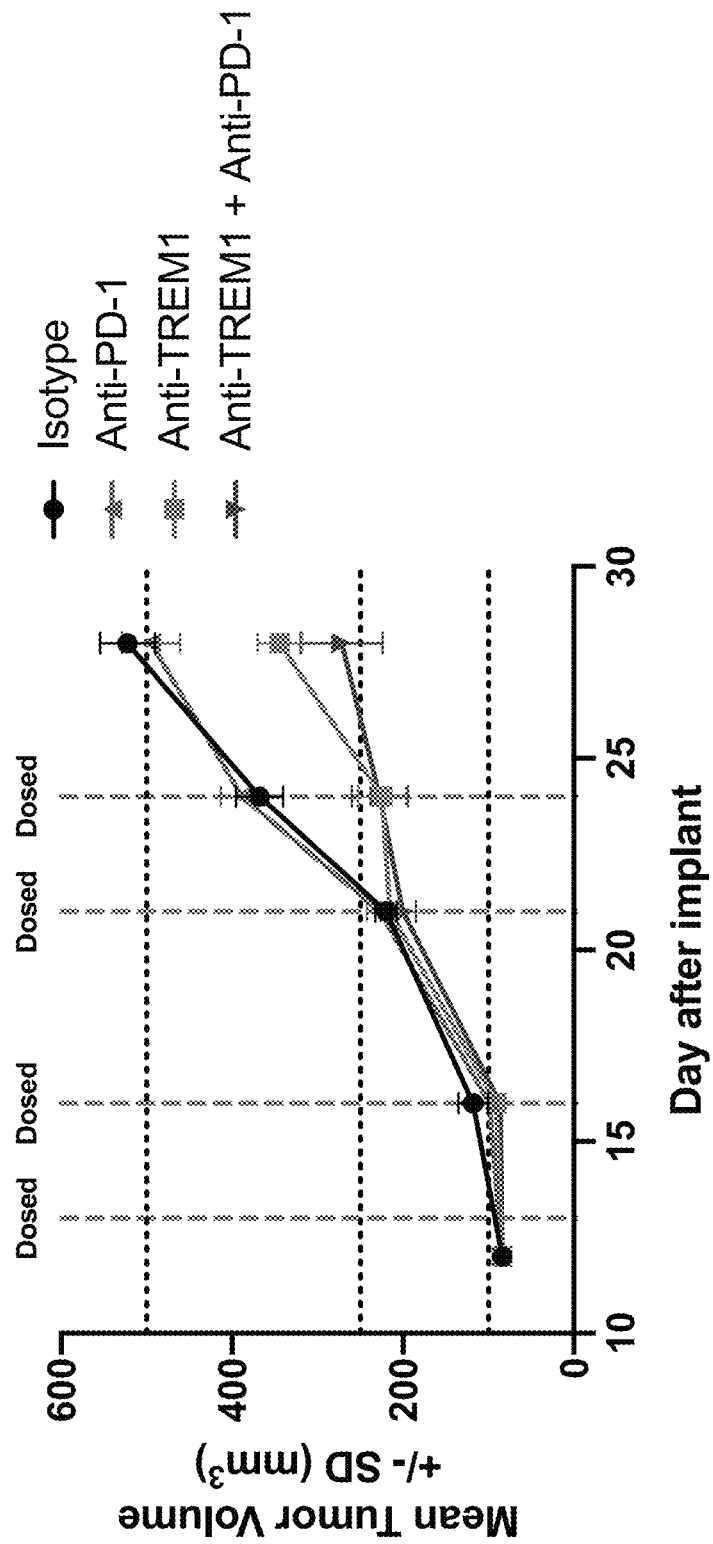
FIG. 30 shows that the afucosylated PI-9067 anti-TREM1 antibody has monotherapeutic activity in the Panc02 tumor model.
Figure 32:
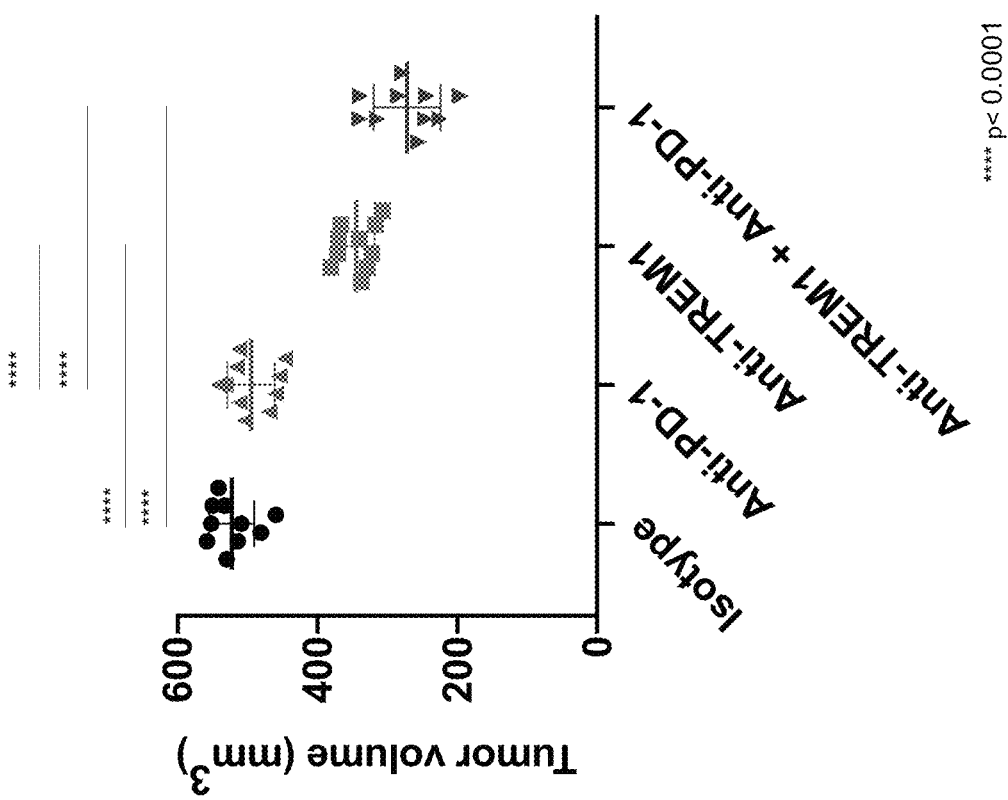
FIG. 32 provides the day 28 tumor volumes for each mouse from each indicated group in the Panc02 tumor model.

In addition, anti-TREM1 antibody therapy has monotherapeutic activity in the Panc02 tumor model. Administration of afucosylated PI-9067L anti-TREM1 antibody alone resulted in a decrease in tumor volume in vivo, as well as in combination with an anti-PD1 antibody (FIG. 30). Individual treatment groups are shown in FIG. 31A-D. Isotype treatment is shown in FIG. 31A, anti-PD-1 alone treatment is shown in FIG. 31B, anti-TREM1 treatment is shown in FIG. 31C, and combination anti-TREM1 and anti-PD-1 treatment is shown in FIG. 31D. Quantification of the mouse tumor volumes in each treatment group at Day 28 is provided in FIG. 32.

Example 13: TREM1 is Expressed Across Different Oncology Indications

Materials and Methods

Flow Cytometry

TREM1 expression was assessed in the microenvironment of human tumors from various indications by flow cytometry. Tumor tissue obtained was either freshly surgically resected (Cooperative Human Tissue Network, CHTN) or previously dissociated and snap frozen (Folio Conversant). Fresh surgically resected tumors were dissociated (Human Tumor Dissociation Kit, Miltenyi Biotec) within 24 hours of being excised from the patient.

Once tumors were dissociated and erythrocytes were removed, single cell suspensions were diluted in PBS (Gibco), washed once, and stained with Zombie NIR (Biolegend) to determine cell viability. Fc receptors were also blocked with a combination of human serum (Jackson Immunoresearch), human FcX (Biolegend), and a peptide-based FcR block solution (Innovex Biosciences). After incubation with FcR blocking reagents, surface receptors on cells were stained with a flow cytometry cocktail encompassing markers for major intratumoral immune subsets as well as a mIgG1 isotype or mouse anti-human TREM1 antibody (clone TREM26, Biolegend). In some cases, cells were also fixed and permeabilized (True-Nuclear Transcription Buffer Set, Biolegend) in order to determine intracellular CD68 expression. All antibodies used for phenotyping were directly conjugated. Data was acquired using an Attune NxT analyzer (ThermoFisher) and analyzed using FlowJo (BD Biosciences), Prism (Graphpad), Excel (Microsoft), and the R computing environment.

LUNG=lung adenocarcinoma, OV=ovarian carcinoma, KID=renal cell carcinoma, PRAD=prostate adenocarcinoma. PAAD=pancreatic adenocarcinoma, BLAD=bladder adenocarcinoma, CRC=colorectal adenocarcinoma, BREAST=breast carcinoma, STAD=stomach adenocarcinoma, SKCM=skin melanoma, HNSC=head and neck carcinoma, TAMs=tumor-associated macrophages, Conv. Monocytes=conventional monocytes.

RNA In Situ Hybridization

RNAscope experiments were performed at Advanced Cell Diagnostics (ACD). Advanced Cell Diagnostics (ACD) performed RNAscope® detection for TREM1 in a set of proprietary TMAs containing tissue from bladder, prostate, melanoma, head and neck, pancreas, colorectal, kidney, lung, ovary, and breast cancers. Sample quality was assessed by staining sections with a positive control probe against PPIB (housekeeping gene) and a negative control probe against the bacterial gene dapB. Staining conditions were optimized for each probe to maximize positive control signal and minimize negative control signal. The TREM1 probe sequence was selected by ACD to have minimal cross-hybridization to off target areas of the genome. RNA in situ hybridization for TREM1, TREM2, CD163, CD8A, and NCAM1 mRNA was performed on automation platform using the RNAscope®LS Duplex Reagent Kit (Advanced Cell Diagnostics, Inc., Newark, CA) according to the manufacturer's instructions. 5 µm formalin fixed, paraffin embedded (FFPE) tissue sections were pretreated with heat and protease prior to hybridization with the target oligo probes. Preamplifier, amplifier, and HRP/AP-labeled oligos were then hybridized sequentially, followed by chromogenic precipitate development. Each sample was quality controlled for RNA integrity with RNAscope® probe specific to PPIB/POLR2A RNA and for background with a probe specific to bacterial dapBRNA. Specific RNA staining signal was identified as green/red, punctate dots. Samples were counterstained with Gill's Hematoxylin. RNA probes against human TREM1 (cat #431508, against 24-1063nt), human TREM2 (cat #420498, against 5-1069nt), human CD163 (cat #417068-C2, against 210-1565nt), human NCAM-1 (cat #421468, against 832-1751nt) and human CD8a (cat #560398, against 871-2342nt) were used. Semi-quantitative scores (0-4) for each probe were defined for all samples by an ACD scientist based on the number of stained dots per cell throughout the section. The scoring criteria were as follows: score 0: no staining or <1 dot/10 cells; score 1: 1-3 dots/cell; score 2: 4-9 dots/cell and no or very few dot clusters; score 3: 10-15 dots/cell and/or <10% dots are in clusters; score 4: >15 dots/cell and/or >10% dots are in clusters. To pass quality control, samples with 2-4 (moderate to high) positive control signal and 0 (undetected) negative control signal were selected for TREM1 quantification. TREM1 positive indications were defined as those that passed quality control and had a TREM1 score of 1 or greater.

Single Cell TREM1 Expression

Dissociated tumor cells (DTCs) from a single human ovarian patient were purchased from Discovery Life Sciences. Cells were flow cytometrically sorted for CD45 positivity to enrich for immune cells and encapsulated for single cell RNA sequencing using 10× Genomics' Chromium Controller. Resulting raw data was sequentially processed using 10×'s CellRanger program and the Seurat module in the R programming language. Cell populations in the resulting t-distributed stochastic neighbor embedding (tSNE) dimensionality reduction were manually annotated using cell-type specific marker genes and TREM1 expression was plotted.

Single cell sequencing data from a single human lung adenocarcinoma patient was downloaded from NCBI's Gene Expression Omnibus (Accession: GSE97168). Raw data was processed using the Seurat module in the R programming language. Cell populations in the resulting t-distributed stochastic neighbor embedding (tSNE) dimensionality reduction were manually annotated using cell-type specific marker genes and TREM1 expression was plotted.

Results

Figure 33:
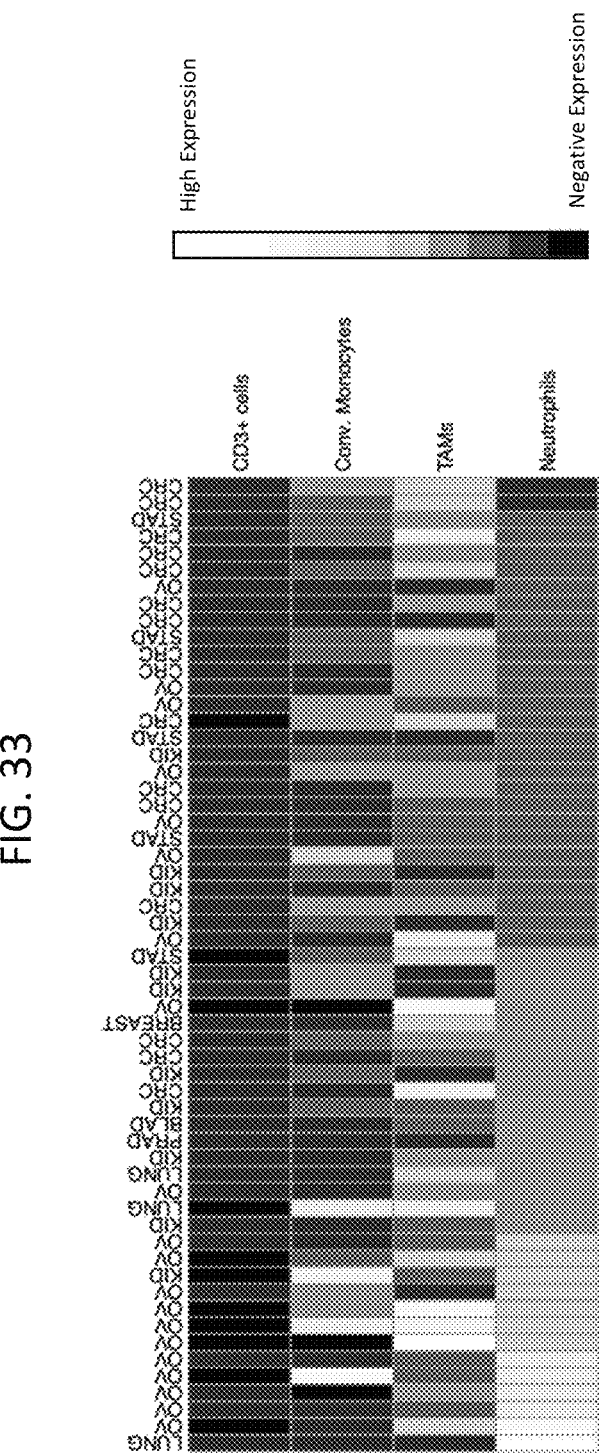
FIG. 33 shows that human TREM1 is expressed across different oncology indications and is restricted to myeloid cells.

TREM1 expression was found exclusively on myeloid cells in the tumor microenvironment of a variety of cancer indications (FIG. 33), including lung adenocarcinoma, ovarian carcinoma, renal cell carcinoma, prostate adenocarcinoma, bladder adenocarcinoma, colorectal adenocarcinoma, breast carcinoma, and stomach adenocarcinoma. TREM1 expression was consistently expressed on neutrophils, TAMs, and/or conventional monocytes and negative on CD3+ cells.

Table 25 also provides quantitation of the TREM1+ tumors as a percentage of the total tumors analyzed. TREM1 was expressed in the majority of the tumors analyzed across multiple tumor types.

TABLE 25

| Flow cytometry | CRC | KID | OV | LU | STAD |
|---|---|---|---|---|---|
| % TREM1⁺ tumors | 94% | 73% | 82% | 91% | 90% |
| Total tumors analyzed | 16 | 11 | 17 | 12 | 10 |

Similar results were seen in the RNA in situ hybridization analysis, shown in Table 26. In most cases, TREM1 was expressed on more than 70% of the tumors analyzed (see e.g., CRC, OV, LU, HNSC, SKCM, PAAD, and PRAD tumors). TREM1 was also expressed in about 40% of the kidney, bladder, and breast tumors analyzed. Thus, TREM1 is expressed in multiple tumor types.

TABLE 26

| RNAScope (FISH) | CRC | KID | OV | LU | BLAD | BREAST | HNSC | SKCM | PAAD | PRAD |
|---|---|---|---|---|---|---|---|---|---|---|
| % TREM1⁺ tumors | 80% | 40% | 71% | 100% | 38% | 40% | 100% | 80% | 86% | 83% |
| Total tumors analyzed | 10 | 10 | 7 | 8 | 8 | 10 | 7 | 10 | 7 | 6 |

A further analysis of single cell sequencing results from CD45+ immune infiltrate sorted from human ovarian tumor dissociated cells showed that TREM1 is predominantly expressed on monocytic myeloid-derived suppressor cells (mMDSCs), immature monocytic myeloid cells that are immune-suppressive (data not shown). In contrast, TREM2 is predominantly expressed on tumor associated macrophages (TAMs). Analysis of single cell sequencing results from a lung adenocarcinoma patient also showed that TREM1 is expressed in human suppressive myeloid populations (data not shown).

Example 14: Anti-TREM1 Antibody Induces a Selective Set of Anti-Cancer Chemokines and Cell Surface Receptors Materials and methods
Sample Preparation Whole blood was sourced from multiple human donors (Stanford Blood Centre) and erythrocytes were removed. The remaining leukocytes were plated at 5×10⁶ cells per well in a 96 well plate. Once plated, cells were incubated with afucosylated hIgG1 isotype or afucosylated PI-4026-5-M100Q (PI64062) for 24 hr in a titration dependent manner. Additional cells were treated with single concentrations of afucosylated hIgG1 isotype or afucosylated PI-4026-5-M100Q (PI64062) for 24 hr for CD80 and CD86 cell surface expression. After 24 hr, supernatants were harvested.

In Vitro Cytokine and Chemokine Detection

For cytokine and chemokine measurements, the samples were assessed in each condition using a Human Proinflammatory and Chemokine Kit (Panel 1, Meso Scale Diagnostics). Data was acquired using Meso Scale Diagnostics Technology and analyzed in Excel (Microsoft) and Prism (Graphpad). EC50 values were calculated based on the titration curves plotted in Prism (Graphpad) and were normalized to nanomolar concentrations.

CD40, HLA-DR, CD80, and CD86 Flow Cytometry

After 24 hr, cells were washed once in PBS and stained with Zombie NIR (Biolegend) to determine cell viability. Fcγ receptors (FcγR) were also blocked with a combination of human serum (Jackson Immunoresearch), human FcX (Biolegend), and a peptide-based FcγR block solution (Innovex Biosciences). After incubation with the FcγR blocking reagents, surface receptors of interest were stained with a flow cytometry cocktail encompassing markers for intratumoral subsets as well as HLA-DR (clone L243), CD40 (clone 5C3), CD80 (clone 2D10, Biolegend cat #306216), and CD86 (clone BU63, Biolegend cat #374212). All antibodies used for phenotyping by flow cytometry were directly conjugated. Data was acquired using an Attune NXT analyzer (ThermoFisher) and analyzed using FlowJo (BD Biosciences), Prism (Graphpad), and Excel (Microsoft). Representative histogram overlays for cell surface HLA-DR, CD40, CD80, and CD86 on CD14+ monocytes are shown.

RNAseq for Cell Sorting

Whole heparinized blood from 5 healthy human donors was treated with 1 mg/ml (~7 nM) of afucosylated PI-4026-5-M100Q (PI64062) or isotype control antibody, respectively, for 16 hours at 37° ° C. at 5% $CO_2$. After the incubation period, blood was transferred and all subsequent steps were carried out on ice. Blood was RBC-lysed and leukocytes were then stained with antibodies against lineage-specific markers. Anti-CD15 (clone W6D3, Biolegend) was used to identify neutrophils, anti-CD14 (clone M5E2, Biolegend) was used to identify monocytes, anti-CD3 (clone UCHT1, Biolegend) was used to identify T cells, and anti-CD56 (clone 5.1H11, Biolegend) was used to identify NK cells. Stained cells were submitted for flow cytometric sorting, yielding pure populations of CD15+ neutrophils, CD14+ monocytes, CD3+ T cells and CD56+NK cells. Total RNA was isolated from each cellular subset-specific sample and submitted for high-throughput RNA sequencing. Subsequent data was aligned to the human genome (GRCh38.p12) and per-gene expression values were tabulated for each sample. The resulting expression matrix was log-normalized using the R package DESeq2 and the 1000 genes with highest variance across all samples were clustered using Euclidean distance and complete linkage. Purity of initial cell sort is indicated by clean separation of cell-types as well as donor-specific separation. Canonical markers for each cell type are indicated on the right.

RNAseq for Immune Activation Markers HLA-DR, CD40, CD80, and CD86

Whole heparinized blood from 5 healthy human donors was treated with 1 mg/ml (~7 nM) of afucosylated PI-4026-5-M100Q (PI64062) or isotype control antibody, respectively, for 16 hours at 37° C. at 5% $CO_2$. After the incubation period, blood was transferred and all subsequent steps were carried out on ice. Blood was RBC-lysed and leukocytes were then stained with antibodies against lineage-specific markers and submitted for flow cytometric sorting, yielding pure populations of CD15+ neutrophils, CD14+ monocytes, CD3+ T cells and CD56+ NK cells. Total RNA was isolated from each cellular subset-specific sample and submitted for high-throughput RNA sequencing. Subsequent data was aligned to the human genome (GRCh38.p12) and per-gene expression values were tabulated for each sample. The resulting expression matrix was reduced to monocyte profiles and counts-per-million normalized. Resulting expression values for HLA-DR. CD40, CD80 and CD86 were plotted across all monocyte-derived samples. Activation markers were specifically expressed and differentially regulated in only monocytes.

Results

Figure 34B:
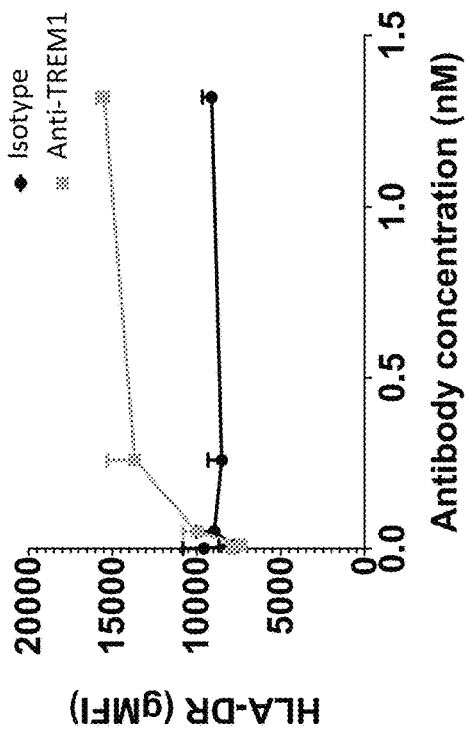
FIG. 34B shows upregulation of HLA-DR surface expression after treatment with afucosylated PI64062.

Afucosylated PI-4026-5-M100Q induced a selective set of chemokines and cytokines in vitro. FIG. 34A provides the relative fold change of the indicated chemokine or cytokine after treatment with PI-4026-5-M100Q as compared to isotype antibody treatment. The cytokines shown in FIG. 34A were detected at greater than 10 pg/ml and were upregulated across experiments from multiple donors.

Figure 34C:
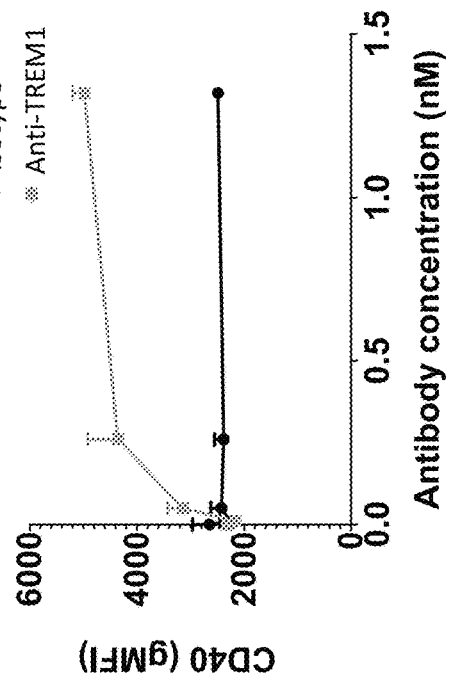
FIG. 34C shows upregulation of CD40 surface expression after treatment with afucosylated PI64062.
Figure 34A:
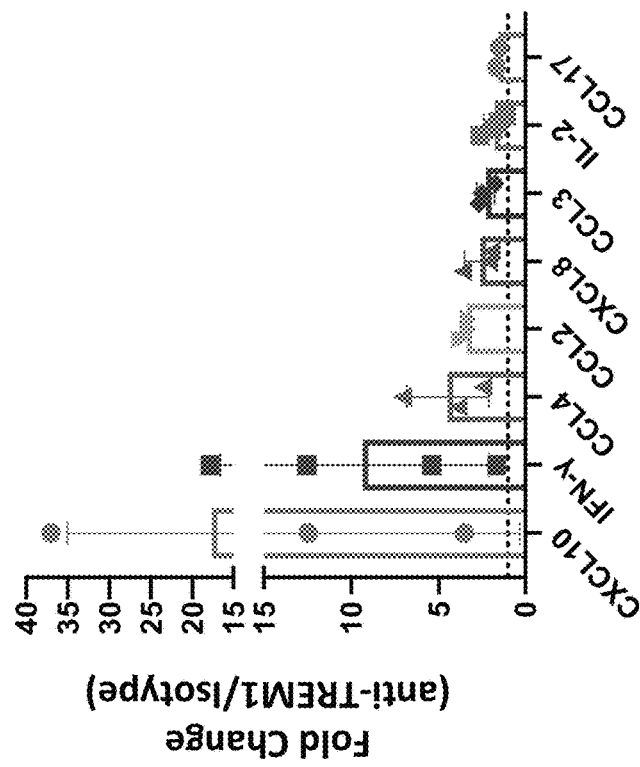
FIG. 34A shows the fold change in cytokines induced by afucosylated PI64062 in human blood cells.

In addition, treatment of cells with afucosylated PI-4026-5-M100Q resulted in a dose dependent increases in HLA-DR surface expression (FIG. 34B) and CD40 (FIG. 34C surface expression on conventional monocytes. HLA-DR and CD40 are co-stimulatory proteins found on antigen presenting cells that play critical roles in antigen presentation. Afucosylated PI-4026-5M100Q upregulate cell surface molecules important for antigen-presentation and lymphocyte activation and also upregulate cytokines responsible for lymphocyte activation and recruitment. These results suggest that the TREM1 antibody can reprogram or activate suppressive myeloid cells into an anti-tumor, pro-inflammatory phenotype.

Figure 35:
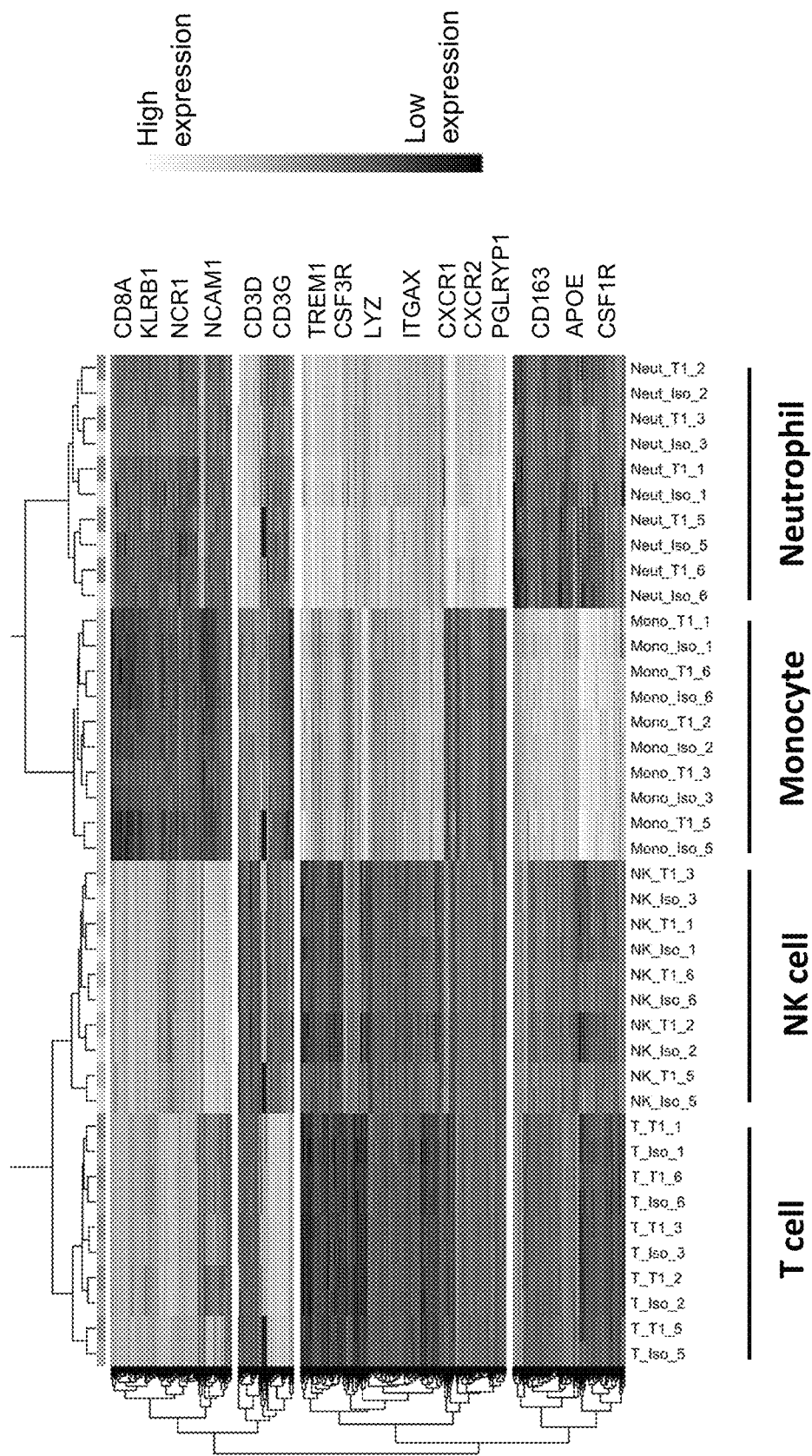
FIG. 35 shows an expression matrix of the 1000 genes with highest variance across blood samples as sorted according to cell type. Gene expression clustering correlated well with sorted immune cell populations.

To confirm these results, the immune signaling genes and pathways induced in cells after treatment with afucosylated PI-4026-M100Q or an isotype control was interrogated via RNAseq. First, RNAseq was performed on cells treated with anti-TREM1 antibody or isotype control and the gene expression of each sample clustered. As shown in FIG. 35, clustering of T cells, NK cells, monocytes, and neutrophils based on RNAseq data correlated well with canonical gene expression each indicated cell population. Thus, the immune cells could be correctly clustered using RNAseq data, regardless of antibody treatment.

Figure 36A:
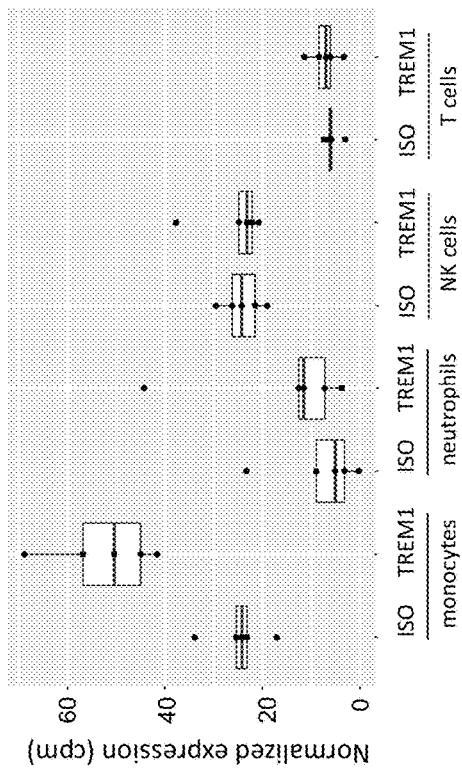
FIG. 36A shows HLA-DR gene expression in the indicated cell types after isotype antibody treatment (ISO) or anti-TREM1 antibody (afucosylated PI64062) treatment.
Figure 36B:
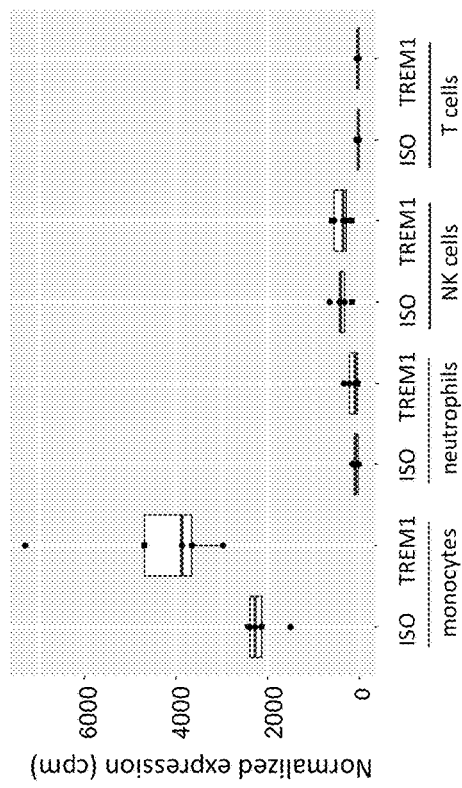
FIG. 36B shows CD40 gene expression in the indicated cell types after isotype antibody treatment (ISO) or anti-TREM1 antibody (afucosylated PI64062) treatment.
Figure 36C:
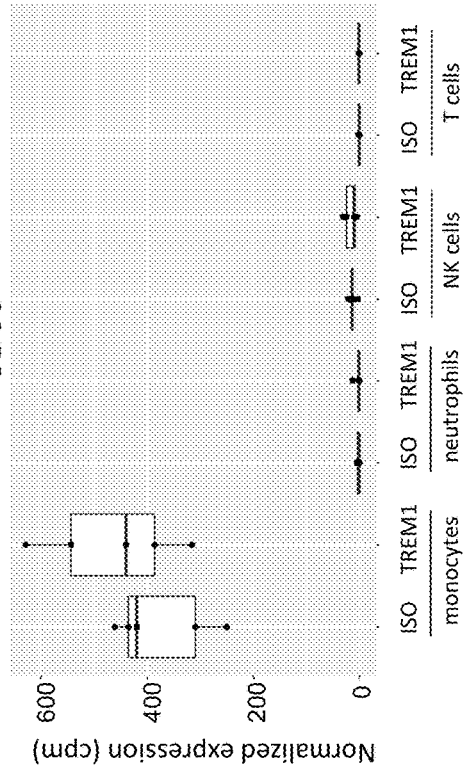
FIG. 36C shows CD80 gene expression in the indicated cell types after isotype antibody treatment (ISO) or anti-TREM1 antibody (afucosylated PI64062) treatment.
Figure 36D:
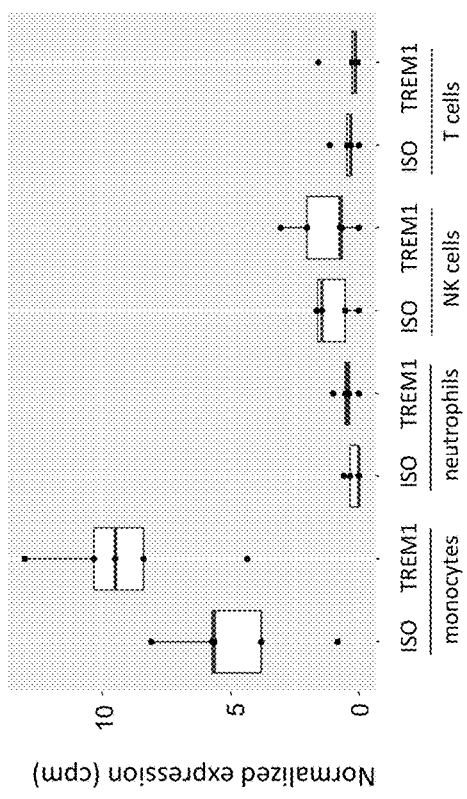
FIG. 36D shows CD86 gene expression in the indicated cell types after isotype antibody treatment (ISO) or anti-TREM1 antibody (afucosylated PI64062) treatment.

Next, anti-TREM1 antibody induction of specific immune cell activation markers was confirmed using RNAseq. HLA-DR, CD40, CD80, and CD86 expression was determined by RNAseq. CD80 and CD86 are additional co-stimulatory proteins found on antigen presenting cells FIG. 36A shows HLA-DR gene expression in the indicated cell types after isotype antibody treatment (ISO) or anti-TREM1 antibody (afucosylated PI64062) treatment. FIG. 36B shows CD40 gene expression in the indicated cell types after isotype antibody treatment (ISO) or anti-TREM1 antibody (afucosylated PI64062) treatment. FIG. 36C shows CD80 gene expression in the indicated cell types after isotype antibody treatment (ISO) or anti-TREM1 antibody (afucosylated PI64062) treatment. FIG. 36D shows CD86 gene expression in the indicated cell types after isotype antibody treatment (ISO) or anti-TREM1 antibody (afucosylated PI64062) treatment. The RNA analysis was further confirmed by flow cytometry analysis for surface expression CD80 and CD86, as well as HLA-DR and CD40 as repeat samples. Representative histogram overlays for cell surface HLA-DR (FIG. 37A), CD40 (FIG. 37B), CD80 (FIG. 37C), and CD86 (FIG. 37D) on CD14+ monocytes are shown, matching the anti-TREM1 induced pattern shown by RNA analyses. Importantly, the cell surface markers induced by anti-TREM1 antibody treatment in the RNAseq samples matched the HLA-DR and CD40 expression initially identified by flow cytometry.

Additional changes in gene expression induced by TREM1 antibody treatment in monocytes, neutrohpils, NK cells, and T cells was also assessed via RNAseq. Genes associated with the IFN response, TNFα signaling, and the inflammatory response were induced by TREM1 antibody treatment in neutrophils, monocytes, NK cells, and T cells. TREM1 antibody induced gene expression changes mainly in neutrophils, monocytes, and NK cells.

Table 27 provides a summary of the immune pathways induced by the TREM1 antibody in different cell types.

TABLE 27

Number of genes selectively induced by TREM1 antibody

| | Monocyte | Neutrophil | NK | T Cell |
|---|---|---|---|---|
| After filtering low-expressed genes (counts per million >2) | 53 | 423 | 20 | 3 |
| Notable pathways induced by TREM1 antibody | IFN Response TNFα signaling In-flammatory response Signaling pathways | IFN Response TNFα signaling In-flammatory response Signaling pathways | TNFα signaling In-flammatory response Signaling pathways | IFN Response TNFα signaling |

Example 15: Anti-TREM1 Antibody Induces a Pro-Inflammatory Response

Materials and Methods

Protein Phosphorylation Quantification

Cells used for phospho-flow analysis were derived from whole blood buffy coats from healthy human donors. Buffy coats were RBC-lysed by two rounds of incubation in BD Pharm Lyse buffer at 37C for 15 min each. Following RBC-lysis, the resulting leukocytes in X-VIVO 15 medium and plated onto 96 multi-well deep-well plates at 5×106 leukocytes/well. Cells were allowed to recover for 2 hrs at 37C, 5% $CO_2$, to decrease the basal phosphorylation levels. Following the recovery period, cells were stimulated PMA (0.1 ug/ml) and ionomycin (1 ug/ml) as a positive control, or with 5 ug/ml of afucosylated PI-4026-5-M100Q or afucosylated hIgG1 isotype for 0, 2, 10, 30, 60, and 90 minutes. Cells were then fixed using pre-warmed BD Cyto Fix buffer for 10 min at 37C. After fixation, the samples were washed twice with FACS buffer (DPBS with 2% FBS, 2 mM EDTA), and permeabilized with 100 ul/sample of BD Perm Buffer III. Samples were then rinsed with FACS buffer, blocked with 50 ul of Innovex and human TrueStain FcX block for 30 min on ice, and washed twice with FACS buffer. Cell pellets were resuspended in the cocktail of antibodies against leukocyte lineage markers and divided into 2 samples for phospho-protein staining. Anti-Phospho-ERK1/2 (Y202/Y204) (Biolegend, clone 4B11B69) and anti-phospho-STAT3 (S727) (Biolegend, clone A16089B) were used. Samples were incubated for 60 minutes at RT with the antibody cocktails including the anti-phospho antibodies. Following incubation, the samples were washed twice with FACS buffer, and then fixed by incubating with 2% paraformaldehyde for 10 min on ice. Samples were washed twice with FACS buffer, resuspended in 200 ul of FACS buffer, and kept at 4C until acquisition on the Attune flow cytometer.

Cell Pathway Induction

Mice bearing MC38 tumors (n=10 per group) were treated with afucosylated PI-9067L or mIgG2a isotype control as described in Example 14 of PCT/US2018/045680. Tumors were harvested on day 19 after implant (48 hours post 2nd treatment). RNA was extracted and sequenced. Differentially induced pathways associated with antibody treatment were assessed using the Broad Institute's Gene Set Enrichment Analysis (GSEA) tool using the c5 collection of gene sets from MSigDB. Significantly upregulated pathways (FDR<0.1) were visualized using the Enrichment Map module in Cytoscape using default parameters.

RNAseq Validation

Whole heparinized blood from 5 healthy human donors was treated with 1 mg/ml (~7 nM) of PY159 and isotype control antibody, respectively, for 16 hours at 37 degrees Celsius at 5% $CO_2$. After the incubation period, blood was transferred and all subsequent steps were carried out on ice. Blood was RBC-lysed and leukocytes were then stained with antibodies against lineage-specific markers and submitted for flow cytometric sorting, yielding pure populations of CD15+ neutrophils, CD14+ monocytes, CD3+ T cells and CD56+NK cells. Total RNA was isolated from each cellular subset-specific sample and submitted for high-throughput RNA sequencing. Subsequent data was aligned to the human genome (GRCh38.p12) and per-gene expression values were tabulated for each sample. Normalization and subsequent differential expression between PY159 and control treated samples were carried out for each cell type using the R package DESeq2. Resulting data for each cellular subset was ordered by fold change, subsetted to include only protein coding genes and passed to Gene Set Enrichment Analysis software (v4.0.0) (available from the Broad Institute.) Pre-ranked analysis was run using default settings against the Broad Institute's Gene Ontology collection (MsigDB c5).

Results

Figure 38A:
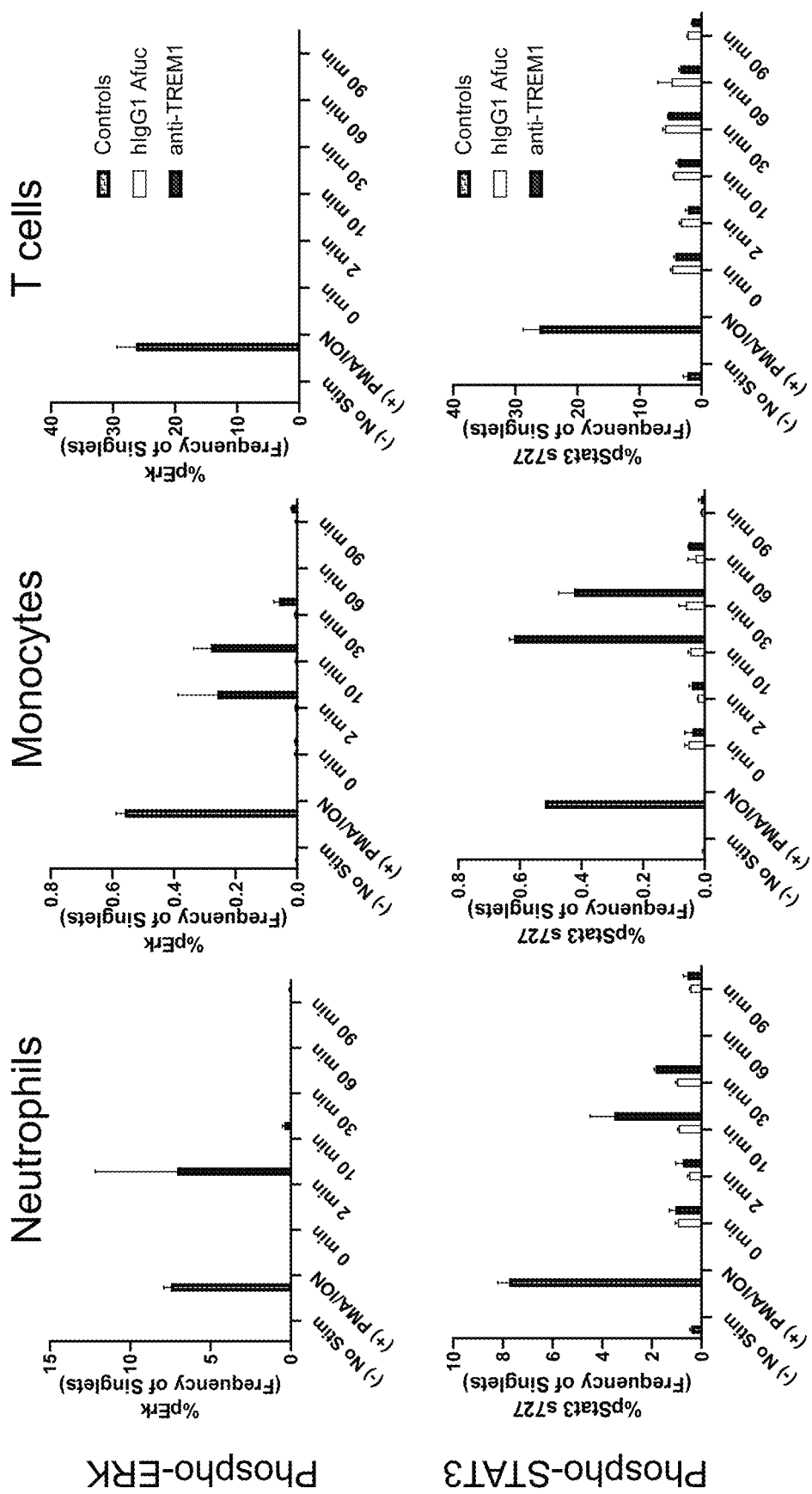
FIG. 38A shows the % of pERK and pSTAT3 in neutrophils, monocytes, or T cells after treatment with isotype control or afucosylated PI64062 antibody.

PI-4026-5-M100Q induced phosphorylation of ERK and STAT3 in monocytes and neutrophils, but not in T cells (FIG. 38A). Only TREM1 antibody induced phosphorylation of ERK in neutrophils or monocytes, no phosphorylation of ERK was observed in hIgG1 treated cells. TREM1 antibody induced higher levels of phosphorylated STAT3 in neutrophils and monocytes, compared to hIgG1 treatment. In the STAT3 panels of FIG. 38A, TREM1 samples are shown as the bars on the right and hIgG1 treated samples are shown in the bars on the left.

Figure 38B:
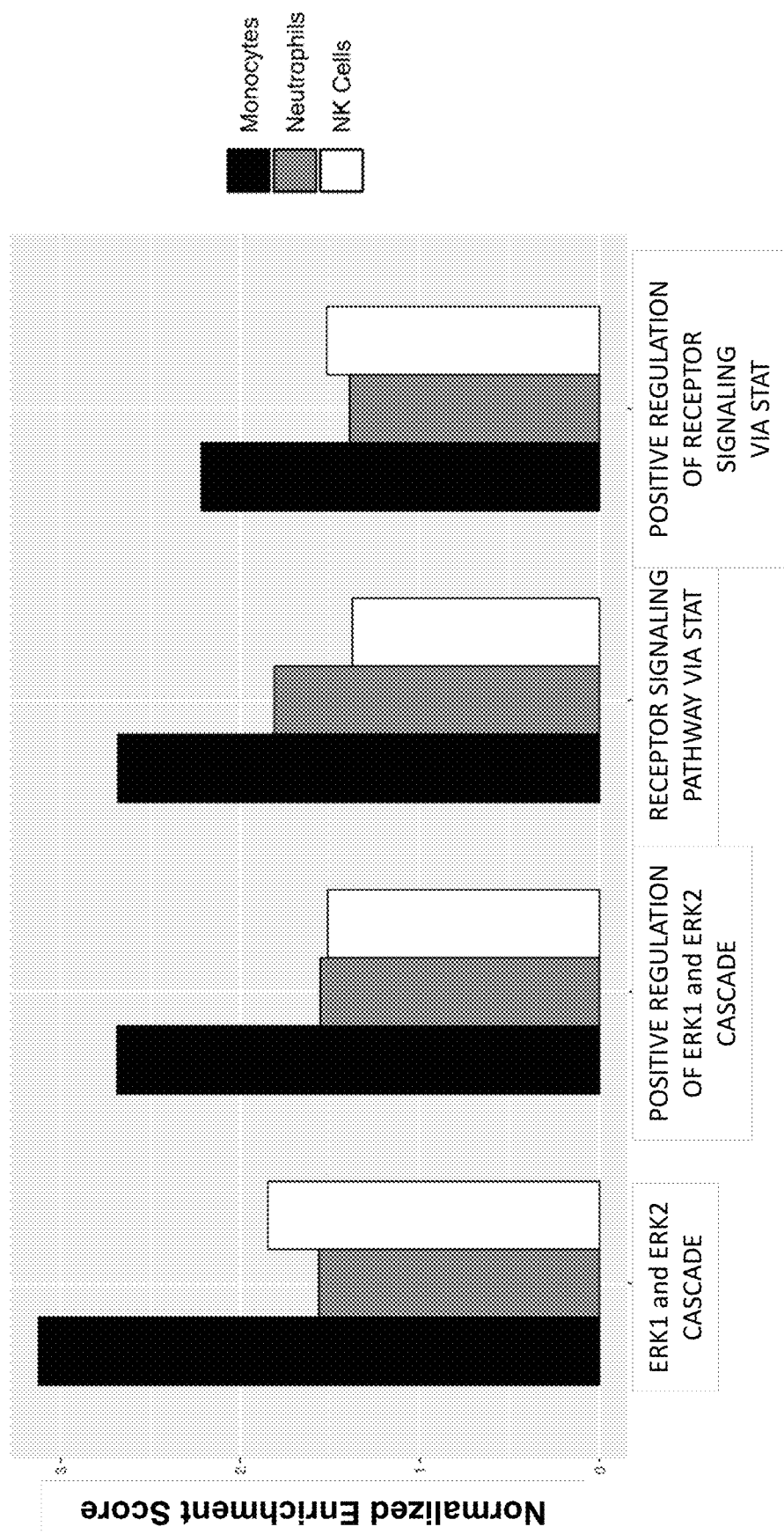
FIG. 38B (*<0.05, **<0.001) shows the results of the RNAseq analysis of the ERK and STAT pathways, showing significant enrichment in genes associated with those pathways in monocytes but not neutrophils or NK cells.

FIG. 38B (*<0.05, **<0.001) shows the results of the RNAseq analysis of the ERK and STAT pathways, showing significant enrichment in genes associated with those pathways in monocytes but not neutrophils or NK cells.

ERK, also known as Mitogen-Activated Protein Kinase (MAPK), activation results in NF-κB activation and expression of a pro-inflammatory response. STAT3 is a transcription factor that is activated by the JAK family signaling proteins and interacts with NF-κB. Activation of STAT3 also results in a pro-inflammatory response. Therefore, the phosphorylation of ERK and STAT3 after TREM1 antibody treatment provides further evidence of agonist activity of the afucsoylated PI-4026-5-M100Q antibody, demonstrating that treatment with the antibody can cross-link TREM1 and induced signaling downstream of TREM1 and its adaptor protein DAP12. This signaling possibly plays a role in reprogramming TREM1+ myeloid cells into pro-inflammatory cells.

The pro-inflammatory response induced by TREM1 antibody treatment in mice and humans was also analyzed. TREM1 antibody treatment in mice resulted in upregulation of pathways associated with immune responses, calcium ion transport, tissue remodeling, metabolism and RNA processing. The immune pathway families include antigen processing and presentation, T cell receptor signaling pathways, TNF responses, TNF superfamily cytokine production, NF-κB signaling, IFNγ production, regulation of IL-6 production, T cell proliferation, the adaptive immune response, lymphocyte mediated immunity, cell adhesion, chemokine activity, chemokine receptor binding, cell chemotaxis, lymphocyte migration, and the ERK1 and ERK2 cascade. Furthermore, treatment with anti-TREM1 antibody in the mouse Py8119 model also showed upregulation of pathways associated with the immune response, such as the innate immune response, cell activation and adhesion, and taxis or locomotion (data not shown).

Figure 39:
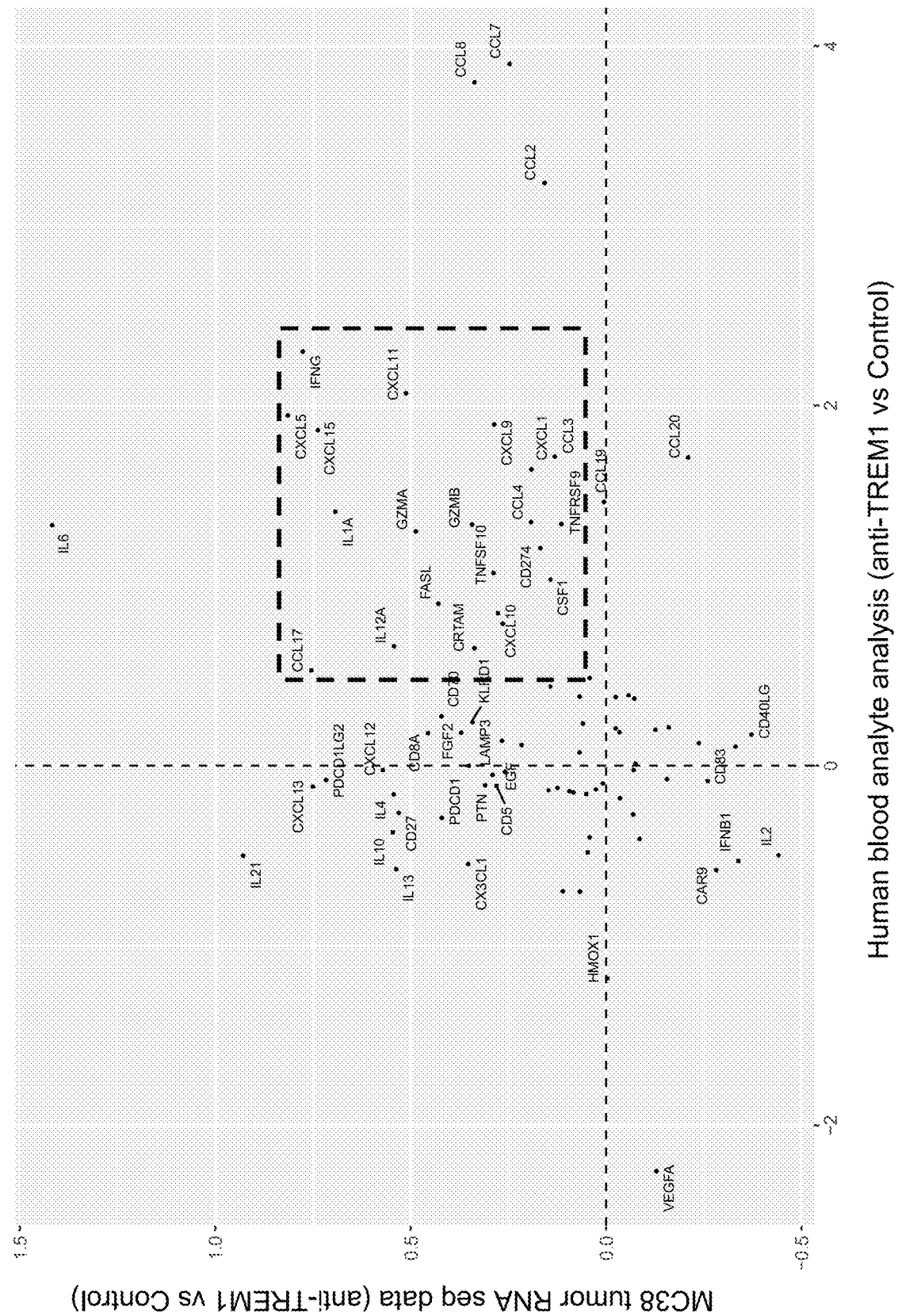
FIG. 39 shows the chemokines and cytokines upregulated by anti-TREM1 antibody in mice or human blood cells.

FIG. 39 shows a graph of genes upregulated in the mouse MC38 tumor model as compared to the chemokines and cytokines induced by PI-4026-5-M100Q in the human blood analyte analysis. In both the mouse in vivo and human blood in vitro data, treatment with anti-TREM1 antibody resulted in upregulation of molecules associated with a pro-inflammatory, T-cell based response.

Table 28 provides a summary of the specific cytokines and chemokines induced in various cell populations by the TREM1 antibody as determined by both protein assays and RNAseq.

TABLE 28

| Protein (O-Link) | RNAseq | Protein (O-Link) | RNAseq |
|---|---|---|---|
| CCL3 (MIP1α) | Monocyte, Neutrophil, NK | TNF α | Neutrophil, NK |
| IL-1a | Monocyte, Neutrophil | GZMH | No change |
| CCL4 (MIP1β) | Monocyte, Neutrophil, NK | IL-12 | Neutrophil, T cell |
| CCL8 (MCP-2) | No change | PD-L1 | Neutrophil |
| CCL20 (MIP3 α) | No change | TNFRSF9 (CD137; 4-1BB) | NK |
| IL-6 | Monocyte | GZMA | No change |
| CCL2 (MCP-1) | No change | CXCL11 | No change |
| CCL7 (MCP-3) | No change | MMP7 | No change |
| CXCL5 (ENA78) | Downregulated in monocytes | CCL23 | Monocyte, Neutrophil |
| CXCL1 (GRO/KC) | No change | CD70 | No change |
| CSF-1 | Monocyte, Neutrophil | CRTAM | NK |
| CCL13 (MCP-4) | Monocyte, Neutrophil | CD8A | No change |
| CCL19 | NK | GZMB | No change |
| IFN-γ | NK | CXCL10 | No change |

Thus, the TREM1 antibody (afucsoylated PI-4026-5-M100Q) induced multiple anti-tumor immune mechanisms in T cells, NK cells, M1-like macrophages that are associated with tumor destruction. In monocytes, TREM1 antibody treatment lead to induction of CXCL10, CXCL9, CCL3, CCL13, IL-6, CSF-1, HLA-DR, CD40, CD86, and CD80. In NK cells, TREM1 antibody treatment lead to induction of IFN-γ, CCL3, CCl4, CCl17, 4-1BB, CRTAM, and CD69. In neutrophils, TREM1 antibody treatment lead to induction of CCL3, CCL4, CCL13, CXCL8, and PD-L1.

A summary table of the TREM1 antibody induced factors, the functions of those factors, and the cell source is shown in Table 29.

TABLE 29

| TREM1-antibody induced factor | Function | Cell Source |
|---|---|---|
| IFN-g, 4-1BB, CXCL9, CXCL10, CCL13 | T cell recruitment and activation | NK cells, Monocytes, Neutrophils |
| IFN-g, CCL3, CCL4, CSF1, CXCL8 | Myeloid cell recruitment and activation | NK cells, Monocytes, Neutrophils |
| IFN-g, CXCL10, 4-1BB | Enhance antigen presentation | NK cells, Monocytes |
| IFN-g, CXCL10, CCL4 | NK cell activation | NK cells, Monocytes, Neutrophils |
| IFN-g, CXCL9, CXCL10 | Required for anti- PD-1 efficacy | NK cells, Monocytes |
| HLA-DR, CD40, CD86, CD80 | T cell activation | Monocytes |

Example 16: In Vivo Anti-TREM1 Therapy Efficacy in Ovarian Model

Antibodies for in vivo use were all tested for endotoxin and used at or below 0.2 EU/mg protein. Anti-PD-1 (clone RMP1-14) was purchased from Absolute Antibody Inc or recombinantly produced as mouse IgG1 D265A format at Pionyr. Mouse IgG1 (clone MOPC-21) and mouse IgG2a (clone C1.18.4) isotype controls were purchased from BioX-Cell or recombinantly made in HEK293 cells at Pionyr. Chimeric mouse IgG2a version of anti-TREM1 antibody (PI-9067L) was produced in HEK293 cells at Pionyr and evaluated for monodispersity and purity by SEC and CE-SDS as well as endotoxin tested.

All experimental procedures involving live animals were approved by the Institutional Animal Care and Use Committees of AJES Life Sciences LLC. 6-8 weeks old female B6(Cg)-Tyrc-2J/J or B6-albino mice were purchased from Jackson Laboratory and used after one week of acclimatization to the animal facility. Mouse ovarian surface epithelial cells overexpressing firefly luciferase known as ID8-Luc (AJES Life Sciences LLC, Stony Brook, NY) were harvested within 3 to 7 subcultures after thaw from liquid nitrogen stock and used for in-vivo experiments. On the day of tumor inoculation, the cells were harvested and used within 45 minutes. To establish intraperitoneal tumors, $5 \times 10^6$ ID8-Luc cells were injected into the lower right abdominal wall. All mice were imaged for in-vivo luciferase activity 20 days following injection for recruitment to the study. Forty tumor-bearing animals were recruited to the study based on average luminescence reading as a surrogate for tumor burden. Four treatment groups were randomly assigned with 10 animals such that the average tumor radiance (p/s/cm2/sr) for each group was $4.7 \times 10^4$. Tumor-bearing animals were treated with indicated antibodies intraperitoneally every 5 days and the luminescence images were captured weekly. Mice were injected intraperitoneally with 0.2 mL of 15 mg/mL D-luciferin (Promega). Ten minutes after D-luciferin injection, the mice were imaged in an instrument equipped with a charge-coupled device camera (IVIS, Xenogen, Alameda, CA). Data was analyzed with Living Image software (Xenogen) and presented as tumor radiance (p/s/cm2/sr) for a region of interest covering the peritoneum.

In this example, PI-9067L was used as an in vivo surrogate for the antibodies described above as it binds to mouse TREM1 and has been shown to provide an anti-cancer therapeutic effect in vivo in PCT/US2018/045680.

Figure 40:
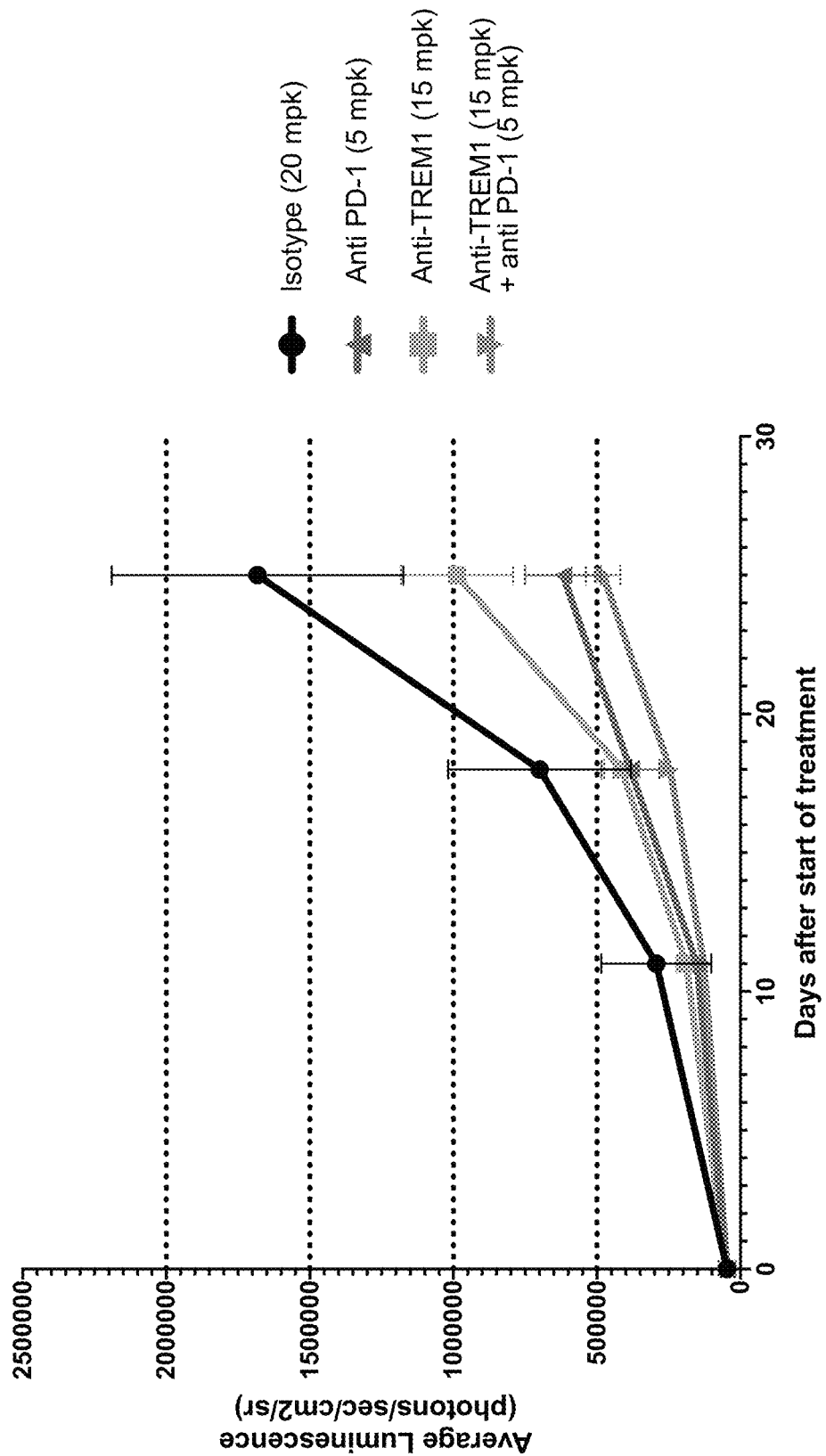
FIG. 40 shows that the afucosylated PI-9067L anti-TREM1 antibody has monotherapeutic activity in the ID8 ovarian tumor model.

As shown in FIG. 40, anti-TREM1 antibody treatment had monotherapeutic and combination therapy efficacy in the orthotopic ID8 ovarian tumor model. Mice treated with anti-TREM1 antibody alone had a decrease in tumor burden, as shown by a decrease in the tumor luminescence compared to isotype control treated mice. Control anti-PD-1 antibody treatment also resulted in a decrease in tumor burden, and the combination of the anti-TREM1 and anti-PD-1 antibodies resulted in the an even greater reduction in tumor burden as compared to anti-TREM1 or anti-PD-1 antibody treatment alone.

In summary of all the in vivo efficacy studies, anti-TREM1 antibodies had monotherapy efficacy in the MC38 colon carcinoma model, resulting in about 44% tumor growth inhibition compared to control; monotherapy efficacy in the Panc02 pancreatic model, resulting in about 43% tumor growth inhibition compared to control; and monotherapy efficacy in the ID8 ovarian model, resulting in about 44% tumor growth inhibition compared to control. Anti-TREM1 antibodies had combination efficacy with anti-PD-1 antibodies in the CTC26 colon carcinoma model, resulting in about 40-45% tumor growth inhibition and a 20-40% cure rate compared to control; combination efficacy with anti-PD-1 antibodies in the Panc02 model, resulting in about 56% tumor growth inhibition compared to control; combination efficacy with anti-PD-1 antibodies in the ID8 ovarian model, resulting in about 62% tumor growth inhibition and 20% cure rate compared to control; and combination efficacy with anti-PD-1 antibodies in the Py8119 breast carcinoma line resulting in about 46% tumor growth inhibition compared to control.

Example 17: Anti-TREM1 Treatment Results in Long-Term, Anti-Tumor Immune Memory BALB/c mice that were tumor-free from previous CT26 tumor model studies after the anti-TREM1 afucolsylated PI-9067L antibody plus anti-PD-1 antibody treatment as described in Example 13 of PCT/US2018/045680 were re-challenged three months later with $1 \times 10^6$ CT26 tumor cells. Tumor volume was measured for 25 days post implant. Age-matched treatment naïve mice received an equivalent number of CT26 cells and tracked for tumor growth during the study period. No additional treatment was provided to the mice during the study period.

Figure 41:
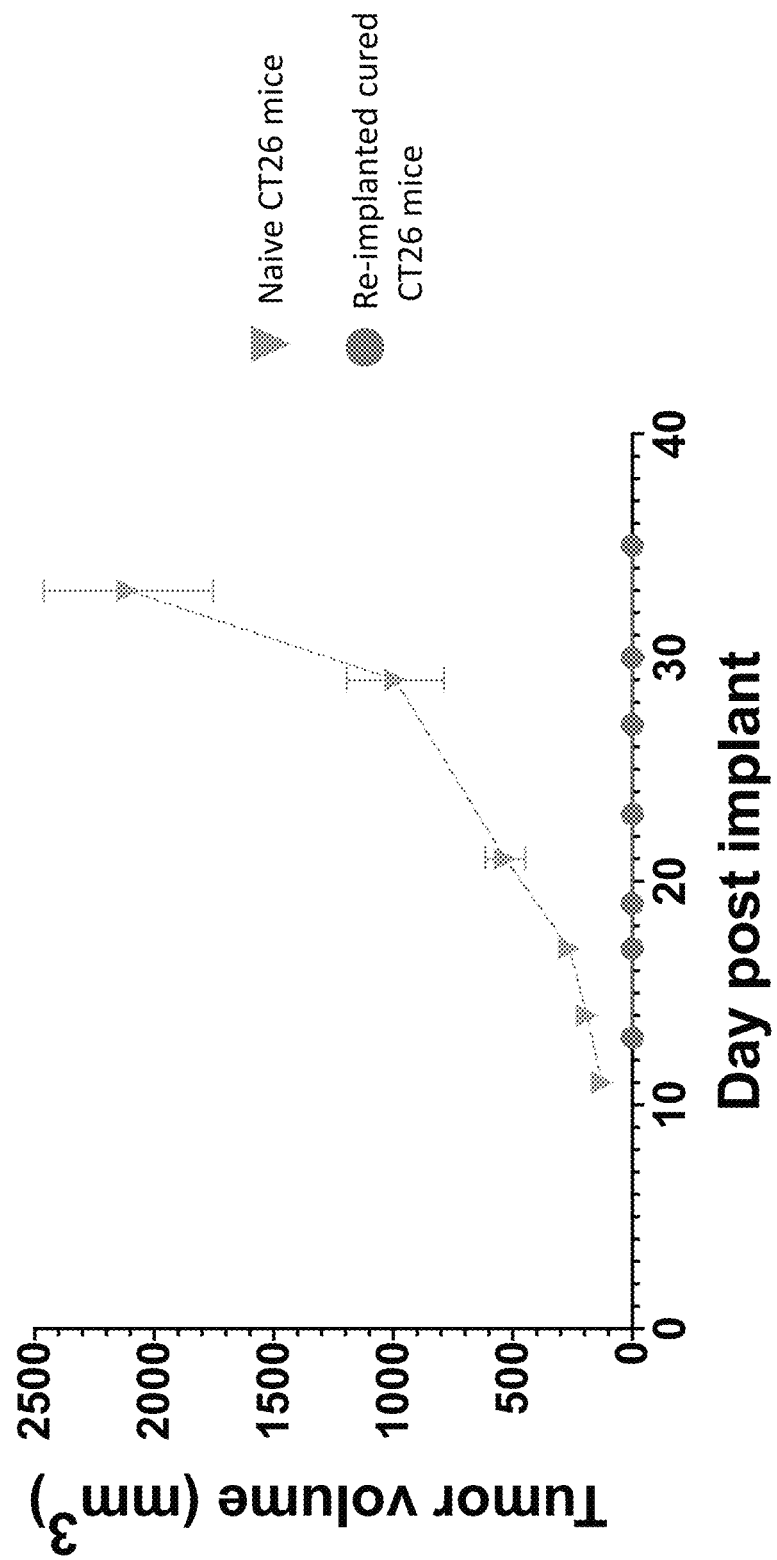
FIG. 41 shows that the afucosylated PI-9067L antibody induces immune memory in re-challenged mice in the CT26 tumor model.

Mice that were cured of their CT26 tumors following treatment with the combination of anti-TREM1 afucolsylated PI-9067L and anti-PD-1 mAb established an effective anti-tumor memory response (FIG. 41). Cured mice were able to reject any new tumor growth even in the absence of additional therapy, indicating long-term immune memory against the original, implanted tumor. This form of long-term immune memory may utilize maintenance of a vigorous CD8+ effector memory response.

Figure 42B:
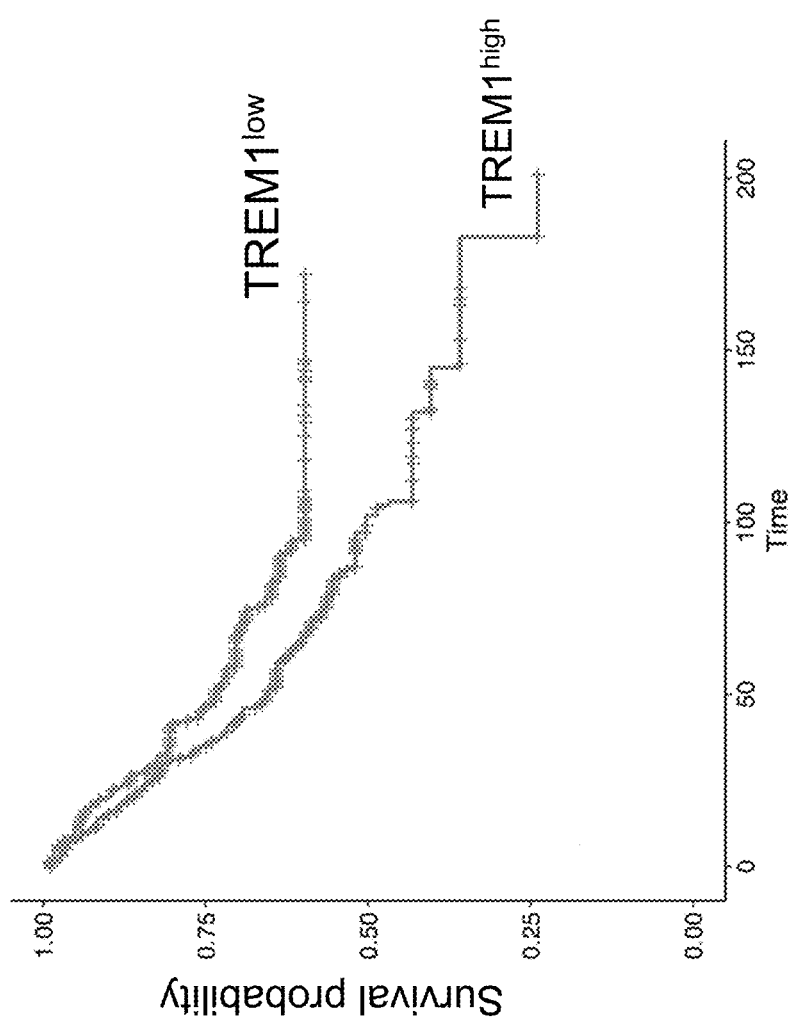
FIG. 42B shows colorectal cancer patient survival probability and TREM1 expression.
Figure 42A:
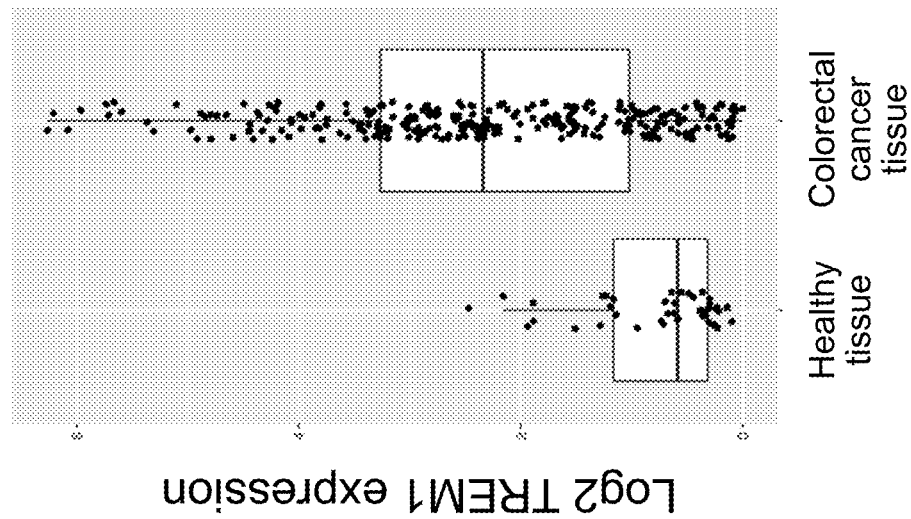
FIG. 42A shows TREM1 expression in colorectal cancer.

Example 18: TREM1 is Expressed in Various Cancers and Inversely Correlates with Patient Survival Level 2, RNAseq data from The Cancer Genome Atlas's cohort of colorectal cancer samples were downloaded from the Broad Institute using firehose_get. RSEM values for TREM1 from both tumor (n=282) and adjacent normal samples (n=41) were converted to log 2 counts per million and plotted in R (FIG. 42A). Prenormalized TREM1 expression profiles and associated clinical data across 566 colorectal tumors were downloaded from NCBI's GEO website (accession GSE39582). Expression profiles were divided into two cohorts based on median level of TREM1. Kaplan-Meier survival curves were plotted for each cohort and the associated logrank test was carried using the survival and survminer packages in R (FIG. 42B).

TREM1 is highly expressed in colorectal cancer (FIG. 42A). In addition, TREM1 expression levels in colorectal cancer inversely correlate with patient survival probability, e.g., patients with high TREM1 expression had a lower longer term survival probability, as compared to patients with lower TREM1 expression, p=0.0081 (FIG. 42B). Inverse correlation of TREM1 expression and patient survival was also observed in breast cancer and pancreatic cancer patients (data not shown). High TREM1 mRNA expression was also observed in NSCLC, HNSCC, ovarian, stomach, and bladder cancers (data not shown).

Example 19: In Vivo Pharmacokinetic Studies

Materials and Methods

Female CD-1 mice were dosed intravenously with increasing doses of 0.1, 1, 10, and 100 mg/kg of afucosylated PI-4928 anti-TREM1 antibody. Plasma was collected at 0.25, 1, 2, 24, 72, 168, and 336 hrs post dosing. Plasma concentrations of the PI-4928 antibody and soluble mouse TREM1 were determined as described below. In this example, PI-4928 was used as an in vivo surrogate for the antibodies described above as it binds to mouse TREM1 and has been shown to provide an anti-cancer therapeutic effect in vivo.

The PI-4928 mouse PK assay is a ligand binding assay (LBA). A 96-well high-binding MSD plate was coated with Fc-tagged recombinant mouse TREM1 (R&D systems #1187-TR). After blocking, samples were added to the plate which bound the TREM1 protein. The presence of the afucoyslated PI-4928 antibody was detected using sulfo-tagged anti-mouse IgG2a secondary antibody (Jackson ImmunoResearch #115-035-206). ECL signal was produced by the secondary antibody after the plate received an electric signal from an MSD plate reader. The ECL signal was detected and quantified by the plate reader.

The PK MSD assay demonstrates great sensitivity with a dynamic range from 300 ng/ml to 0.41 ng/ml. When the minimal required dilution (MRD) of 1:20 is used, the LLOQ of this assay is 8.2 ng/ml and ULOQ is 6000 ng/mL. The assay is qualified for detecting afucosylated PI-4928 antibodies in BALB/c $K_2$EDTA plasma.

Mouse soluble TREM1 (msTREM1) was quantified via a sandwich immunoassay developed on the MSD platform. Biotinylated goat anti-mTREM1 polyclonal antibodies (R&D systems #AF1187) were used as capture agents and bound to precoated streptavidin plate. After washing, samples containing mTREM1 proteins were added to the plate. The bound TREM1 proteins were detected by a sulfo-tagged mIgG2a antibody against mTREM1 (antibody developed in-house).

The MSD sTREM1 assay has a dynamic range of 10 ng/ml to 14 pg/mL. The LLOQ and LOD of this assay are 14 pg/mL and 1 pg/mL, respectively. This sTREM1 assay is able to detect circulating TREM1 proteins in plasma samples from BalB/c, C57BL/6 and CD1 strains. In addition, this assay detects sTREM1 protein in the presence of the anti-TREM1 antibody PI-4928.

Blood cell counts were also determined on days 7 and 14. Blood was collected in K2EDTA tubes and analyzed on the Heska Element HT5 to determine differential white blood cell counts and red blood cell parameters.

Results

Afucosylated PI-4928 antibody had dose dependent pharmacokinetics in mice (FIG. 43A). As shown in FIG. 43B, treatment with anti-TREM1 antibody resulted in a dose dependent accumulation of soluble mouse TREM1 protein in plasma, indicating that PI-4928 antibody also stabilized soluble mouse TREM1 protein.

In addition, administration of afucolsylated PI-4928 did not cause any significant change in mouse blood cell counts of neutrophils, monocytes, eosinophils, or basophils (FIGS. 44A and 44B) or serum chemistry (FIGS. 44C and 44D) tested on day 7 and day 14. Red blood cell parameters including hemoglobin (HGB), hematocrit (HCT), mean cell volume (MCV), mean cell hemoglobin (MCH), mean cell hemoglobin concentration (MCHC), and red blood cell distribution (RDW-CV) were measured.

Example 20: In Vivo Anti-TREM1 Therapy Efficacy in Breast Cancer Model

Materials and Methods

Figure 45A:
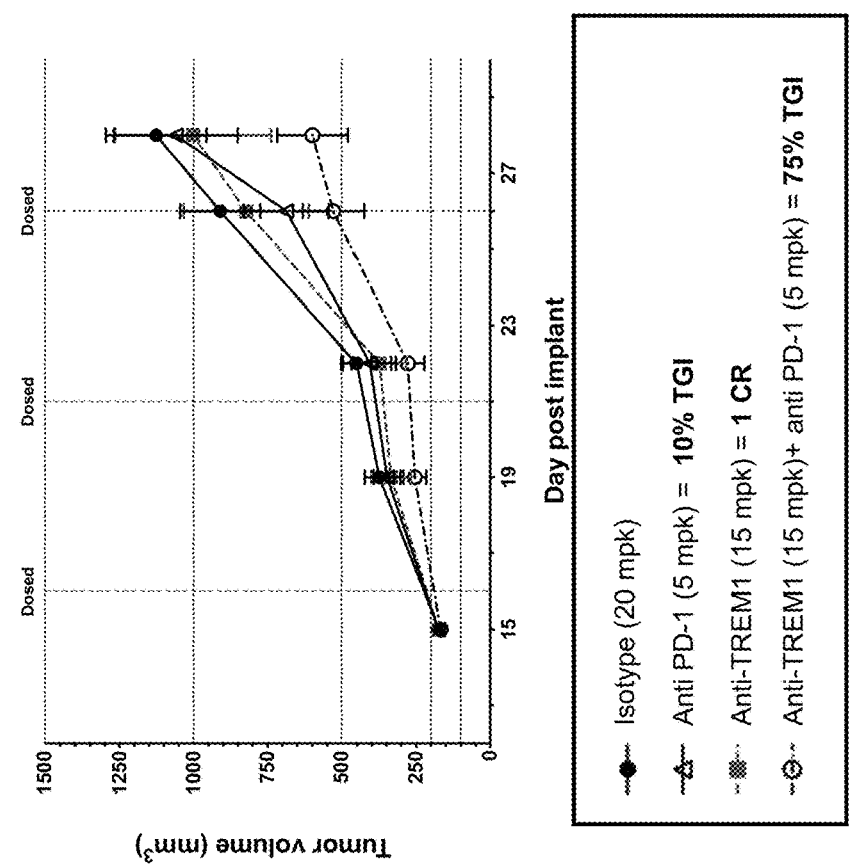
FIG. 45A show the anti-tumor efficacy of anti-TREM1, anti-PD-1, or a combination of anti-TREM1 and anti-PD-1 treatments in small subcutaneous EMT6 tumor-bearing female BALB/c mice.
Figure 45B:
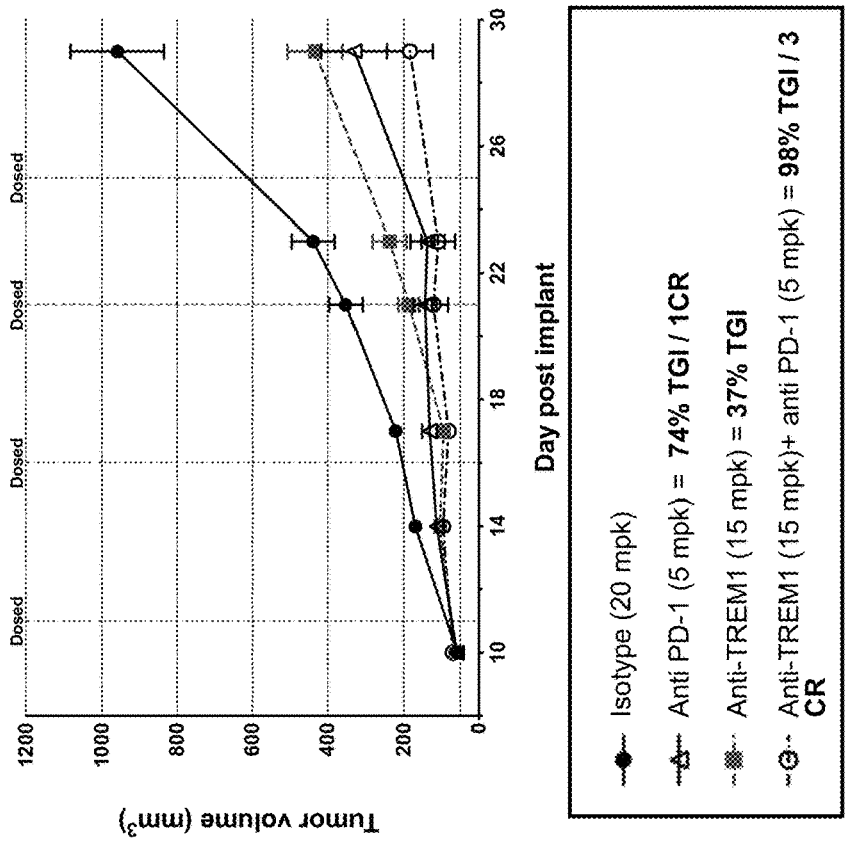
FIG. 45B show the anti-tumor efficacy of anti-TREM1, anti-PD-1, or a combination of anti-TREM1 and anti-PD-1 treatments in large subcutaneous EMT6 tumor-bearing female BALB/c mice.

Female BALB/c mice at about eight weeks of age were obtained from Taconic. Mouse mammary tumor cell line EMT6 (CRL-2755) was obtained from American Type Culture Collection, and cultured according to their guidelines. Low passage cells were resuspended at $1\times10^7$ cells/ml in serum-free culture medium. The tumor cell suspension was subcutaneously injected on the shaved right ventral flank of BALB/c mice. Tumor volume growth was monitored via perpendicular tumor diameter measurements and calculated using the formula $(mm^3)=0.5\times(length)\times(width)^2$. For drug treatments, mice were dosed intraperitoneally with mouse anti-mouse isotype control IgG2a (Clone C1.18.4 at 15 mg/kg), anti-mouse isotype control IgG1 (Clone MOPC-21 at 15 mg/kg), anti-mouse PD-1 (Pionyr Pi-0004-AB at 5 mg/kg), anti-mouse TREM1 (Clone Pi-9067L at 15 mg/kg), or a combination of anti-TREM1 antibody and anti-PD-1 antibody. Anti-PD-1 (clone RMP1-14) was purchased from BioXCell (West Lebanon, NH, USA) or recombinantly produced as mouse IgG1 D265A format. Treatment was initiated when the group average tumor volume was an average of 62 cubic mm (FIG. 45A) or and average of 173 cubic mm (FIG. 45B). The vertical lines indicate days when antibodies were administered intraperitoneally. All studies were conducted in accordance with the Explora Biolabs institutional animal care and use committee under the protocol AUP0606. Mice were housed under conditions outlined in the NIH Guide for Care and Use of Laboratory Animals in compliance with the USDA Laboratory Animal Welfare Act. The animals were allowed ad libitum access to Lab Diet rodent chow and water. Mice were monitored a minimum of twice per week by the investigator or veterinary staff for clinical abnormalities which may require euthanasia. Mice showing a net body weight loss >20% compared to baseline weight measurement were euthanized.

Results

FIGS. 44A and 44B show the anti-tumor efficacy of anti-TREM1, anti-PD-1, or a combination of anti-TREM1 and anti-PD-1 treatments in subcutaneous EMT6 tumor-bearing female BALB/c mice. FIG. 44A shows the tumor volumes during treatment of mice with "small" tumors of 62 $mm^3$. FIG. 44B shows the tumor volumes during treatment of mice with "large" tumors of 173 $mm^3$. In the small tumors, anti-TREM1 antibody treatment alone or in combination with anti-PD-1 antibody showed anti-tumor efficacy. Anti-TREM1 antibody treatment resulted in 47% tumor growth inhibition, anti-PD-1 antibody treatment resulted in 65% tumor growth inhibition and 2 complete regression, and the combination of anti-TREM1 antibody and anti-PD-1 antibody treatment resulted in 91% tumor growth inhibition and 3 complete regressions (FIG. 44A). In the large tumors, anti-TREM1 antibody treatment resulted in 1 complete remission, anti-PD-1 antibody treatment resulted in 10% tumor growth inhibition, and the combination of anti-TREM1 antibody and anti-PD-1 antibody treatment resulted in 75% tumor growth inhibition (FIG. 44A). Thus, the anti-TREM1 antibody shows both monotherapeutic and combination therapeutic efficacy.

All references, issued patents and patent applications cited within the body of the instant specification are hereby incorporated by reference in their entirety, for all purposes.

While the invention has been particularly shown and described with reference to a preferred embodiment and various alternate embodiments, it will be understood by persons skilled in the relevant art that various changes in form and details can be made therein without departing from the spirit and scope of the invention.

SEQUENCE LISTING

| SEQ ID NO | Name | Sequence |
|---|---|---|
| 1 | Human TREM1 | MRKTRLWGLLWMLFVSELRAATKLTEEKYELKEGQTLDVKCDYTLEKFASSQKAWQIIRD GEMPKTLACTERPSKNSHPVQVGRIILEDYHDHGLLRVRMVNLQVEDSGLYQCVIYQPPK EPHMLFDRIRLVVTKGFSGTPGSNENSTQNVYKIPPTTTKALCPLYTSPRTVTQAPPKST ADVSTPDSEINLTNVTDIIRVPVFNIVILLAGGFLSKSLVFSVLFAVTLRSFVP |
| 2 | Mouse TREM1 | MRKAGLWGLLCVFFVSEVKAAIVLEEERYDLVEGQTLTVKCPFNIMKYANSQKAWQRLPD GKEPLTLVVTQRPFTRPSEVHMGKFTLKHDPSEAMLQVQMTDLQVTDSGLYRCVIYHPPN DPVVLFHPVRLVVTKGSSDVFTPVIIPITRLTERPILITTKYSPSDTTTTRSLPKPTAVV SSPGLGVTIINGTDADSVSTSSVTISVICGLLSKSLVFIILFIVTKRTFG |
| 3 | 4026 VH-1 100X | QVQLVQSGAEVKKPGASVKVSCKASGYTFTDYVINWVRQAPGQGLEWMGEIYPGSGSTFYAQKF QGRVTMTRDTSTSTVYMELSSLRSEDTAVYYCARRXAAMDYWGQGTLVTVSS |
| 4 | 4026 VH-2 100X | QVQLVQSGAEVKKPGASVKVSCKASGYTFTDYVINWVRQAPGQGLEWMGEIYPGSGSTFYAQKF QGRVTMTADTSTSTVYMELSSLRSEDTAVYYCTRRXAAMDYWGQGTLVTVSS |
| 5 | 4026 VH-3 100X | QVQLVQSGAEVKKPGASVKMSCKASGYTFTDYVINWVRQAPGQGLEWIGEIYPGSGSTFYAQKF QGRATLTADTSTSTAYMEVSSLRSEDTAVYYCTRRXAAMDYWGQGTLVTVSS |
| 6 | 4026 VH-4 100X | QVQLVQSGAEVKKPGASVKMSCKASGYTFTDYVINWVRQAPGQGLEWIGEIYPGSGSTFYAQKF QGRATLTADKSTSTAYMEVSSLRSEDTAVYYCTRRXAAMDYWGQGTLVTVSS |
| 7 | 4026 VH-1 M100 | QVQLVQSGAEVKKPGASVKVSCKASGYTFTDYVINWVRQAPGQGLEWMGEIYPGSGSTFYAQKF QGRVTMTRDTSTSTVYMELSSLRSEDTAVYYCARRMAAMDYWGQGTLVTVSS |
| 8 | 4026 VH-2 M100 | QVQLVQSGAEVKKPGASVKVSCKASGYTFTDYVINWVRQAPGQGLEWMGEIYPGSGSTFYAQKF QGRVTMTADTSTSTVYMELSSLRSEDTAVYYCTRRMAAMDYWGQGTLVTVSS |
| 9 | 4026 VH-3 M100 | QVQLVQSGAEVKKPGASVKMSCKASGYTFTDYVINWVRQAPGQGLEWIGEIYPGSGSTFYAQKF QGRATLTADTSTSTAYMEVSSLRSEDTAVYYCTRRMAAMDYWGQGTLVTVSS |
| 10 | 4026 VH-4 M100 | QVQLVQSGAEVKKPGASVKMSCKASGYTFTDYVINWVRQAPGQGLEWIGEIYPGSGSTFYAQKF QGRATLTADKSTSTAYMEVSSLRSEDTAVYYCTRRMAAMDYWGQGTLVTVSS |
| 11 | 4026 VH-1 M100L | QVQLVQSGAEVKKPGASVKVSCKASGYTFTDYVINWVRQAPGQGLEWMGEIYPGSGSTFYAQKF QGRVTMTRDTSTSTVYMELSSLRSEDTAVYYCARRLAAMDYWGQGTLVTVSS |
| 12 | 4026 VH-2 M100L | QVQLVQSGAEVKKPGASVKVSCKASGYTFTDYVINWVRQAPGQGLEWMGEIYPGSGSTFYAQKF QGRVTMTADTSTSTVYMELSSLRSEDTAVYYCTRRLAAMDYWGQGTLVTVSS |
| 13 | 4026 VH-3 M100L | QVQLVQSGAEVKKPGASVKMSCKASGYTFTDYVINWVRQAPGQGLEWIGEIYPGSGSTFYAQKF QGRATLTADTSTSTAYMEVSSLRSEDTAVYYCTRRLAAMDYWGQGTLVTVSS |
| 14 | 4026 VH-4 M100L | QVQLVQSGAEVKKPGASVKMSCKASGYTFTDYVINWVRQAPGQGLEWIGEIYPGSGSTFYAQKF QGRATLTADKSTSTAYMEVSSLRSEDTAVYYCTRRLAAMDYWGQGTLVTVSS |
| 15 | 4026 VH-1 M100Q | QVQLVQSGAEVKKPGASVKVSCKASGYTFTDYVINWVRQAPGQGLEWMGEIYPGSGSTFYAQKF QGRVTMTRDTSTSTVYMELSSLRSEDTAVYYCARRQAAMDYWGQGTLVTVSS |
| 16 | 4026 VH-2 M100Q | QVQLVQSGAEVKKPGASVKVSCKASGYTFTDYVINWVRQAPGQGLEWMGEIYPGSGSTFYAQKF QGRVTMTADTSTSTVYMELSSLRSEDTAVYYCTRRQAAMDYWGQGTLVTVSS |
| 17 | 4026 VH-3 M100Q | QVQLVQSGAEVKKPGASVKMSCKASGYTFTDYVINWVRQAPGQGLEWIGEIYPGSGSTFYAQKF QGRATLTADTSTSTAYMEVSSLRSEDTAVYYCTRRQAAMDYWGQGTLVTVSS |
| 18 | 4026 VH-4 M100Q | QVQLVQSGAEVKKPGASVKMSCKASGYTFTDYVINWVRQAPGQGLEWIGETYPGSGSTFYAQKF QGRATLTADKSTSTAYMEVSSLRSEDTAVYYCTRRQAAMDYWGQGTLVTVSS |

SEQUENCE LISTING

| SEQ ID NO | Name | Sequence |
|---|---|---|
| 19 | 4026 VL-1 | DIQMTQSPSSLSASVGDRVTITCSASSSVSYMHWYQQKPGKAPKLLIYTTSNLASGVPSRFSGS GSGTDFTLTISSLQPEDFATYYCHQWSGYPTFGQGTKLEIK |
| 20 | 4026 VL-2 | DIQLTQSPSSLSASVGDRVTITCSASSSVSYMHWYQQKPGKAPKLLLYTTSNLASGVPSRFSGS GSGTDYTLTISSLQPEDFATYYCHQWSGYPTFGQGTKLEIK |
| 21 | 4026 VL-3 | DIQLTQSPSSLSASVGDRITLTCSASSSVSYMHWYQQKPGKAPKLLLYTTSNLASGVPSRFSGS GSGTDYTLTISSVQPEDFATYYCHQWSGYPTFGQGTKLEIK |
| 22 | 4026 VL-4 | DIQLTQSPSSLSASVGDRITLTCSASSSVSYMHWYQQKPGKAPKLLLYTTSNLASGVPSRFSGS GSGTDYTLTISSVQPEDAATYYCHQWSGYPTFGQGTKLEIK |
| 23 | CDR H1 | GYTFTDYVIN |
| 24 | CDR H2 | EIYPGSGSTF |
| 25 | CDR H3 | RMAAMDY |
| 26 | CDR L1 | SASSSVSYMH |
| 27 | CDR L2 | TTSNLAS |
| 28 | CDR L3 | HQWSGYPT |
| 29 | CDR H3 Consensus | RXAAMDY |
| 30 | CDR H3 M100I | RIAAMDY |
| 31 | CDR H3 M100E | REAAMDY |
| 32 | CDR H3 M100L | RLAAMDY |
| 33 | CDR H3 M100Q | RQAAMDY |
| 34 | 4026-5 Heavy chain M100Q | QVQLVQSGAEVKKPGASVKMSCKASGYTFTDYVINWVRQAPGQGLEWIGEIYPGSGSTFYAQKF QGRATLTADTSTSTAYMEVSSLRSEDTAVYYCTRRQAAMDYWGQGTLVTVSSASTKGPSVFPLA PSSKSTSGGTAALGCLVKDYFPEPVTVSWNSGALTSGVHTFPAVLQSSGLYSLSSVVTVPSSSL GTQTYICNVNHKPSNTKVDKKVEPKSCDKTHTCPPCPAPELLGGPSVFLFPPKPKDTLMISRTP EVTCVVVDVSHEDPEVKFNWYVDGVEVHNAKTKPREEQYNSTYRVVSVLTVLHQDWLNGKEYKC KVSNKALPAPIEKTISKAKGQPREPQVYTLPPSRDELTKNQVSLTCLVKGFYPSDIAVEWESNG QPENNYKTTPPVLDSDGSFFLYSKLTVDKSRWQQGNVFSCSVMHEALHNHYTQKSLSLSPGK |
| 35 | 4026-5 light chain M100Q | DIQLTQSPSSLSASVGDRVTITCSASSSVSYMHWYQQKPGKAPKLLLYTTSNLASGVPSRFSGS GSGTDYTLTISSLQPEDFATYYCHQWSGYPTFGQGTKLEIKRTVAAPSVFIFPPSDEQLKSGTA SVVCLLNNFYPREAKVQWKVDNALQSGNSQESVTEQDSKDSTYSLSSTLTLSKADYEKHKVYAC EVTHQGLSSPVTKSFNRGEC |
| 36 | 4026-5 heavy chain M100L | QVQLVQSGAEVKKPGASVKMSCKASGYTFTDYVINWVRQAPGQGLEWIGEIYPGSGSTFYAQKF QGRATLTADTSTSTAYMEVSSLRSEDTAVYYCTRRLAAMDYWGQGTLVTVSSASTKGPSVFPLA PSSKSTSGGTAALGCLVKDYFPEPVTVSWNSGALTSGVHTFPAVLQSSGLYSLSSVVTVPSSSL GTQTYICNVNHKPSNTKVDKKVEPKSCDKTHTCPPCPAPELLGGPSVFLFPPKPKDTLMISRTP EVTCVVVDVSHEDPEVKFNWYVDGVEVHNAKTKPREEQYNSTYRVVSVLTVLHQDWLNGKEYKC KVSNKALPAPIEKTISKAKGQPREPQVYTLPPSRDELTKNQVSLTCLVKGFYPSDIAVEWESNG QPENNYKTTPPVLDSDGSFFLYSKLTVDKSRWQQGNVFSCSVMHEALHNHYTQKSLSLSPGK |
| 37 | 4026-5 light chain M100L | DIQLTQSPSSLSASVGDRVTITCSASSSVSYMHWYQQKPGKAPKLLLYTTSNLASGVPSRFSGS GSGTDYTLTISSLQPEDFATYYCHQWSGYPTFGQGTKLEIKRTVAAPSVFIFPPSDEQLKSGTA SVVCLLNNFYPREAKVQWKVDNALQSGNSQESVTEQDSKDSTYSLSSTLTLSKADYEKHKVYAC EVTHQGLSSPVTKSFNRGEC |
| 38 | 4026-5 heavy chain M100M | QVQLVQSGAEVKKPGASVKMSCKASGYTFTDYVINWVRQAPGQGLEWIGEIYPGSGSTFYAQKF QGRATLTADTSTSTAYMEVSSLRSEDTAVYYCTRRMAAMDYWGQGTLVTVSSASTKGPSVFPLA PSSKSTSGGTAALGCLVKDYFPEPVTVSWNSGALTSGVHTFPAVLQSSGLYSLSSVVTVPSSSL GTQTYICNVNHKPSNTKVDKKVEPKSCDKTHTCPPCPAPELLGGPSVFLFPPKPKDTLMISRTP EVTCVVVDVSHEDPEVKFNWYVDGVEVHNAKTKPREEQYNSTYRVVSVLTVLHQDWLNGKEYKC KVSNKALPAPIEKTISKAKGQPREPQVYTLPPSRDELTKNQVSLTCLVKGFYPSDIAVEWESNG QPENNYKTTPPVLDSDGSFFLYSKLTVDKSRWQQGNVFSCSVMHEALHNHYTQKSLSLSPGK |

-continued

SEQUENCE LISTING

| SEQ ID NO | Name | Sequence |
|---|---|---|
| 39 | 4026-5 light chain M100M | DIQLTQSPSSLSASVGDRVTITCSASSSVSYMHWYQQKPGKAPKLLLYTTSNLASGVPSRFSGS GSGTDYTLTISSLQPEDFATYYCHQWSGYPTFGQGTKLEIKRTVAAPSVFIFPPSDEQLKSGTA SVVCLLNNFYPREAKVQWKVDNALQSGNSQESVTEQDSKDSTYSLSSTLTLSKADYEKHKVYAC EVTHQGLSSPVTKSFNRGEC |
| 40 | 4026 CH | ASTKGPSVFPLAPSSKSTSGGTAALGCLVKDYFPEPVTVSWNSGALTSGVHTFPAVLQSSGLYS LSSVVTVPSSSLGTQTYICNVNHKPSNTKVDKKVEPKSCDKTHTCPPCPAPELLGGPSVFLFPP KPKDTLMISRTPEVTCVVVDVSHEDPEVKFNWYVDGVEVHNAKTKPREEQYNSTYRVVSVLTVL HQDWLNGKEYKCKVSNKALPAPIEKTISKAKGQPREPQVYTLPPSRDELTKNQVSLTCLVKGFY PSDIAVEWESNGQPENNYKTTPPVLDSDGSFFLYSKLTVDKSRWQQGNVFSCSVMHEALHNHYT QKSLSLSPGK |
| 41 | 4026 CL | RTVAAPSVFIFPPSDEQLKSGTASVVCLLNNFYPREAKVQWKVDNALQSGNSQESVTEQDSKDS TYSLSSTLTLSKADYEKHKVYACEVTHQGLSSPVTKSFNRGEC |
| 42 | hTREM1 residues 21-34 | ATKLTEEKYELKEG |
| 43 | hTREM1 residues 103-109 | LQVEDSG |
| 44 | hTREM1 residues 128-136 | RIRLVVTKG |
| 45 | hIgG1 | ASTKGPSVFPLAPSSKSTSGGTAALGCLVKDYFPEPVTVSWNSGALTSGVHTFPAVLQSSGLYS LSSVVTVPSSSLGTQTYICNVNHKPSNTKVDKKVEPKSCDKTHTCPPCPAPELLGGPSVFLFPP KPKDTLMISRTPEVTCVVVDVSHEDPEVKFNWYVDGVEVHNAKTKPREEQYNSTYRVVSVLTVL HQDWLNGKEYKCKVSNKALPAPIEKTISKAKGQPREPQVYTLPPSRDELTKNQVSLTCLVKGFY PSDIAVEWESNGQPENNYKTTPPVLDSDGSFFLYSKLTVDKSRWQQGNVFSCSVMHEALHNHYT QKSLSLSPGK |
| 46 | mIgG1 | AKTTPPSVYPLAPGSAAQTNSMVTLGCLVKGYFPEPVTVTWNSGSLSSGVHTFPAVLQSD LYTLSSSVTVPSSPRPSETVTCNVAHPASSTKVDKKIVPRDCGCKPCICTVPEVSSVFIF PPKPKDVLTITLTPKVTCVVVDISKDDPEVQFSWFVDDVEVHTAQTQPREEQFNSTFRSV SELPIMHQDWLNGKEEKCRVNSAAFPAPIEKTISKTKGRPKAPQVYTIPPPKEQMAKDKV SLTCMITDFFPEDITVEWQWNGQPAENYKNTQPIMNTNGSYFVYSKLNVQKSNWEAGNTF TCSVLHEGLHNHHTEKSLSHSPGK |
| 47 | hIgG4 | ASTKGPSVFPLAPCSRSTSESTAALGCLVKDYFPEPVTVSWNSGALTSGVHTFPAVLQSS GLYSLSSVVTVPSSSLGTKTYTCNVDHKPSNTKVDKRVESKYGPPCPSCPAPEFLGGPSV FLFPPKPKDTLMISRTPEVTCVVVDVSQEDPEVQFNWYVDGVEVHNAKTKPREEQFNSTY RVVSVLTVLHQDWLNGKEYKCKVSNKGLPSSIEKTISKAKGQPREPQVYTLPPSQEEMTK NQVSLTCLVKGFYPSDIAVEWESNGQPENNYKTTPPVLDSDGSFFLYSRLTVDKSRWQEG NVFSCSVMHEALHNHYTQKSLSLSLGK |
| 48 | 4170 mAb Heavy Chain | EVQLVESGGGLVQPGGSLKLSCAASGFTFSTYAMHWVRQASGKGLEWVGRIRTKSSNYATYYAA SVKGRFTISRDDSKNTAYLQMNSLKTEDTAVYYCTRDMGIRRQFAYWGQGTLVTVSSASTKGPS VFPLAPSSKSTSGGTAALGCLVKDYFPEPVTVSWNSGALTSGVHTFPAVLQSSGLYSLSSVVTV PSSSLGTQTYICNVNHKPSNTKVDKKVEPKSCDKTHTCPPCPAPELLGGPSVFLFPPKPKDTLM ISRTPEVTCVVVDVSHEDPEVKFNWYVDGVEVHNAKTKPREEQYNSTYRVVSVLTVLHQDWLNG KEYKCKVSNKALPAPIEKTISKAKGQPREPQVYTLPPSRDELTKNQVSLTCLVKGFYPSDIAVE WESNGQPENNYKTTPPVLDSDGSFFLYSKLTVDKSRWQQGNVFSCSVMHEALHNHYTQKSLSLS PGK |
| 49 | 4170 mAb light chain | DIVLTQSPDSLAVSLGERATINCRASESVDTFDYSFLHWYQQKPGQPPKLLIYRASNLESGVPD RFSGSGSGTDFTLTISSLQAEDVAVYYCQQSNEDPYTFGQGTKLEIKRTVAAPSVFIFPPSDEQ LKSGTASVVCLLNNEYPREAKVQWKVDNALQSGNSQESVTEQDSKDSTYSLSSTLTLSKADYEK HKVYACEVTHQGLSSPVTKSFNRGEC |
| 50 | TREM-26 mAb heavy chain | QVQLQQSGPELVKPGTSVKMSCKASGYTFTDYVINWVKQRTGQGLEWIGEIYPGSGSTFYHEKF KGKATLTADKSSNTAYMQVSSLTSEDSAVYFCTRRMAAMDYWGQGTSVTVSSAKTTPPSVYPLA PGSAAQTNSMVTLGCLVKGYFPEPVTVTWNSGSLSSGVHTFPAVLQSDLYTLSSSVTVPSSTWP SETVTCNVAHPASSTKVDKKIVPRDCGCKPCICTVPEVSSVFLFPPKPKDVLTITLTPKVTCVV VDISKDDPEVQFSWFVDDVEVHTAQTQPREEQFNSTFRSVSELPIMHQDWLNGKEEKCRVNSAA FPAPIEKTLSKTKGRPKAPQVYTLPPPKEQMAKDKVSLTCMITDFFPEDITVEWQWNGQPAENY KNTQPIMDTDGSYFVYSKLNVQKSNWEAGNTFTCSVLHEGLHNHHTEKSLSHSPGK |
| 51 | TREM-26 mAb light chain | QIVLTQSPAIMSASLGEEITLTCSASSSVSYMHWYQQKSGTSPKLLLYTTSNLASGVPSRFSGT GSGTFYSLTISSVEAEDAADYYCHQWSGYPTFGGGTKLEIKRADAAPTVSIFPPSSEQLTSGGA SVVCFLNNFYPKDINVKWKIDGSERQNGVLNSWTDQDSKDSTYSMSSTLTLTKDEYERHNSYTC EATHKTSTSPIVKSFNRNEC |

SEQUENCE LISTING

| SEQ ID NO | Name | Sequence |
|---|---|---|
| 52 | TREM-26 VH | QVQLQQSGPELVKPGTSVKMSCKASGYTFTDYVINWVKQRTGQGLEWIGEIYPGSGSTFYHEKF KGKATLTADKSSNTAYMQVSSLTSEDSAVYFCTRRMAAMDYWGQGTSVTVSS |
| 53 | TREM-26 VL | QIVLTQSPAIMSASLGEEITLTCSASSSVSYMHWYQQKSGTSPKLLLYTTSNLASGVPSRFSGT GSGTFYSLTISSVEAEDAADYYCHQWSGYPTFGGGTKLEIK |
| 54 | Pi-4928 heavy chain | QVQLKESGPGLVQPSQTLSLTCTVSGFSITSSNVYWFRQPPGKGLEWMGNIWGDGSTDYNSSLK SRLTLSRDTSKNQVFLKINSLQSEDTATYFCTRSWEYYFDHWGQGVVVTVSSAKTTAPSVYPLA PVCGDTTGSSVTLGCLVKGYFPEPVTLTWNSGSLSSGVHTFPAVLQSDLYTLSSSVTVTSSTWP SQSITCNVAHPASSTKVDKKIEPRGPTIKPCPPCKCPAPNLLGGPSVFIFPPKIKDVLMISLSP IVTCVVVDVSEDDPDVQISWFVNNVEVHTAQTQTHREDYNSTLRVVSALPIQHQDWMSGKEEKC KVNNKDLPAPIERTISKPKGSVRAPQVYVLPPPEEEMTKKQVTLTCMVTDFMPEDIYVEWTNNG KTELNYKNTEPVLDSDGSYFMYSKLRVEKKNWVERNSYSCSVVHEGLHNHHTTKSFSRTPGK |
| 55 | Pi-4928 light chain | DIVLTQSPALAVSPGQRATLSCRASQSVTLSNVNLMNWYQQKPGQQPKLLIYHASNLASGIPTR FSGSGSGTDFTLTIDPVQADDIAAYYCQQSGESPRTFGGGTKVELKRADAAPTVSIFPPSSEQL TSGGASVVCFLNNFYPKDINVKWKIDGSERQNGVLNSWTDQDSKDSTYSMSSTLTLTKDEYERH NSYTCEATHKTSTSPIVKSFNRNEC |
| 56 | Pi-9067s heavy chain | EVQLVESGGGLVQPGGSLRLSCAASGFDIYSYSIHWVRQAPGKGLEWVAYIYPSYGYTSYADSV KGRFTISADTSKNTAYLQMNSLRAEDTAVYYCARGAVAALDYWGQGTLVTVSSASTKGPSVFPL APSSKSTSGGTAALGCLVKDYFPEPVTVSWNSGALTSGVHTFPAVLQSSGLYSLSSVVTVPSSS LGTQTYICNVNHKPSNTKVDKKVEPKSCDKTHTCPPCPAPNLLGGPSVFIFPPKIKDVLMISLS PIVTCVVVDVSEDDPDVQISWFVNNVEVHTAQTQTHREDYNSTLRVVSALPIQHQDWMSGKEFK CKVNNKDLPAPIERTISKPKGSVRAPQVYVLPPPEEEMTKKQVTLTCMVTDFMPEDIYVEWTNN GKTELNYKNTEPVLDSDGSYFMYSKLRVEKKNWVERNSYSCSVVHEGLHNHHTTKSFSRTPGK |
| 57 | Pi-9067s light chain | DIQMTQSPSSLSASVGDRVTITCRASQSVSSAVAWYQQKPGKAPKLLIYSASSLYSGVPSRFSG SRSGTDFTLTISSLQPEDFATYYCQQYGVSGYSLITFGQGTKVEIKRTVAAPSVFIFPPSDEQL KSGTASVVCLLNNFYPREAKVQWKVDNALQSGNSQESVTEQDSKDSTYSLSSTLTLSKADYEKH KVYACEVTHQGLSSPVTKSFNRGEC |
| 58 | Pi-9067L heavy chain | EVQLVESGGGLVQPGGSLRLSCAASGFDIYSYSIHWVRQAPGKGLEWVAYIYPSYGYTSYADSV KGRFTISADTSKNTAYLQMNSLRAEDTAVYYCARGAVAALDYWGQGTLVTVSSAKTTAPSVYPL APVCGDTTGSSVTLGCLVKGYFPEPVTLTWNSGSLSSGVHTFPAVLQSDLYTLSSSVTVTSSTW PSQSITCNVAHPASSTKVDKKIEPRGPTIKPCPPCKCPAPNLLGGPSVFIFPPKIKDVLMISLS PIVTCVVVDVSEDDPDVQISWFVNNVEVHTAQTQTHREDYNSTLRVVSALPIQHQDWMSGKEFK CKVNNKDLPAPIERTISKPKGSVRAPQVYVLPPPEEEMTKKQVTLTCMVTDEMPEDIYVEWTNN GKTELNYKNTEPVLDSDGSYFMYSKLRVEKKNWVERNSYSCSVVHEGLHNHHTTKSFSRTPGK |
| 59 | Pi-9067L light chain | DIQMTQSPSSLSASVGDRVTITCRASQSVSSAVAWYQQKPGKAPKLLIYSASSLYSGVPSRFSG SRSGTDFTLTISSLQPEDFATYYCQQYGVSGYSLITFGQGTKVEIKRADAAPTVSIFPPSSEQL TSGGASVVCFLNNFYPKDINVKWKIDGSERQNGVLNSWTDQDSKDSTYSMSSTLTLTKDEYERH NSYTCEATHKTSTSPIVKSFNRNEC |

The invention claimed is:

1. A method of increasing an immune response in a subject comprising administering to the subject an isolated antibody that binds to TREM1 (SEQ ID NO: 1) comprising a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein:
   a CDR-H1 comprises the sequence set forth in SEQ ID NO: 23,
   b CDR-H2 comprises the sequence set forth in SEQ ID NO: 24,
   c CDR-H3 comprises the sequence set forth in SEQ ID NO: 29, wherein X is glutamine (Q), leucine (L), isoleucine (I), or glutamic acid (E),
   d CDR-L1 comprises the sequence set forth in SEQ ID NO: 26,
   e CDR-L2 comprises the sequence set forth in SEQ ID NO: 27, and
   f CDR-L3 comprises the sequence set forth in SEQ ID NO: 28.

2. The method of claim 1, wherein the VH sequence comprises the sequence selected from the sequences set forth in SEQ ID NO: 16, 17, or 18; and the VL sequence comprises the sequence selected from the sequences set forth in SEQ ID NOs: 20, 21, or 22.

3. The method of claim 1, wherein the VH sequence comprises the sequence set forth in SEQ ID NO: 17, and the VL sequence comprises the sequence set forth in SEQ ID NO: 20.

4. The method of claim 1, wherein the antibody comprises a heavy chain sequence set forth in SEQ ID NO: 34 and a light chain sequence set forth in SEQ ID NO: 35.

5. The method of claim 1, wherein the antibody is afucosylated.

6. The method of claim 1, wherein the antibody is humanized.

7. The method of claim 1, wherein the subject has previously received, is concurrently receiving, or will subsequently receive an immunotherapy, wherein the immunotherapy is at least one of: a checkpoint inhibitor; a checkpoint inhibitor of T cells; anti-PD1 antibody; anti-PDL1 antibody; anti-CTLA4 antibody; adoptive T cell therapy; CAR-T cell therapy; a dendritic cell vaccine; a monocyte vaccine; a toll-like receptor ligand; a cytokine; a cytotoxic therapy; a chemotherapy; a radiotherapy; a small molecule inhibitor; a small molecule agonist; an immunomodulator; and an epigenetic modulator.

8. The method of claim 7, wherein the immunotherapy is an anti-PD1 antibody, an anti-PDL1 antibody, or an anti-CTLA4 antibody.

9. The method of claim 1, wherein the CDR-H3 comprises the sequence set forth in SEQ ID NO: 33.

10. The method of claim 1, wherein the CDR-H3 comprises the sequence set forth in SEQ ID NO: 32.

11. The method of claim 1, wherein the VH sequence comprises the sequence selected from the sequences set forth in SEQ ID NO: 12, 13, or 14; and the VL sequence comprises the sequence selected from the sequences set forth in SEQ ID NOs: 20, 21, or 22.

12. The method of claim 1, wherein the antibody is afucosylated, and wherein the VH sequence comprises the sequence set forth in SEQ ID NO: 17, and the VL sequence comprises the sequence set forth in SEQ ID NO: 20.

13. The method of claim 1, wherein the antibody is afucosylated, and the antibody comprises the heavy chain sequence set forth in SEQ ID NO: 34 and the light chain sequence set forth in SEQ ID NO: 35.

14. A method of treating cancer in a subject, comprising administering to the subject an isolated antibody that binds to TREM1 (SEQ ID NO: 1) comprising a variable heavy chain (VH) sequence comprising three heavy chain CDR sequences, CDR-H1, CDR-H2, and CDR-H3, and a variable light chain (VL) sequence comprising three light chain CDR sequences, CDR-L1, CDR-L2, and CDR-L3, wherein:
   a CDR-H1 comprises the sequence set forth in SEQ ID NO: 23,
   b CDR-H2 comprises the sequence set forth in SEQ ID NO: 24,
   c CDR-H3 comprises the sequence set forth in SEQ ID NO: 29, wherein X is glutamine (Q), leucine (L), isoleucine (I), or glutamic acid (E),
   d CDR-L1 comprises the sequence set forth in SEQ ID NO: 26,
   e CDR-L2 comprises the sequence set forth in SEQ ID NO: 27, and f CDR-L3 comprises the sequence set forth in SEQ ID NO: 28.

15. The method of claim 14, wherein the VH sequence comprises the sequence selected from the sequences set forth in SEQ ID NO: 16, 17, or 18; and the VL sequence comprises the sequence selected from the sequences set forth in SEQ ID NOs: 20, 21, or 22.

16. The method of claim 14, wherein the VH sequence comprises the sequence set forth in SEQ ID NO: 17, and the VL sequence comprises the sequence set forth in SEQ ID NO: 20.

17. The method of claim 14, wherein the antibody comprises a heavy chain sequence set forth in SEQ ID NO: 34 and a light chain sequence set forth in SEQ ID NO: 35.

18. The method of claim 14, wherein the antibody is afucosylated.

19. The method of claim 14, wherein the antibody is humanized.

20. The method of claim 14, wherein the subject has previously received, is concurrently receiving, or will subsequently receive an immunotherapy, wherein the immunotherapy is at least one of: a checkpoint inhibitor; a checkpoint inhibitor of T cells; anti-PD1 antibody; anti-PDL1 antibody; anti-CTLA4 antibody; adoptive T cell therapy; CAR-T cell therapy; a dendritic cell vaccine; a monocyte vaccine; a toll-like receptor ligand; a cytokine; a cytotoxic therapy; a chemotherapy; a radiotherapy; a small molecule inhibitor; a small molecule agonist; an immunomodulator; and an epigenetic modulator.

21. The method of claim 20, wherein the immunotherapy is an anti-PD1 antibody, an anti-PDL1 antibody, or an anti-CTLA4 antibody.

* * * * *

SEQUENCE LISTING

<160> NUMBER OF SEQ ID NOS: 59

<210> SEQ ID NO 1
<211> LENGTH: 234
<212> TYPE: PRT
<213> ORGANISM: Homo sapiens

<400> SEQUENCE: 1

Met Arg Lys Thr Arg Leu Trp Gly Leu Leu Trp Met Leu Phe Val Ser
1               5                   10                  15

Glu Leu Arg Ala Ala Thr Lys Leu Thr Glu Glu Lys Tyr Glu Leu Lys
                20                  25                  30

Glu Gly Gln Thr Leu Asp Val Lys Cys Asp Tyr Thr Leu Glu Lys Phe
            35                  40                  45

Ala Ser Ser Gln Lys Ala Trp Gln Ile Ile Arg Asp Gly Glu Met Pro
        50                  55                  60

Lys Thr Leu Ala Cys Thr Glu Arg Pro Ser Lys Asn Ser His Pro Val

-continued

```
                65                  70                  75                  80
        Gln Val Gly Arg Ile Ile Leu Glu Asp Tyr His Asp His Gly Leu Leu
                        85                  90                  95

Arg Val Arg Met Val Asn Leu Gln Val Glu Asp Ser Gly Leu Tyr Gln
                        100                 105                 110

Cys Val Ile Tyr Gln Pro Pro Lys Glu Pro His Met Leu Phe Asp Arg
                        115                 120                 125

Ile Arg Leu Val Val Thr Lys Gly Phe Ser Gly Thr Pro Gly Ser Asn
                        130                 135                 140

Glu Asn Ser Thr Gln Asn Val Tyr Lys Ile Pro Pro Thr Thr Thr Lys
        145                 150                 155                 160

Ala Leu Cys Pro Leu Tyr Thr Ser Pro Arg Thr Val Thr Gln Ala Pro
                        165                 170                 175

Pro Lys Ser Thr Ala Asp Val Ser Thr Pro Asp Ser Glu Ile Asn Leu
                        180                 185                 190

Thr Asn Val Thr Asp Ile Ile Arg Val Pro Val Phe Asn Ile Val Ile
                        195                 200                 205

Leu Leu Ala Gly Gly Phe Leu Ser Lys Ser Leu Val Phe Ser Val Leu
                        210                 215                 220

Phe Ala Val Thr Leu Arg Ser Phe Val Pro
        225                 230

<210> SEQ ID NO 2
<211> LENGTH: 230
<212> TYPE: PRT
<213> ORGANISM: Mus musculus

<400> SEQUENCE: 2

Met Arg Lys Ala Gly Leu Trp Gly Leu Leu Cys Val Phe Phe Val Ser
        1               5                   10                  15

Glu Val Lys Ala Ala Ile Val Leu Glu Glu Arg Tyr Asp Leu Val
                        20                  25                  30

Glu Gly Gln Thr Leu Thr Val Lys Cys Pro Phe Asn Ile Met Lys Tyr
                        35                  40                  45

Ala Asn Ser Gln Lys Ala Trp Gln Arg Leu Pro Asp Gly Lys Glu Pro
                        50                  55                  60

Leu Thr Leu Val Val Thr Gln Arg Pro Phe Thr Arg Pro Ser Glu Val
        65                  70                  75                  80

His Met Gly Lys Phe Thr Leu Lys His Asp Pro Ser Glu Ala Met Leu
                        85                  90                  95

Gln Val Gln Met Thr Asp Leu Gln Val Thr Asp Ser Gly Leu Tyr Arg
                        100                 105                 110

Cys Val Ile Tyr His Pro Pro Asn Asp Pro Val Val Leu Phe His Pro
                        115                 120                 125

Val Arg Leu Val Val Thr Lys Gly Ser Ser Asp Val Phe Thr Pro Val
                        130                 135                 140

Ile Ile Pro Ile Thr Arg Leu Thr Glu Arg Pro Ile Leu Ile Thr Thr
        145                 150                 155                 160

Lys Tyr Ser Pro Ser Asp Thr Thr Thr Arg Ser Leu Pro Lys Pro
                        165                 170                 175

Thr Ala Val Val Ser Pro Gly Leu Gly Val Thr Ile Ile Asn Gly
                        180                 185                 190

Thr Asp Ala Asp Ser Val Ser Ser Val Thr Ile Ser Val Ile
                        195                 200                 205
```

```
Cys Gly Leu Leu Ser Lys Ser Leu Val Phe Ile Ile Leu Phe Ile Val
    210                 215                 220

Thr Lys Arg Thr Phe Gly
225                 230

<210> SEQ ID NO 3
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (100)..(100)
<223> OTHER INFORMATION: Any amino acid

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Val Ile Asn Trp Val Arg Gln Ala Pro Gly Gln Gly Leu Glu Trp Met
        35                  40                  45

Gly Glu Ile Tyr Pro Gly Ser Gly Ser Thr Phe Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Xaa Ala Ala Met Asp Tyr Trp Gly Gln Gly Thr Leu Val
            100                 105                 110

Thr Val Ser Ser
            115

<210> SEQ ID NO 4
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (100)..(100)
<223> OTHER INFORMATION: Any amino acid

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Val Ile Asn Trp Val Arg Gln Ala Pro Gly Gln Gly Leu Glu Trp Met
        35                  40                  45

Gly Glu Ile Tyr Pro Gly Ser Gly Ser Thr Phe Tyr Ala Gln Lys Phe
    50                  55                  60

Gln Gly Arg Val Thr Met Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Arg Xaa Ala Ala Met Asp Tyr Trp Gly Gln Gly Thr Leu Val
```

```
                100             105             110

Thr Val Ser Ser
        115

<210> SEQ ID NO 5
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (100)..(100)
<223> OTHER INFORMATION: Any amino acid

<400> SEQUENCE: 5

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Val Ile Asn Trp Val Arg Gln Ala Pro Gly Gln Gly Leu Glu Trp Ile
        35                  40                  45

Gly Glu Ile Tyr Pro Gly Ser Gly Ser Thr Phe Tyr Ala Gln Lys Phe
    50                  55                  60

Gln Gly Arg Ala Thr Leu Thr Ala Asp Thr Ser Thr Ser Thr Ala Tyr
65                  70                  75                  80

Met Glu Val Ser Ser Leu Arg Ser Glu Asp Thr Ala Val Tyr Tyr Cys
                85                  90                  95

Thr Arg Arg Xaa Ala Ala Met Asp Tyr Trp Gly Gln Gly Thr Leu Val
            100                 105                 110

Thr Val Ser Ser
        115

<210> SEQ ID NO 6
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (100)..(100)
<223> OTHER INFORMATION: Any amino acid

<400> SEQUENCE: 6

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Val Ile Asn Trp Val Arg Gln Ala Pro Gly Gln Gly Leu Glu Trp Ile
        35                  40                  45

Gly Glu Ile Tyr Pro Gly Ser Gly Ser Thr Phe Tyr Ala Gln Lys Phe
    50                  55                  60

Gln Gly Arg Ala Thr Leu Thr Ala Asp Lys Ser Thr Ser Thr Ala Tyr
65                  70                  75                  80

Met Glu Val Ser Ser Leu Arg Ser Glu Asp Thr Ala Val Tyr Tyr Cys
                85                  90                  95

Thr Arg Arg Xaa Ala Ala Met Asp Tyr Trp Gly Gln Gly Thr Leu Val
            100                 105                 110
```

Thr Val Ser Ser
        115

<210> SEQ ID NO 7
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Val Ile Asn Trp Val Arg Gln Ala Pro Gly Gln Gly Leu Glu Trp Met
            35                  40                  45

Gly Glu Ile Tyr Pro Gly Ser Gly Ser Thr Phe Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Met Ala Ala Met Asp Tyr Trp Gly Gln Gly Thr Leu Val
                100                 105                 110

Thr Val Ser Ser
        115

<210> SEQ ID NO 8
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Val Ile Asn Trp Val Arg Gln Ala Pro Gly Gln Gly Leu Glu Trp Met
            35                  40                  45

Gly Glu Ile Tyr Pro Gly Ser Gly Ser Thr Phe Tyr Ala Gln Lys Phe
        50                  55                  60

Gln Gly Arg Val Thr Met Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Arg Met Ala Ala Met Asp Tyr Trp Gly Gln Gly Thr Leu Val
                100                 105                 110

Thr Val Ser Ser
        115

<210> SEQ ID NO 9
<211> LENGTH: 116
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 9

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Val Ile Asn Trp Val Arg Gln Ala Pro Gly Gln Gly Leu Glu Trp Ile
        35                  40                  45

Gly Glu Ile Tyr Pro Gly Ser Gly Ser Thr Phe Tyr Ala Gln Lys Phe
    50                  55                  60

Gln Gly Arg Ala Thr Leu Thr Ala Asp Thr Ser Thr Ser Thr Ala Tyr
65                  70                  75                  80

Met Glu Val Ser Ser Leu Arg Ser Glu Asp Thr Ala Val Tyr Tyr Cys
                85                  90                  95

Thr Arg Arg Met Ala Ala Met Asp Tyr Trp Gly Gln Gly Thr Leu Val
            100                 105                 110

Thr Val Ser Ser
        115

<210> SEQ ID NO 10
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Val Ile Asn Trp Val Arg Gln Ala Pro Gly Gln Gly Leu Glu Trp Ile
        35                  40                  45

Gly Glu Ile Tyr Pro Gly Ser Gly Ser Thr Phe Tyr Ala Gln Lys Phe
    50                  55                  60

Gln Gly Arg Ala Thr Leu Thr Ala Asp Lys Ser Thr Ser Thr Ala Tyr
65                  70                  75                  80

Met Glu Val Ser Ser Leu Arg Ser Glu Asp Thr Ala Val Tyr Tyr Cys
                85                  90                  95

Thr Arg Arg Met Ala Ala Met Asp Tyr Trp Gly Gln Gly Thr Leu Val
            100                 105                 110

Thr Val Ser Ser
        115

<210> SEQ ID NO 11
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Asp Tyr
             20                  25                  30

Val Ile Asn Trp Val Arg Gln Ala Pro Gly Gln Gly Leu Glu Trp Met
         35                  40                  45

Gly Glu Ile Tyr Pro Gly Ser Gly Ser Thr Phe Tyr Ala Gln Lys Phe
     50                  55                  60

Gln Gly Arg Val Thr Met Thr Arg Asp Thr Ser Ser Thr Val Tyr
 65                  70                  75                  80

Met Glu Leu Ser Ser Leu Arg Ser Glu Asp Thr Ala Val Tyr Tyr Cys
             85                  90                  95

Ala Arg Arg Leu Ala Ala Met Asp Tyr Trp Gly Gln Gly Thr Leu Val
            100                 105                 110

Thr Val Ser Ser
        115

<210> SEQ ID NO 12
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
             20                  25                  30

Val Ile Asn Trp Val Arg Gln Ala Pro Gly Gln Gly Leu Glu Trp Met
         35                  40                  45

Gly Glu Ile Tyr Pro Gly Ser Gly Ser Thr Phe Tyr Ala Gln Lys Phe
     50                  55                  60

Gln Gly Arg Val Thr Met Thr Ala Asp Thr Ser Thr Ser Thr Val Tyr
 65                  70                  75                  80

Met Glu Leu Ser Ser Leu Arg Ser Glu Asp Thr Ala Val Tyr Tyr Cys
             85                  90                  95

Thr Arg Arg Leu Ala Ala Met Asp Tyr Trp Gly Gln Gly Thr Leu Val
            100                 105                 110

Thr Val Ser Ser
        115

<210> SEQ ID NO 13
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Ala Glu Val Lys Lys Pro Gly Ala
 1               5                  10                  15

Ser Val Lys Met Ser Cys Lys Ala Ser Gly Tyr Thr Phe Thr Asp Tyr
             20                  25                  30

Val Ile Asn Trp Val Arg Gln Ala Pro Gly Gln Gly Leu Glu Trp Ile
         35                  40                  45

Gly Glu Ile Tyr Pro Gly Ser Gly Ser Thr Phe Tyr Ala Gln Lys Phe
     50                  55                  60
```

```
Gln Gly Arg Ala Thr Leu Thr Ala Asp Thr Ser Thr Ser Thr Ala Tyr
65                  70                  75                  80

Met Glu Val Ser Ser Leu Arg Ser Glu Asp Thr Ala Val Tyr Tyr Cys
                85                  90                  95

Thr Arg Arg Leu Ala Ala Met Asp Tyr Trp Gly Gln Gly Thr Leu Val
            100                 105                 110

Thr Val Ser Ser
        115

<210> SEQ ID NO 14
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Val Ile Asn Trp Val Arg Gln Ala Pro Gly Gln Gly Leu Glu Trp Ile
        35                  40                  45

Gly Glu Ile Tyr Pro Gly Ser Gly Ser Thr Phe Tyr Ala Gln Lys Phe
    50                  55                  60

Gln Gly Arg Ala Thr Leu Thr Ala Asp Lys Ser Thr Ser Thr Ala Tyr
65                  70                  75                  80

Met Glu Val Ser Ser Leu Arg Ser Glu Asp Thr Ala Val Tyr Tyr Cys
                85                  90                  95

Thr Arg Arg Leu Ala Ala Met Asp Tyr Trp Gly Gln Gly Thr Leu Val
            100                 105                 110

Thr Val Ser Ser
        115

<210> SEQ ID NO 15
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Val Ile Asn Trp Val Arg Gln Ala Pro Gly Gln Gly Leu Glu Trp Met
        35                  40                  45

Gly Glu Ile Tyr Pro Gly Ser Gly Ser Thr Phe Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Gln Ala Ala Met Asp Tyr Trp Gly Gln Gly Thr Leu Val
            100                 105                 110
```

Thr Val Ser Ser
        115

<210> SEQ ID NO 16
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Val Ile Asn Trp Val Arg Gln Ala Pro Gly Gln Gly Leu Glu Trp Met
        35                  40                  45

Gly Glu Ile Tyr Pro Gly Ser Gly Ser Thr Phe Tyr Ala Gln Lys Phe
    50                  55                  60

Gln Gly Arg Val Thr Met Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Arg Gln Ala Ala Met Asp Tyr Trp Gly Gln Gly Thr Leu Val
            100                 105                 110

Thr Val Ser Ser
        115

<210> SEQ ID NO 17
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Val Ile Asn Trp Val Arg Gln Ala Pro Gly Gln Gly Leu Glu Trp Ile
        35                  40                  45

Gly Glu Ile Tyr Pro Gly Ser Gly Ser Thr Phe Tyr Ala Gln Lys Phe
    50                  55                  60

Gln Gly Arg Ala Thr Leu Thr Ala Asp Thr Ser Thr Ser Thr Ala Tyr
65                  70                  75                  80

Met Glu Val Ser Ser Leu Arg Ser Glu Asp Thr Ala Val Tyr Tyr Cys
                85                  90                  95

Thr Arg Arg Gln Ala Ala Met Asp Tyr Trp Gly Gln Gly Thr Leu Val
            100                 105                 110

Thr Val Ser Ser
        115

<210> SEQ ID NO 18
<211> LENGTH: 116
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 18

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Val Ile Asn Trp Val Arg Gln Ala Pro Gly Gln Gly Leu Glu Trp Ile
        35                  40                  45

Gly Glu Ile Tyr Pro Gly Ser Gly Ser Thr Phe Tyr Ala Gln Lys Phe
    50                  55                  60

Gln Gly Arg Ala Thr Leu Thr Ala Asp Lys Ser Thr Ser Thr Ala Tyr
65                  70                  75                  80

Met Glu Val Ser Ser Leu Arg Ser Glu Asp Thr Ala Val Tyr Tyr Cys
                85                  90                  95

Thr Arg Arg Gln Ala Ala Met Asp Tyr Trp Gly Gln Gly Thr Leu Val
            100                 105                 110

Thr Val Ser Ser
        115

<210> SEQ ID NO 19
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

His Trp Tyr Gln Gln Lys Pro Gly Lys Ala Pro Lys Leu Leu Ile Tyr
        35                  40                  45

Thr Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys His Gln Trp Ser Gly Tyr Pro Thr Phe
                85                  90                  95

Gly Gln Gly Thr Lys Leu Glu Ile Lys
            100                 105

<210> SEQ ID NO 20
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

His Trp Tyr Gln Gln Lys Pro Gly Lys Ala Pro Lys Leu Leu Leu Tyr

```
                35                  40                  45
Thr Thr Ser Asn Leu Ala Ser Gly Val Pro Ser Arg Phe Ser Gly Ser
        50                  55                  60
Gly Ser Gly Thr Asp Tyr Thr Leu Thr Ile Ser Ser Leu Gln Pro Glu
65                  70                  75                  80
Asp Phe Ala Thr Tyr Tyr Cys His Gln Trp Ser Gly Tyr Pro Thr Phe
                85                  90                  95
Gly Gln Gly Thr Lys Leu Glu Ile Lys
            100                 105

<210> SEQ ID NO 21
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Gln Leu Thr Gln Ser Pro Ser Ser Leu Ser Ala Ser Val Gly
1               5                   10                  15
Asp Arg Ile Thr Leu Thr Cys Ser Ala Ser Ser Ser Val Ser Tyr Met
            20                  25                  30
His Trp Tyr Gln Gln Lys Pro Gly Lys Ala Pro Lys Leu Leu Leu Tyr
        35                  40                  45
Thr Thr Ser Asn Leu Ala Ser Gly Val Pro Ser Arg Phe Ser Gly Ser
    50                  55                  60
Gly Ser Gly Thr Asp Tyr Thr Leu Thr Ile Ser Ser Val Gln Pro Glu
65                  70                  75                  80
Asp Phe Ala Thr Tyr Tyr Cys His Gln Trp Ser Gly Tyr Pro Thr Phe
                85                  90                  95
Gly Gln Gly Thr Lys Leu Glu Ile Lys
            100                 105

<210> SEQ ID NO 22
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Gln Leu Thr Gln Ser Pro Ser Ser Leu Ser Ala Ser Val Gly
1               5                   10                  15
Asp Arg Ile Thr Leu Thr Cys Ser Ala Ser Ser Ser Val Ser Tyr Met
            20                  25                  30
His Trp Tyr Gln Gln Lys Pro Gly Lys Ala Pro Lys Leu Leu Leu Tyr
        35                  40                  45
Thr Thr Ser Asn Leu Ala Ser Gly Val Pro Ser Arg Phe Ser Gly Ser
    50                  55                  60
Gly Ser Gly Thr Asp Tyr Thr Leu Thr Ile Ser Ser Val Gln Pro Glu
65                  70                  75                  80
Asp Ala Ala Thr Tyr Tyr Cys His Gln Trp Ser Gly Tyr Pro Thr Phe
                85                  90                  95
Gly Gln Gly Thr Lys Leu Glu Ile Lys
            100                 105
```

```
<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Tyr Thr Phe Thr Asp Tyr Val Ile Asn
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Glu Ile Tyr Pro Gly Ser Gly Ser Thr Phe
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Met Ala Ala Met Asp Tyr
1               5

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Ala Ser Ser Ser Val Ser Tyr Met His
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Thr Ser Asn Leu Ala Ser
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28
```

```
His Gln Trp Ser Gly Tyr Pro Thr
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Leu, Gln, Met, Ile, or Glu

<400> SEQUENCE: 29

Arg Xaa Ala Ala Met Asp Tyr
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Ile Ala Ala Met Asp Tyr
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Glu Ala Ala Met Asp Tyr
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Leu Ala Ala Met Asp Tyr
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Gln Ala Ala Met Asp Tyr
1               5
```

<210> SEQ ID NO 34
<211> LENGTH: 446
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

```
Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Val Ile Asn Trp Val Arg Gln Ala Pro Gly Gln Gly Leu Glu Trp Ile
        35                  40                  45

Gly Glu Ile Tyr Pro Gly Ser Gly Ser Thr Phe Tyr Ala Gln Lys Phe
    50                  55                  60

Gln Gly Arg Ala Thr Leu Thr Ala Asp Thr Ser Thr Ser Thr Ala Tyr
65                  70                  75                  80

Met Glu Val Ser Ser Leu Arg Ser Glu Asp Thr Ala Val Tyr Tyr Cys
                85                  90                  95

Thr Arg Arg Gln Ala Ala Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365
```

```
Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445
```

<210> SEQ ID NO 35
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
                20                  25                  30

His Trp Tyr Gln Gln Lys Pro Gly Lys Ala Pro Lys Leu Leu Leu Tyr
            35                  40                  45

Thr Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys His Gln Trp Ser Gly Tyr Pro Thr Phe
                85                  90                  95

Gly Gln Gly Thr Lys Leu Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210
```

<210> SEQ ID NO 36
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Gln Val Gln Leu Val Gln Ser Gly Ala Glu Val Lys Lys Pro Gly Ala
  1               5                  10                  15

Ser Val Lys Met Ser Cys Lys Ala Ser Gly Tyr Thr Phe Thr Asp Tyr
             20                  25                  30

Val Ile Asn Trp Val Arg Gln Ala Pro Gly Gln Gly Leu Glu Trp Ile
         35                  40                  45

Gly Glu Ile Tyr Pro Gly Ser Gly Ser Thr Phe Tyr Ala Gln Lys Phe
 50                  55                  60

Gln Gly Arg Ala Thr Leu Thr Ala Asp Thr Ser Thr Ser Thr Ala Tyr
 65                  70                  75                  80

Met Glu Val Ser Ser Leu Arg Ser Glu Asp Thr Ala Val Tyr Tyr Cys
             85                  90                  95

Thr Arg Arg Leu Ala Ala Met Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
```

```
                420             425             430
Asn His Tyr Thr Gln Lys Ser Leu Ser Leu Ser Pro Gly Lys
        435             440             445

<210> SEQ ID NO 37
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

His Trp Tyr Gln Gln Lys Pro Gly Lys Ala Pro Lys Leu Leu Leu Tyr
        35                  40                  45

Thr Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys His Gln Trp Ser Gly Tyr Pro Thr Phe
                85                  90                  95

Gly Gln Gly Thr Lys Leu Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210

<210> SEQ ID NO 38
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Val Ile Asn Trp Val Arg Gln Ala Pro Gly Gln Gly Leu Glu Trp Ile
        35                  40                  45

Gly Glu Ile Tyr Pro Gly Ser Gly Ser Thr Phe Tyr Ala Gln Lys Phe
```

```
             50                 55                  60
Gln Gly Arg Ala Thr Leu Thr Ala Asp Thr Ser Thr Ser Thr Ala Tyr
 65                  70                  75                  80

Met Glu Val Ser Ser Leu Arg Ser Glu Asp Thr Ala Val Tyr Tyr Cys
                 85                  90                  95

Thr Arg Arg Met Ala Ala Met Asp Tyr Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 39
<211> LENGTH: 212
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 39

Asp Ile Gln Leu Thr Gln Ser Pro Ser Leu Ser Ala Ser Val Gly
1               5                   10                  15

Asp Arg Val Thr Ile Thr Cys Ser Ala Ser Ser Val Ser Tyr Met
            20                  25                  30

His Trp Tyr Gln Gln Lys Pro Gly Lys Ala Pro Lys Leu Leu Tyr
        35                  40                  45

Thr Thr Ser Asn Leu Ala Ser Gly Val Pro Ser Arg Phe Ser Gly
50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys His Gln Trp Ser Gly Tyr Pro Thr Phe
            85                  90                  95

Gly Gln Gly Thr Lys Leu Glu Ile Lys Arg Thr Val Ala Ala Pro Ser
        100                 105                 110

Val Phe Ile Phe Pro Pro Ser Asp Glu Gln Leu Lys Ser Gly Thr Ala
    115                 120                 125

Ser Val Val Cys Leu Leu Asn Asn Phe Tyr Pro Arg Glu Ala Lys Val
130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
            165                 170                 175

Leu Thr Leu Ser Lys Ala Asp Tyr Glu Lys His Lys Val Tyr Ala Cys
        180                 185                 190

Glu Val Thr His Gln Gly Leu Ser Ser Pro Val Thr Lys Ser Phe Asn
    195                 200                 205

Arg Gly Glu Cys
    210

<210> SEQ ID NO 40
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
        100                 105                 110
```

```
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 41
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 42
<211> LENGTH: 14
<212> TYPE: PRT
```

<213> ORGANISM: Homo sapiens

<400> SEQUENCE: 42

Ala Thr Lys Leu Thr Glu Glu Lys Tyr Glu Leu Lys Glu Gly
1               5                   10

<210> SEQ ID NO 43
<211> LENGTH: 7
<212> TYPE: PRT
<213> ORGANISM: Homo sapiens

<400> SEQUENCE: 43

Leu Gln Val Glu Asp Ser Gly
1               5

<210> SEQ ID NO 44
<211> LENGTH: 9
<212> TYPE: PRT
<213> ORGANISM: Homo sapiens

<400> SEQUENCE: 44

Arg Ile Arg Leu Val Val Thr Lys Gly
1               5

<210> SEQ ID NO 45
<211> LENGTH: 330
<212> TYPE: PRT
<213> ORGANISM: Homo sapiens

<400> SEQUENCE: 45

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

```
Gln Pro Arg Glu Pro Gln Val Tyr Thr Leu Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 46
<211> LENGTH: 324
<212> TYPE: PRT
<213> ORGANISM: Mus musculus

<400> SEQUENCE: 46

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
            35                  40                  45

Gly Val His Thr Phe Pro Ala Val Leu Gln Ser Asp Leu Tyr Thr Leu
        50                  55                  60

Ser Ser Ser Val Thr Val Pro Ser Ser Pro Arg Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
            115                 120                 125

Thr Ile Thr Leu Thr Pro Lys Val Thr Cys Val Val Val Asp Ile Ser
        130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
            195                 200                 205

Ile Glu Lys Thr Ile Ser Lys Thr Lys Gly Arg Pro Lys Ala Pro Gln
        210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270
```

```
Pro Ile Met Asn Thr Asn Gly Ser Tyr Phe Val Tyr Ser Lys Leu Asn
        275                 280                 285

Val Gln Lys Ser Asn Trp Glu Ala Gly Asn Thr Phe Thr Cys Ser Val
290                 295                 300

Leu His Glu Gly Leu His Asn His His Thr Glu Lys Ser Leu Ser His
305                 310                 315                 320

Ser Pro Gly Lys

<210> SEQ ID NO 47
<211> LENGTH: 327
<212> TYPE: PRT
<213> ORGANISM: Homo sapiens

<400> SEQUENCE: 47

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320
```

Leu Ser Leu Ser Leu Gly Lys
            325

<210> SEQ ID NO 48
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Thr Tyr
            20                  25                  30

Ala Met His Trp Val Arg Gln Ala Ser Gly Lys Gly Leu Glu Trp Val
        35                  40                  45

Gly Arg Ile Arg Thr Lys Ser Ser Asn Tyr Ala Thr Tyr Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg Asp Met Gly Ile Arg Arg Gln Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val

```
                    340                 345                 350
Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
        450

<210> SEQ ID NO 49
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Thr Phe
            20                  25                  30

Asp Tyr Ser Phe Leu His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 50
<211> LENGTH: 440
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Val Gln Leu Gln Gln Ser Gly Pro Glu Leu Val Lys Pro Gly Thr
1               5                   10                  15

Ser Val Lys Met Ser Cys Lys Ala Ser Gly Tyr Thr Phe Thr Asp Tyr
            20                  25                  30

Val Ile Asn Trp Val Lys Gln Arg Thr Gly Gln Gly Leu Glu Trp Ile
        35                  40                  45

Gly Glu Ile Tyr Pro Gly Ser Gly Ser Thr Phe Tyr His Glu Lys Phe
    50                  55                  60

Lys Gly Lys Ala Thr Leu Thr Ala Asp Lys Ser Ser Asn Thr Ala Tyr
65                  70                  75                  80

Met Gln Val Ser Ser Leu Thr Ser Glu Asp Ser Ala Val Tyr Phe Cys
                85                  90                  95

Thr Arg Arg Met Ala Ala Met Asp Tyr Trp Gly Gln Gly Thr Ser Val
            100                 105                 110

Thr Val Ser Ser Ala Lys Thr Thr Pro Pro Ser Val Tyr Pro Leu Ala
        115                 120                 125

Pro Gly Ser Ala Ala Gln Thr Asn Ser Met Val Thr Leu Gly Cys Leu
    130                 135                 140

Val Lys Gly Tyr Phe Pro Glu Pro Val Thr Val Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Pro Ser Ser Thr Trp Pro
            180                 185                 190

Ser Glu Thr Val Thr Cys Asn Val Ala His Pro Ala Ser Ser Thr Lys
        195                 200                 205

Val Asp Lys Lys Ile Val Pro Arg Asp Cys Gly Cys Lys Pro Cys Ile
    210                 215                 220

Cys Thr Val Pro Glu Val Ser Ser Val Phe Leu Phe Pro Pro Lys Pro
225                 230                 235                 240

Lys Asp Val Leu Thr Ile Thr Leu Thr Pro Lys Val Thr Cys Val Val
                245                 250                 255

Val Asp Ile Ser Lys Asp Asp Pro Glu Val Gln Phe Ser Trp Phe Val
            260                 265                 270

Asp Asp Val Glu Val His Thr Ala Gln Thr Gln Pro Arg Glu Glu Gln
        275                 280                 285

Phe Asn Ser Thr Phe Arg Ser Val Ser Glu Leu Pro Ile Met His Gln
    290                 295                 300

Asp Trp Leu Asn Gly Lys Glu Phe Lys Cys Arg Val Asn Ser Ala Ala
305                 310                 315                 320

Phe Pro Ala Pro Ile Glu Lys Thr Leu Ser Lys Thr Lys Gly Arg Pro
                325                 330                 335

Lys Ala Pro Gln Val Tyr Thr Leu Pro Pro Lys Glu Gln Met Ala
            340                 345                 350

Lys Asp Lys Val Ser Leu Thr Cys Met Ile Thr Asp Phe Phe Pro Glu
        355                 360                 365

Asp Ile Thr Val Glu Trp Gln Trp Asn Gly Gln Pro Ala Glu Asn Tyr
    370                 375                 380
```

```
Lys Asn Thr Gln Pro Ile Met Asp Thr Asp Gly Ser Tyr Phe Val Tyr
385                 390                 395                 400

Ser Lys Leu Asn Val Gln Lys Ser Asn Trp Glu Ala Gly Asn Thr Phe
            405                 410                 415

Thr Cys Ser Val Leu His Glu Gly Leu His Asn His Thr Glu Lys
            420                 425                 430

Ser Leu Ser His Ser Pro Gly Lys
        435                 440

<210> SEQ ID NO 51
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Ile Val Leu Thr Gln Ser Pro Ala Ile Met Ser Ala Ser Leu Gly
1               5                   10                  15

Glu Glu Ile Thr Leu Thr Cys Ser Ala Ser Ser Ser Val Ser Tyr Met
            20                  25                  30

His Trp Tyr Gln Gln Lys Ser Gly Thr Ser Pro Lys Leu Leu Leu Tyr
        35                  40                  45

Thr Thr Ser Asn Leu Ala Ser Gly Val Pro Ser Arg Phe Ser Gly Thr
    50                  55                  60

Gly Ser Gly Thr Phe Tyr Ser Leu Thr Ile Ser Ser Val Glu Ala Glu
65                  70                  75                  80

Asp Ala Ala Asp Tyr Tyr Cys His Gln Trp Ser Gly Tyr Pro Thr Phe
                85                  90                  95

Gly Gly Gly Thr Lys Leu Glu Ile Lys Arg Ala Asp Ala Ala Pro Thr
            100                 105                 110

Val Ser Ile Phe Pro Pro Ser Ser Glu Gln Leu Thr Ser Gly Gly Ala
        115                 120                 125

Ser Val Val Cys Phe Leu Asn Asn Phe Tyr Pro Lys Asp Ile Asn Val
    130                 135                 140

Lys Trp Lys Ile Asp Gly Ser Glu Arg Gln Asn Gly Val Leu Asn Ser
145                 150                 155                 160

Trp Thr Asp Gln Asp Ser Lys Asp Ser Thr Tyr Ser Met Ser Ser Thr
                165                 170                 175

Leu Thr Leu Thr Lys Asp Glu Tyr Glu Arg His Asn Ser Tyr Thr Cys
            180                 185                 190

Glu Ala Thr His Lys Thr Ser Thr Ser Pro Ile Val Lys Ser Phe Asn
        195                 200                 205

Arg Asn Glu Cys
    210

<210> SEQ ID NO 52
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Val Gln Leu Gln Gln Ser Gly Pro Glu Leu Val Lys Pro Gly Thr
1               5                   10                  15
```

```
Ser Val Lys Met Ser Cys Lys Ala Ser Gly Tyr Thr Phe Thr Asp Tyr
            20                  25                  30

Val Ile Asn Trp Val Lys Gln Arg Thr Gly Gln Gly Leu Glu Trp Ile
        35                  40                  45

Gly Glu Ile Tyr Pro Gly Ser Gly Ser Thr Phe Tyr His Glu Lys Phe
    50                  55                  60

Lys Gly Lys Ala Thr Leu Thr Ala Asp Lys Ser Ser Asn Thr Ala Tyr
65                  70                  75                  80

Met Gln Val Ser Ser Leu Thr Ser Glu Asp Ser Ala Val Tyr Phe Cys
                85                  90                  95

Thr Arg Arg Met Ala Ala Met Asp Tyr Trp Gly Gln Gly Thr Ser Val
                100                 105                 110

Thr Val Ser Ser
        115

<210> SEQ ID NO 53
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Ile Val Leu Thr Gln Ser Pro Ala Ile Met Ser Ala Ser Leu Gly
1               5                   10                  15

Glu Glu Ile Thr Leu Thr Cys Ser Ala Ser Ser Ser Val Ser Tyr Met
            20                  25                  30

His Trp Tyr Gln Gln Lys Ser Gly Thr Ser Pro Lys Leu Leu Leu Tyr
        35                  40                  45

Thr Thr Ser Asn Leu Ala Ser Gly Val Pro Ser Arg Phe Ser Gly Thr
    50                  55                  60

Gly Ser Gly Thr Phe Tyr Ser Leu Thr Ile Ser Ser Val Glu Ala Glu
65                  70                  75                  80

Asp Ala Ala Asp Tyr Tyr Cys His Gln Trp Ser Gly Tyr Pro Thr Phe
                85                  90                  95

Gly Gly Gly Thr Lys Leu Glu Ile Lys
                100                 105

<210> SEQ ID NO 54
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Ile Thr Ser Ser
            20                  25                  30

Asn Val Tyr Trp Phe Arg Gln Pro Pro Gly Lys Gly Leu Glu Trp Met
        35                  40                  45

Gly Asn Ile Trp Gly Asp Gly Ser Thr Asp Tyr Asn Ser Ser Leu Lys
    50                  55                  60

Ser Arg Leu Thr Leu Ser Arg Asp Thr Ser Lys Asn Gln Val Phe Leu
65                  70                  75                  80
```

```
Lys Ile Asn Ser Leu Gln Ser Glu Asp Thr Ala Thr Tyr Phe Cys Thr
                85                  90                  95

Arg Ser Trp Glu Tyr Tyr Phe Asp His Trp Gly Gln Gly Val Val Val
            100                 105                 110

Thr Val Ser Ser Ala Lys Thr Thr Ala Pro Ser Val Tyr Pro Leu Ala
        115                 120                 125

Pro Val Cys Gly Asp Thr Thr Gly Ser Ser Val Thr Leu Gly Cys Leu
    130                 135                 140

Val Lys Gly Tyr Phe Pro Glu Pro Val Thr Leu Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Ser Val Thr Val Thr Ser Ser Thr Trp Pro
            180                 185                 190

Ser Gln Ser Ile Thr Cys Asn Val Ala His Pro Ala Ser Ser Thr Lys
        195                 200                 205

Val Asp Lys Lys Ile Glu Pro Arg Gly Pro Thr Ile Lys Pro Cys Pro
210                 215                 220

Pro Cys Lys Cys Pro Ala Pro Asn Leu Leu Gly Gly Pro Ser Val Phe
225                 230                 235                 240

Ile Phe Pro Pro Lys Ile Lys Asp Val Leu Met Ile Ser Leu Ser Pro
                245                 250                 255

Ile Val Thr Cys Val Val Val Asp Val Ser Glu Asp Asp Pro Asp Val
            260                 265                 270

Gln Ile Ser Trp Phe Val Asn Asn Val Glu Val His Thr Ala Gln Thr
        275                 280                 285

Gln Thr His Arg Glu Asp Tyr Asn Ser Thr Leu Arg Val Val Ser Ala
    290                 295                 300

Leu Pro Ile Gln His Gln Asp Trp Met Ser Gly Lys Glu Phe Lys Cys
305                 310                 315                 320

Lys Val Asn Asn Lys Asp Leu Pro Ala Pro Ile Glu Arg Thr Ile Ser
                325                 330                 335

Lys Pro Lys Gly Ser Val Arg Ala Pro Gln Val Tyr Val Leu Pro Pro
            340                 345                 350

Pro Glu Glu Glu Met Thr Lys Lys Gln Val Thr Leu Thr Cys Met Val
        355                 360                 365

Thr Asp Phe Met Pro Glu Asp Ile Tyr Val Glu Trp Thr Asn Asn Gly
    370                 375                 380

Lys Thr Glu Leu Asn Tyr Lys Asn Thr Glu Pro Val Leu Asp Ser Asp
385                 390                 395                 400

Gly Ser Tyr Phe Met Tyr Ser Lys Leu Arg Val Glu Lys Lys Asn Trp
                405                 410                 415

Val Glu Arg Asn Ser Tyr Ser Cys Ser Val Val His Glu Gly Leu His
            420                 425                 430

Asn His His Thr Thr Lys Ser Phe Ser Arg Thr Pro Gly Lys
        435                 440                 445

<210> SEQ ID NO 55
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 55

Asp Ile Val Leu Thr Gln Ser Pro Ala Leu Ala Val Ser Pro Gly Gln
1               5                   10                  15

Arg Ala Thr Leu Ser Cys Arg Ala Ser Gln Ser Val Thr Leu Ser Asn
            20                  25                  30

Val Asn Leu Met Asn Trp Tyr Gln Gln Lys Pro Gly Gln Gln Pro Lys
        35                  40                  45

Leu Leu Ile Tyr His Ala Ser Asn Leu Ala Ser Gly Ile Pro Thr Arg
    50                  55                  60

Phe Ser Gly Ser Gly Ser Gly Thr Asp Phe Thr Leu Thr Ile Asp Pro
65                  70                  75                  80

Val Gln Ala Asp Asp Ile Ala Ala Tyr Tyr Cys Gln Gln Ser Gly Glu
                85                  90                  95

Ser Pro Arg Thr Phe Gly Gly Gly Thr Lys Val Glu Leu Lys Arg Ala
            100                 105                 110

Asp Ala Ala Pro Thr Val Ser Ile Phe Pro Pro Ser Ser Glu Gln Leu
        115                 120                 125

Thr Ser Gly Gly Ala Ser Val Val Cys Phe Leu Asn Asn Phe Tyr Pro
    130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
        195                 200                 205

Val Lys Ser Phe Asn Arg Asn Glu Cys
    210                 215

<210> SEQ ID NO 56
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Ile Tyr Ser Tyr
            20                  25                  30

Ser Ile His Trp Val Arg Gln Ala Pro Gly Lys Gly Leu Glu Trp Val
        35                  40                  45

Ala Tyr Ile Tyr Pro Ser Tyr Gly Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ala Val Ala Ala Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

```
Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Val Asp Val Ser Glu Asp Asp Pro Asp
            260                 265                 270

Val Gln Ile Ser Trp Phe Val Asn Asn Val Glu Val His Thr Ala Gln
        275                 280                 285

Thr Gln Thr His Arg Glu Asp Tyr Asn Ser Thr Leu Arg Val Val Ser
290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
        355                 360                 365

Val Thr Asp Phe Met Pro Glu Asp Ile Tyr Val Glu Trp Thr Asn Asn
370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
            420                 425                 430

His Asn His His Thr Thr Lys Ser Phe Ser Arg Thr Pro Gly Lys
        435                 440                 445

<210> SEQ ID NO 57
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45
```

Tyr Ser Ala Ser Ser Leu Tyr Ser Gly Val Pro Ser Arg Phe Ser Gly
            50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Gly Val Ser Gly Tyr
                    85                  90                  95

Ser Leu Ile Thr Phe Gly Gln Gly Thr Lys Val Glu Ile Lys Arg Thr
                100                 105                 110

Val Ala Ala Pro Ser Val Phe Ile Phe Pro Pro Ser Asp Glu Gln Leu
                115                 120                 125

Lys Ser Gly Thr Ala Ser Val Val Cys Leu Leu Asn Asn Phe Tyr Pro
            130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
                180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
            210                 215

<210> SEQ ID NO 58
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asp Ile Tyr Ser Tyr
                 20                  25                  30

Ser Ile His Trp Val Arg Gln Ala Pro Gly Lys Gly Leu Glu Trp Val
             35                  40                  45

Ala Tyr Ile Tyr Pro Ser Tyr Gly Tyr Thr Ser Tyr Ala Asp Ser Val
         50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gly Ala Val Ala Ala Leu Asp Tyr Trp Gly Gln Gly Thr Leu
                100                 105                 110

Val Thr Val Ser Ser Ala Lys Thr Thr Ala Pro Ser Val Tyr Pro Leu
            115                 120                 125

Ala Pro Val Cys Gly Asp Thr Thr Gly Ser Ser Val Thr Leu Gly Cys
            130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp 180                 185                 190

Pro Ser Gln Ser Ile Thr Cys Asn Val Ala His Pro Ala Ser Ser Thr
            195                 200                 205

Lys Val Asp Lys Lys Ile Glu Pro Arg Gly Pro Thr Ile Lys Pro Cys
            210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Val Asp Val Ser Glu Asp Asp Pro Asp
            260                 265                 270

Val Gln Ile Ser Trp Phe Val Asn Asn Val Glu Val His Thr Ala Gln
            275                 280                 285

Thr Gln Thr His Arg Glu Asp Tyr Asn Ser Thr Leu Arg Val Val Ser
            290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
            355                 360                 365

Val Thr Asp Phe Met Pro Glu Asp Ile Tyr Val Glu Trp Thr Asn Asn
370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
            420                 425                 430

His Asn His His Thr Thr Lys Ser Phe Ser Arg Thr Pro Gly Lys
            435                 440                 445

<210> SEQ ID NO 59
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Val Ser Gly Tyr
                85                  90                  95

```
Ser Leu Ile Thr Phe Gly Gln Gly Thr Lys Val Glu Ile Lys Arg Ala
            100                 105                 110

Asp Ala Ala Pro Thr Val Ser Ile Phe Pro Pro Ser Ser Glu Gln Leu
        115                 120                 125

Thr Ser Gly Gly Ala Ser Val Val Cys Phe Leu Asn Asn Phe Tyr Pro
        130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
        195                 200                 205

Val Lys Ser Phe Asn Arg Asn Glu Cys
        210                 215
```